(12) United States Patent
Kambourakis et al.

(10) Patent No.: US 9,506,090 B2
(45) Date of Patent: Nov. 29, 2016

(54) METHOD FOR SYNTHESIZING FDCA AND DERIVATES THEREOF

(71) Applicant: SYNTHETIC GENOMICS, INC., La Jolla, CA (US)

(72) Inventors: Spiros Kambourakis, San Diego, CA (US); Benjamin M. Griffin, San Diego, CA (US); Kevin V. Martin, Solana Beach, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 0 days.

(21) Appl. No.: 14/033,300

(22) Filed: Sep. 20, 2013

(65) Prior Publication Data

US 2014/0106414 A1    Apr. 17, 2014

Related U.S. Application Data

(60) Provisional application No. 61/704,408, filed on Sep. 21, 2012.

(51) Int. Cl.
| | | |
|---|---|---|
| C12P 7/58 | (2006.01) | |
| C07D 307/68 | (2006.01) | |
| C12P 17/12 | (2006.01) | |

(52) U.S. Cl.
CPC .......... *C12P 7/58* (2013.01); *C07D 307/68* (2013.01); *C12P 17/12* (2013.01)

(58) Field of Classification Search
None
See application file for complete search history.

(56) References Cited

U.S. PATENT DOCUMENTS

| | | |
|---|---|---|
| 3,184,479 A | 5/1965 | Matter |
| 3,203,963 A | 8/1965 | Hales |
| 3,326,944 A | 6/1967 | Lew |
| 5,298,411 A | 3/1994 | Sogabe et al. |
| 7,385,081 B1 | 6/2008 | Gong |
| 7,411,078 B2 | 8/2008 | Miura et al. |
| 8,242,292 B2 | 8/2012 | Yutaka et al. |
| 2010/0075381 A1 | 3/2010 | Ito et al. |
| 2011/0124065 A1 | 5/2011 | Moon et al. |
| 2011/0183382 A1 | 7/2011 | Schmalisch et al. |
| 2012/0264179 A1 | 10/2012 | Burgard et al. |
| 2014/0171683 A1 | 6/2014 | Sieber et al. |
| 2014/0295508 A1 | 10/2014 | Yoshikuni et al. |
| 2015/0152452 A1 | 6/2015 | Kalum et al. |

FOREIGN PATENT DOCUMENTS

| | | |
|---|---|---|
| EP | 2 683 815 B1 | 5/2015 |
| GB | 957 985 | 5/1964 |
| WO | WO 2010/072902 A1 | 7/2010 |
| WO | WO 2011/043661 A1 | 4/2011 |
| WO | WO 2013/049711 A1 | 4/2013 |
| WO | WO 2013/151428 A1 | 10/2013 |
| WO | WO 2013/183610 A1 | 12/2013 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Otera et al. Esterification: Methods, Reactions, and Applications, Second Edition. Chapter 1. 2010 Wiley-VCH Verlag GmbH & Co. KGaA. Published Online Feb. 2, 2010.*
Palmer et al. Biochemistry. Oct. 13, 1998;37(41):14350-7.*
Gandini et al. Prog. Polym. Sci., 1997, 22, 1203-1379.*
Heuts et al.: *"Discovery, characterization, and kinetic analysis of an alditol oxidase from Streptomyces coelicolor"*; J. Biol. Chem, Jul. 13, 2007, vol. 28, pp. 20283-20291.
PubChem. Glucuronic Acid (CID 23677976) Feb. 5, 2008 [retrieved Dec. 1, 2013]. Available on the internet: <URL:http://pubchem.ncbi.nlm.nih.gov/summary.cgi?cid=23677976&loc=ec_rcs>.
International Search Report regarding PCT/US2013/061036.

(Continued)

*Primary Examiner* — Christian Fronda
(74) *Attorney, Agent, or Firm* — DLA Piper LLP (US)

(57) ABSTRACT

The present invention provides methods for producing a product of one or more enzymatic pathways. The pathways used in the methods of the invention involve one or more conversion steps such as, for example, an enzymatic conversion of guluronic acid into D-glucarate (Step 7); an enzymatic conversion of 5-ketogluconate (5-KGA) into L-Iduronic acid (Step 15); an enzymatic conversion of L-Iduronic acid into Idaric acid Step 7b); and an enzymatic conversion of 5-ketocluconate into 4,6-dihydroxy 2,5-diketo hexanoate (2,5-DDH) (Step 16). In some embodiments the methods of the invention produce 2,5-furandicarboxylic acid (FDCA) as a product. The methods include both enzymatic and chemical conversions as steps. Various pathways are also provided for converting glucose into 5-dehdyro-4-deoxy-glucarate (DDG), and for converting glucose into 2,5-furandicarboxylic acid (FDCA). The methods also involve the use of engineered enzymes that perform reactions with high specificity and efficiency. Additional products that can be produce include metabolic products such as, but not limited to, guluronic acid, L-iduronic acid, idaric acid, glucaric acid. Any of the products can be produced using glucose as a substrate or using any intermediate in any of the methods or pathways of the invention.

24 Claims, 15 Drawing Sheets

(56) References Cited

OTHER PUBLICATIONS

Aden, A. et al.: "*Top Value Added Chemicals From Biomass vol. I—Results of Screening for Potential Candidates from Sugars and Synthesis Gas*"; DOE National Renewable Enrgy Lab, Aug. 2004, DOE/GO 102004-1993; 76 pages.

De Jong, E. et al.: "*Furandicarboxylic Acid (FDCA), A Versatile Building Block fors Very Interesting Class of Polyesters*"; American Chemical Society, Aug. 6, 2012, pp. 1-13.

Tong, Xinli et al.: "*Biomass into chemicals: Conversion of sugars to furan derivatives by catalytic processes*"; Applied Catalysis A: General, 385 (2010), pp. 1-13.

Wikipedia: "*2,5-Furandicarboxylic acid*"; Wikipedia The Free Encyclopedia, Aug. 3, 2012, 5 pgs, http://en.wikipedia.org/wiki/2,5-Furandicarboxylic_acid.

International Search Report issued on Sep. 8, 2015, regarding PCT/US2015/021848.

Chica et al.: "*Semi-rational approaches to engineering enzyme activity: combining the benefits of directed evolution and rational design*"; Curr Opin Biotechnol. Aug. 2005;16(4):378-84.

Sen, S. et al.: "*Developments in Directed Evolution for Improving Enzyme Functions*"; Appl Biochem Biotechnol. Dec. 2007;143(3):212-23.

Dirkx et al.: "*The oxidation of gluconic acid with platinum on carbon as catalyst*"; J. Catalysis, 1981, vol. 67, 1981, pp. 14-20.

Extended European Search Report issued on May 16, 2016, regarding EP 13 83 8235.

McKinlay et al.: "*A genomic perspective on the potential of Actinobacillus succinogenes for industrial succinate production*"; BMC Genomics, vol. 11, 2010, pp. 1(680)-16(695).

Takase et al.: "*Molecular identification of unsaturated uronate reductase prerequisite for alginate metabolism in Spingomonas sp. A1*"; Biochimica et Biophysica Acta, vol. 1804, 2010, pp. 1925-1936.

* cited by examiner

Scheme 6

SEQUENCE LISTING

<160> NUMBER OF SEQ ID NOS: 72

<210> SEQ ID NO 1
<211> LENGTH: 267
<212> TYPE: PRT
<213> ORGANISM: Agrobacterium tumefaciens

<400> SEQUENCE: 1

Met Ala Met Lys Arg Leu Leu Val Thr Gly Ala Ala Gly Gln Leu Gly
1               5                   10                  15

Arg Val Met Arg Lys Arg Leu Ala Ser Met Ala Glu Ile Val Arg Leu
                20                  25                  30

Ala Asp Leu Ala Pro Leu Asp Pro Ala Gly Pro Asn Glu Glu Cys Met
            35                  40                  45

Gln Cys Asp Leu Ala Asp Ala Asp Ala Val Asp Ala Met Val Ala Gly
        50                  55                  60

Cys Asp Gly Ile Val His Leu Gly Gly Ile Ser Val Glu Lys Pro Phe
65                  70                  75                  80

Glu Gln Ile Leu Gln Gly Asn Ile Ile Gly Leu Tyr Asn Leu Tyr Glu
                85                  90                  95

Ala Ala Arg Ala His Gly Gln Pro Arg Ile Ile Phe Ala Ser Ser Asn
            100                 105                 110

His Thr Ile Gly Tyr Tyr Pro Gln Thr Glu Arg Leu Gly Pro Asp Val
        115                 120                 125

Pro Phe Arg Pro Asp Gly Leu Tyr Gly Val Ser Lys Cys Phe Gly Glu
    130                 135                 140

Ser Leu Ala Arg Met Tyr Phe Glu Lys Phe Gly Gln Glu Thr Ala Leu
145                 150                 155                 160

Val Arg Ile Gly Ser Cys Thr Pro Glu Pro Leu Asn Tyr Arg Met Leu
                165                 170                 175

Ser Thr Trp Phe Ser His Asp Asp Phe Val Ser Leu Ile Glu Ala Ala
            180                 185                 190

Phe Arg Ala Pro Val Leu Gly Cys Pro Ile Val Trp Gly Ala Ser Ala
        195                 200                 205

Asn Asp Ala Ser Trp Trp Asp Asn Ser His Leu Gly Phe Ile Gly Trp
    210                 215                 220

Lys Pro Lys Asp Asn Ala Glu Ala Phe Arg Arg Lys Ile Ala Glu Thr
225                 230                 235                 240

Thr Pro Gln Pro Asp Ala Arg Asp Pro Ile Val Arg Phe Gln Gly Gly
                245                 250                 255

Val Phe Val Asp Asn Pro Ile Phe Lys Glu Thr
            260                 265

<210> SEQ ID NO 2
<211> LENGTH: 266
<212> TYPE: PRT
<213> ORGANISM: Rhizobium lupini

<400> SEQUENCE: 2

```
Met Lys Arg Leu Leu Ile Thr Gly Ala Ala Gly Ala Leu Gly Arg Val
1               5                   10                  15

Met Arg Glu Arg Leu Ala Pro Met Ala Thr Ile Leu Arg Leu Ser Asp
            20                  25                  30

Ile Ala Pro Ile Gly Ala Ala Arg Gln Asn Glu Glu Ile Val Gln Cys
        35                  40                  45

Asp Leu Ala Asp Ala Lys Ala Val His Ala Leu Val Glu Asp Cys Asp
    50                  55                  60

Gly Ile Val His Leu Gly Gly Val Ser Val Glu Arg Lys Phe Ser Gln
65                  70                  75                  80

Ile Val Ala Gly Asn Ile Val Gly Leu Tyr Asn Leu Tyr Glu Ala Ala
                85                  90                  95

Arg Ala His Arg Met Pro Arg Ile Val Phe Ala Ser Ser Asn His Thr
            100                 105                 110

Ile Gly Phe Tyr Pro Gln Thr Glu Arg Leu Ser Val Asp His Pro Tyr
        115                 120                 125

Arg Pro Asp Gly Leu Tyr Gly Val Ser Lys Cys Phe Gly Glu Ser Leu
130                 135                 140

Ala His Met Tyr His Glu Lys Phe Gly Gln Glu Thr Ala Leu Val Arg
145                 150                 155                 160

Ile Gly Ser Cys Val Thr Glu Pro Val Asn His Arg Met Leu Ser Thr
                165                 170                 175

Trp Leu Ser Tyr Asp Asp Phe Val Ser Leu Ile Glu Ala Val Phe Arg
            180                 185                 190

Ala Pro Lys Leu Gly Cys Pro Val Ile Trp Gly Ala Ser Asn Asn Asp
        195                 200                 205

Ala Gly Trp Trp Asp Asn Ser Ala Ala Gly Phe Leu Gly Trp Lys Pro
210                 215                 220

Lys Asp Asn Ala Glu Ile Phe Arg Ser Lys Ile Glu Ala Ala Cys Glu
225                 230                 235                 240

Arg Pro Gly Ser Asp Asp Pro Ala Ala Arg Trp Gln Gly Gly Leu Phe
                245                 250                 255

Thr Gln Asp Pro Ile Phe Pro Glu Asp Glu
            260                 265
```

<210> SEQ ID NO 3
<211> LENGTH: 272
<212> TYPE: PRT
<213> ORGANISM: Pseudomonas sp.

<400> SEQUENCE: 3

```
Met Thr Thr Ala Tyr Thr Pro Phe Asn Arg Leu Leu Leu Thr Gly Ala
1               5                   10                  15

Ala Gly Gly Leu Gly Lys Val Leu Arg Glu Ser Leu Arg Pro Tyr Ala
            20                  25                  30

Asn Val Leu Arg Val Ser Asp Ile Ala Ala Met Ser Pro Ala Thr Gly
        35                  40                  45

Ala His Glu Glu Val Gln Val Cys Asp Leu Ala Asp Lys Ala Ala Val
    50                  55                  60

His Gln Leu Val Glu Gly Val Asp Ala Ile Leu His Phe Gly Gly Val
65                  70                  75                  80

Ser Val Glu Arg Pro Phe Glu Glu Ile Leu Gly Ala Asn Ile Cys Gly
                85                  90                  95
```

-continued

```
Val Phe His Ile Tyr Glu Ala Ala Arg Arg His Gly Val Lys Arg Val
             100                 105                 110

Ile Phe Ala Ser Ser Asn His Val Ile Gly Phe Tyr Lys Gln Asp Glu
         115                 120                 125

Thr Ile Asp Ala Asn Cys Pro Arg Arg Pro Asp Ser Tyr Tyr Gly Leu
    130                 135                 140

Ser Lys Ser Tyr Gly Glu Asp Met Ala Ser Phe Tyr Phe Asp Arg Tyr
145                 150                 155                 160

Gly Ile Glu Thr Val Ser Ile Arg Ile Gly Ser Ser Phe Pro Glu Pro
                165                 170                 175

His Asn Arg Arg Met Met Ser Thr Trp Leu Ser Phe Ala Asp Leu Thr
            180                 185                 190

Gln Leu Leu Glu Arg Ala Leu Tyr Thr Pro Asn Val Gly His Thr Val
        195                 200                 205

Val Tyr Gly Met Ser Ala Asn Lys Asn Val Trp Trp Asp Asn His Leu
    210                 215                 220

Ala Ala His Leu Gly Phe Gln Pro Lys Asp Ser Ser Glu Val Phe Arg
225                 230                 235                 240

Ala Gln Ile Asp Ala Gln Pro Met Pro Ala Ala Asp Pro Ala Met
                245                 250                 255

Val Phe Gln Gly Gly Ala Phe Val Ala Ala Gly Pro Phe Gly Asp Asp
            260                 265                 270
```

<210> SEQ ID NO 4
<211> LENGTH: 804
<212> TYPE: DNA
<213> ORGANISM: Agrobacterium Tumefaciens

<400> SEQUENCE: 4

| | | |
|---|---|---|
| atggcaatga aacggcttct tgttaccggt gctgcgggcc agcttggccg cgttatgcgc | 60 |
| aaacgccttg catcgatggc cgagatcgtt cgccttgccg atctcgcccc gctcgatccg | 120 |
| gcaggcccga acgaggaatg catgcaatgc gaccttgcgg atgcagacgc cgttgacgcc | 180 |
| atggttgccg gttgcgacgg catcgttcac ctcggcggca tatcggtgga gaagcctttc | 240 |
| gaacaaatcc ttcagggcaa catcatcggg ctgtataatc tctatgaggc cgcccgcgcc | 300 |
| cacggccagc cgcgcatcat cttcgccagt tcgaaccata cgatcggtta ttacccgcag | 360 |
| acggagaggc ttggaccgga tgttcccttc cgcccggatg gctttacgg cgtctccaaa | 420 |
| tgtttcggcg agagccttgc ccgcatgtat ttcgagaaat tcggccagga gaccgcactt | 480 |
| gtccgcatcg ctcctgcac gccggaaccc cttaattacc gcatgctgtc cacctggttt | 540 |
| tcgcatgacg atttcgtctc gctgatcgag gcggcgttcc gcgcccccgt gctcggctgc | 600 |
| cccatcgtct gggggcgtc ggccaacgat gcgagctggt gggacaattc gcatctcggc | 660 |
| tttattggat ggaaaccgaa ggacaatgcc gaggccttcc gccggaagat tgccgaaacg | 720 |
| acgccgcagc cggacgcgcg cgaccccgatt gtccgctttc agggtggcgt gtttgtcgac | 780 |
| aacccgatct tcaaggagac gtga | 804 |

<210> SEQ ID NO 5
<211> LENGTH: 801
<212> TYPE: DNA
<213> ORGANISM: Rhizobium lupini

<400> SEQUENCE: 5
atgaagagac ttctgattac cggcgcagcg ggtgcactgg gccgcgtgat gcgggaaagg     60

```
ctcgcaccca tggcaacgat tctgcgcctt tccgatatcg ccccgattgg agcggcccgc    120
cagaacgagg aaatcgtcca gtgcgatctt gccgatgcca aagcagtgca tgctctggtc    180
gaagattgcg acgggatcgt ccatctcggt ggcgtctcag tagagcgcaa gttctcgcag    240
atcgtcgccg gcaacatcgt cggcctttac aatctctacg aagccgcacg cgcgcatcgg    300
atgccgcgca tcgtctttgc aagttccaat cacaccatcg gcttttatcc gcaaaccgaa    360
cggttgtcgg tggaccatcc ctatcgtccg acgggctct acggcgtatc gaaatgtttc     420
ggcgagtctc tggcgcatat gtaccatgag aagttcgggc aggagacggc actcgtgcgc    480
atcgggtcct gcgtgaccga accggtcaac catcgcatgc tttccacctg gctttcctac    540
gatgatttcg tctcgcttat cgaggccgta ttccgtgcgc cgaaactcgg ctgccccgtc    600
atctggggcg cgtcgaacaa cgatgcagga tggtgggaca attccgccgc cggctttctc    660
ggctggaagc cgaaagacaa tgccgaaatc ttccgttcga agatcgaagc cgcttgcgaa    720
cgccccggtt ctgatgatcc ggccgcccgc tggcaaggcg ggctcttcac gcaggacccg    780
atcttcccag aggacgagta a                                              801

<210> SEQ ID NO 6
<211> LENGTH: 819
<212> TYPE: DNA
<213> ORGANISM: Pseudomonas sp.

<400> SEQUENCE: 6
atgaccacag cctacacccc cttcaatcgc ctgctactca ccggagcggc aggcggcctc     60
ggcaaggtcc tgcgcgaaag cctgcgacct tatgccaacg tcctgcgcgt ctccgacatc    120
gcggccatga gccctgccac aggcgcccat gaagaagtcc aggtctgcga cctcgccgat    180
aaagcggcgg tccatcaact ggtcgaaggc gtcgacgcaa tcctgcactt cggtggcgta    240
tcggtggagc ggcccttcga ggaaatcctc ggggccaata tctgcggcgt gtttcatatc    300
tatgaagcgg cgccggca tggcgtaaag cgggtgatct tcgccagctc caaccacgtc     360 atcggtttt ataagcagga cgaaaccatc gacgccaact gcccgcgccg ccccgacagc     420
tactacggtc tgtccaagtc ctacggcgaa gacatggcca gcttctactt cgaccgctac    480
ggcatcgaga ccgtgagcat ccgcatcggc tcctcgttcc ccgagccgca caatcgccgc    540
atgatgagca cctggctgag cttttgccga ctgacgcagc tgctcgaacg cgcgctgtac    600 accccccaacg tcggccacac cgtggtctac ggcatgtccg ctaacaagaa cgtctggtgg    660
gacaaccacc tggccgcgca cctgggcttc aaccgaagg acagctccga ggtgttccgt    720
gcgcagatcg atgcccagcc gatgcccgcc gccgatgacc cggcgatggt ctttcaaggc    780
ggcgcctttg tcgcagccgg gccgttcggc gacgactga                           819

<210> SEQ ID NO 7
<211> LENGTH: 274
<212> TYPE: PRT
<213> ORGANISM: Rhizobium sp.

<400> SEQUENCE: 7

Met Leu Asn Val Glu Thr Arg His Ala Val His Ala Asp His Ala Arg
1               5                   10                  15

Ser Leu Asp Thr Glu Gly Leu Arg Arg His Phe Leu Ala Gln Gly Leu
            20                  25                  30

Phe Ala Glu Gly Glu Ile Arg Leu Ile Tyr Thr His Tyr Asp Arg Phe
        35                  40                  45
```

```
Val Met Gly Gly Ala Val Pro Asp Gly Ala Pro Leu Val Leu Asp His
    50              55                  60

Val Glu Glu Thr Lys Thr Pro Gly Phe Leu Asp Arg Arg Glu Met Gly
65                  70                  75                  80

Ile Val Asn Ile Gly Ala Glu Gly Ser Val His Ala Gly Asn Glu Ser
                85                  90                  95

Trp Ser Leu Asn Arg Gly Asp Val Leu Tyr Leu Gly Met Gly Ala Gly
                100                 105                 110

Pro Val Thr Phe Glu Gly Ala Gly Arg Phe Tyr Leu Val Ser Ala Pro
            115                 120                 125

Ala His Arg Ser Leu Pro Asn Arg Leu Val Thr Pro Ala Asp Ser Lys
    130                 135                 140

Glu Val Lys Leu Gly Ala Leu Glu Thr Ser Asn Lys Arg Thr Ile Asn
145                 150                 155                 160

Gln Phe Ile His Pro Leu Val Met Glu Ser Cys Gln Leu Val Leu Gly
                165                 170                 175

Tyr Thr Thr Leu Glu Asp Gly Ser Val Trp Asn Thr Met Pro Ala His
            180                 185                 190

Val His Asp Arg Arg Met Glu Ala Tyr Leu Tyr Phe Gly Met Asp Glu
    195                 200                 205

Thr Ser Arg Val Leu His Leu Met Gly Glu Pro Gln Gln Thr Arg His
210                 215                 220

Leu Phe Val Ala Asn Glu Gly Ala Ile Ser Pro Pro Trp Ser Ile
225                 230                 235                 240

His Ala Gly Ala Gly Ile Gly Ser Tyr Thr Phe Ile Trp Ala Met Ala
                245                 250                 255

Gly Asp Asn Val Asp Tyr Thr Asp Met Glu Phe Ile Gln Pro Gly Asp
            260                 265                 270

Leu Arg

<210> SEQ ID NO 8
<211> LENGTH: 278
<212> TYPE: PRT
<213> ORGANISM: Escherichia coli K-12

<400> SEQUENCE: 8

Met Asp Val Arg Gln Ser Ile His Ser Ala His Ala Lys Thr Leu Asp
1               5                   10                  15

Thr Gln Gly Leu Arg Asn Glu Phe Leu Val Glu Lys Val Phe Val Ala
                20                  25                  30

Asp Glu Tyr Thr Met Val Tyr Ser His Ile Asp Arg Ile Ile Val Gly
            35                  40                  45

Gly Ile Met Pro Ile Thr Lys Thr Val Ser Val Gly Gly Glu Val Gly
    50                  55                  60

Lys Gln Leu Gly Val Ser Tyr Phe Leu Glu Arg Arg Glu Leu Gly Val
65                  70                  75                  80

Ile Asn Ile Gly Gly Ala Gly Thr Ile Thr Val Asp Gly Gln Cys Tyr
                85                  90                  95

Glu Ile Gly His Arg Asp Ala Leu Tyr Val Gly Lys Gly Ala Lys Glu
                100                 105                 110

Val Val Phe Ala Ser Ile Asp Thr Gly Thr Pro Ala Lys Phe Tyr Tyr
            115                 120                 125

Asn Cys Ala Pro Ala His Thr Thr Tyr Pro Thr Lys Lys Val Thr Pro
    130                 135                 140
```

Asp Glu Val Ser Pro Val Thr Leu Gly Asp Asn Leu Thr Ser Asn Arg
145                 150                 155                 160

Arg Thr Ile Asn Lys Tyr Phe Val Pro Asp Val Leu Glu Thr Cys Gln
            165                 170                 175

Leu Ser Met Gly Leu Thr Glu Leu Ala Pro Gly Asn Leu Trp Asn Thr
            180                 185                 190

Met Pro Cys His Thr His Glu Arg Arg Met Glu Val Tyr Phe Tyr Phe
            195                 200                 205

Asn Met Asp Asp Asp Ala Cys Val Phe His Met Met Gly Gln Pro Gln
        210                 215                 220

Glu Thr Arg His Ile Val Met His Asn Glu Gln Ala Val Ile Ser Pro
225                 230                 235                 240

Ser Trp Ser Ile His Ser Gly Val Gly Thr Lys Ala Tyr Thr Phe Ile
            245                 250                 255

Trp Gly Met Val Gly Glu Asn Gln Val Phe Asp Asp Met Asp His Val
            260                 265                 270

Ala Val Lys Asp Leu Arg
            275

<210> SEQ ID NO 9
<211> LENGTH: 278
<212> TYPE: PRT
<213> ORGANISM: Rhizobium sp.

<400> SEQUENCE: 9

Met Thr Met Lys Ile Leu Tyr Gly Ala Gly Pro Glu Asp Val Lys Gly
1               5                   10                  15

Tyr Asp Thr Gln Arg Leu Arg Asp Ala Phe Leu Leu Asp Asp Leu Phe
            20                  25                  30

Ala Asp Asp Arg Val Ser Phe Thr Tyr Thr His Val Asp Arg Leu Ile
        35                  40                  45

Leu Gly Gly Ala Val Pro Val Thr Thr Ser Leu Thr Phe Gly Ser Gly
    50                  55                  60

Thr Glu Ile Gly Thr Pro Tyr Leu Leu Ser Ala Arg Glu Met Gly Ile
65                  70                  75                  80

Ala Asn Leu Gly Gly Thr Gly Thr Ile Glu Val Asp Gly Gln Arg Phe
            85                  90                  95

Thr Leu Glu Asn Arg Asp Val Leu Tyr Val Gly Arg Gly Ala Arg Gln
            100                 105                 110

Met Thr Ala Ser Ser Leu Ser Ala Glu Arg Pro Ala Arg Phe Tyr Met
            115                 120                 125

Asn Ser Val Pro Ala Gly Ala Asp Phe Pro His Arg Leu Ile Thr Arg
        130                 135                 140

Gly Glu Ala Lys Pro Leu Asp Leu Gly Asp Ala Arg Arg Ser Asn Arg
145                 150                 155                 160

Arg Arg Leu Ala Met Tyr Ile His Pro Glu Val Ser Pro Ser Cys Leu
            165                 170                 175

Leu Leu Met Gly Ile Thr Asp Leu Ala Glu Gly Ser Ala Trp Asn Thr
            180                 185                 190

Met Pro Pro His Leu His Glu Arg Arg Met Glu Ala Tyr Cys Tyr Phe
            195                 200                 205

Asp Leu Ser Pro Glu Asp Arg Val Ile His Met Met Gly Arg Pro Asp
        210                 215                 220

Glu Thr Arg His Leu Val Val Ala Asp Gly Glu Ala Val Leu Ser Pro
225                 230                 235                 240

```
Ala Trp Ser Ile His Met Gly Ala Gly Thr Gly Pro Tyr Ala Phe Val
                245                 250                 255

Trp Gly Met Thr Gly Glu Asn Gln Glu Tyr Asn Asp Val Ala Pro Val
            260                 265                 270

Ala Val Ala Asp Leu Lys
            275

<210> SEQ ID NO 10
<211> LENGTH: 274
<212> TYPE: PRT
<213> ORGANISM: Pannonibacter phragmitetus

<400> SEQUENCE: 10

Met Leu Thr Val Glu Thr Arg His Ala Ile Asp Pro Gln Thr Ala Lys
1               5                   10                  15

Arg Met Asp Thr Glu Glu Leu Arg Lys His Phe His Met Gly Ser Leu
                20                  25                  30

Phe Ala Ala Gly Glu Ile Arg Leu Val Tyr Thr His Tyr Asp Arg Met
            35                  40                  45

Ile Val Gly Ala Ala Val Pro Ser Gly Ala Pro Leu Val Leu Asp Gln
    50                  55                  60

Val Lys Glu Cys Gly Thr Ala Ser Ile Leu Asp Arg Arg Glu Met Ala
65                  70                  75                  80

Val Val Asn Val Gly Ala Ser Gly Lys Val Ser Ala Ala Gly Glu Thr
                85                  90                  95

Tyr Ala Met Glu Arg Gly Asp Val Leu Tyr Leu Pro Leu Gly Ser Gly
            100                 105                 110

Lys Val Thr Phe Glu Gly Glu Gly Arg Phe Tyr Ile Leu Ser Ala Pro
        115                 120                 125

Ala His Ala Ala Tyr Pro Ala Arg Leu Ile Arg Ile Gly Glu Ala Glu
    130                 135                 140

Lys Val Lys Leu Gly Ser Ala Glu Thr Ser Asn Asp Arg Thr Ile Tyr
145                 150                 155                 160

Gln Phe Val His Pro Ala Val Met Thr Ser Cys Gln Leu Val Val Gly
                165                 170                 175

Tyr Thr Gln Leu His Asn Gly Ser Val Trp Asn Thr Met Pro Ala His
            180                 185                 190

Val His Asp Arg Arg Met Glu Ala Tyr Leu Tyr Phe Asp Met Lys Pro
        195                 200                 205

Glu Gln Arg Val Phe His Phe Met Gly Glu Pro Gln Glu Thr Arg His
    210                 215                 220

Leu Val Met Lys Asn Glu Asp Ala Val Val Ser Pro Pro Trp Ser Ile
225                 230                 235                 240

His Cys Gly Ala Gly Thr Gly Ser Tyr Thr Phe Ile Trp Ala Met Ala
                245                 250                 255

Gly Asp Asn Val Asp Tyr Lys Val Glu Met Val Ala Met Glu Asp
            260                 265                 270

Leu Arg

<210> SEQ ID NO 11
<211> LENGTH: 271
<212> TYPE: PRT
<213> ORGANISM: Bacillus subtilis

<400> SEQUENCE: 11
```

```
Met Ser Tyr Leu Leu Arg Lys Pro Gln Ser Asn Glu Val Ser Asn Gly
1               5                   10                  15

Val Lys Leu Val His Glu Val Thr Lys Ser Asn Ser Asp Leu Thr Tyr
            20                  25                  30

Val Glu Phe Lys Val Leu Asp Leu Ala Ser Gly Ser Ser Tyr Ala Glu
        35                  40                  45

Glu Leu Lys Lys Gln Glu Ile Cys Ile Val Ala Val Thr Gly Asn Ile
    50                  55                  60

Thr Val Thr Asp His Glu Ser Thr Phe Glu Asn Ile Gly Thr Arg Glu
65                  70                  75                  80

Ser Val Phe Glu Arg Lys Pro Thr Asp Ser Val Tyr Ile Ser Asn Asp
                85                  90                  95

Arg Ser Phe Glu Ile Thr Ala Val Ser Asp Ala Arg Val Ala Leu Cys
            100                 105                 110

Tyr Ser Pro Ser Glu Lys Gln Leu Pro Thr Lys Leu Ile Lys Ala Glu
        115                 120                 125

Asp Asn Gly Ile Glu His Arg Gly Lys Phe Ser Asn Lys Arg Thr Val
    130                 135                 140

His Asn Ile Leu Pro Asp Ser Asp Pro Ser Ala Asn Ser Leu Leu Val
145                 150                 155                 160

Val Glu Val Tyr Thr Asp Ser Gly Asn Trp Ser Ser Tyr Pro Pro His
                165                 170                 175

Lys His Asp Gln Asp Asn Leu Pro Glu Ser Phe Leu Glu Thr
            180                 185                 190

Tyr Tyr His Glu Leu Asp Pro Gly Gln Gly Phe Val Phe Gln Arg Val
        195                 200                 205

Tyr Thr Asp Asp Arg Ser Ile Asp Glu Thr Met Thr Val Glu Asn Glu
    210                 215                 220

Asn Val Val Ile Val Pro Ala Gly Tyr His Pro Val Gly Val Pro Asp
225                 230                 235                 240

Gly Tyr Thr Ser Tyr Tyr Leu Asn Val Met Ala Gly Pro Thr Arg Lys
                245                 250                 255

Trp Lys Phe His Asn Asp Pro Ala His Glu Trp Ile Leu Glu Arg
            260                 265                 270

<210> SEQ ID NO 12
<211> LENGTH: 269
<212> TYPE: PRT
<213> ORGANISM: Ochrobactrum anthropi

<400> SEQUENCE: 12

Met Ala Asn Leu Leu Arg Lys Pro Asn Gly Thr His Gly Lys Val His
1               5                   10                  15

Asp Ile Thr Pro Glu Asn Ala Lys Trp Gly Tyr Val Gly Phe Gly Leu
            20                  25                  30

Phe Arg Leu Lys Ser Gly Glu Ser Val Ser Glu Lys Thr Gly Ser Thr
        35                  40                  45

Glu Val Ile Leu Val Leu Val Glu Gly Lys Ala Lys Ile Ser Ala Ser
    50                  55                  60

Gly Glu Asp Phe Gly Glu Met Gly Glu Arg Leu Asn Val Phe Glu Lys
65                  70                  75                  80

Leu Pro Pro His Cys Leu Tyr Val Pro Ala Glu Ser Asp Trp His Ala
                85                  90                  95

Thr Ala Thr Asp Cys Val Leu Ala Val Cys Thr Ala Pro Gly Lys
            100                 105                 110
```

```
Pro Gly Arg Lys Ala Gln Lys Leu Gly Pro Glu Ser Leu Thr Leu Glu
        115                 120                 125

Gln Arg Gly Lys Gly Ala Asn Thr Arg Phe Ile His Asn Ile Ala Met
130                 135                 140

Glu Ser Arg Asp Val Ala Asp Ser Leu Leu Val Thr Glu Val Phe Thr
145                 150                 155                 160

Pro Gln Gly Asn Trp Ser Ser Tyr Pro Pro His Arg His Asp Glu Asp
                165                 170                 175

Asn Phe Pro Asp Met Thr Tyr Leu Glu Glu Thr Tyr Tyr His Arg Leu
            180                 185                 190

Asn Pro Ala Gln Gly Phe Gly Phe Gln Arg Val Phe Thr Glu Asp Gly
        195                 200                 205

Ser Leu Asp Glu Thr Met Ala Val Ser Asp Gly Asp Val Val Leu Val
    210                 215                 220

Pro Lys Gly His His Pro Cys Gly Ala Pro Tyr Gly Tyr Glu Met Tyr
225                 230                 235                 240

Tyr Leu Asn Val Met Ala Gly Pro Leu Arg Lys Trp Arg Phe Lys Asn
                245                 250                 255

His Pro Asp His Asp Trp Ile Phe Lys Arg Asp Asn Pro
            260                 265

<210> SEQ ID NO 13
<211> LENGTH: 268
<212> TYPE: PRT
<213> ORGANISM: Halomonas titanicae

<400> SEQUENCE: 13

Met Ala Ser Leu Leu Val Arg Pro Thr Ala Pro Asp Ala Gln Gly Thr
1               5                   10                  15

Val Ile Asp Val Thr Pro Glu Ser Ala Gly Trp Thr His Val Gly Phe
            20                  25                  30

Arg Val His Lys Leu Ala Lys Gly Gln Arg Leu Glu Ala Ser Ser Asp
        35                  40                  45

Asp Gln Glu Val Cys Leu Val Leu Thr Gly Arg Ala Thr Val Thr
50                  55                  60

Cys Gly Glu His Arg Phe Glu Asp Ile Gly Gln Arg Met Asp Ile Phe
65                  70                  75                  80

Glu Gln Ile Pro Pro Tyr Ala Val Tyr Leu Pro Asp His Val Ser Tyr
                85                  90                  95

Ala Val Glu Ala Thr Thr Asp Leu Glu Leu Ala Val Cys Thr Ala Pro
            100                 105                 110

Gly His Gly Asn His Ala Pro Arg Leu Ile Ala Pro Asp Asn Ile Lys
        115                 120                 125

Gln Ser Thr Arg Gly Gln Gly Thr Asn Thr Arg His Val His Asp Ile
130                 135                 140

Leu Pro Glu Thr Glu Pro Ala Asp Ser Leu Leu Val Val Glu Val Phe
145                 150                 155                 160

Thr Pro Ala Gly Asn Trp Ser Ser Tyr Pro Pro His Lys His Asp Val
                165                 170                 175

Asp Asn Leu Pro His Glu Ser His Leu Glu Thr Tyr Tyr His Arg
            180                 185                 190

Ile Asn Pro Glu Gln Gly Phe Ala Phe Gln Arg Val Tyr Thr Asp Asp
        195                 200                 205

Arg Ser Leu Asp Glu Thr Met Ala Val Glu Asn Gly Cys Cys Val Leu
```

```
                210                 215                 220
Val Pro Lys Gly Tyr His Pro Val Gly Ala Ser His Gly Tyr Ser Leu
225                 230                 235                 240

Tyr Tyr Leu Asn Val Met Ala Gly Pro Lys Arg Ala Trp Lys Phe His
                245                 250                 255

Asn Asp Pro Asp His Glu Trp Leu Met Asn Ala Gly
            260                 265

<210> SEQ ID NO 14
<211> LENGTH: 264
<212> TYPE: PRT
<213> ORGANISM: Acidiphilium multivorum

<400> SEQUENCE: 14

Met Pro Asp Leu Leu Arg Lys Pro Phe Gly Thr His Gly Lys Val His
1               5                   10                  15

Asp Ile Thr Pro Ala Ala Ala Gly Trp Arg His Val Gly Phe Gly Leu
                20                  25                  30

Tyr Arg Leu Arg Ala Gly Glu Phe Ala Ala Glu Ala Thr Gly Gly Asn
            35                  40                  45

Glu Val Ile Leu Val Met Val Glu Gly Lys Ala Ser Ile Arg Ala Ala
50                  55                  60

Gly Arg Asp Trp Gly Val Leu Gly Glu Arg Met Ser Val Phe Glu Lys
65                  70                  75                  80

Ser Pro Pro His Ser Leu Tyr Val Pro Asn Gly Ala Glu Trp Ala Leu
                85                  90                  95

Val Ala Glu Thr Asp Cys Ile Val Ala Val Cys Ser Ala Pro Gly Arg
            100                 105                 110

Gly Gly His Ala Ala Arg Arg Ile Gly Pro Glu Gly Ile Val Leu Thr
        115                 120                 125

Ala Arg Gly Glu Gly Thr Asn Thr Arg His Ile Asn Asn Ile Ala Met
130                 135                 140

Glu Ala Glu Asp Tyr Cys Asp Ala Leu Leu Val Thr Glu Val Phe Thr
145                 150                 155                 160

Pro Ala Gly His Trp Ser Ser Tyr Pro Ser His Arg His Asp Glu Asp
                165                 170                 175

Asp Asp Pro Arg Ile Thr Tyr Leu Glu Glu Thr Tyr Tyr His Arg Leu
            180                 185                 190

Asn Pro Ala Ser Gly Phe Gly Val Gln Arg Val Tyr Thr Asp Asp Arg
        195                 200                 205

Ala Leu Asp Gln Thr Met Ala Val Ser Asp Gly Asp Val Val Leu Val
210                 215                 220

Pro Arg Gly His His Pro Cys Ala Ala Pro Tyr Gly Ile Glu Met Tyr
225                 230                 235                 240

Tyr Leu Asn Val Met Ala Gly Pro Leu Arg Lys Trp Arg Phe Leu Pro
                245                 250                 255

Asp Pro Glu Leu Gly Ile Ala Lys
            260

<210> SEQ ID NO 15
<211> LENGTH: 271
<212> TYPE: PRT
<213> ORGANISM: Lactobacillus casei

<400> SEQUENCE: 15

Met Ser Leu Leu Tyr His Lys Gln Asn Gln Glu Leu Ser Ser Gly Val
```

```
            1               5                   10                  15
        Arg Leu Ile Gln Asp Val Asn Ala Ser Asn Ser Pro Met Lys Tyr Thr
                        20                  25                  30

Ala Val Lys Val Leu Glu Phe Ser Ala Asp Ser Ser Tyr Glu Glu Thr
                        35                  40                  45

Leu Glu Ala Phe Glu Ala Gly Ile Val Val Leu Gly Lys Val Thr
                50                      55                  60

Ile Thr Ala Asp Asp Gln Thr Phe Glu Asp Val Gly Gln Arg Thr Ser
        65                      70                  75                  80

Ile Phe Asp Lys Ile Pro Thr Asp Ser Val Tyr Val Ser Thr Gly Leu
                        85                  90                  95

Ala Phe Gly Ile Arg Ala Lys Gln Ala Ala Lys Ile Leu Ile Ala Tyr
                        100                 105                 110

Ala Pro Thr Asn Gln Thr Phe Pro Val Arg Leu Ile Arg Gly Asn Ile
                        115                 120                 125

His Gln Val Glu His Arg Gly Lys Tyr Asn Asn Lys Arg Leu Val Gln
                    130                 135                 140

Asn Ile Leu Pro Asp Asn Leu Pro Phe Ala Asp Lys Leu Leu Leu Val
        145                 150                 155                 160

Glu Val Tyr Thr Asp Ser Ala Asn Trp Ser Ser Tyr Pro Pro His Arg
                        165                 170                 175

His Asp His Asp Leu Pro Ala Glu Ser Leu Leu Glu Glu Ile Tyr
                    180                 185                 190

Tyr His Glu Met Arg Pro Lys Gln Gly Phe Val Phe Gln Arg Val Tyr
                    195                 200                 205

Thr Asp Asp Leu Ser Leu Asp Glu Thr Met Ala Val Gln Asn Gln Asp
                210                 215                 220

Val Val Val Val Pro Lys Gly Tyr His Pro Val Gly Val Pro Asp Gly
        225                 230                 235                 240

Tyr Asp Ser Tyr Tyr Leu Asn Val Met Ala Gly Pro Thr Arg Val Trp
                        245                 250                 255

His Phe His Asn Ala Pro Glu His Ala Trp Ile Ile Asp Arg Gln
                    260                 265                 270

<210> SEQ ID NO 16
<211> LENGTH: 466
<212> TYPE: PRT
<213> ORGANISM: Bacteroides sp.

<400> SEQUENCE: 16

Met Lys Lys Phe Met Asp Glu Asn Phe Leu Gln Thr Glu Thr Ala
        1               5                   10                  15

Gln Lys Leu Tyr His Asn His Ala Asn Met Pro Ile Phe Asp Tyr
                        20                  25                  30

His Cys His Ile Asn Pro Lys Asp Ile Ala Glu Asp Arg Met Phe Lys
                        35                  40                  45

Thr Ile Thr Glu Ile Trp Leu Tyr Gly Asp His Tyr Lys Trp Arg Ala
                50                      55                  60

Met Arg Thr Asn Gly Val Asp Glu Arg Phe Cys Thr Gly Asp Ala Ser
        65                      70                  75                  80

Asp Trp Glu Lys Phe Glu Lys Trp Ala Glu Thr Val Pro His Thr Leu
                        85                  90                  95

Arg Asn Pro Leu Tyr His Trp Thr His Leu Glu Leu Lys Lys Phe Phe
                        100                 105                 110
```

Gly Ile Asn Glu Ile Leu Ser Pro Lys Asn Ala Arg Glu Ile Tyr Asp
115                 120                 125

Ala Cys Asn Glu Lys Leu Gln Thr Pro Ala Tyr Ser Cys Arg Asn Ile
130                 135                 140

Ile Arg Met Ala Asn Val His Thr Ile Cys Thr Thr Asp Asp Pro Val
145                 150                 155                 160

Asp Thr Leu Glu Tyr His Gln Ile Lys Glu Asp Gly Phe Glu Val
                165                 170                 175

Ala Val Leu Pro Ala Trp Arg Pro Asp Lys Ala Met Met Val Glu Asp
            180                 185                 190

Pro Lys Phe Phe Asn Asp Tyr Met Asp Gln Leu Ala Glu Ala Gly
                195                 200                 205

Ile His Ile Glu Ser Phe Glu Asp Leu Met Glu Ala Leu Asp Thr Arg
            210                 215                 220

His Gln Tyr Phe His Asp Asn Gly Cys Arg Leu Ser Asp His Gly Leu
225                 230                 235                 240

Asp Thr Val Phe Ala Glu Asp Tyr Thr Glu Glu Ile Lys Ala Ile
                245                 250                 255

Phe Lys Lys Ile Arg Gly Gly Ser Arg Leu Ser Glu Thr Glu Ile Leu
            260                 265                 270

Lys Phe Lys Ser Cys Met Leu Tyr Glu Tyr Gly Val Met Asp His Ser
275                 280                 285

Arg Gly Trp Thr Gln Gln Leu His Ile Gly Ala Gln Arg Asn Asn Asn
            290                 295                 300

Thr Arg Leu Phe Lys Lys Leu Gly Pro Asp Thr Gly Phe Asp Ser Ile
305                 310                 315                 320

Gly Asp Lys Pro Ile Ala Glu Pro Leu Ala Lys Leu Leu Asp Arg Leu
                325                 330                 335

Asp Gln Glu Asn Lys Leu Cys Lys Thr Val Leu Tyr Asn Leu Asn Pro
            340                 345                 350

Arg Asp Asn Glu Leu Tyr Ala Thr Met Leu Gly Asn Phe Gln Asp Gly
            355                 360                 365

Ser Val Pro Gly Lys Ile Gln Tyr Gly Ser Gly Trp Trp Phe Leu Asp
370                 375                 380

Gln Lys Asp Gly Met Ile Lys Gln Met Asn Ala Leu Ser Asn Leu Gly
385                 390                 395                 400

Leu Leu Ser Arg Phe Val Gly Met Leu Thr Asp Ser Arg Ser Phe Leu
            405                 410                 415

Ser Tyr Thr Arg His Glu Tyr Phe Arg Arg Thr Leu Cys Asn Leu Leu
            420                 425                 430

Gly Asn Asp Val Glu Asn Gly Glu Ile Pro Ala Asp Met Glu Leu Leu
            435                 440                 445

Gly Ser Met Val Glu Asn Ile Cys Phe Asn Asn Ala Lys Asn Tyr Phe
450                 455                 460

Asn Phe
465

<210> SEQ ID NO 17
<211> LENGTH: 451
<212> TYPE: PRT
<213> ORGANISM: Thermotoga maritima MSB8

<400> SEQUENCE: 17

Met Phe Leu Gly Glu Asp Tyr Leu Leu Thr Asn Arg Ala Ala Val Arg
1               5                   10                  15

-continued

Leu Phe Asn Glu Val Lys Asp Leu Pro Ile Val Asp Pro His Asn His
            20                  25                  30

Leu Asp Ala Lys Asp Ile Val Glu Asn Lys Pro Trp Asn Asp Ile Trp
            35                  40                  45

Glu Val Glu Gly Ala Thr Asp His Tyr Val Trp Glu Leu Met Arg Arg
            50                  55                  60

Cys Gly Val Ser Glu Glu Tyr Ile Thr Gly Ser Arg Ser Asn Lys Glu
65                      70                  75                  80

Lys Trp Leu Ala Leu Ala Lys Val Phe Pro Arg Phe Val Gly Asn Pro
                85                  90                  95

Thr Tyr Glu Trp Ile His Leu Asp Leu Trp Arg Arg Phe Asn Ile Lys
            100                 105                 110

Lys Val Ile Ser Glu Glu Thr Ala Glu Glu Ile Trp Glu Glu Thr Lys
            115                 120                 125

Lys Lys Leu Pro Glu Met Thr Pro Gln Lys Leu Leu Arg Asp Met Lys
130                 135                 140

Val Glu Ile Leu Cys Thr Thr Asp Pro Val Ser Thr Leu Glu His
145                 150                 155                 160

His Arg Lys Ala Lys Glu Ala Val Glu Gly Val Thr Ile Leu Pro Thr
            165                 170                 175

Trp Arg Pro Asp Arg Ala Met Asn Val Asp Lys Glu Gly Trp Arg Glu
            180                 185                 190

Tyr Val Glu Lys Met Gly Glu Arg Tyr Gly Glu Asp Thr Ser Thr Leu
            195                 200                 205

Asp Gly Phe Leu Asn Ala Leu Trp Lys Ser His Glu His Phe Lys Glu
            210                 215                 220

His Gly Cys Val Ala Ser Asp His Ala Leu Leu Glu Pro Ser Val Tyr
225                 230                 235                 240

Tyr Val Asp Glu Asn Arg Ala Arg Ala Val His Glu Lys Ala Phe Ser
            245                 250                 255

Gly Glu Lys Leu Thr Gln Asp Glu Ile Asn Asp Tyr Lys Ala Phe Met
            260                 265                 270

Met Val Gln Phe Gly Lys Met Asn Gln Glu Thr Asn Trp Val Thr Gln
            275                 280                 285

Leu His Ile Gly Ala Leu Arg Asp Tyr Arg Asp Ser Leu Phe Lys Thr
            290                 295                 300

Leu Gly Pro Asp Ser Gly Gly Asp Ile Ser Thr Asn Phe Leu Arg Ile
305                 310                 315                 320

Ala Glu Gly Leu Arg Tyr Phe Leu Asn Glu Phe Asp Gly Lys Leu Lys
            325                 330                 335

Ile Val Leu Tyr Val Leu Asp Pro Thr His Leu Pro Thr Ile Ser Thr
            340                 345                 350

Ile Ala Arg Ala Phe Pro Asn Val Tyr Val Gly Ala Pro Trp Trp Phe
            355                 360                 365

Asn Asp Ser Pro Phe Gly Met Glu Met His Leu Lys Tyr Leu Ala Ser
            370                 375                 380

Val Asp Leu Leu Tyr Asn Leu Ala Gly Met Val Thr Asp Ser Arg Lys
385                 390                 395                 400

Leu Leu Ser Phe Gly Ser Arg Thr Glu Met Phe Arg Arg Val Leu Ser
            405                 410                 415

Asn Val Val Gly Glu Met Val Glu Lys Gly Gln Ile Pro Ile Lys Glu
            420                 425                 430

```
Ala Arg Glu Leu Val Lys His Val Ser Tyr Asp Gly Pro Lys Ala Leu
        435                 440                 445

Phe Phe Gly
    450

<210> SEQ ID NO 18
<211> LENGTH: 427
<212> TYPE: PRT
<213> ORGANISM: Bacillus halodurans

<400> SEQUENCE: 18

Met Ser Ile Asn Ser Arg Glu Val Leu Ala Glu Lys Val Lys Asn Ala
1               5                   10                  15

Val Asn Asn Gln Pro Val Thr Asp Met His Thr His Leu Phe Ser Pro
            20                  25                  30

Asn Phe Gly Glu Ile Leu Leu Trp Asp Ile Asp Glu Leu Leu Thr Tyr
        35                  40                  45

His Tyr Leu Val Ala Glu Val Met Arg Trp Thr Asp Val Ser Ile Glu
    50                  55                  60

Ala Phe Trp Ala Met Ser Lys Arg Glu Gln Ala Asp Leu Ile Trp Glu
65                  70                  75                  80

Glu Leu Phe Ile Lys Arg Ser Pro Val Ser Glu Ala Cys Arg Gly Val
                85                  90                  95

Leu Thr Cys Leu Gln Gly Leu Gly Leu Asp Pro Ala Thr Arg Asp Leu
            100                 105                 110

Gln Val Tyr Arg Glu Tyr Phe Ala Lys Lys Thr Ser Glu Glu Gln Val
        115                 120                 125

Asp Thr Val Leu Gln Leu Ala Asn Val Ser Asp Val Val Met Thr Asn
    130                 135                 140

Asp Pro Phe Asp Asp Asn Glu Arg Ile Ser Trp Leu Glu Gly Lys Gln
145                 150                 155                 160

Pro Asp Ser Arg Phe His Ala Ala Leu Arg Leu Asp Pro Leu Leu Asn
                165                 170                 175

Glu Tyr Glu Gln Thr Lys His Arg Leu Arg Asp Trp Gly Tyr Lys Val
            180                 185                 190

Asn Asp Glu Trp Asn Glu Gly Ser Ile Gln Glu Val Lys Arg Phe Leu
        195                 200                 205

Thr Asp Trp Ile Glu Arg Met Asp Pro Val Tyr Met Ala Val Ser Leu
    210                 215                 220

Pro Pro Thr Phe Ser Phe Pro Glu Glu Ser Asn Arg Gly Arg Ile Ile
225                 230                 235                 240

Arg Asp Cys Leu Leu Pro Val Ala Glu Lys His Asn Ile Pro Phe Ala
                245                 250                 255

Met Met Ile Gly Val Lys Lys Arg Val His Pro Ala Leu Gly Asp Ala
            260                 265                 270

Gly Asp Phe Val Gly Lys Ala Ser Met Asp Gly Val Glu His Leu Leu
        275                 280                 285

Arg Glu Tyr Pro Asn Asn Lys Phe Leu Val Thr Met Leu Ser Arg Glu
    290                 295                 300

Asn Gln His Glu Leu Val Val Leu Ala Arg Lys Phe Ser Asn Leu Met
305                 310                 315                 320

Ile Phe Gly Cys Trp Trp Phe Met Asn Asn Pro Glu Ile Ile Asn Glu
                325                 330                 335

Met Thr Arg Met Arg Met Glu Met Leu Gly Thr Ser Phe Ile Pro Gln
            340                 345                 350
```

```
His Ser Asp Ala Arg Val Leu Glu Gln Leu Ile Tyr Lys Trp His His
            355                 360                 365

Ser Lys Ser Ile Ile Ala Glu Val Leu Ile Asp Lys Tyr Asp Asp Ile
    370                 375                 380

Leu Gln Ala Gly Trp Glu Val Thr Glu Glu Ile Lys Arg Asp Val
385                 390                 395                 400

Ala Asp Leu Phe Ser Arg Asn Phe Trp Arg Phe Val Gly Arg Asn Asp
            405                 410                 415

His Val Thr Ser Val Lys Val Glu Gln Gln Thr
            420                 425

<210> SEQ ID NO 19
<211> LENGTH: 473
<212> TYPE: PRT
<213> ORGANISM: Bacillus subtilis

<400> SEQUENCE: 19

Met Glu Pro Phe Met Gly Lys Asn Phe Leu Leu Lys Asn Glu Thr Ala
1               5                   10                  15

Val Ser Leu Tyr His Asn Tyr Ala Lys Asp Met Pro Ile Ile Asp Tyr
            20                  25                  30

His Cys His Leu Ser Pro Lys Glu Ile Tyr Glu Asn Lys Thr Phe Gln
        35                  40                  45

Asn Ile Thr Glu Ala Trp Leu Tyr Gly Asp His Tyr Lys Trp Arg Ile
    50                  55                  60

Met Arg Ala Asn Gly Ile Glu Glu Thr Tyr Ile Thr Gly Asp Ala Pro
65                  70                  75                  80

Asp Glu Glu Lys Phe Met Ala Trp Ala Lys Thr Val Pro Met Ala Ile
            85                  90                  95

Gly Asn Pro Leu Tyr Asn Trp Thr His Leu Glu Leu Gln Arg Phe Phe
            100                 105                 110

Gly Ile Tyr Glu Ile Leu Asn Glu Lys Ser Gly Ser Ala Ile Trp Lys
            115                 120                 125

Gln Thr Asn Lys Leu Leu Lys Gly Glu Gly Phe Gly Ala Arg Asp Leu
    130                 135                 140

Ile Val Lys Ser Asn Val Lys Val Cys Thr Thr Asp Asp Pro Val
145                 150                 155                 160

Asp Ser Leu Glu Tyr His Leu Leu Leu Lys Glu Asp Lys Asp Phe Pro
            165                 170                 175

Val Ser Val Leu Pro Gly Phe Arg Pro Asp Lys Gly Leu Glu Ile Asn
            180                 185                 190

Arg Glu Gly Phe Pro Glu Trp Val Gln Ala Leu Glu Asp Ala Ala Ala
        195                 200                 205

Ile Ser Ile Thr Thr Tyr Asp Glu Phe Leu Lys Ala Leu Glu Lys Arg
    210                 215                 220

Val Arg Phe Phe His Ser Ala Gly Gly Arg Val Ser Asp His Ala Ile
225                 230                 235                 240

Asp Thr Met Val Phe Ala Glu Thr Thr Lys Glu Glu Ala Gly Arg Ile
            245                 250                 255

Phe Ser Asp Arg Leu Gln Gly Thr Glu Val Ser Cys Glu Asp Glu Lys
            260                 265                 270

Lys Phe Lys Thr Tyr Thr Leu Gln Phe Leu Cys Gly Leu Tyr Ala Glu
        275                 280                 285

Leu Asp Trp Ala Met Gln Phe His Ile Asn Ala Leu Arg Asn Thr Asn
```

```
            290                 295                 300
Thr Lys Met Met Lys Arg Leu Gly Pro Asp Thr Gly Tyr Asp Ser Met
305                 310                 315                 320

Asn Asp Glu Glu Ile Ala Lys Pro Leu Tyr Lys Leu Leu Asn Ser Val
                325                 330                 335

Glu Met Lys Asn Gln Leu Pro Lys Thr Ile Leu Tyr Ser Leu Asn Pro
            340                 345                 350

Asn Asp Asn Tyr Val Ile Ala Ser Met Ile Asn Ser Phe Gln Asp Gly
        355                 360                 365

Ile Thr Pro Gly Lys Ile Gln Phe Gly Thr Ala Trp Trp Phe Asn Asp
370                 375                 380

Thr Lys Asp Gly Met Leu Asp Gln Met Lys Ala Leu Ser Asn Val Gly
385                 390                 395                 400

Leu Phe Ser Arg Phe Ile Gly Met Leu Thr Asp Ser Arg Ser Phe Leu
                405                 410                 415

Ser Tyr Thr Arg His Glu Tyr Phe Arg Arg Ile Val Cys Asn Leu Ile
            420                 425                 430

Gly Glu Trp Val Glu Asn Gly Glu Val Pro Arg Asp Met Glu Leu Leu
        435                 440                 445

Gly Ser Ile Val Gln Gly Ile Cys Tyr Asp Asn Ala Lys His Tyr Phe
450                 455                 460

Gln Phe Gln Glu Glu Lys Ala Asn Val
465                 470

<210> SEQ ID NO 20
<211> LENGTH: 825
<212> TYPE: DNA
<213> ORGANISM: Rhizobium sp.

<400> SEQUENCE: 20
atgctcaacg tggaaacgag gcacgccgtt cacgcggatc acgcgagatc actcgacaca      60
gagggcctgc gccggcactt cctggcccag ggcctgtttg cggagggcga gatacggctg     120
atctatacgc attatgatcg attcgtcatg ggaggcgccg tgccggacgg cgcgccactt     180
gtgctcgatc atgtcgagga gacgaaaacg ccgggctttc tcgaccgacg ggagatggga     240
atcgtcaata tcggtgctga gggcagcgtg catgccggca acgaaagctg gtcgctgaac     300
cgtggtgacg tactttatct cggcatgggg gcgggaccgg tcaccttcga aggggctggg     360
cgcttctacc tcgtctcggc accggcgcat cgcagcctgc ccaaccggct cgtcacgccg     420
gccgacagca aggaggtcaa gcttggcgct ctcgagactt ccaacaaacg caccatcaat     480
cagttcattc atcccctggt catggaaagc tgccagctcg tgctgggata taccacgctg     540
gaggacggct cggtctggaa taccatgccc gcgcatgtgc acgaccgacg catggaggcc     600
tatctctatt tcggcatgga tgagacatcg cgggttctgc atctgatggg cgagccgcag     660
caaacgaggc atctcttcgt cgccaatgag aagggggcga tctctccgcc gtggtccatc     720
catgcgggag caggcattgg cagctatacc ttcatctggg ccatggcggg cgacaatgtc     780
gattataccg acatggagtt catccagccg ggagatcttc gatga                    825

<210> SEQ ID NO 21
<211> LENGTH: 837
<212> TYPE: DNA
<213> ORGANISM: Escherichia coli

<400> SEQUENCE: 21
```

| | |
|---|---|
| atggacgtaa gacagagcat ccacagtgcg cacgcaaaaa cgctggatac ccaagggctg | 60 |
| cgcaatgaat ttttggttga aaaggtattt gtcgccgatg agtacaccat ggtttacagc | 120 |
| cacattgacc gaattattgt tggcggcatt atgccgataa ctaaaacggt tccgttggc | 180 |
| ggggaagttg gtaaacaact cggcgtaagc tatttccttg aacgtcgcga gttaggtgtt | 240 |
| atcaatattg gcggtgccgg tacgattact gtcgatggcc aatgctatga aatcggtcac | 300 |
| cgcgacgccc tgtatgttgg taaaggtgca aaagaagttg tctttgccag tattgatacc | 360 |
| ggcactccgg cgaagtttta ttacaattgc gcaccgcgc atacgacgta tcccaccaaa | 420 |
| aaagtcacac cggacgaagt atctccagtc acgttaggcg ataacctcac cagtaaccgt | 480 |
| cgcacgatta acaaatattt tgtcccggat gtactggaaa cctgccaatt gagtatgggg | 540 |
| ctgacggagc tggctccggg taacttgtgg aacaccatgc cgtgtcacac ccacgagcgc | 600 |
| cggatggaag tttatttcta tttcaatatg gatgatgacg cctgcgtttt ccacatgatg | 660 |
| gggcagccgc aagaaacgcg tcatattgtg atgcataacg agcaggcggt gatctccccg | 720 |
| agctggtcga tccattccgg tgtcggaacc aaagcttata cctttatctg gggcatggtc | 780 |
| ggtgaaaacc aggtctttga tgatatggac catgtggccg ttaaagattt gcgctag | 837 |

<210> SEQ ID NO 22
<211> LENGTH: 837
<212> TYPE: DNA
<213> ORGANISM: Rhizobium sp.

<400> SEQUENCE: 22

| | |
|---|---|
| atgacgatga agatactcta cggcgccgga ccggaggatg tgaaagggta tgacacgcag | 60 |
| cgcctgcgcg acgccttcct gctggacgac ctcttcgccg acgccgggt cagtttcaca | 120 |
| tatacccatg tcgatcgcct catcctcggc ggggccgtcc cggtgacgac gagcctcacc | 180 |
| ttcggctccg gcacggagat cggaacgccc tacctgcttt ccgcccgcga gatggggatc | 240 |
| gccaatctcg gcggcacggg cacgatcgag gtggatggcc agcgcttcac gctcgaaaac | 300 |
| cgcgacgtgc tctatgtcgg tcgcggcgcc cggcagatga ccgcctccag cctgtcggcg | 360 |
| gagaggccag cccgcttcta catgaattcc gtgcccgccg cgccgatt ccgcaccgt | 420 |
| ctgatcaccc gcggagaggc caagcccctc gatctcggcg atgcgcgccg ctcgaacagg | 480 |
| cgccggctcg caatgtacat ccatccggag gtctcgccgt cctgcctgct gctcatgggc | 540 |
| atcaccgatc ttgccgaggg cagcgcctgg aacaccatgc cgccgcatct gcacgagcgg | 600 |
| cggatggagc cctattgcta cttcgatctc tcgcccgagg accgggtcat ccacatgatg | 660 |
| ggtcggccgg acgaaacccg ccaccttgtc gtggccgacg gcgaggcggt cctctctccc | 720 |
| gcctggtcga tccatatggg tgccgggacg ggccctacg ccttcgtctg ggcatgacc | 780 |
| ggcgaaaacc aggaatacaa cgacgtcgct cccgtagccg tggctgatct caaatga | 837 |

<210> SEQ ID NO 23
<211> LENGTH: 825
<212> TYPE: DNA
<213> ORGANISM: Pannonibacter phragmitetus

<400> SEQUENCE: 23

| | |
|---|---|
| atgctgaccg tcgaaacccg ccacgccatt gatccgcaga ccgcaaagcg gatggacacg | 60 |
| gaagagctgc gcaagcattt ccacatgggc agcctgtttg ctgccggtga atccgcctc | 120 |
| gtctacaccc actatgaccg catgatcgtc ggcgctgccg tgcctcgggg cgcgccgctg | 180 |
| gtgctggatc aggtcaagga atgcggcacc gccagcatcc tcgaccgccg cgagatggct | 240 |

```
gtcgtcaacg tcggcgccag cggcaaggtc tctgcagcag gcgaaaccta cgccatggaa    300
cgcggcgacg tgctctatct gccgctgggc tccggcaagg tgaccttcga aggcgaaggc    360
cgcttctaca ttctctccgc tccggcccac gctgcttacc cggcccgcct gatccgcatc    420
ggcgaggccg agaaggtcaa gctcggctcg gccgagacct ccaacgaccg caccatctac    480
cagttcgtgc atccggcggt gatgacttcc tgccaactcg tcgtcggcta cacccagctg    540
cacaacggct ctgtctggaa caccatgccc gccacgtgc atgaccggcg catggaggcc     600
tatctctatt tcgacatgaa gccggagcag cgcgtgttcc acttcatggg cgagccgcag    660
gaaacccgcc atctggtcat gaagaacgag gatgcggtgg tctccccgcc ctggtccatc    720
cactgcggcg caggcaccgg cagctacacc ttcatctggg ccatggccgg cgacaacgtc    780
gactacaagg acgtggaaat ggtcgccatg gaggatctgc ggtga                    825

<210> SEQ ID NO 24
<211> LENGTH: 816
<212> TYPE: DNA
<213> ORGANISM: Bacillus subtilis

<400> SEQUENCE: 24
atgagttatt tgttgcgtaa gccgcagtcg aatgaagtgt ctaatggggt caaactggtg     60
cacgaagtaa cgaaatccaa ctctgatctc acctatgtag agtttaaagt gttagatctc    120
gcttccggtt ccagctatgc agaagaattg aaaaaacagg aaatctgtat tgtcgcggta    180
acgggaaaca ttacagtgac cgatcacgag tcgactttg agaatatcgg cacgcgtgaa     240
agcgtattcg aacgaaaacc gacagacagc gtctatattt caaatgaccg ttcctttgag    300
atcacagcgg tcagcgacgc aagagtggcg ctttgctatt ctccatcgga aaaacagctt    360
ccgacaaagc tgatcaaagc ggaagacaat ggcattgagc atcgcgggaa gttttcaaac    420
aaacgtactg ttcacaacat tcttccggat tcagacccct cagctaacag cctattagta    480
gttgaagtct atacagacag cggcaactgg tccagctatc cgcctcataa acatgatcaa    540
gacaatttgc cggaggaatc tttttttagaa gaaacgtact accatgagtt agacccggga    600
cagggctttg tgtttcagcg tgtatacaca gatgaccgct cgattgacga cacaatgact    660
gtagaaaatg aaaacgttgt catcgttcct gcaggatacc acccggtagg cgtgccggac    720
ggatacacat cctactattt aaatgtcatg gcagggccga cgcggaaatg gaagtttcat    780
aatgacccgg cgcatgagtg gattttagaa cgttaa                              816

<210> SEQ ID NO 25
<211> LENGTH: 810
<212> TYPE: DNA
<213> ORGANISM: Ochrobactrum anthropi

<400> SEQUENCE: 25
atggccaatt tgttgcgcaa gcccaacggc acgcatggca aggtccacga catcactccg     60
gaaaacgcca atggggtta tgtcgggttc gggctctttc gtctcaaatc cggcgagagt     120
gtctccgaaa agaccggatc gacggaggtg atccttgttc ttgtggaagg caaggcaaag    180
atttccgctt ctggcgagga tttcggcgag atgggtgaac gcttaaacgt gttcgagaaa    240
ctgccgccac actgcctcta tgtgcctgct gaaagcgact ggcatgcaac cgccacgaca    300
gattgtgttc tggctgtttg caccgcaccg ggcaagccag gccgcaaggc acagaagctt    360
gggccggaaa gcttgacact tgaacaacgc ggaaaaggtg ccaatacccg ctttatccat    420
```

```
aatatcgcaa tggaaagccg cgatgttgcc gatagccttc ttgttaccga ggtattcaca    480
ccgcagggaa actggtcgtc ctatccaccc cacagacacg acgaagacaa ttttccggat    540
atgacctatc tggaagagac ctattatcac cgtctcaacc cggcgcaggg cttcggcttc    600
cagcgtgttt tcaccgaaga cggaagcctt gatgaaacca tggcggtctc tgacggagac    660
gtcgtgcttg taccaaaagg ccaccatcca tgtggcgcgc cctatggcta cgagatgtat    720
tatctcaatg tgatggccgg tcccttgcgc aaatggcgct tcaagaacca tcccgaccat    780
gactggattt tcaaacgcga caatccgtaa                                    810

<210> SEQ ID NO 26
<211> LENGTH: 807
<212> TYPE: DNA
<213> ORGANISM: Halomonas titanicae

<400> SEQUENCE: 26
atggcttccc tactggtacg ccccaccgcc ccagatgccc agggcaccgt gattgacgtt     60
acccctgaat ctgctggctg gacgcacgtt ggctttcggg tgcataaact cgccaagggc    120
cagcgcctgg aggccagcag cgatgatcag gaagtctgcc tggtgctgct caccggtcgc    180
gccacggtaa cttgcggcga gcaccgcttt gaagatattg ccagcgtat  ggatatttt     240 gagcagatcc ctccctatgc ggtttaccta cctgaccatg ttagctacgc ggtggaagcg    300
accacagact tagagctagc ggtgtgcacc gcccctgggc atggcaacca tgccccacgg    360
ctcatcgcgc ctgacaacat caagcaaagc acccgtggcc agggcaccaa cacccgccat    420
gttcacgata ttctgccgga aaccgagccc gccgatagcc tattagtagt cgaagtattc    480
acacctgcgg gtaactggtc gagctacccg ccccacaaac acgatgtgga taacttaccc    540
cacgaatcac atctggaaga gacctactac caccgcatta cccctgaaca agggttcgcc    600
ttccagcgcg tttacaccga tgaccgcagc cttgatgaaa ccatggcggt ggaaaacggc    660
tgctgtgtgt tggttcccaa gggttaccat ccggtgggcg cctcccatgg ctactcgctc    720
tactacttaa atgtgatggc ggggcccaag cgggcatgga aatttcacaa cgaccccgac    780
cacgaatggc tgatgaacgc tggatag                                       807

<210> SEQ ID NO 27
<211> LENGTH: 795
<212> TYPE: DNA
<213> ORGANISM: Acidiphilium multivorum

<400> SEQUENCE: 27
atgccggact tactgagaaa accgtttggc acccatggca aagtgcacga tattacccca     60
gcagcagcag gttggagaca tgttggtttt ggcttatatc gcttaagagc gggcgaattt    120
gcagcagaag cgacaggcgg caatgaagtt attctggtga tggttgaggg caaagcgtct    180
attagagcag caggcagaga ttggggcgtt ttaggcgaac gtatgagcgt cttcgaaaaa    240
agtccaccac attccctgta tgtcccgaat ggtgcagaat gggccttagt agccgaaaca    300
gattgcattg tagcagtgtg tagcgctccg ggtagaggag tcatgctgc  aagaagaatt    360 ggtcctgaag gtattgtgtt aaccgccaga ggtgaaggca ccaatacacg ccacatcaac    420
aacatcgcca tggaagccga agattattgt gatgccctgt tagtcaccga agtgttcacc    480
ccagccggcc attggagctc ttatccatct catcgtcatg atgaagacga cgatccgcgc    540
atcacctatt tagaagagac ctactatcat cgcttaaatc ctgcctcggg ctttggcgtt    600
caacgcgtct ataccgatga tcgcgcctta gatcaaacca tggcggtttc tgatggcgat    660
```

```
gttgttttag ttcctcgcgg ccatcatccg tgtgcagccc cgtatggtat tgaaatgtat    720
tacctgaacg tcatggccgg cccgttacgt aaatggcgct ttttacctga tcctgaactt    780
ggcattgcga aataa                                                     795
```

```
<210> SEQ ID NO 28
<211> LENGTH: 816
<212> TYPE: DNA
<213> ORGANISM: Lactobacillus casei

<400> SEQUENCE: 28
atgtctctgc tgtaccacaa gcagaaccag gaactgagta gtggtgtgcg cctgatccaa     60
gatgttaatg ccagcaatag cccgatgaaa tataccgccg tgaaagtgct ggagtttagc    120
gccgatagca gctatgagga aaccttagag gcctttgaag ccggcattgt tgtgttagag    180
ggcaaagtga ccatcaccgc cgacgatcaa accttcgaag atgtgggtca agaacctcg    240 atcttcgaca aaatcccgac cgatagcgtt tatgtgtcta ccggtttagc cttcggtatt    300
cgcgccaaac aagccgccaa aatcttaatc gcgtatgctc cgaccaatca gaccttccca    360
gttcgcttaa ttcgcggcaa tatccaccag gtggaacatc gcggcaagta caacaacaaa    420
cgcttagtgc agaacattct cccggataat ctcccgttcg ccgataaatt actgctggtt    480
gaggtgtaca ccgatagcgc caattggagc tcctatccgc cgcatagaca tgatcacgat    540
gatttaccgg ccgaaagtct gttagaggag atctactatc acgaaatgcg cccgaagcag    600
ggcttcgtct ttcaacgcgt gtataccgat gatctgagtc tggatgagac catggccgtt    660
caaaatcaag atgttgtcgt tgtcccgaaa ggctatcatc cggttggtgt ccccgacggc    720
tatgattcgt attacctgaa cgtgatggcc ggcccgacaa gagtgtggca ttttcataat    780
gctccggaac atgcctggat tattgatcgc cagtaa                              816
```

```
<210> SEQ ID NO 29
<211> LENGTH: 1401
<212> TYPE: DNA
<213> ORGANISM: Bacteroides sp.

<400> SEQUENCE: 29
atgaaaaaat ttatggatga aaattttctg ttgcaaaccg aaacagcgca gaaattgtat     60
cataatcacg cggcaaacat gccgattttc gattaccact gccacattaa ccccaaagac    120
atcgcggaag accggatgtt taaaaccatc accgaaatct ggttgtacgg cgatcattat    180
aaatggcgcg ccatgcgtac aaacggcgtt gacgagcgct tttgcaccgg cgatgcaagc    240
gattgggaaa agtttgaaaa gtgggccgaa acggttcctc ataccctgcg taatccgctt    300
tatcactgga cacacctgga gctaaagaaa tttttcggga ttaacgagat cctgagtccg    360
aaaaatgccc gggaaattta tgatgcctgt aacgaaaaac tgcaaacgcc cgcgtatagt    420
tgccgcaaca tcatccggat ggccaatgtg catacaatct gtaccaccga cgacccggtt    480
gacacactgg aatatcatca gcaaattaaa gaagacggct ttgaagtggc ggttttacct    540
gcctggcgtc cggataaagc gatgatggtg gaagacccga agttctttaa cgactatatg    600
gaccagttgg ccgaagctgc cggtatccat atcgaatcgt tgaggatttt gatggaagcc    660
ttggatacgc gtcaccagta ttttcatgat aatggttgcc gtttgtccga ccacgggctg    720
gataccgttt ttgctgaaga ttatacgag gaagaaatta agcgatctt caaaaaaatc    780 cgtggcggca gcaggcttag cgaaacggaa atcctgaaat tcaagtcctg catgttgtac    840
```

```
gaatatgggg tgatggacca ttcgcgcggc tggacacaac aattgcacat ggcgcacaa      900 cgcaacaaca acacccgttt gttcaaaaaa ttaggtcccg acactggttt cgattcgatt      960
ggcgataagc cgatcgctga accattggcc aaattgctcg accgcctgga tcaggaaaac     1020
aaattgtgca aaacggtttt gtataatctg aatccgcgtg ataacgagtt gtacgctacc     1080
atgttgggca actttcagga cggatcggtt cccgggaaaa ttcaatacgg ctcgggttgg     1140
tggtttctcg atcagaaaga cggcatgatt aaacagatga atgcccttttc caatctgggt     1200 ttgctgagcc gtttcgtagg catgctgacc gactcaagga gcttcctttc gtacacccgt     1260
cacgaatatt tccgtcgtac cctttgcaac ctgcttggga tgatgttga aaacggggag     1320 attccggcag atatggagct tttgggcagt atggttgaga atatttgttt taataacgcg     1380
aagaactatt ttaattttta g                                                1401

<210> SEQ ID NO 30
<211> LENGTH: 1356
<212> TYPE: DNA
<213> ORGANISM: Thermotoga maritima MSB8

<400> SEQUENCE: 30
atgtttctgg gcgaagacta tctgctgacc aatcgtgcgg cagttcgtct gttcaacgaa       60
gtgaaagatc tgccgatcgt tgatccgcat aaccacctgg atgcgaaaga tatcgtggaa      120
aacaaaccgt ggaacgacat ctgggaagtg aaggtgcga ccgatcacta tgtgtgggaa      180
ctgatgcgtc gttgtggtgt tagcgaagaa tatattaccg gctctcgtag caacaaagaa      240
aaatggctgg cgctggcgaa agtgtttccg cgttttgtgg gtaatccgac gtacgaatgg      300
atccacctgg atctgtggcg tcgtttcaac atcaaaaaag tcatcagcga agaaaccgcg      360
gaagaaatct gggaagaaac caaaaaaaaa ctgccggaga tgaccccgca gaaactgctg      420
cgcgacatga agtggaaat cctgtgcacc accgatgatc cggtgtctac cctggaacat      480
caccgtaaag cgaaagaagc cgtggaaggc gtgaccattt taccgacctg gcgtccggat      540
cgtgcaatga atgttgataa agaaggttgg cgtgaatatg ttgaaaaat gggtgaacgc      600 tatggcgaag ataccagcac cctggatggt tttctgaatg ccctgtggaa aagccacgaa      660
cacttcaaag aacacggctg tgtggcgagc gatcatgcgc tgctggaacc gagcgtgtac      720
tacgtggatg aaaaccgcgc gcgtgcagtt catgaaaaag cattttctgg tgaaaaactg      780
actcaagatg aaatcaacga ctataaagcg ttcatgatgg tgcagttcgg caaaatgaac      840
caggaaacca ctgggtgac ccagctgcac attggtgccc tgcgcgatta ccgcgatagc      900
ctgttcaaaa ccctgggccc ggattctggt ggcgatatca gcaccaactt tctgcgtatt      960
gctgaaggtc tgcgttattt tctgaacgaa tttgatggta aactgaaaat tgtgctgtac     1020
gtgctggatc cgacccattt accgaccatt tcgaccattg cacgtgcgtt cccgaacgtg     1080
tatgtgggtg caccgtggtg gttcaacgat agcccgttcg gcatggaaat gcacctgaaa     1140
tacctggcga gcgttgatct gctgtacaat ctggctggta tggttaccga ttcacgtaaa     1200
ttactgagtt ttggttctcg taccgaaatg tttcgtcgcg ttctgtctaa tgtggttggc     1260
gaaatggtgg aaaaaggcca gatcccgatc aaagaagcgc gcgaactggt gaaacacgtg     1320
agctacgacg gcccgaaagc cctgttcttt ggctga                                1356

<210> SEQ ID NO 31
<211> LENGTH: 1284
<212> TYPE: DNA
<213> ORGANISM: Bacillus halodurans
```

<400> SEQUENCE: 31

```
atgagcatca acagccgtga agttctggcg gaaaaagtga aaaacgcggt gaacaaccag    60
ccggttaccg atatgcatac ccacctgttt agcccgaact ttggcgaaat tctgctgtgg   120
gacatcgatg aactgctgac ctatcactac ctggttgcgg aagttatgcg ttggaccgat   180
gtgagcattg aagcgttttg ggcaatgagc aaacgtgaac aggccgatct gatttgggaa   240
gaactgttca tcaaacgcag cccggtgagc gaagcatgtc gtggcgttct gacctgttta   300
caaggtttag gtctggatcc ggcaactcgt gatttacagg tgtatcgtga atacttcgcc   360
aaaaaaacca gcgaggaaca ggtggatacc gttctgcagc tggcaaatgt gagcgatgtg   420
gtgatgacca atgatccgtt cgatgataat gaacgcatca gctggctgga aggcaaacag   480
ccggatagcc gctttcatgc agcgttacgt ctggatccgc tgctgaatga atatgaacag   540
accaaacatc gtctgcgtga ttggggttat aaagtgaacg acgaatggaa cgaaggcagc   600
atccaggaag tgaaacgctt tctgaccgac tggattgaac gtatggatcc ggtgtatatg   660
gcggtgagct taccgccgac cttcagcttt ccggaagaat cgaaccgtgg ccgcattatc   720
cgtgattgtc tgttaccggt tgcagaaaaa cataacatcc cgtttgcaat gatgattggc   780
gtgaaaaaac gcgtgcatcc ggcgttaggt gatgcaggcg attttgtggg taaagcaagt   840
atggatggcg ttgaacacct gctgcgcgaa tacccgaaca caaaattcct ggtgaccatg   900
ctgagccgcg aaaaccagca cgaactggtg ttctggcgc gtaaatttag taacctgatg   960
attttttggtt gttggtggtt tatgaacaac ccggagatca tcaacgaaat gacccgcatg  1020
cgcatggaaa tgctgggtac cagctttatc ccgcagcaca gcgatgcccg tgttctggaa  1080
cagctgatct ataaatggca ccacagcaaa agcatcatcg cggaagtcct gatcgacaaa  1140
tacgacgaca tcctgcaagc aggttgggaa gttaccgaag aagaaatcaa acgtgatgtg  1200
gcagatctgt ttagccgcaa cttttggcgc tttgtgggcc gtaacgatca cgtgaccagc  1260
gtgaaagtgg aacagcagac ctga                                        1284
```

<210> SEQ ID NO 32
<211> LENGTH: 1422
<212> TYPE: DNA
<213> ORGANISM: Bacillus halodurans

<400> SEQUENCE: 32

```
atggaaccgt ttatgggcaa aaacttcctg ctgaaaaacg agaccgcggt gagcctgtac    60
cacaactacg cgaaagatat gccgatcatc gactaccatt gccatctgag cccgaaagaa   120
atctacgaga acaaaaacctt ccagaacatc accgaagcgt ggctgtacgg cgatcactac   180
aaatggcgca tcatgcgtgc gaatggcatc gaagaaacct atattaccgg tgatgcaccg   240
gacgaagaaa aattcatggc gtgggcgaaa accgtgccga tggccattgg taatccgctg   300
tataactgga cccatctgga actgcaacgt ttttttggca tctacgaaat cctgaacgaa   360
aaaagcggca gcgcgatctg gaaacagacc aacaaactgc tgaaaggcga aggctttggt   420
gcgcgtgatc tgatcgtgaa aagcaacgtt aaagtggtgt gcaccaccga cgatccggtg   480
gattctctgg aataccatct gctgctgaaa gaagacaaag acttcccggt tagcgtttta   540
ccgggttttc gtccggataa aggtctggaa atcaaccgtg aaggctttcc ggaatgggtt   600
caagccctgg aagatgcggc cgcaattagc attacgacct atgatgaatt tctgaaagcg   660
ctggaaaaac gcgtgcgctt cttccatagt gcgggtggtc gtgttagcga tcatgcaatc   720
```

```
gataccatgg ttttcgccga aaccaccaaa gaagaagcgg gtcgcatttt tagtgatcgt    780
ctgcaaggca ccgaagttag ctgcgaagac gagaaaaaat tcaaaaccta caccctgcag    840
tttctgtgtg gcctgtatgc cgaactggac tgggcaatgc agtttcacat caacgcgctg    900
cgcaacacca acaccaaaat gatgaaacgc ctgggtccgg ataccggtta tgatagcatg    960
aacgatgaag aaatcgcgaa accgctgtac aaactgctga acagcgtgga aatgaaaaac   1020
caactgccga aaaccatcct gtacagcctg aacccgaacg acaactacgt gatcgcgagc   1080
atgatcaaca gcttccagga tggcatcacc ccgggcaaaa ttcagtttgg caccgcatgg   1140
tggttcaacg ataccaaaga tggtatgctg gatcagatga aagcactgag caatgtgggc   1200
ctgtttagcc gttttattgg catgctgacc gatagccgta gctttctgag ctatacccgt   1260
cacgaatact ttcgccgcat tgtgtgtaac ctgatcggcg aatgggtgga aaacggcgaa   1320
gttccgcgcg atatggaact gctgggtagt attgtgcaag gtatttgcta cgataacgcg   1380
aaacattact tccagttcca ggaggaaaaa gcgaacgtgt ga                      1422
```

<210> SEQ ID NO 33
<211> LENGTH: 593
<212> TYPE: PRT
<213> ORGANISM: Achromobacter piechaudii

<400> SEQUENCE: 33

```
Met Ser Gln Thr Pro Arg Lys Leu Arg Ser Gln Lys Trp Phe Asp Asp
1               5                   10                  15

Pro Ala His Ala Asp Met Thr Ala Ile Tyr Val Glu Arg Tyr Leu Asn
            20                  25                  30

Tyr Gly Leu Thr Arg Gln Glu Leu Gln Ser Gly Arg Pro Ile Ile Gly
        35                  40                  45

Ile Ala Gln Thr Gly Ser Asp Leu Ala Pro Cys Asn Arg His His Leu
    50                  55                  60

Ala Leu Ala Glu Arg Val Lys Ala Gly Ile Arg Asp Ala Gly Gly Ile
65                  70                  75                  80

Pro Met Glu Phe Pro Val His Pro Leu Ala Glu Gln Gly Arg Arg Pro
                85                  90                  95

Thr Ala Ala Leu Asp Arg Asn Leu Ala Tyr Leu Gly Leu Val Glu Ile
            100                 105                 110

Leu His Gly Tyr Pro Leu Asp Gly Val Val Leu Thr Thr Gly Cys Asp
        115                 120                 125

Lys Thr Thr Pro Ala Cys Leu Met Ala Ala Thr Val Asp Leu Pro
    130                 135                 140

Ala Ile Val Leu Ser Gly Gly Pro Met Leu Asp Gly Trp His Asp Gly
145                 150                 155                 160

Gln Arg Val Gly Ser Gly Thr Val Ile Trp His Ala Arg Asn Leu Met
                165                 170                 175

Ala Ala Gly Lys Leu Asp Tyr Glu Gly Phe Met Thr Leu Ala Thr Ala
            180                 185                 190

Ser Ser Pro Ser Val Gly His Cys Asn Thr Met Gly Thr Ala Leu Ser
        195                 200                 205

Met Asn Ser Leu Ala Glu Ala Leu Gly Met Ser Leu Pro Thr Cys Ala
    210                 215                 220

Ser Ile Pro Ala Pro Tyr Arg Glu Arg Ala Gln Met Ala Tyr Ala Thr
225                 230                 235                 240

Gly Met Arg Ile Cys Asp Met Val Arg Glu Asp Leu Arg Pro Ser His
                245                 250                 255
```

```
Ile Leu Thr Arg Gln Ala Phe Glu Asn Ala Ile Val Val Ala Ser Ala
            260                 265                 270

Leu Gly Ala Ser Thr Asn Cys Pro Pro His Leu Ile Ala Met Ala Arg
        275                 280                 285

His Ala Gly Ile Asp Leu Ser Leu Asp Asp Trp Gln Arg Leu Gly Glu
    290                 295                 300

Asp Val Pro Leu Leu Val Asn Cys Val Pro Ala Gly Glu His Leu Gly
305                 310                 315                 320

Glu Gly Phe His Arg Ala Gly Val Pro Ala Val Met His Glu Leu
                325                 330                 335

Phe Ala Ala Gly Arg Leu His Pro Asp Cys Pro Thr Val Ser Gly Lys
                340                 345                 350

Thr Ile Gly Asp Ile Ala Ala Gly Ala Lys Thr Arg Asp Ala Asp Val
            355                 360                 365

Ile Arg Ser Cys Ala Ala Pro Leu Lys His Arg Ala Gly Phe Ile Val
        370                 375                 380

Leu Ser Gly Asn Phe Phe Asp Ser Ala Ile Ile Lys Met Ser Val Val
385                 390                 395                 400

Gly Glu Ala Phe Arg Arg Ala Tyr Leu Ser Glu Pro Gly Ser Glu Asn
                405                 410                 415

Ala Phe Glu Ala Arg Ala Ile Val Phe Glu Gly Pro Glu Asp Tyr His
                420                 425                 430

Ala Arg Ile Glu Asp Pro Ala Leu Asn Ile Asp Glu His Cys Ile Leu
            435                 440                 445

Val Ile Arg Gly Ala Gly Thr Val Gly Tyr Pro Gly Ser Ala Glu Val
        450                 455                 460

Val Asn Met Ala Pro Pro Ser His Leu Ile Lys Arg Gly Val Asp Ser
465                 470                 475                 480

Leu Pro Cys Leu Gly Asp Gly Arg Gln Ser Gly Thr Ser Gly Ser Pro
                485                 490                 495

Ser Ile Leu Asn Met Ser Pro Glu Ala Ala Val Gly Gly Leu Ala
            500                 505                 510

Leu Leu Arg Thr Gly Asp Lys Ile Arg Val Asp Leu Asn Gln Arg Ser
        515                 520                 525

Val Thr Ala Leu Val Asp Asp Ala Glu Met Ala Arg Arg Lys Gln Glu
        530                 535                 540

Pro Pro Tyr Gln Ala Pro Ala Ser Gln Thr Pro Trp Gln Glu Leu Tyr
545                 550                 555                 560

Arg Gln Leu Val Gly Gln Leu Ser Thr Gly Cys Leu Glu Pro Ala
                565                 570                 575

Thr Leu Tyr Leu Lys Val Ile Glu Thr Arg Gly Asp Pro Arg His Ser
            580                 585                 590

His

<210> SEQ ID NO 34
<211> LENGTH: 602
<212> TYPE: PRT
<213> ORGANISM: Acinetobacter sp.

<400> SEQUENCE: 34

Met Ser Glu Arg Ile Lys Lys Met Asn Asp Gln Asn Lys Arg Ile Phe
1               5                   10                  15

Leu Arg Ser Gln Glu Trp Phe Asp Pro Glu His Ala Asp Met Thr
            20                  25                  30
```

```
Ala Leu Tyr Val Glu Arg Tyr Met Asn Tyr Gly Leu Thr Arg Ala Glu
         35                  40                  45

Leu Gln Ser Gly Arg Pro Ile Gly Ile Ala Gln Thr Gly Ser Asp
 50                  55                  60

Leu Thr Pro Cys Asn Arg His His Lys Glu Leu Ala Glu Arg Val Lys
 65                  70                  75                  80

Ala Gly Ile Arg Asp Ala Gly Gly Ile Pro Met Glu Phe Pro Val His
                 85                  90                  95

Pro Ile Ala Glu Gln Thr Arg Arg Pro Thr Ala Ala Leu Asp Arg Asn
                100                 105                 110

Leu Ala Tyr Leu Gly Leu Val Glu Ile Leu His Gly Tyr Pro Leu Asp
            115                 120                 125

Gly Val Val Leu Thr Thr Gly Cys Asp Lys Thr Thr Pro Ala Cys Leu
130                 135                 140

Met Ala Ala Thr Thr Asp Ile Pro Ala Ile Val Leu Ser Gly Gly
145                 150                 155                 160

Pro Met Leu Asp Gly His Phe Lys Gly Glu Leu Ile Gly Ser Gly Thr
                165                 170                 175

Val Leu Trp His Ala Arg Asn Leu Leu Ala Thr Gly Glu Ile Asp Tyr
                180                 185                 190

Glu Gly Phe Met Glu Met Thr Thr Ser Ala Ser Pro Ser Val Gly His
            195                 200                 205

Cys Asn Thr Met Gly Thr Ala Leu Ser Met Asn Ala Leu Ala Glu Ala
            210                 215                 220

Leu Gly Met Ser Leu Pro Thr Cys Ala Ser Ile Pro Ala Pro Tyr Arg
225                 230                 235                 240

Glu Arg Gly Gln Met Ala Tyr Met Thr Gly Lys Arg Ile Cys Glu Met
                245                 250                 255

Val Leu Glu Asp Leu Arg Pro Ser Lys Ile Met Asn Lys Gln Ser Phe
                260                 265                 270

Glu Asn Ala Ile Ala Val Ala Ser Ala Leu Gly Ala Ser Ser Asn Cys
            275                 280                 285

Pro Pro His Leu Ile Ala Ile Ala Arg His Met Gly Ile Glu Leu Ser
            290                 295                 300

Leu Glu Asp Trp Gln Arg Val Gly Glu Asn Ile Pro Leu Ile Val Asn
305                 310                 315                 320

Cys Met Pro Ala Gly Lys Tyr Leu Gly Glu Gly Phe His Arg Ala Gly
                325                 330                 335

Gly Val Pro Ala Val Leu His Glu Leu Gln Lys Ala Ser Val Leu His
                340                 345                 350

Glu Gly Cys Ala Ser Val Ser Gly Lys Thr Met Gly Glu Ile Ala Lys
            355                 360                 365

Asn Ala Lys Thr Ser Asn Val Asp Val Ile Phe Pro Tyr Glu Gln Pro
370                 375                 380

Leu Lys His Gly Ala Gly Phe Ile Val Leu Ser Gly Asn Phe Phe Asp
385                 390                 395                 400

Ser Ala Ile Met Lys Met Ser Val Val Gly Glu Ala Phe Lys Lys Thr
                405                 410                 415

Tyr Leu Ser Asp Pro Asn Gly Glu Asn Ser Phe Glu Ala Arg Ala Ile
            420                 425                 430

Val Phe Glu Gly Pro Glu Asp Tyr His Ala Arg Ile Asn Asp Pro Ala
435                 440                 445
```

```
Leu Asp Ile Asp Glu His Cys Ile Leu Val Ile Arg Gly Ala Gly Thr
450                 455                 460

Val Gly Tyr Pro Gly Ser Ala Glu Val Val Asn Met Ala Pro Pro Ala
465                 470                 475                 480

Glu Leu Ile Lys Lys Gly Ile Asp Ser Leu Pro Cys Leu Gly Asp Gly
            485                 490                 495

Arg Gln Ser Gly Thr Ser Ala Ser Pro Ser Ile Leu Asn Met Ser Pro
                500                 505                 510

Glu Ala Ala Val Gly Gly Ile Ala Leu Leu Lys Thr Asn Asp Arg
                515                 520                 525

Leu Arg Ile Asp Leu Asn Lys Arg Ser Val Asn Val Leu Ile Ser Asp
530                 535                 540

Glu Glu Leu Glu Gln Arg Arg Arg Glu Trp Lys Pro Thr Val Ser Ser
545                 550                 555                 560

Ser Gln Thr Pro Trp Gln Glu Met Tyr Arg Asn Met Val Gly Gln Leu
                565                 570                 575

Ser Thr Gly Gly Cys Leu Glu Pro Ala Thr Leu Tyr Met Arg Val Ile
                580                 585                 590

Asn Gln Asp Asn Leu Pro Arg His Ser His
                595                 600

<210> SEQ ID NO 35
<211> LENGTH: 593
<212> TYPE: PRT
<213> ORGANISM: Achromobacter xylosoxidans

<400> SEQUENCE: 35

Met Ser Gln Thr Pro Arg Lys Leu Arg Ser Gln Lys Trp Phe Asp Asp
1               5                   10                  15

Pro Ala His Ala Asp Met Thr Ala Ile Tyr Val Glu Arg Tyr Leu Asn
                20                  25                  30

Tyr Gly Leu Thr Arg Gln Glu Leu Gln Ser Gly Arg Pro Ile Ile Gly
            35                  40                  45

Ile Ala Gln Thr Gly Ser Asp Leu Ala Pro Cys Asn Arg His His Leu
50                  55                  60

Ala Leu Ala Glu Arg Ile Lys Ala Gly Ile Arg Asp Ala Gly Gly Ile
65                  70                  75                  80

Pro Met Glu Phe Pro Val His Pro Leu Ala Glu Gln Gly Arg Arg Pro
                85                  90                  95

Thr Ala Ala Leu Asp Arg Asn Leu Ala Tyr Leu Gly Leu Val Glu Ile
                100                 105                 110

Leu His Gly Tyr Pro Leu Asp Gly Val Val Leu Thr Thr Gly Cys Asp
            115                 120                 125

Lys Thr Thr Pro Ala Cys Leu Met Ala Ala Ala Thr Val Asp Ile Pro
            130                 135                 140

Ala Ile Val Leu Ser Gly Gly Pro Met Leu Asp Gly Trp His Asp Gly
145                 150                 155                 160

Gln Arg Val Gly Ser Gly Thr Val Ile Trp His Ala Arg Asn Leu Met
                165                 170                 175

Ala Ala Gly Lys Leu Asp Tyr Glu Gly Phe Met Thr Leu Ala Thr Ala
                180                 185                 190

Ser Ser Pro Ser Ile Gly His Cys Asn Thr Met Gly Thr Ala Leu Ser
            195                 200                 205

Met Asn Ser Leu Ala Glu Ala Leu Gly Met Ser Leu Pro Thr Cys Ala
210                 215                 220
```

Ser Ile Pro Ala Pro Tyr Arg Glu Arg Gly Gln Met Ala Tyr Ala Thr
225                 230                 235                 240

Gly Leu Arg Ile Cys Asp Met Val Arg Glu Asp Leu Arg Pro Ser His
            245                 250                 255

Val Leu Thr Arg Gln Ala Phe Glu Asn Ala Ile Val Val Ala Ser Ala
        260                 265                 270

Leu Gly Ala Ser Ser Asn Cys Pro Pro His Leu Ile Ala Met Ala Arg
    275                 280                 285

His Ala Gly Ile Asp Leu Ser Leu Asp Asp Trp Gln Arg Leu Gly Glu
290                 295                 300

Asp Val Pro Leu Leu Val Asn Cys Val Pro Ala Gly Glu His Leu Gly
305                 310                 315                 320

Glu Gly Phe His Arg Ala Gly Val Pro Ala Val Leu His Glu Leu
                325                 330                 335

Ala Ala Ala Gly Arg Leu His Met Asp Cys Ala Thr Val Ser Gly Lys
            340                 345                 350

Thr Ile Gly Glu Ile Ala Ala Ala Lys Thr Asn Ala Asp Val
        355                 360                 365

Ile Arg Ser Cys Asp Ala Pro Leu Lys His Arg Ala Gly Phe Ile Val
    370                 375                 380

Leu Ser Gly Asn Phe Phe Asp Ser Ala Ile Ile Lys Met Ser Val Val
385                 390                 395                 400

Gly Glu Ala Phe Arg Arg Ala Tyr Leu Ser Glu Pro Gly Ser Glu Asn
                405                 410                 415

Ala Phe Glu Ala Arg Ala Ile Val Phe Glu Gly Pro Glu Asp Tyr His
            420                 425                 430

Ala Arg Ile Glu Asp Pro Thr Leu Asn Ile Asp Glu His Cys Ile Leu
        435                 440                 445

Val Ile Arg Gly Ala Gly Thr Val Gly Tyr Pro Gly Ser Ala Glu Val
    450                 455                 460

Val Asn Met Ala Pro Pro Ser His Leu Leu Lys Arg Gly Ile Asp Ser
465                 470                 475                 480

Leu Pro Cys Leu Gly Asp Gly Arg Gln Ser Gly Thr Ser Ala Ser Pro
                485                 490                 495

Ser Ile Leu Asn Met Ser Pro Glu Ala Ala Val Gly Gly Leu Ala
            500                 505                 510

Leu Leu Arg Thr Gly Asp Arg Ile Arg Val Asp Leu Asn Gln Arg Ser
        515                 520                 525

Val Ile Ala Leu Val Asp Gln Thr Glu Met Glu Arg Arg Lys Leu Glu
    530                 535                 540

Pro Pro Tyr Gln Ala Pro Glu Ser Gln Thr Pro Trp Gln Glu Leu Tyr
545                 550                 555                 560

Arg Gln Leu Val Gly Gln Leu Ser Thr Gly Gly Cys Leu Glu Pro Ala
                565                 570                 575

Thr Leu Tyr Leu Lys Val Val Glu Thr Arg Gly Asp Pro Arg His Ser
            580                 585                 590

His

<210> SEQ ID NO 36
<211> LENGTH: 1782
<212> TYPE: DNA
<213> ORGANISM: Achromobacter piechaudii

<400> SEQUENCE: 36

```
atgtctcaga cacccc gcaa gttgcgcagc cagaaatggt tcgacgaccc tgcgcatgcc      60
gatatgacgg cgatttacgt cgagcgttat ctgaattacg gcctgacgcg gcaagagttg     120
cagtccgggc ggccgatcat cggcatcgcc cagaccggca gcgatctggc gccctgcaac     180
cgccatcacc tggcgctggc cgagcgcgtc aaagcgggca tccgggacgc gggcggcatc     240
ccgatggagt tccccgtgca cccgctggcc gaacaaggcc ggcggcccac ggccgcgctg     300
gaccgcaacc tggcctatct gggcctggtc gaaatcctgc acggctaccc cttggacggg     360
gtggtgctga cgactggctg cgacaagacc acgcctgcct gcctgatggc cgccgccacg     420
gtcgacctgc ccgccatcgt gctgtccggc ggccccatgc tggacggctg cacgacggc      480 cagcgcgtcg gttccggcac cgtcatctgg cacgcgcgca acctgatggc ggccggcaag     540
cttgattacg aaggcttcat gacgctggcc accgcgtctt cgccgtcggt cggccactgc     600
aacaccatgg gcacggcgtt gtcgatgaat cgctggccg aagcgctggg catgtcgctg      660
cccacctgcg ccagcattcc cgcccctac gcgaacgcg cccagatggc ctacgccacc       720
ggcatgcgca tctgcgacat ggtgcgcgaa gacctgcgac cctcccacat cctgacacgg     780
caggcattcg agaacgccat cgtcgtggca tcggcgctgg gcgcgtccac caattgcccg     840
ccgcacctga tcgcgatggc ccgccacgcc ggcatcgacc ttagcctgga cgactggcag     900
cgcctgggtg aagacgtgcc gctgctggtc aactgcgtgc cggcgggcga gcatctgggc     960
gagggcttcc accgcgcggg cggcgtcccc gcggtcatgc atgaactgtt cgccgccggg    1020
cgccttcacc ccgactgccc caccgtatcc ggcaagacca tcggggacat cgccgcgggc    1080
gccaagaccc gcgacgccga cgtcatccgc agctgcgccg cccccgctgaa acaccgggca   1140 ggcttcatcg tgctgtcggg caatttcttc gacagcgcca tcatcaagat gtcggtcgta    1200
ggcgaagcgt tccgccgcgc ctacctgtcc gaacccggct cagagaacgc cttcgaggcc    1260
cgcgccatcg tgttcgaagg ccccgaggac taccacgcgc gcatcgaaga cccggcgctg    1320
aacatcgacg aacactgcat ccttgtcatc cgcggcgccg gcaccgtggg ctacccgggc    1380
agcgccgaag tggtcaacat ggcgccgccg tcccacctga tcaagcgcgg cgtggattcc    1440
ctgccgtgcc tggggatgg caggcaaagc ggcacttccg gcagcccgtc cattttgaac     1500
atgtcccctg aagcagcagt cgggggagga ttggcgctgc tgcgcaccgg cgacaagatc    1560
cgtgtcgatc tgaaccagcg cagcgtcacc gccttggtcg acgacgcgga aatggcaaga    1620
cggaagcaag aaccgcccta ccaggcaccg gcctcgcaaa cgccctggca agagctgtac    1680
cggcaactgg tcgccagtt gtcgacgggc ggctgcctgg agcccgcgac gctatatctg    1740
aaagtcatcg aaacgcgcgg cgatccccgg cactctcact ga                       1782
```

<210> SEQ ID NO 37
<211> LENGTH: 1809
<212> TYPE: DNA
<213> ORGANISM: Acinetobacter sp.

<400> SEQUENCE: 37

```
atgagtgaaa ggatcaaaaa aatgaatgat caaataaaac ggatttttt acgtagccaa       60 gaatggtttg atgatcctga acatgctgac atgacagcac tctatgttga gcgttatatg     120
aattatggcc tgacccgtgc cgagctacaa tcaggccgcc cgattattgg tattgcacaa     180
actggcagtg atttaactcc atgtaaccgt caccacaaag aacttgctga acgggttaaa     240
gcaggtattc gagatgcggg aggtattccc atggaattcc ccgttcaccc gattgcagaa     300
```

```
caaacccgtc gccctactgc tgcacttgat agaaatttag cttacttagg cttagttgaa    360
atattgcatg ttatccgct tgatggtgtg gtgctaacca caggttgtga caaaactaca    420
cctgcttgtt taatggctgc cgcaacgaca gatataccag ccattgtgtt gtctggtgga    480
ccaatgctag atggtcattt taaaggtgag ttaattggtt ctgggactgt gctttggcat    540
gcaagaaatt tacttgccac gggtgaaatt gattatgaag ggttcatgga aatgaccact    600
tcagcatcgc cttcggtcgg acattgcaac accatgggca ctgcacttcc tatgaatgcc    660
ttggcagaag ctttgggcat gtctttaccg acatgtgcaa gtattccagc gccgtatcgc    720
gaacgagggc aaatggccta tatgacaggc aaaagaattt gtgaaatggt tttagaagat    780
ttacgccctt ctaaaatcat gaacaaacaa tcatttgaaa atgccatcgc ggtagcttca    840
gcattagggg catcaagtaa ttgccctcct cacctcattg caattgcccg tcatatgggc    900
attgagctca gtttagaaga ctggcaacgc gttggggaga acattcctct cattgtgaac    960
tgtatgcctg cgggtaaata tttaggtgaa ggttttcacc gtgctggcgg tgttcctgct   1020
gttttgcatg aattacaaaa ggccagcgtt ttacatgaag gctgtgcatc agtcagcggt   1080
aaaacgatgg gagaaattgc taaaaatgct aaaacctcca atgtagatgt tattttccca   1140
tatgaacaac cattaaaaca tggtgcaggt tttattgtgc ttagtggcaa tttcttcgac   1200
agcgccatta tgaaaatgtc tgttgtgggt gaagcattta agaaaaccta tttatctgac   1260
ccaaatgggg aaaatagctt tgaagcacgg gcaatcgttt ttgaagggcc agaggactac   1320
catgcacgaa ttaatgatcc agccttagac attgatgaac attgtatttt ggtcattcgt   1380
ggcgctggaa cagtgggcta tccaggtagt gcagaagttg taaatatggc tccacccgca   1440
gagttaatta aaaaaggcat cgattcactg ccttgcttag gagatggccg ccaaagtggt   1500
acgtctgcca gccttctat tttaaatatg tcacccgaag cggcggtagg cggtggaatt   1560
gcattattaa agaccaatga ccgtttacgc attgatctca ataaacgctc cgtcaacgta   1620
ctcatttctg acgaagagtt agaacaacgc cgccgtgagt ggaaaccgac ggtctcttca   1680
tctcaaacac cttggcaaga aatgtatcgc aacatggtgg gtcaattatc cactggcggt   1740
tgtttggaac ctgcaacttt atatatgcga gtcataaatc aagacaacct tccaagacac   1800
tctcattaa                                                           1809

<210> SEQ ID NO 38
<211> LENGTH: 1782
<212> TYPE: DNA
<213> ORGANISM: Achromobacter xylosoxidans

<400> SEQUENCE: 38
atgagccaaa caccgcgtaa attacgcagc cagaagtggt tgacgatcc tgcacatgcc      60
gatatgaccg ccatctatgt tgaacgctac ctgaactatg gcttaacccg ccaagaactg    120
caaagtggtc gccgattat tggtattgcc caaaccggca gcgatttagc cccgtgtaat    180
cgccatcatt tagccttagc cgaacgcatt aaagcaggca ttagagatgc aggcggcatt    240
cctatggaat ttcccgttca tccgctggcc gaacaaggta gacgtcctac agcagcatta    300
gatcgcaatt tagcctattt aggcctggtg gaaattttac acggctatcc cctgacggt    360
gtggtgctga caaccggttg cgataaaaca acaccggcgt gtttaatggc agctgcaaca    420
gttgatattc cggcgatcgt gttatcaggt ggtccgatgt tagatggctg gcatgatggc    480
caaagagttg gcagtggtac cgtgatttgg catgcacgaa atttaatggc agcaggcaaa    540
ctggattatg aaggcttcat gaccctggcg acagcctctt ctccgagtat tggacactgt    600
```

```
aataccatgg gcacagcctt aagcatgaat agtctggcag aagccctggg tatgtcttta    660
ccgacctgtg cgtctattcc agccccgtat agagaacgcg gtcaaatggc gtatgctact    720
ggtttacgca tttgcgatat ggtgcgcgaa gatttacgcc cgtcacatgt tttaacccgc    780
caagccttcg aaaatgccat tgttgttgcc tcagccttag gtgcaagctc taattgtccc    840
cctcatttaa ttgccatggc ccgtcatgcc ggtatcgact taagcctgga tgactggcaa    900
cgcttaggcg aagatgttcc gttactggtc aattgtgtgc ctgccggtga acatttaggt    960
gaaggatttc atcgcgcggg tggtgttcct gctgttttac atgaattagc tgccgcaggt   1020
cgtttacata tggattgtgc taccgtttct ggcaagacca tcggcgaaat tgcagctgcc   1080
gcaaaaacca acaacgcaga cgtgattcgc tcgtgtgatg ccccgttaaa acatagagcc   1140
ggctttattg tgttaagcgg caatttcttc gactccgcca tcatcaagat gtccgttgtg   1200
ggtgaagcct ttcgcagagc ctatttaagt gaacctggca gcgaaaatgc ctttgaagcc   1260
cgtgccatcg tgtttgaagg cccggaagac tatcatgccc gcattgaaga tccgaccctg   1320
aatattgatg aacactgcat tctggtgatt cgcggcgcag gtaccgttgg ttatcctggt   1380
agtgctgaag ttgtgaatat ggccccgccg agccatttat taaaacgcgg tattgattca   1440
ttaccttgcc tgggagatgg ccgccaaagt ggtacctcag ctagtccgtc tatcctgaat   1500
atgagccctg aagccgccgt tggaggaggt ttagcattat taagaaccgg tgatcgcatt   1560
cgcgtcgatc tgaatcaacg ctcagtcatt gcattagtcg accagaccga aatggaacgc   1620
cgcaaattag aaccaccgta tcaagcacct gaaagccaaa ccccgtggca gaactgtat    1680
cgccaattag tcggtcaact gtcaacaggc ggctgcctgg aaccagccac cttatattta   1740
aaagtcgtgg aaacccgtgg agatcctcgt catagccatt aa                      1782
```

<210> SEQ ID NO 39
<211> LENGTH: 451
<212> TYPE: PRT
<213> ORGANISM: Terriglobuds roseus

<400> SEQUENCE: 39

```
Met Asp Arg Arg Glu Leu Leu Lys Thr Ser Ala Leu Leu Met Ala Ala
1               5                   10                  15

Ala Pro Leu Ala Arg Ala Ala Asn Val Pro Glu Asp His Ala Asn Val
            20                  25                  30

Pro Arg Thr Asn Trp Ser Lys Asn Phe His Tyr Ser Thr Ser Arg Val
        35                  40                  45

Tyr Ala Pro Thr Thr Pro Glu Glu Val Pro Ala Ile Val Leu Glu Asn
    50                  55                  60

Gly His Leu Lys Gly Leu Gly Ser Arg His Cys Phe Asn Asn Ile Ala
65                  70                  75                  80

Asp Ser Gln Tyr Ala Gln Ile Ser Met Arg Glu Val Lys Gly Ile Gln
                85                  90                  95

Ile Asp Glu Ala Ala Gln Thr Val Thr Val Gly Ala Gly Ile Ala Tyr
            100                 105                 110

Gly Glu Leu Ala Pro Val Leu Asp Lys Ala Gly Phe Ala Leu Ala Asn
        115                 120                 125

Leu Ala Ser Leu Pro His Ile Ser Val Gly Gly Thr Ile Ala Thr Ala
    130                 135                 140

Thr His Gly Ser Gly Val Gly Asn Lys Asn Leu Ser Ser Ala Thr Arg
145                 150                 155                 160
```

```
Ala Ile Glu Ile Val Lys Ala Asp Gly Ser Ile Leu Arg Leu Ser Arg
             165                 170                 175

Asp Thr Asp Gly Glu Arg Phe Arg Met Ala Val Val His Leu Gly Ala
        180                 185                 190

Leu Gly Val Leu Thr Lys Val Thr Leu Asp Ile Val Pro Arg Phe Asp
        195                 200                 205

Met Ser Gln Val Val Tyr Arg Asn Leu Ser Phe Asp Gln Leu Glu His
    210                 215                 220

Asn Leu Asp Thr Ile Leu Ser Ser Gly Tyr Ser Val Ser Leu Phe Thr
225                 230                 235                 240

Asp Trp Gln Arg Asn Arg Val Asn Gln Val Trp Ile Lys Asp Lys Ala
                245                 250                 255

Thr Ala Asp Ala Pro Gln Lys Pro Leu Pro Pro Met Phe Tyr Gly Ala
            260                 265                 270

Thr Leu Gln Thr Ala Lys Leu His Pro Ile Asp Asp His Pro Ala Asp
        275                 280                 285

Ala Cys Thr Glu Gln Met Gly Ser Val Gly Pro Trp Tyr Leu Arg Leu
    290                 295                 300

Pro His Phe Lys Met Glu Phe Thr Pro Ser Ser Gly Glu Glu Leu Gln
305                 310                 315                 320

Thr Glu Tyr Phe Val Ala Arg Lys Asp Gly Tyr Arg Ala Ile Arg Ala
                325                 330                 335

Val Glu Lys Leu Arg Asp Lys Ile Thr Pro His Leu Phe Ile Thr Glu
            340                 345                 350

Ile Arg Thr Ile Ala Ala Asp Asp Leu Pro Met Ser Met Ala Tyr Gln
        355                 360                 365

Arg Asp Ser Met Ala Ile His Phe Thr Trp Lys Pro Glu Glu Pro Thr
    370                 375                 380

Val Arg Lys Leu Leu Pro Glu Ile Glu Ala Ala Leu Ala Pro Phe Gly
385                 390                 395                 400

Val Arg Pro His Trp Gly Lys Ile Phe Glu Ile Pro Pro Ser Tyr Leu
                405                 410                 415

His Lys Gln Tyr Pro Ala Leu Pro Arg Phe Arg Ala Met Ala Gln Ala
            420                 425                 430

Leu Asp Pro Gly Gly Lys Phe Arg Asn Ala Tyr Leu Asp Arg Asn Ile
        435                 440                 445

Phe Gly Ala
    450

<210> SEQ ID NO 40
<211> LENGTH: 450
<212> TYPE: PRT
<213> ORGANISM: Granulicella mallensis

<400> SEQUENCE: 40

Met Asp Lys Arg Asp Phe Leu Lys Gly Ser Ala Thr Thr Ala Val Ala
1               5                   10                  15

Leu Met Met Gly Leu Asn Glu Ser Lys Ala Phe Ala Asp Asp Ser Val
            20                  25                  30

Pro Arg Thr Asn Trp Ser Gly Asn Tyr His Tyr Ser Thr Asn Lys Val
        35                  40                  45

Leu Gln Pro Ala Ser Val Ala Glu Thr Gln Asp Ala Val Arg Ser Val
    50                  55                  60

Ala Gly Val Arg Ala Leu Gly Thr Arg His Ser Phe Asn Gly Ile Ala
65                  70                  75                  80
```

```
Asp Ser Gln Ile Ala Gln Ile Ser Thr Leu Lys Leu Lys Asp Val Ser
                85                  90                  95

Leu Asp Ala Lys Ser Ser Thr Val Thr Val Gly Ala Gly Ile Arg Tyr
            100                 105                 110

Gly Asp Leu Ala Val Gln Leu Asp Ala Lys Gly Phe Ala Leu His Asn
        115                 120                 125

Leu Ala Ser Leu Pro His Ile Ser Val Gly Gly Ala Cys Ala Thr Ala
    130                 135                 140

Thr His Gly Ser Gly Met Gly Asn Gly Asn Leu Ala Thr Ala Val Lys
145                 150                 155                 160

Ala Val Glu Phe Val Ala Ala Asp Gly Ser Val His Thr Leu Ser Arg
                165                 170                 175

Asp Arg Asp Gly Asp Arg Phe Ala Gly Ser Val Gly Leu Gly Ala
                180                 185                 190

Leu Gly Val Val Thr His Leu Thr Leu Gln Val Gln Pro Arg Phe Glu
        195                 200                 205

Met Thr Gln Val Val Tyr Arg Asp Leu Pro Phe Ser Glu Leu Glu His
    210                 215                 220

His Leu Pro Glu Ile Met Gly Ala Gly Tyr Ser Val Ser Leu Phe Thr
225                 230                 235                 240

Asp Trp Gln Asn Gly Arg Ala Gly Glu Val Trp Ile Lys Arg Arg Val
                245                 250                 255

Asp Gln Gly Gly Ala Ser Ala Pro Pro Ala Arg Phe Phe Asn Ala Thr
                260                 265                 270

Leu Ala Thr Thr Lys Leu His Pro Ile Leu Asp His Pro Ala Glu Ala
        275                 280                 285

Cys Thr Asp Gln Leu Asn Thr Val Gly Pro Trp Tyr Glu Arg Leu Pro
    290                 295                 300

His Phe Lys Leu Asn Phe Thr Pro Ser Ser Gly Gln Glu Leu Gln Thr
305                 310                 315                 320

Glu Phe Phe Val Pro Phe Asp Arg Gly Tyr Asp Ala Ile Arg Ala Val
                325                 330                 335

Glu Thr Leu Arg Asp Val Ile Thr Pro His Leu Tyr Ile Thr Glu Leu
            340                 345                 350

Arg Ala Val Ala Ala Asp Asp Leu Trp Met Ser Met Ala Tyr Gln Arg
        355                 360                 365

Pro Ser Leu Ala Ile His Phe Thr Trp Lys Pro Glu Thr Asp Ala Val
    370                 375                 380

Leu Lys Leu Leu Pro Gln Ile Glu Ala Lys Leu Ala Pro Phe Gly Ala
385                 390                 395                 400

Arg Pro His Trp Ala Lys Val Phe Thr Met Lys Ser Ser His Val Ala
                405                 410                 415

Pro Leu Tyr Pro Arg Leu Lys Asp Phe Leu Val Leu Ala Lys Ser Phe
            420                 425                 430

Asp Pro Lys Gly Lys Phe Gln Asn Ala Phe Leu Gln Asp His Val Asp
        435                 440                 445

Ile Ala
    450

<210> SEQ ID NO 41
<211> LENGTH: 414
<212> TYPE: PRT
<213> ORGANISM: Streptomyces acidiscabies
```

```
<400> SEQUENCE: 41

Met Thr Ala Ser Val Thr Asn Trp Ala Gly Asn Ile Ser Phe Val Ala
1               5                   10                  15

Lys Asp Val Val Arg Pro Gly Val Glu Ala Leu Arg Lys Val Val
            20                  25                  30

Ala Gly Asn Asp Arg Val Arg Val Leu Gly Ser Gly His Ser Phe Asn
        35                  40                  45

Arg Ile Ala Glu Pro Gly Ala Asp Gly Val Leu Val Ser Leu Asp Ala
    50                  55                  60

Leu Pro Gln Val Ile Asp Val Asp Thr Glu Arg Arg Thr Val Arg Val
65                  70                  75                  80

Gly Gly Gly Val Lys Tyr Ala Glu Leu Ala Arg His Val Asn Glu Ser
                85                  90                  95

Gly Leu Ala Leu Pro Asn Met Ala Ser Leu Pro His Ile Ser Val Ala
            100                 105                 110

Gly Ser Val Ala Thr Gly Thr His Gly Ser Gly Val Asn Asn Gly Pro
        115                 120                 125

Leu Ala Thr Pro Val Arg Glu Val Glu Leu Leu Thr Ala Asp Gly Ser
    130                 135                 140

Leu Val Thr Ile Gly Lys Asp Asp Ala Arg Phe Pro Gly Ala Val Thr
145                 150                 155                 160

Ser Leu Gly Ala Leu Gly Val Val Ala Leu Thr Leu Asp Leu Glu
                165                 170                 175

Pro Ala Tyr Gly Val Glu Gln Tyr Thr Phe Thr Glu Leu Pro Leu Glu
            180                 185                 190

Gly Leu Asp Phe Glu Ala Val Ala Ser Ala Ala Tyr Ser Val Ser Leu
        195                 200                 205

Phe Thr Asp Trp Arg Glu Ala Gly Phe Arg Gln Val Trp Val Lys Arg
    210                 215                 220

Arg Ile Asp Glu Pro Tyr Ala Gly Phe Pro Trp Ala Ala Pro Ala Thr
225                 230                 235                 240

Glu Lys Leu His Pro Val Pro Gly Met Pro Ala Glu Asn Cys Thr Asp
                245                 250                 255

Gln Phe Gly Ala Ala Gly Pro Trp His Glu Arg Leu Pro His Phe Lys
            260                 265                 270

Ala Glu Phe Thr Pro Ser Ser Gly Asp Glu Leu Gln Ser Glu Tyr Leu
        275                 280                 285

Leu Pro Arg Glu His Ala Leu Ala Ala Leu Asp Ala Val Gly Asn Val
    290                 295                 300

Arg Glu Thr Val Ser Thr Val Leu Gln Ile Cys Glu Val Arg Thr Ile
305                 310                 315                 320

Ala Ala Asp Thr Gln Trp Leu Ser Pro Ala Tyr Gly Arg Asp Ser Val
                325                 330                 335

Ala Leu His Phe Thr Trp Thr Asp Asp Met Asp Ala Val Leu Pro Ala
            340                 345                 350

Val Arg Ala Val Glu Ser Ala Leu Asp Gly Phe Gly Ala Arg Pro His
        355                 360                 365

Trp Gly Lys Val Phe Thr Thr Ala Pro Ala Leu Arg Glu Arg Tyr
    370                 375                 380

Pro Arg Leu Asp Asp Phe Arg Thr Leu Arg Asp Glu Leu Asp Pro Ala
385                 390                 395                 400

Gly Lys Phe Thr Asn Ala Phe Val Arg Asp Val Leu Glu Gly
                405                 410
```

```
<210> SEQ ID NO 42
<211> LENGTH: 427
<212> TYPE: PRT
<213> ORGANISM: Actinomycetales

<400> SEQUENCE: 42
```

| | | | | | | | | | | | | | | |
|---|---|---|---|---|---|---|---|---|---|---|---|---|---|---|
| Met | Thr | Leu | Glu | Arg | Asn | Trp | Ala | Gly | Thr | His | Thr | Phe | Ala | Ala | Pro |
| 1 | | | | 5 | | | | | 10 | | | | | 15 | |
| Arg | Ile | Val | Asn | Ala | Thr | Ser | Ile | Asp | Glu | Val | Arg | Ala | Leu | Val | Ala |
| | | | 20 | | | | | 25 | | | | | 30 | | |
| Glu | Ala | Ala | Arg | Thr | Gly | Thr | Arg | Val | Arg | Ala | Leu | Gly | Thr | Arg | His |
| | | 35 | | | | | 40 | | | | | 45 | | | |
| Ser | Phe | Thr | Asp | Leu | Ala | Asp | Ser | Asp | Gly | Thr | Leu | Ile | Thr | Val | Leu |
| | 50 | | | | | 55 | | | | | 60 | | | | |
| Asp | Ile | Pro | Ala | Asp | Pro | Val | Phe | Asp | Glu | Ala | Ala | Gly | Ser | Val | Thr |
| 65 | | | | | 70 | | | | | 75 | | | | | 80 |
| Ile | Gly | Ala | Gly | Thr | Arg | Tyr | Gly | Ile | Ala | Ala | Ala | Trp | Leu | Ala | Glu |
| | | | | 85 | | | | | 90 | | | | | 95 | |
| His | Gly | Leu | Ala | Phe | His | Asn | Met | Gly | Ser | Leu | Pro | His | Ile | Ser | Val |
| | | | 100 | | | | | 105 | | | | | 110 | | |
| Gly | Gly | Ala | Ile | Ala | Thr | Gly | Thr | His | Gly | Ser | Gly | Asn | Asp | Asn | Gly |
| | | 115 | | | | | 120 | | | | | 125 | | | |
| Ile | Leu | Ser | Ser | Ala | Val | Ser | Gly | Leu | Glu | Tyr | Val | Asp | Ala | Thr | Gly |
| | 130 | | | | | 135 | | | | | 140 | | | | |
| Glu | Leu | Val | His | Val | Arg | Arg | Gly | Asp | Pro | Gly | Phe | Asp | Gly | Leu | Val |
| 145 | | | | | 150 | | | | | 155 | | | | | 160 |
| Val | Gly | Leu | Gly | Ala | Tyr | Gly | Ile | Val | Val | Arg | Val | Thr | Val | Asp | Val |
| | | | | 165 | | | | | 170 | | | | | 175 | |
| Gln | Pro | Ala | Tyr | Arg | Val | Arg | Gln | Asp | Val | Tyr | Arg | Asp | Val | Pro | Trp |
| | | | 180 | | | | | 185 | | | | | 190 | | |
| Asp | Ala | Val | Leu | Ala | Asp | Phe | Glu | Gly | Val | Thr | Gly | Gly | Ala | Tyr | Ser |
| | | 195 | | | | | 200 | | | | | 205 | | | |
| Val | Ser | Ile | Phe | Thr | Asn | Trp | Leu | Gly | Asp | Thr | Val | Glu | Gln | Ile | Trp |
| | 210 | | | | | 215 | | | | | 220 | | | | |
| Trp | Lys | Thr | Arg | Leu | Val | Ala | Gly | Asp | Asp | Glu | Leu | Pro | Val | Pro |
| 225 | | | | | 230 | | | | | 235 | | | | | 240 |
| Glu | Ser | Trp | Leu | Gly | Val | Gln | Arg | Asp | Ser | Leu | Thr | Ala | Gly | Asn | Leu |
| | | | 245 | | | | | 250 | | | | | 255 | | |
| Val | Glu | Thr | Asp | Pro | Asp | Asn | Leu | Thr | Leu | Gln | Gly | Gly | Val | Pro | Gly |
| | | | 260 | | | | | 265 | | | | | 270 | | |
| Asp | Trp | Trp | Glu | Arg | Leu | Pro | His | Phe | Arg | Leu | Glu | Ser | Thr | Pro | Ser |
| | | 275 | | | | | 280 | | | | | 285 | | | |
| Asn | Gly | Asp | Glu | Ile | Gln | Thr | Glu | Tyr | Phe | Ile | Asp | Arg | Ala | Asp | Gly |
| | 290 | | | | | 295 | | | | | 300 | | | | |
| Pro | Ala | Ala | Ile | Thr | Ala | Leu | Arg | Ala | Leu | Gly | Asp | Arg | Ile | Ala | Pro |
| 305 | | | | | 310 | | | | | 315 | | | | | 320 |
| Leu | Leu | Leu | Val | Thr | Glu | Leu | Arg | Thr | Ala | Ala | Pro | Asp | Lys | Leu | Trp |
| | | | | 325 | | | | | 330 | | | | | 335 | |
| Leu | Ser | Gly | Ala | Tyr | His | Arg | Glu | Met | Leu | Ala | Val | His | Phe | Thr | Trp |
| | | | 340 | | | | | 345 | | | | | 350 | | |
| Arg | Asn | Leu | Pro | Glu | Glu | Val | Arg | Ala | Val | Leu | Pro | Ala | Ile | Glu | Glu |
| | | 355 | | | | | 360 | | | | | 365 | | | |
| Ala | Leu | Ala | Pro | Phe | Asp | Ala | Arg | Pro | His | Trp | Gly | Lys | Leu | Asn | Leu |

```
                    370                 375                 380
Leu Thr Ala Glu Arg Ile Ala Glu Val Val Pro Arg Leu Ala Asp Ala
385                 390                 395                 400

Arg Asp Leu Phe Glu Glu Leu Asp Pro Ala Gly Thr Phe Ser Asn Ala
                405                 410                 415

His Leu Glu Arg Ile Gly Val Arg Leu Pro Arg
            420                 425
```

<210> SEQ ID NO 43
<211> LENGTH: 419
<212> TYPE: PRT
<213> ORGANISM: Frankia sp.

<400> SEQUENCE: 43

```
Met Arg Asp Ala Ala Ala Asn Trp Ala Gly Asn Val Arg Phe Gly
1               5                   10                  15

Ala Ala Arg Val Val Ala Pro Glu Ser Val Gly Glu Leu Gln Glu Ile
                20                  25                  30

Val Ala Gly Ser Arg Lys Ala Arg Ala Leu Gly Thr Gly His Ser Phe
            35                  40                  45

Ser Arg Ile Ala Asp Thr Asp Gly Thr Leu Ile Ala Thr Ala Arg Leu
50                  55                  60

Pro Arg Arg Ile Gln Ile Asp Asp Gly Ser Val Thr Val Ser Gly Gly
65                  70                  75                  80

Ile Arg Tyr Gly Asp Leu Ala Arg Glu Leu Ala Pro Asn Gly Trp Ala
                85                  90                  95

Leu Arg Asn Leu Gly Ser Leu Pro His Ile Ser Val Ala Gly Ala Cys
                100                 105                 110

Ala Thr Gly Thr His Gly Ser Gly Asp Arg Asn Gly Ser Leu Ala Thr
            115                 120                 125

Ser Val Ala Ala Leu Glu Leu Val Thr Ala Ser Gly Glu Leu Val Ser
130                 135                 140

Val Arg Arg Gly Asp Glu Asp Phe Asp Gly His Val Ile Ala Leu Gly
145                 150                 155                 160

Ala Leu Gly Val Thr Val Ala Val Thr Leu Asp Leu Val Pro Gly Phe
                165                 170                 175

Gln Val Arg Gln Leu Val Tyr Glu Gly Leu Thr Arg Asp Thr Leu Leu
            180                 185                 190

Glu Ser Val Gln Glu Ile Phe Ala Ala Ser Tyr Ser Val Ser Val Phe
            195                 200                 205

Thr Gly Trp Asp Pro Glu Ser Ser Gln Leu Trp Leu Lys Gln Arg Val
210                 215                 220

Asp Gly Pro Gly Asp Asp Gly Glu Pro Ala Glu Arg Phe Gly Ala
225                 230                 235                 240

Arg Leu Ala Thr Arg Pro Leu His Pro Val Pro Gly Ile Asp Pro Thr
                245                 250                 255

His Thr Thr Gln Gln Leu Gly Val Pro Gly Pro Trp His Glu Arg Leu
            260                 265                 270

Pro His Phe Arg Leu Asp Phe Thr Pro Ser Ala Gly Asp Glu Leu Gln
            275                 280                 285

Thr Glu Tyr Phe Val Ala Arg Glu His Ala Ala Ala Ile Glu Ala
290                 295                 300

Leu Phe Ala Ile Gly Ala Val Arg Pro Ala Leu Gln Ile Ser Glu
305                 310                 315                 320
```

-continued

```
Ile Arg Thr Val Ala Asp Ala Leu Trp Leu Ser Pro Ala Tyr Arg
            325                 330                 335

Arg Asp Val Met Ala Leu His Phe Thr Trp Ile Ser Ala Glu Gly Thr
            340                 345                 350

Val Met Pro Ala Val Ala Ala Val Glu Arg Ala Leu Ala Pro Phe Asp
            355                 360                 365

Pro Val Pro His Trp Gly Lys Val Phe Ala Leu Pro Pro Ala Ala Val
            370                 375                 380

Arg Ala Gly Tyr Pro Arg Ala Ala Glu Phe Leu Ala Leu Ala Ala Arg
385                 390                 395                 400

Arg Asp Pro Glu Ala Val Phe Arg Asn Gln Tyr Leu Asp Ala Tyr Leu
                405                 410                 415

Pro Ala Ala

<210> SEQ ID NO 44
<211> LENGTH: 413
<212> TYPE: PRT
<213> ORGANISM: Propionibacteriacaeae

<400> SEQUENCE: 44

Met Thr Gln Arg Asn Trp Ala Gly Asn Val Ser Tyr Ser Ser Ser Arg
1               5                   10                  15

Val Ala Glu Pro Ala Ser Val Asp Asp Leu Thr Ala Leu Val Glu Ser
            20                  25                  30

Glu Pro Arg Val Arg Pro Leu Gly Ser Arg His Cys Phe Asn Asp Ile
        35                  40                  45

Ala Asp Thr Pro Gly Val His Val Ser Leu Ala Arg Leu Arg Gly Glu
    50                  55                  60

Glu Pro Arg Leu Thr Ala Pro Gly Thr Leu Arg Thr Pro Ala Trp Leu
65                  70                  75                  80

Arg Tyr Gly Asp Leu Val Pro Val Leu Arg Glu Ala Gly Ala Ala Leu
                85                  90                  95

Ala Asn Leu Ala Ser Leu Pro His Ile Ser Val Ala Gly Ala Val Gln
            100                 105                 110

Thr Gly Thr His Gly Ser Gly Asp Arg Ile Gly Thr Leu Ala Thr Gln
        115                 120                 125

Val Ser Ala Leu Glu Leu Val Thr Gly Thr Gly Glu Val Leu Arg Leu
    130                 135                 140

Glu Arg Gly Glu Pro Asp Phe Asp Gly Ala Val Val Gly Leu Gly Ala
145                 150                 155                 160

Leu Gly Val Leu Thr His Val Glu Leu Asp Val Ser Pro Ala Arg Asp
                165                 170                 175

Val Ala Gln His Val Tyr Glu Gly Val Arg Leu Asp Asp Val Leu Ala
            180                 185                 190

Asp Leu Gly Ala Val Thr Gly Ala Gly Asp Ser Val Ser Met Phe Thr
        195                 200                 205

His Trp Gln Asp Pro Ala Val Val Ser Gln Val Trp Val Lys Ser Gly
    210                 215                 220

Gly Asp Val Asp Asp Ala Ala Ile Arg Asp Ala Gly Gly Arg Pro Ala
225                 230                 235                 240

Asp Gly Pro Arg His Pro Ile Ala Gly Ile Asp Pro Thr Pro Cys Thr
                245                 250                 255

Pro Gln Leu Gly Glu Pro Gly Trp Tyr Asp Arg Leu Pro His Phe
            260                 265                 270
```

```
Arg Leu Glu Phe Thr Pro Ser Val Gly Glu Glu Leu Gln Ser Glu Tyr
            275                 280                 285

Leu Val Asp Arg Asp Asp Ala Val Asp Ala Ile Arg Ala Val Gln Asp
        290                 295                 300

Leu Ala Pro Arg Ile Ala Pro Leu Leu Phe Val Cys Glu Ile Arg Thr
305                 310                 315                 320

Met Ala Ser Asp Gly Leu Trp Leu Ser Pro Ala Gln Gly Arg Asp Thr
                325                 330                 335

Val Gly Leu His Phe Thr Trp Arg Pro Asp Glu Ser Ala Val Arg Gln
            340                 345                 350

Leu Leu Pro Glu Ile Glu Arg Ala Leu Pro Ala Ser Ala Arg Pro His
        355                 360                 365

Trp Gly Lys Val Phe Thr Leu Pro Gly His Asp Val Ala Ala Arg Tyr
    370                 375                 380

Pro Arg Trp Ala Asp Phe Val Ala Leu Arg Arg Arg Leu Asp Pro Glu
385                 390                 395                 400

Arg Arg Phe Ala Asn Ala Tyr Leu Glu Arg Leu Gly Leu
                405                 410

<210> SEQ ID NO 45
<211> LENGTH: 420
<212> TYPE: PRT
<213> ORGANISM: Streptomyces sp.

<400> SEQUENCE: 45

Met Thr Pro Ala Glu Lys Asn Trp Ala Gly Asn Ile Thr Phe Gly Ala
1               5                   10                  15

Lys Arg Leu Cys Val Pro Arg Ser Val Arg Glu Leu Arg Glu Thr Val
            20                  25                  30

Ala Ala Ser Gly Ala Val Arg Pro Leu Gly Thr Arg His Ser Phe Asn
        35                  40                  45

Thr Val Ala Asp Thr Ser Gly Asp His Val Ser Leu Ala Gly Leu Pro
    50                  55                  60

Arg Val Val Asp Ile Asp Val Pro Gly Arg Ala Val Ser Leu Ser Ala
65                  70                  75                  80

Gly Leu Arg Phe Gly Glu Phe Ala Ala Glu Leu His Ala Arg Gly Leu
                85                  90                  95

Ala Leu Ala Asn Leu Gly Ser Leu Pro His Ile Ser Val Ala Gly Ala
            100                 105                 110

Val Ala Thr Gly Thr His Gly Ser Gly Val Gly Asn Arg Ser Leu Ala
        115                 120                 125

Gly Ala Val Arg Ala Leu Ser Leu Val Thr Ala Asp Gly Glu Thr Arg
    130                 135                 140

Thr Leu Arg Arg Thr Asp Glu Asp Phe Ala Gly Ala Val Val Ser Leu
145                 150                 155                 160

Gly Ala Leu Gly Val Val Thr Ser Leu Glu Leu Asp Leu Val Pro Ala
                165                 170                 175

Phe Glu Val Arg Gln Trp Val Tyr Glu Asp Leu Pro Glu Ala Thr Leu
            180                 185                 190

Ala Ala Arg Phe Asp Glu Val Met Ser Ala Ala Tyr Ser Val Ser Val
        195                 200                 205

Phe Thr Asp Trp Arg Pro Gly Pro Val Gly Gln Val Trp Leu Lys Gln
    210                 215                 220

Arg Val Gly Asp Glu Gly Ala Arg Ser Val Met Pro Ala Glu Trp Leu
225                 230                 235                 240
```

```
Gly Ala Arg Leu Ala Asp Gly Pro Arg His Pro Val Pro Gly Met Pro
                245                 250                 255

Ala Gly Asn Cys Thr Ala Gln Gln Gly Val Pro Gly Pro Trp His Glu
            260                 265                 270

Arg Leu Pro His Phe Arg Met Glu Phe Thr Pro Ser Asn Gly Asp Glu
        275                 280                 285

Leu Gln Ser Glu Tyr Phe Val Ala Arg Ala Asp Ala Val Ala Ala Tyr
    290                 295                 300

Glu Ala Leu Ala Arg Leu Arg Asp Arg Ile Ala Pro Val Leu Gln Val
305                 310                 315                 320

Ser Glu Leu Arg Thr Val Ala Ala Asp Leu Trp Leu Ser Pro Ala
                325                 330                 335

His Gly Arg Asp Ser Val Ala Phe His Phe Thr Trp Val Pro Asp Ala
                340                 345                 350

Ala Ala Val Ala Pro Val Ala Gly Ala Ile Glu Glu Ala Leu Ala Pro
            355                 360                 365

Phe Gly Ala Arg Pro His Trp Gly Lys Val Phe Ser Thr Ala Pro Glu
    370                 375                 380

Val Leu Arg Thr Leu Tyr Pro Arg Tyr Ala Asp Phe Glu Glu Leu Val
385                 390                 395                 400

Gly Arg His Asp Pro Glu Gly Thr Phe Arg Asn Ala Phe Leu Asp Arg
                405                 410                 415

Tyr Phe Arg Arg
            420

<210> SEQ ID NO 46
<211> LENGTH: 419
<212> TYPE: PRT
<213> ORGANISM: Paenibacillus sp.

<400> SEQUENCE: 46

Met Gly Asp Lys Leu Asn Trp Ala Gly Asn Tyr Arg Tyr Arg Ser Met
1               5                   10                  15

Glu Leu Leu Glu Pro Lys Ser Leu Glu Glu Val Lys Asp Leu Val Val
                20                  25                  30

Ser Arg Thr Ser Ile Arg Val Leu Gly Ser Cys His Ser Phe Asn Gly
            35                  40                  45

Ile Ala Asp Thr Gly Gly Ser His Leu Ser Leu Arg Lys Met Asn Arg
        50                  55                  60

Val Ile Asp Leu Asp Arg Val Gln Arg Thr Val Thr Val Glu Gly Gly
65                  70                  75                  80

Ile Arg Tyr Gly Asp Leu Cys Arg Tyr Leu Asn Asp His Gly Tyr Ala
                85                  90                  95

Leu His Asn Leu Ala Ser Leu Pro His Ile Ser Val Ala Gly Ala Val
                100                 105                 110

Ala Thr Ala Thr His Gly Ser Gly Asp Leu Asn Ala Ser Leu Ala Ser
            115                 120                 125

Ser Val Arg Ala Ile Glu Leu Met Lys Ser Asp Gly Glu Val Thr Val
        130                 135                 140

Leu Thr Arg Gly Thr Asp Pro Glu Phe Asp Gly Ala Val Val Gly Leu
145                 150                 155                 160

Gly Gly Leu Gly Val Val Thr Lys Leu Lys Leu Asp Leu Val Pro Ser
                165                 170                 175

Phe Gln Val Ser Gln Thr Val Tyr Asp Arg Leu Pro Phe Ser Ala Leu
```

```
            180                 185                 190
Asp His Gly Ile Asp Glu Ile Leu Ser Ser Ala Tyr Ser Val Ser Leu
            195                 200                 205

Phe Thr Asp Trp Ala Glu Pro Ile Phe Asn Gln Val Trp Val Lys Arg
            210                 215                 220

Lys Val Gly Ile Asn Gly Glu Asp Glu Thr Ser Pro Asp Phe Phe Gly
225                 230                 235                 240

Ala Leu Pro Ala Pro Glu Lys Arg His Met Val Leu Gly Gln Ser Val
            245                 250                 255

Val Asn Cys Ser Glu Gln Met Gly Asp Pro Gly Pro Trp Tyr Glu Arg
            260                 265                 270

Leu Pro His Phe Arg Met Glu Phe Thr Pro Ser Ala Gly Asn Glu Leu
            275                 280                 285

Gln Ser Glu Tyr Phe Val Pro Arg Arg His Ala Val Glu Ala Met Arg
            290                 295                 300

Ala Leu Gly Lys Leu Arg Asp Arg Ile Ala Pro Leu Leu Phe Ile Ser
305                 310                 315                 320

Glu Ile Arg Thr Ile Ala Ser Asp Thr Phe Trp Met Ser Pro Cys Tyr
            325                 330                 335

Arg Gln Asp Ser Val Gly Leu His Phe Thr Trp Lys Pro Asp Trp Glu
            340                 345                 350

Arg Val Arg Gln Leu Leu Pro Leu Ile Glu Arg Leu Glu Pro Phe
            355                 360                 365

Ala Ala Arg Pro His Trp Ala Lys Leu Phe Thr Met Glu Ser Glu Met
            370                 375                 380

Ile Gln Ala Arg Tyr Glu Arg Leu Ala Asp Phe Arg Gln Leu Leu Leu
385                 390                 395                 400

Arg Tyr Asp Pro Ile Gly Lys Phe Arg Asn Thr Phe Leu Asp His Tyr
            405                 410                 415

Ile Met His

<210> SEQ ID NO 47
<211> LENGTH: 1356
<212> TYPE: DNA
<213> ORGANISM: Terriglobuds roseus

<400> SEQUENCE: 47
atggatcgtc gtgaactgct gaaaacctct gcactgctga tggcagcagc accgttagca      60
cgtgcagcaa atgttccgga agatcatgca aatgttccgc gtaccaattg agcaaaaaac     120
ttccactata gcaccagccg cgtttatgca ccgactaccc cggaagaagt tccggcaatt     180
gttctggaaa atggtcatct gaaggtctg ggttctcgtc actgcttcaa caacatcgcc      240
gatagccagt atgcgcagat cagcatgcgc gaagttaaag gcattcagat cgatgaagcc     300
gcacaaaccg ttaccgtggg tgcaggtatt gcgtatggtg aattagcacc ggtgctggat     360
aaagcgggtt ttgcactggc aaatttagca agtttaccgc atatcagcgt gggtggcacc     420
attgcaaccg caacacatgg ctctggcgtt ggtaacaaaa acctgtcttc tgcaacccgt     480
gcaattgaaa tcgtgaaagc ggatggcagc attctgcgtc tgtcgcgtga tactgatggt     540
gaacgttttc gtatggcggt ggttcatctg ggtgcattag gtgttttaac caaagttacc     600
ctggatatcg tgccgcgctt cgatatgtct caggtggtgt atcgcaacct gtcctttgat     660
cagctggaac acaacctgga taccattctg agctctggct atagcgttag cctgttcacc     720
gactggcagc gtaatcgtgt taatcaggtg tggatcaaag ataaagcgac cgcggatgca     780
```

```
ccgcaaaaac cgttacctcc gatgttttat ggtgcgaccc tgcaaaccgc aaaactgcat    840
ccgatcgatg atcatccggc agatgcatgt accgaacaaa tgggtagtgt tggtccgtgg    900
tatttacgtc tgccgcattt caaaatggag tttaccccga gcagcggtga agaattacag    960
accgaatact tcgtggcgcg caaagatggc tatcgcgcaa ttcgtgccgt ggaaaaactg   1020
cgcgataaaa ttaccccgca cctgtttatc accgaaatcc gcaccattgc agcagatgat   1080
ctgccgatga gcatggcata tcaacgtgac agtatgcgca ttcattttac ctggaaaccg   1140
gaagaaccga ccgtgcgtaa attactgccg gaaatcgaag cagcactggc gccgtttggt   1200
gttcgtccgc attggggcaa aattttgaa attccgccga gctatctgca taaacagtat   1260
ccggcactgc gcgttttcg cgcaatggca caggcattag atcctggtgg caaatttcgt   1320
aatgcatatc tggatcgtaa catctttggc gcgtag                             1356
```

<210> SEQ ID NO 48
<211> LENGTH: 1353
<212> TYPE: DNA
<213> ORGANISM: Granulicella mallensis
<400> SEQUENCE: 48

```
atggacaaac gcgatttcct gaaaggtagc gcaaccaccg cagttgcact gatgatgggt     60
ctgaatgaaa gcaaagcgtt tgcggatgat agcgttccgc gtaccaattg gagcggcaac    120
taccattata gcaccaacaa agtgctgcag ccggcaagtg ttgcagaaac ccaagatgca    180
gttcgtagtg ttcaggtgt tcgtgcatta ggtactcgtc atagctttaa cggcatcgcg     240
gatagccaga ttgcccagat tagtaccctg aaactgaaag atgtgagcct ggatgcgaaa    300
agctcgaccg tgaccgttgg tgcaggtatt cgttatggtg atctggcggt tcagctggat    360
gcgaaaggtt ttgctctgca taatctggca agtctgccgc atatttctgt tggtggtgca    420
tgtgcaactg cgacccatgg ttcaggtatg ggtaatggta atttagcaac cgcagttaaa    480
gcggtggaat ttgttgcggc ggatggtagc gtgcataccc tgtctcgtga tcgtgatggt    540
gatcgttttg cgggctctgt tgttggtctg ggtgcattag gtgttgttac ccatttaacc    600
ctgcaagttc agccacgttt cgaaatgacc caggtggtgt accgtgatct gccatttagt    660
gaactggaac atcatctgcc ggaaattatg ggtgccggtt atagcgtgtc cctgtttacc    720
gattggcaga atggtcgtgc aggtgaagtg tggatcaaac gtcgcgtgga tcaaggtggt    780
gcaagtgctc ctccagctcg ttttttttaat gcaaccttag caaccaccaa actgcacccg    840
atcctggatc atcctgctga agcatgtacc gatcagttaa ataccgtagg tccgtggtat    900
gaacgtttac cgcacttcaa actgaacttc accccgagca gtggccaaga attacagacc    960 gagttttttcg tgccgttcga tcgcggctat gacgccattc gtgccgttga aactttacgt   1020
gatgtgatta ccccgcacct gtatatcacc gaactgcgtg cagttgcagc tgatgattta   1080
tggatgagca tggcatatca acgtccgagt ctggcaatcc attttacctg gaaccggaa    1140 accgatgcag tgctgaaatt actgccgcag attgaagcga aactggcccc gtttggtgct   1200
cgtccgcatt gggcaaaagt ttttaccatg aaaagcagcc atgtggcacc gctgtatccg   1260
cgcctgaaag attttctggt tctggcaaaa tcctttgatc cgaaaggcaa attccaaaac   1320
gcgtttctgc aggaccatgt ggacatcgca tag                                 1353
```

<210> SEQ ID NO 49
<211> LENGTH: 1245
<212> TYPE: DNA

<213> ORGANISM: Streptomyces acidiscabies

<400> SEQUENCE: 49

```
atgaccgcat ctgtgaccaa ttgggcgggt aacatcagct ttgtggcgaa agatgttgtt      60
cgtccgggtg gtgttgaagc actgcgtaaa gttgttgcgg gtaatgatcg tgttcgtgtt     120
ctgggttctg gtcatagctt taaccgtatc gctgaaccgg gtgctgatgg tgttctggtt     180
agcctggatg cattaccgca agtgattgat gttgataccg aacgtcgtac cgtgcgtgtt     240
ggtggtggtg ttaaatacgc ggaactggct cgtcatgtga atgaatctgg tctggcactg     300
ccgaatatgg catctctgcc gcatatttct gttgcaggtt ctgttgcaac tggtacccat     360
ggttctggtg tgaataatgg cccgttagca accccggttc gtgaagttga attattaacc     420
gcggatggct ctctggtgac catcggtaaa gatgatgcgc gttttccggg tgcagttact     480
tctctgggtg cgctgggtgt tgttgttgca ctgaccttag atttagaacc ggcgtatggt     540
gttgaacagt atacctttac cgaattaccg ctggaaggtc tggacttcga agcagttgcg     600
agtgcagcat attctgttag cctgttcacc gattggcgtg aagctggttt tcgccaagtt     660
tgggtgaaaac gccgcattga tgaaccgtac gcgggctttc cgtgggcagc accggcaact     720
gaaaaattac atccggttcc gggtatgcca gcagaaaatt gtactgatca atttggtgca     780
gcaggtccat ggcatgaacg tttaccgcat tttaaagcgg aatttacccc gtctagcggt     840
gatgaattac agagcgaata tctgctgccg cgtgaacatg cactggcggc actggatgca     900
gtgggcaacg tgcgtgaaac cgtttctacc gtgctgcaga tttgcgaagt cgtaccatt      960
gcagcagata cccagtggtt aagtccggct tatggtcgtg atagtgttgc attacatttt    1020
acttggaccg atgatatgga tgcagttttta cctgcagttc gtgccgttga aagcgcgctg    1080
gatggctttg tgctcgcccc gcattgggt aaagtgttta ccaccgcacc ggcagcatta    1140
cgtgaacgtt atccgcgtct ggatgatttt cgtaccctgc gtgatgaatt agatccggca    1200
ggcaaattta ctaatgcatt tgttcgtgat gttctggaag ttag                      1245
```

<210> SEQ ID NO 50
<211> LENGTH: 1284
<212> TYPE: DNA
<213> ORGANISM: Actinomycetales

<400> SEQUENCE: 50

```
atgaccctgg aacgtaattg ggcaggtacc cataccttg cagcaccgcg tattgttaat       60
gcaaccagca tcgatgaagt tcgtgcgtta gtggcagaag cagcacgtac cggtacccgt     120
gttcgtgcat taggtactcg tcattctttt accgatctgg cagatagcga tggtacccctg    180
attaccgtgc tggatattcc ggcagatcca gtttttcgatg aagcagcagg tagcgttacc    240
attggtgcag gtacccgtta tggtattgca gcagcatggt tagcagaaca tggtctggcg    300
tttcacaaca tgggtagcct gccgcatatt agcgttggtg gtgcaattgc aaccggtacc    360
catggtagtg gtaatgataa cggcattctg agtagcgcag ttagtggtct ggaatatgtt    420
gatgcgaccg gtgaactggt tcatgtgcgt cgtggtgatc ctggttttga tggtctggtt    480
gttggtttag cgcgtatgg tattgtggtt cgtgtgacgg tggatgttca accggcatat    540
cgtgttcgcc aggatgtgta tcgtgatgtt ccgtgggatg cagttctggc agattttgaa    600
ggtgttacag gtgtgcgta tagcgttagc atctttacca actggctggg tgatacggtg    660
gaacagattt ggtggaaaac ccgtctggtt gcaggtgatg atgaactgcc ggtggttccg    720
gaaagctggc tgggtgttca acgtgattct ttaaccgcag gtaatctggt tgaaaccgat    780
```

```
ccggataatt taaccctgca aggtggtgtt ccgggtgatt ggtgggaacg tttaccgcat      840
tttcgtctgg aaagtacccc gtctaatggt gatgaaatcc agaccgaata cttcatcgat      900
cgcgcggatg gtccggcggc aattaccgca ctgcgtgcat taggtgatcg tattgctccg      960
ttactgttag ttaccgaatt acgtaccgca gctccagata aactgtggct gagtggcgca     1020
tatcatcgcg aaatgttagc ggtccatttt acctggcgta atttaccgga agaagtgcgt     1080
gcagttttac cagcgatcga agaagccctg gcgccgtttg atgctcgtcc gcattgggg      1140 aaactgaatc tgttaaccgc agaacgtatt gcagaagttg ttccgcgtct ggctgatgca     1200
cgtgatctgt ttgaagaact ggacccggct ggtacctttt ctaatgctca tctggaacgt     1260
attggtgttc gtttaccgcg ttag                                            1284
```

<210> SEQ ID NO 51
<211> LENGTH: 1260
<212> TYPE: DNA
<213> ORGANISM: Frankia sp.

<400> SEQUENCE: 51

```
atgcgtgatg cagcagcagc aaattgggca ggtaatgtgc gttttggtgc agcacgtgtt       60
gttgcaccgg aaagtgttgg tgaactgcag gaaattgttg caggtagccg taaagcacgt      120
gcattaggta ccggtcatag ctttagccgt attgcagata ccgatggtac cctgattgct      180
accgcacgtt taccacgtcg tattcagatc gatgatggca gcgttaccgt ttctggtggt      240
atccgttatg gcgatctggc ccgtgaatta gcaccgaatg gttgggcatt acgtaatctg      300
ggttctttac cgcacatttc agttgcaggt gcatgtgcaa ccggtaccca tggttcaggt      360
gatcgtaatg gtagtctggc aacctctgtt gcagcgttag aattagttac cgcgtctggt      420
gaattagtga gcgttcgtcg tggcgatgaa gatttcgatg ccatgtgat tgcgctgggt      480 gcactgggtg ttactgttgc agttaccctg gatttagttc cgggttttca ggttcgtcag      540
ctggtgtatg aaggtctgac ccgtgatacc ttactggaaa gtgtgcagga aatctttgct      600
gcgagctata gtgttagcgt gtttaccggt tgggacccgg aaagttctca actgtggctg      660
aaacagcgcg ttgatggtcc gggcgatgat ggtgaaccac cggcagaacg ttttggtgca      720
cgtttagcaa ctcgtccgtt acatccagtt ccgggtattg atccgactca tactactcaa      780
caattaggtg ttccaggtcc gtggcatgaa cgtttaccgc atttcgtct ggattttacc      840 ccttctgcag gtgatgaact gcaaaccgaa tacttcgtgg cccgcgaaca tgcagcggcg      900
gcgattgaag cactgtttgc gattggtgcg gttgttcgtc cggcattaca aattagcgaa      960
attcgtaccg ttgcagctga tgcattatgg ctgtctccgg catatcgtcg tgatgttatg     1020
gcgttacatt ttacctggat tagcgcagaa ggtaccgtta tgccagcagt tgcagcagtg     1080
gaacgtgcac tggcgccgtt tgatccggtt cctcattggg gtaaagtttt tgcgctgccg     1140
ccagcagcag ttcgtgctgg ttatcctcgt gcagcagaat ttttagcatt agcagctcgt     1200
cgtgatccgg aagcagtttt tcgtaatcag tatttagatg catatttacc ggcagcatag     1260
```

<210> SEQ ID NO 52
<211> LENGTH: 1242
<212> TYPE: DNA
<213> ORGANISM: Propionibacteriaceae

<400> SEQUENCE: 52

```
atgacccagc gtaattgggc gggtaatgtg agctatagta gcagccgtgt tgcagaacca       60
```

```
gcaagtgtgg atgatttaac cgcactggtt gaaagtgaac cgcgtgttcg tccgttaggt      120
agtcgtcatt gcttcaacga tatcgccgat accccaggtg ttcatgtttc tctggcacgt      180
ctgcgtggtg aagaaccgcg tttaacagca ccgggtacct tacgtactcc agcttggtta      240
cgttatggtg atttagttcc ggttctgcgt gaagcaggtg cagcattagc aaatttagca      300
tctctgccgc atattagcgt tgcaggtgca gttcaaaccg tacccatgg ttcaggtgat       360 cgtattggca ctctggcaac ccaagttagc gccctggaat tagtgaccgg caccggtgaa      420
gttttacgct tagaacgtgg tgaacctgat tttgatggtg cggttgttgg tttaggtgcg      480
ttaggtgttc tgactcatgt ggaattagat gttagtccgg cgcgtgatgt tgcacagcac      540
gtgtatgaag gtgttcgtct ggatgatgtt ctggcggatt taggcgcggt tactggcgca      600
ggtgattcgg tgagcatgtt tacccattgg caagatccgg cagttgttag tcaggtttgg      660
gttaaaagtg gcggtgatgt ggatgatgca gcaattcgtg atgcaggtgg tcgtccggca      720
gatggtccgc gtcatccaat tgcaggtatt gatccgactc catgtactcc acaattaggt      780
gaaccaggtc cgtggtatga tcgtctgccg catttctcgtc tggaattac cccgagtgtt      840 ggtgaagaac tgcaaagtga atatctggtt gatcgcgatg atgccgttga tgcaattcgt      900
gcggtgcagg atttagcccc gcgtattgcg ccgctgctgt tgtttgcga aattcgtacc      960 atggcaagtg atggtttatg gctgagcccg gcacaaggtc gtgataccgt tggtctgcat     1020
tttacctggc gtcctgatga atctgcagtt cgtcaattat taccggaaat tgaacgtgct     1080
ttaccggcaa gtgctcgtcc gcattgggt aaagtgttta ccctgccggg ccatgatgtt     1140
gcagcacgtt atccgcgttg ggcagatttt gttgcattac gtcgtcgttt agatccggaa     1200
cgtcgtttcg cgaatgcata cctggaacgt ttaggtctgt ag                       1242

<210> SEQ ID NO 53
<211> LENGTH: 1263
<212> TYPE: DNA
<213> ORGANISM: Streptomyces sp.

<400> SEQUENCE: 53
atgactccgg cggaaaaaaa ttgggcgggc aacatcacct ttggtgcaaa acgtctgtgt       60
gttccgcgtt ctgttcgtga actgcgtgaa accgttgcag catctggtgc agttcgtccg      120
ttaggtactc gtcatagctt taataccgtt gcagatacca gtggtgatca tgttagtctg      180
gcaggtttac cgcgtgttgt ggacatcgat gttccgggtc gtgcagtttc tctgtctgct      240
ggtctgcgtt ttggtgaatt tgcggctgaa ttacatgcac gtggtctggc gctggcaaat      300
ttaggttctc tgccgcatat tagcgttgca ggtgcagttg caaccggtac tcatggttct      360
ggtgttggta tcgttctttt agcaggtgca gttcgtgctt tatctctggt aaccgccgat      420
ggtgaaaccc gtaccttacg tcgtaccgat gaagattttg caggtgcagt ggtttctctg      480
ggtgcactgg gtgttgttac ttctctggaa ctggatttag ttccggcgtt cgaagtgcgt      540
cagtgggtgt acgaagatct gccggaagca actttagcag ctcgttttga tgaagttatg      600
tcagcagcgt atagcgtgtc cgtgttcacc gattggcgtc cgggtcctgt tggtcaagtt      660
tggctgaaac aacgtgttgg tgatgaaggt gctcgtagtg ttatgccagc agaatggtta      720
ggtgcacgtt tagcagatgg tccgcgtcat ccagttccag gtatgcctgc aggtaattgt      780
acagcacaac aaggtgttcc aggtccgtgg catgaacgtt taccgcattt tcgcatggaa      840 tttacccccgt ctaacggcga tgaactgcaa agcgaatatt ttgtggcgcg tgcagatgca      900
gttgcagcgt atgaagcatt agcacgtctg cgtgatcgta ttgcgccggt tctgcaagtt      960
```

```
agcgaattac gtaccgttgc agcagatgat ctgtggctga gtccggcaca tggtcgtgat   1020
agtgttgcgt ttcattttac ctgggttccg gatgcagcag cagttgcacc ggttgcaggt   1080
gctattgaag aagcattagc accgtttggt gcacgtccac attggggtaa agttttagc    1140 accgcaccgg aagttttacg taccttatat ccgcgttatg ccgatttcga gaactggtg   1200 ggccgccatg atccggaagg cacctttcgt aatgcatttt tagatcgcta ctttcgtcgc   1260
tag                                                                1263

<210> SEQ ID NO 54
<211> LENGTH: 1260
<212> TYPE: DNA
<213> ORGANISM: Paenibacillus sp.

<400> SEQUENCE: 54
atgggcgata aactgaattg ggcgggcaac tatcgttatc gcagcatgga actgctggaa    60
ccgaaaagcc tggaagaagt gaaagatctg gtggttagcc gtaccagcat cgtgttctg   120 ggtagctgtc atagctttaa cggcattgcg gataccggtg gtagtcatct gagtctgcgc   180
aaaatgaacc gcgtgattga tctggatcgt gttcagcgta ccgttaccgt tgaaggtggt   240
attcgttacg gtgatctgtg ccgctatctg aacgatcatg gttatgccct gcataatctg   300
gcaagcttac gcacatcag cgttgcaggt gcagttgcaa ccgcaaccca tggttctggt   360
gatctgaatg caagtctggc aagctctgtt cgtgcaattg aactgatgaa agcgatggc   420 gaagttacgg ttctgacccg tggtaccgat ccggaatttg atggtgcagt tgttggtctg   480
ggtggtttag tgttgtgac caaactgaaa ctggatctgg ttccgagctt tcaggtgtcg   540
cagaccgtgt atgatcgtct gccgtttagc gcactggatc atggcatcga tgaaattctg   600
agtagtgcat atagcgttag cctgttcacc gattgggcgg aaccgatctt taatcaggtg   660
tgggtgaaac gcaaagtggg cattaacggc gaagatgaaa ccagtccgga tttttttggc   720
gcattaccgg caccggaaaa acgccacatg gttctgggtc agagcgtggt gaattgcagc   780
gaacaaatgg gtgatcctgg tccgtggtat gaacgtttac cgcattttcg catggaattt   840
accccgagtg caggcaatga attacagagc gaatattttg tgccgcgtcg tcatgcggtt   900
gaagcaatgc gtgcgttagg taaactgcgt gatcgtattg caccactgct gttcatcagc   960
gaaatccgca ccattgcgag cgataccttc tggatgagcc gtgttatcg tcaggattct   1020 gttggtctgc attttacctg gaaaccggat tgggaacgtg ttcgtcagtt attaccgctg   1080
attgaacgtg aactggaacc gtttgcggca cgtccgcatt gggcgaaact gtttaccatg   1140
gaaagcgaaa tgattcaggc gcgctatgaa cgtctggcgg attttcgtca gctgctgctg   1200
cgttatgatc cgattggcaa attccgtaac acctttctgg atcactacat catgcactaa   1260

<210> SEQ ID NO 55
<211> LENGTH: 205
<212> TYPE: PRT
<213> ORGANISM: Thermus thermophilus

<400> SEQUENCE: 55
```

Met Glu Ala Thr Leu Pro Val Leu Asp Ala Lys Thr Ala Ala Leu Lys
1               5                  10                  15

Arg Arg Ser Ile Arg Arg Tyr Arg Lys Asp Pro Val Pro Glu Gly Leu
            20                  25                  30

Leu Arg Glu Ile Leu Glu Ala Ala Leu Arg Ala Pro Ser Ala Trp Asn
        35                  40                  45

Leu Gln Pro Trp Arg Ile Val Val Arg Asp Pro Ala Thr Lys Arg
    50                  55                  60

Ala Leu Arg Glu Ala Ala Phe Gly Gln Ala His Val Glu Glu Ala Pro
65                  70                  75                  80

Val Val Leu Val Leu Tyr Ala Asp Leu Glu Asp Ala Leu Ala His Leu
                85                  90                  95

Asp Glu Val Ile His Pro Gly Val Gln Gly Glu Arg Arg Glu Ala Gln
            100                 105                 110

Lys Gln Ala Ile Gln Arg Ala Phe Ala Ala Met Gly Gln Glu Ala Arg
        115                 120                 125

Lys Ala Trp Ala Ser Gly Gln Ser Tyr Ile Leu Leu Gly Tyr Leu Leu
    130                 135                 140

Leu Leu Leu Glu Ala Tyr Gly Leu Gly Ser Val Pro Met Leu Gly Phe
145                 150                 155                 160

Asp Pro Glu Arg Val Lys Ala Ile Leu Gly Leu Pro Ser His Ala Ala
                165                 170                 175

Ile Pro Ala Leu Val Ala Leu Gly Tyr Pro Ala Glu Glu Gly Tyr Pro
            180                 185                 190

Ser His Arg Leu Pro Leu Glu Arg Val Val Leu Trp Arg
        195                 200                 205

<210> SEQ ID NO 56
<211> LENGTH: 618
<212> TYPE: DNA
<213> ORGANISM: Thermus thermophilus

<400> SEQUENCE: 56
atggaagcaa ccttaccggt gttagacgcg aaaaccgcag cactgaaacg tcgtagcatt      60
cgccgttatc gcaaagatcc agttccggaa ggtttactgc gcgaaattct ggaagcagca     120
ttacgtgcac cgtctgcatg gaatttacaa ccgtggcgta ttgtggtggt tcgtgatccg     180
gcaactaaac gtgcattacg tgaagcagca tttggtcaag cccatgtgga agaagcaccg     240
gttgttctgg ttctgtacgc agatctggaa gatgcactgg cacatctgga tgaagtgatt     300
catccgggcg ttcaaggtga acgtcgtgaa gcgcagaaac aagcaattca gcgtgcattt     360
gcagcaatgg gtcaggaagc tcgtaaagct tgggcaagcg gtcaaagtta tattctgctg     420
ggttatctgc tgctgctgct ggaagcatat ggtctgggtt ctgttccgat gctgggtttt     480
gatcctgaac gtgttaaagc gattctgggc ctgccgtcac atgcagcgat tccggcatta     540
gttgcactgg gttatccggc tgaagaaggt tatccgagtc atcgtttacc gctggaacgt     600
gttgttttat ggcgttga                                                   618

<210> SEQ ID NO 57
<211> LENGTH: 247
<212> TYPE: PRT
<213> ORGANISM: Agrobacterium sp.

<400> SEQUENCE: 57

Met Lys Asn Pro Phe Ser Leu Gln Gly Arg Lys Ala Leu Val Thr Gly
1               5                   10                  15

Ala Asn Thr Gly Leu Gly Gln Ala Ile Ala Val Gly Leu Ala Ala Ala
            20                  25                  30

Gly Ala Glu Val Val Cys Ala Ala Arg Arg Ala Pro Asp Glu Thr Leu
        35                  40                  45

Glu Met Ile Ala Ser Asp Gly Gly Lys Ala Ser Ala Leu Ser Ile Asp

```
            50                  55                  60
Phe Ala Asp Pro Leu Ala Ala Lys Asp Ser Phe Ala Gly Ala Gly Phe
65                  70                  75                  80

Asp Ile Leu Val Asn Asn Ala Gly Ile Ile Arg Arg Ala Asp Ser Val
                85                  90                  95

Glu Phe Ser Glu Leu Asp Trp Asp Glu Val Met Asp Val Asn Leu Lys
            100                 105                 110

Ala Leu Phe Phe Thr Thr Gln Ala Phe Ala Lys Glu Leu Leu Ala Lys
        115                 120                 125

Gly Arg Ser Gly Lys Val Val Asn Ile Ala Ser Leu Leu Ser Phe Gln
    130                 135                 140

Gly Gly Ile Arg Val Pro Ser Tyr Thr Ala Ala Lys His Gly Val Ala
145                 150                 155                 160

Gly Leu Thr Lys Leu Leu Ala Asn Glu Trp Ala Ala Lys Gly Ile Asn
                165                 170                 175

Val Asn Ala Ile Ala Pro Gly Tyr Ile Glu Thr Asn Asn Thr Glu Ala
            180                 185                 190

Leu Arg Ala Asp Ala Ala Arg Asn Lys Ala Ile Leu Glu Arg Ile Pro
        195                 200                 205

Ala Gly Arg Trp Gly Arg Ser Glu Asp Ile Ala Gly Ala Ala Val Phe
    210                 215                 220

Leu Ser Ser Ala Ala Ala Asp Tyr Val His Gly Ala Ile Leu Asn Val
225                 230                 235                 240

Asp Gly Gly Trp Leu Ala Arg
                245

<210> SEQ ID NO 58
<211> LENGTH: 198
<212> TYPE: PRT
<213> ORGANISM: Agrobacterium tumefaciens

<400> SEQUENCE: 58

Met Ile Ala Gly Val Gly Gly Glu Ala Arg Glu Leu Ala Leu Asp Leu
1               5                   10                  15

Ser Asp Pro Met Ala Ala Lys Asp Val Phe Ala Glu Gly Ala Tyr Asp
            20                  25                  30

Leu Leu Ile Asn Asn Ala Gly Ile Ile Arg Arg Ala Asp Ala Val Asp
        35                  40                  45

Phe Ser Glu Asp Asp Trp Asp Ala Val Met Asp Val Asn Leu Lys Ala
    50                  55                  60

Val Phe Phe Thr Ser Gln Ala Phe Ala Arg Ala Leu Met Ser Arg Asn
65                  70                  75                  80

Ala Ser Gly Lys Ile Val Asn Ile Ala Ser Leu Leu Ser Phe Gln Gly
                85                  90                  95

Gly Ile Arg Val Ala Ser Tyr Thr Ala Ala Lys His Gly Val Ala Gly
            100                 105                 110

Ile Thr Arg Leu Leu Ala Asn Glu Trp Ala Ser Arg Gly Ile Asn Val
        115                 120                 125

Asn Ala Ile Ala Pro Gly Tyr Ile Ala Thr Asn Asn Thr Glu Ala Leu
    130                 135                 140

Arg Ala Asp Glu Glu Arg Asn Ala Ala Ile Leu Ala Arg Ile Pro Ala
145                 150                 155                 160

Gly Arg Trp Gly Arg Ala Glu Asp Ile Ala Gly Thr Ala Val Tyr Leu
                165                 170                 175
```

```
Cys Ser Pro Ala Ala Asp Tyr Val His Gly Ala Ile Leu Asn Val Asp
            180                 185                 190

Gly Gly Trp Leu Ala Arg
        195
```

<210> SEQ ID NO 59
<211> LENGTH: 253
<212> TYPE: PRT
<213> ORGANISM: Escherichia coli

<400> SEQUENCE: 59

```
Met Ile Leu Ser Ala Phe Ser Leu Glu Gly Lys Val Ala Val Val Thr
1               5                   10                  15

Gly Cys Asp Thr Gly Leu Gly Gln Gly Met Ala Leu Gly Leu Ala Gln
            20                  25                  30

Ala Gly Cys Asp Ile Val Gly Ile Asn Ile Val Glu Pro Thr Glu Thr
        35                  40                  45

Ile Glu Gln Val Thr Ala Leu Gly Arg Arg Phe Leu Ser Leu Thr Ala
    50                  55                  60

Asp Leu Arg Lys Ile Asp Gly Ile Pro Ala Leu Leu Asp Arg Ala Val
65                  70                  75                  80

Ala Glu Phe Gly His Ile Asp Ile Leu Val Asn Asn Ala Gly Leu Ile
                85                  90                  95

Arg Arg Glu Asp Ala Leu Glu Phe Ser Glu Lys Asp Trp Asp Asp Val
            100                 105                 110

Met Asn Leu Asn Ile Lys Ser Val Phe Phe Met Ser Gln Ala Ala Ala
        115                 120                 125

Lys His Phe Ile Ala Gln Gly Asn Gly Gly Lys Ile Ile Asn Ile Ala
    130                 135                 140

Ser Met Leu Ser Phe Gln Gly Gly Ile Arg Val Pro Ser Tyr Thr Ala
145                 150                 155                 160

Ser Lys Ser Gly Val Met Gly Val Thr Arg Leu Met Ala Asn Glu Trp
                165                 170                 175

Ala Lys His Asn Ile Asn Val Asn Ala Ile Ala Pro Gly Tyr Met Ala
            180                 185                 190

Thr Asn Asn Thr Gln Gln Leu Arg Ala Asp Glu Gln Arg Ser Ala Glu
        195                 200                 205

Ile Leu Asp Arg Ile Pro Ala Gly Arg Trp Gly Leu Pro Ser Asp Leu
    210                 215                 220

Met Gly Pro Ile Val Phe Leu Ala Ser Ser Ala Ser Asp Tyr Val Asn
225                 230                 235                 240

Gly Tyr Thr Ile Ala Val Asp Gly Gly Trp Leu Ala Arg
                245                 250
```

<210> SEQ ID NO 60
<211> LENGTH: 254
<212> TYPE: PRT
<213> ORGANISM: Sphingomonas sp.

<400> SEQUENCE: 60

```
Met Pro Gly Met Thr Thr Pro Phe Asp Leu His Gly Lys Thr Ala Ile
1               5                   10                  15

Val Thr Gly Ala Asn Thr Gly Ile Gly Gln Ala Ile Ala Leu Ser Leu
            20                  25                  30

Ala Gln Ala Gly Ala Asp Ile Ala Ala Val Gly Arg Thr Pro Ala Gln
        35                  40                  45
```

Asp Thr Val Asp Gln Val Arg Ala Leu Gly Arg Arg Ala Asp Ile Ile
    50                  55                  60

Ser Ala Asp Leu Ser Thr Ile Glu Pro Val Gln Arg Val Leu Asp Glu
 65                  70                  75                  80

Thr Leu Glu Lys Leu Gly Ala Leu Asp Ile Leu Val Asn Asn Ala Gly
                 85                  90                  95

Ile Ile Arg Arg Ala Asp Ser Val Asp Phe Thr Glu Asp Trp Asp
                100                 105                 110

Ala Val Ile Asp Thr Asn Leu Lys Thr Thr Phe Phe Leu Cys Gln Ala
            115                 120                 125

Ala Gly Arg His Met Leu Ala Gln Gly Ala Gly Lys Ile Ile Asn Ile
    130                 135                 140

Ala Ser Leu Leu Ser Phe Gln Gly Gly Ile Arg Val Pro Ser Tyr Thr
145                 150                 155                 160

Ala Ser Lys Ser Gly Val Ala Gly Leu Thr Lys Leu Leu Ala Asn Glu
                165                 170                 175

Trp Ala Ala Lys Gly Val Asn Val Asn Ala Ile Ala Pro Gly Tyr Ile
            180                 185                 190

Ala Thr Asn Asn Thr Ala Ala Leu Gln Ala Asp Glu Thr Arg Asn Arg
    195                 200                 205

Gln Ile Gln Glu Arg Ile Pro Ala Gly Arg Trp Gly Asp Pro Ala Asp
210                 215                 220

Ile Gly Gly Ala Ala Val Phe Leu Ala Ser Ala Ala Asp Tyr Ile
225                 230                 235                 240

His Gly His Thr Leu Ala Val Asp Gly Gly Trp Leu Ala Arg
                245                 250

<210> SEQ ID NO 61
<211> LENGTH: 246
<212> TYPE: PRT
<213> ORGANISM: Hoeflea phototrophica

<400> SEQUENCE: 61

Met Asn Pro Phe Ser Leu Glu Gly Lys Thr Ala Leu Val Thr Gly Ala
1               5                   10                  15

Asn Thr Gly Ile Gly Gln Ala Ile Ala Met Ala Leu Gly Arg Ala Gly
                20                  25                  30

Ala Asp Val Ile Cys Ala Gly Arg Ser Ser Cys Ala Glu Thr Val Ala
            35                  40                  45

Leu Ile Ala Gly Ser Lys Gly Lys Ala Arg Glu Leu Val Leu Asp Phe
    50                  55                  60

Ala Asp Pro Met Ala Ala Arg Asp Val Phe Ala Ala Glu Pro Val Asp
 65                  70                  75                  80

Ile Leu Val Asn Asn Ala Gly Ile Ile Arg Arg Ala Asp Ala Val Asp
                 85                  90                  95

Phe Thr Glu Ala Asp Trp Asp Glu Val Met Asp Val Asn Leu Lys Ala
            100                 105                 110

Val Phe Phe Thr Cys Gln Ala Phe Gly Lys Ala Val Leu Gly Arg Gly
        115                 120                 125

Gly Asn Gly Lys Ile Val Asn Ile Ala Ser Leu Leu Ser Phe Gln Gly
    130                 135                 140

Gly Ile Arg Val Pro Ser Tyr Thr Ala Ser Lys His Gly Val Ala Gly
145                 150                 155                 160

Ile Thr Lys Leu Leu Ala Asn Glu Trp Ala Ala Lys Gly Ile Asn Val
                165                 170                 175

```
Asn Ala Ile Ala Pro Gly Tyr Ile Glu Thr Asn Asn Thr Glu Ala Leu
            180                 185                 190

Arg Ala Asp Pro Val Arg Asn Lys Ala Ile Leu Glu Arg Ile Pro Ala
        195                 200                 205

Gly Arg Trp Gly Gln Ala Ser Asp Ile Gly Ala Ala Val Phe Leu
    210                 215                 220

Ala Ser Pro Ala Ala Asn Tyr Ile His Gly Ala Val Leu Asn Val Asp
225                 230                 235                 240

Gly Gly Trp Leu Ala Arg
                245

<210> SEQ ID NO 62
<211> LENGTH: 744
<212> TYPE: DNA
<213> ORGANISM: Agrobacterium sp.

<400> SEQUENCE: 62
atgaagaatc cctttcgct tcagggcgt aaggcgctcg tcaccggcgc gaatacgggg       60
cttggccagg cgattgcggt tgggctcgcc gcggccggtg cggaggtggt ctgcgccgcc     120
cgccgcgcgc cggatgaaac gctggagatg atcgccagcg acggcggcaa ggccagcgca     180
ttgtccatcg atttttgccga tccgctggcg gcgaaggaca gttttgccgg cgccggtttc     240
gatattctcg tcaacaatgc cggtatcatc cgccgtgccg attccgtcga gttctccgaa     300
ctcgactggg acgaggtgat ggacgtcaat ctcaaggcgc tgtttttcac cacccaggct     360
tttgcgaaag agctgctggc gaaaggccgg tccggcaagg tggtcaatat cgcttcgctc     420 cttcctttc agggcggtat tcgcgtgccg tcctatacgg cggcgaaaca tggtgtcgcc     480
ggcctaacca aactcctggc gaatgaatgg ccgccaagg gcatcaatgt gaatgccatt     540
gcgcccggtt atatcgaaac caacaatacc gaggcgctac gcgccgatgc ggctcgtaac     600
aaggccattc tcgagcgcat cccggccggc cgctgggggc gctcggaaga catcgccggg     660
gcggcggttt tcctgtcatc tgcggcggcg gactatgtgc atggcgccat tctcaacgtc     720
gatggcggct ggctggcgcg ctga                                            744

<210> SEQ ID NO 63
<211> LENGTH: 597
<212> TYPE: DNA
<213> ORGANISM: Agrobacterium tumefaciens

<400> SEQUENCE: 63
atgatcgccg gcgtgggggg agaagcaagg gagctggcgc tcgatctgtc cgatcccatg       60
gcggcaaaag atgttttttgc tgaaggcgct tacgacctcc tcatcaacaa tgccggcatc     120
atccgccgtg ccgatgcagt cgatttctcc gaggatgact gggacgcggt gatggacgtg     180
aacctgaaag ccgtcttctt cacctcgcaa gcctttgcgc gggctctcat gtccagaaac     240
gcaagcggaa agatcgttaa cattgcatcc cttctgtcgt ttcaaggcgg cattcgcgtt     300
gcctcctaca cggccgccaa gcacggtgtg gcaggcatca ccagactgtt ggcaaacgaa     360
tgggcgtccc gcggcatcaa cgtcaatgcg atagcgcccg gttacattgc cacgaacaac     420
acggaagcgc ttcgagccga cgaggagcgc aacgcggcga tcctcgcacg cattccggct     480
ggccgctggg gcggggcgga ggatattgcg ggtactgctg tctatctttg ttcgccggca     540
gccgattatg ttcatggcgc cattctaaac gtcgatggcg gttggctcgc gcgctga       597
```

<210> SEQ ID NO 64
<211> LENGTH: 762
<212> TYPE: DNA
<213> ORGANISM: Escherichia coli

<400> SEQUENCE: 64

| | | | | | |
|---|---|---|---|---|---|
| atgattttaa | gtgcattttc | tctcgaaggt | aaagttgcgg | tcgtcactgg | ttgtgatact | 60 |
| ggactgggtc | aggggatggc | gttggggctg | gcgcaagcgg | gctgtgacat | tgttggcatt | 120 |
| aacatcgttg | aaccgactga | aaccatcgag | caggtcacag | cgctggggcg | tcgtttttta | 180 |
| agcctgaccg | ccgatctgcg | aaagattgat | ggtattccag | cactgctgga | tcgcgcggta | 240 |
| gcggagtttg | gtcatattga | tatcctggtg | aataacgccg | gattgattcg | ccgcgaagat | 300 |
| gctctcgagt | tcagcgaaaa | ggactgggac | gatgtcatga | acctgaatat | caagagcgta | 360 |
| ttcttcatgt | ctcaggcagc | ggcgaaacac | tttatcgcgc | aaggcaatgg | cggcaagatt | 420 |
| atcaatatcg | cgtcaatgct | ctccttccag | ggcgggatcc | gtgtgccttc | ttataccgca | 480 |
| tcaaaaagcg | cgtgatgggg | tgtgacgcga | ttgatgcga | acgaatgggc | taaacacaac | 540 |
| attaatgtta | atgcgatagc | cccgggttac | atggcgacca | caatactca | acaactacgg | 600 |
| gcagatgaac | aacgtagcgc | ggaaattctc | gaccgcattc | cagctggtcg | ttggggactg | 660 |
| ccgagtgacc | tgatggggcc | gatagtgttc | cttgcctcca | gcgcttcaga | ttatgtgaat | 720 |
| ggttatacca | ttgccgtgga | tggcggttgg | ctggcgcgtt | aa | | 762 |

<210> SEQ ID NO 65
<211> LENGTH: 765
<212> TYPE: DNA
<213> ORGANISM: Sphingomonas sp.

<400> SEQUENCE: 65

| | | | | | |
|---|---|---|---|---|---|
| atgcccggca | tgaccactcc | tttcgatctt | catggcaaga | ccgcgatcgt | caccggcgcc | 60 |
| aataccggca | tcggccaggc | cattgccctg | tcgctcgcgc | aggccggcgc | ggatatcgcc | 120 |
| gccgtcggcc | gcacgcccgc | acaggacacg | gtcgatcagg | tccgcgcgct | cggccgccgg | 180 |
| gcggacatta | tctcggccga | cctttcgacc | atcgaaccgg | tccagcgcgt | cctcgacgaa | 240 |
| acgctggaaa | agcttggtgc | cttggacata | ctggtcaaca | tgccggcat | catccgccgc | 300 |
| gccgacagcg | tcgatttcac | cgaggaggat | tgggacgcgg | tgatcgacac | caatctcaag | 360 |
| accaccttct | tcctctgtca | ggccgccggt | cgccacatgc | ttgcccaagg | cgctggcaag | 420 |
| atcatcaaca | tcgcctcgct | tcttcctc | cagggcggca | ttcgcgtgcc | gagctacacc | 480 |
| gcgtccaaaa | gcgcgtcgc | gggcctgacc | aagctgctcg | ccaacgaatg | gcggccaag | 540 |
| ggcgtcaatg | tgaacgccat | cgcgccgggc | tatatcgcca | ccaacaacac | cgccgcgctc | 600 |
| caggccgacg | aaacccgcaa | ccgccagatc | caggagcgca | tcccggctgg | ccgctggggc | 660 |
| gaccccgccg | acattggcgg | cgcggccgtg | ttcctggcgt | ccagcgccgc | cgattatatc | 720 |
| catggccaca | cgctcgccgt | cgacggcggc | tggctcgcgc | gctga | | 765 |

<210> SEQ ID NO 66
<211> LENGTH: 741
<212> TYPE: DNA
<213> ORGANISM: Hoeflea phototrophica

<400> SEQUENCE: 66

| | | | | | |
|---|---|---|---|---|---|
| atgaaccct | tctcgcttga | gggcaagacc | gcccttgtga | ccggtgccaa | tacgggcatc | 60 |
| ggtcaggcca | tcgccatggc | gcttggccgc | gccggggcgg | acgtcatctg | cgcgggacgc | 120 |

```
tcgtcctgtg cggagaccgt tgccctcatc gctggcagca agggcaaggc gcgcgaactg    180
gtgctcgact cgccgaccc gatggccgcc cgtgacgtgt cgccgccga accggtggac    240 atcctcgtca acaacgcggg catcatccgg cgcgccgatg cagtggattt caccgaggcc    300
gactgggatg aggtgatgga cgtgaacctg aaggccgtgt cttcacctg ccaggccttc    360 ggcaaggccg ttcttggccg tggaggaaac ggcaagatcg tcaacattgc ctcgctcctg    420
tcattccagg gtggtatccg ggtgccgtcc tacacggcct cgaagcatgg tgttgcaggc    480
atcaccaagc ttctggccaa cgaatgggcg gcgaagggca tcaatgtgaa tgccatcgcc    540
cccggttaca tcgaaacgaa caataccgaa gcactgcggg cggacccggt gcgcaacaag    600
gccatccttg agcgtatccc tgccggccgc tggggccagg cctcggacat cggcgaagcc    660
gccgtgttcc ttgcctctcc ggctgccaat tacatccatg gtgcagtgct gaatgttgac    720
ggaggctggc ttgcccgctg a                                              741
```

<210> SEQ ID NO 67
<211> LENGTH: 446
<212> TYPE: PRT
<213> ORGANISM: Escherichia coli

<400> SEQUENCE: 67

```
Met Ser Ser Gln Phe Thr Thr Pro Val Val Thr Glu Met Gln Val Ile
1               5                   10                  15

Pro Val Ala Gly His Asp Ser Met Leu Met Asn Leu Ser Gly Ala His
            20                  25                  30

Ala Pro Phe Phe Thr Arg Asn Ile Val Ile Ile Lys Asp Asn Ser Gly
        35                  40                  45

His Thr Gly Val Gly Glu Ile Pro Gly Gly Glu Lys Ile Arg Lys Thr
    50                  55                  60

Leu Glu Asp Ala Ile Pro Leu Val Val Gly Lys Thr Leu Gly Glu Tyr
65                  70                  75                  80

Lys Asn Val Leu Thr Leu Val Arg Asn Thr Phe Ala Asp Arg Asp Ala
                85                  90                  95

Gly Gly Arg Gly Leu Gln Thr Phe Asp Leu Arg Thr Thr Ile His Val
            100                 105                 110

Val Thr Gly Ile Glu Ala Ala Met Leu Asp Leu Leu Gly Gln His Leu
        115                 120                 125

Gly Val Asn Val Ala Ser Leu Leu Gly Asp Gly Gln Gln Arg Ser Glu
    130                 135                 140

Val Glu Met Leu Gly Tyr Leu Phe Phe Val Gly Asn Arg Lys Ala Thr
145                 150                 155                 160

Pro Leu Pro Tyr Gln Ser Gln Pro Asp Asp Ser Cys Asp Trp Tyr Arg
                165                 170                 175

Leu Arg His Glu Glu Ala Met Thr Pro Asp Ala Val Val Arg Leu Ala
            180                 185                 190

Glu Ala Ala Tyr Glu Lys Tyr Gly Phe Asn Asp Phe Lys Leu Lys Gly
        195                 200                 205

Gly Val Leu Ala Gly Glu Glu Ala Glu Ser Ile Val Ala Leu Ala
    210                 215                 220

Gln Arg Phe Pro Gln Ala Arg Ile Thr Leu Asp Pro Asn Gly Ala Trp
225                 230                 235                 240

Ser Leu Asn Glu Ala Ile Lys Ile Gly Lys Tyr Leu Lys Gly Ser Leu
                245                 250                 255

Ala Tyr Ala Glu Asp Pro Cys Gly Ala Glu Gln Gly Phe Ser Gly Arg
```

```
                260                 265                 270
Glu Val Met Ala Glu Phe Arg Arg Ala Thr Gly Leu Pro Thr Ala Thr
                275                 280                 285
Asn Met Ile Ala Thr Asp Trp Arg Gln Met Gly His Thr Leu Ser Leu
            290                 295                 300
Gln Ser Val Asp Ile Pro Leu Ala Asp Pro His Phe Trp Thr Met Gln
305                 310                 315                 320
Gly Ser Val Arg Val Ala Gln Met Cys His Glu Phe Gly Leu Thr Trp
                325                 330                 335
Gly Ser His Ser Asn Asn His Phe Asp Ile Ser Leu Ala Met Phe Thr
            340                 345                 350
His Val Ala Ala Ala Pro Gly Lys Ile Thr Ala Ile Asp Thr His
        355                 360                 365
Trp Ile Trp Gln Glu Gly Asn Gln Arg Leu Thr Lys Glu Pro Phe Glu
        370                 375                 380
Ile Lys Gly Gly Leu Val Gln Val Pro Glu Lys Pro Gly Leu Gly Val
385                 390                 395                 400
Glu Ile Asp Met Asp Gln Val Met Lys Ala His Glu Leu Tyr Gln Lys
                405                 410                 415
His Gly Leu Gly Ala Arg Asp Asp Ala Met Gly Met Gln Tyr Leu Ile
            420                 425                 430
Pro Gly Trp Thr Phe Asp Asn Lys Arg Pro Cys Met Val Arg
        435                 440                 445

<210> SEQ ID NO 68
<211> LENGTH: 446
<212> TYPE: PRT
<213> ORGANISM: Pseudomonas stutzeri

<400> SEQUENCE: 68

Met Thr Thr Ala Met Ser Gly Thr Pro Arg Ile Thr Glu Leu Thr Val
1               5                   10                  15
Val Pro Val Ala Gly Gln Asp Ser Met Leu Met Asn Leu Ser Gly Ala
            20                  25                  30
His Gly Pro Trp Phe Thr Arg Asn Ile Leu Ile Leu Lys Asp Ser Ala
        35                  40                  45
Gly His Val Gly Val Gly Glu Val Pro Gly Gly Glu Ala Ile Arg Gln
    50                  55                  60
Thr Leu Asp Asp Ala Arg Ala Leu Leu Val Gly Glu Pro Ile Gly Gln
65                  70                  75                  80
Tyr Asn Ala Leu Leu Gly Lys Val Arg Arg Ala Phe Ala Asp Arg Asp
                85                  90                  95
Ala Gly Gly Arg Gly Leu Gln Thr Phe Asp Leu Arg Ile Ala Ile His
            100                 105                 110
Ala Val Thr Ala Leu Glu Ser Ala Leu Leu Asp Leu Gly Gln His
        115                 120                 125
Leu Glu Val Pro Val Ala Ala Leu Leu Gly Glu Gly Gln Gln Arg Asp
    130                 135                 140
Glu Val Glu Met Leu Gly Tyr Leu Phe Phe Ile Gly Asp Arg Asn Arg
145                 150                 155                 160
Thr Asp Leu Gly Tyr Arg Asp Glu Ser Asn Ser Asp Asp Ala Trp Phe
                165                 170                 175
Arg Val Arg Asn Glu Glu Ala Met Thr Pro Glu Arg Ile Val Arg Gln
            180                 185                 190
```

Ala Glu Ala Ala Tyr Glu Arg Tyr Gly Phe Lys Asp Phe Lys Leu Lys
            195                 200                 205

Gly Gly Val Leu Arg Gly Glu Glu Val Glu Ala Ile Arg Ala Leu
210                 215                 220

Ala Gln Arg Phe Pro Asp Ala Arg Val Thr Leu Asp Pro Asn Gly Ala
225                 230                 235                 240

Trp Ser Leu Asp Glu Ala Ser Gly Leu Cys Arg Asp Leu His Gly Val
            245                 250                 255

Leu Ala Tyr Ala Glu Asp Pro Cys Gly Ala Glu Asn Gly Tyr Ser Gly
            260                 265                 270

Arg Glu Val Met Ala Glu Phe Arg Arg Ala Thr Gly Leu Pro Thr Ala
            275                 280                 285

Thr Asn Met Ile Ala Thr Asp Trp Arg Gln Met Ser His Ala Val Cys
290                 295                 300

Leu His Ser Val Asp Ile Pro Leu Ala Asp Pro His Phe Trp Thr Met
305                 310                 315                 320

Ala Gly Ser Val Arg Val Ala Gln Met Cys Ala Asp Phe Gly Leu Thr
            325                 330                 335

Trp Gly Ser His Ser Asn Asn His Phe Asp Ile Ser Leu Ala Met Phe
            340                 345                 350

Thr His Val Ala Ala Ala Pro Gly Arg Val Thr Ala Ile Asp Thr
            355                 360                 365

His Trp Ile Trp Gln Asp Gly Gln His Leu Thr Arg Glu Pro Leu Lys
            370                 375                 380

Ile Val Ser Gly Lys Val Ala Val Pro Gln Lys Pro Gly Leu Gly Val
385                 390                 395                 400

Glu Leu Asp Trp Asp Ala Leu Glu Gln Ala His Ala His Tyr Gln Glu
            405                 410                 415

Lys Gly Leu Gly Ala Arg Asp Asp Ala Ile Ala Met Gln Tyr Leu Ile
            420                 425                 430

Pro Asn Trp Thr Phe Asn Asn Lys Lys Pro Cys Met Val Arg
            435                 440                 445

<210> SEQ ID NO 69
<211> LENGTH: 1341
<212> TYPE: DNA
<213> ORGANISM: Escherichia coli

<400> SEQUENCE: 69
atgagttctc aatttacgac gcctgttgtt actgaaatgc aggttatccc ggtggcgggt      60
catgacagta tgctgatgaa tctgagtggt gcacacgcac cgttctttac gcgtaatatt     120
gtgattatca agataattc tggtcacact ggcgtagggg aaattcccgg cggcgagaaa     180
atccgtaaaa cgctggaaga tgcgattccg ctggtggtag gtaaaacgct gggtgaatac     240
aaaaacgttc tgacgctggt gcgtaatact tttgccgatc gtgatgctgg tgggcgcggt     300
ttgcagacat ttgacctacg taccactatt catgtagtta ccgggataga agcggcaatg     360
ctggatctgc tggggcagca tctgggggta acgtggcat cgctgctggg cgatggtcaa     420
cagcgtagcg aagtcgaaat gctcggttat ctgttcttcg tcggtaatcg caaagccacg     480
ccgctgccgt atcaaagcca gccggatgac tcatgcgact ggtatcgcct gcgtcatgaa     540
gaagcgatga cgccggatgc ggtggtgcgc ctggcggaag cggcatatga aaaatatggc     600
ttcaacgatt tcaaactgaa gggcggtgta ctggccgggg aagaagaggc cgagtctatt     660
gtggcactgg cgcaacgctt cccgcaggcg cgtattacgc tcgatcctaa cggtgcctgg     720

```
tcgctgaacg aagcgattaa aatcggtaaa tacctgaaag gttcgctggc ttatgcagaa    780
gatccgtgtg gtgcggagca aggtttctcc gggcgtgaag tgatggcaga gttccgtcgc    840
gcgacaggtc taccgactgc aaccaatatg atcgccaccg actggcggca aatgggccat    900
acgctctccc tgcaatccgt tgatatcccg ctggcggatc cgcatttctg gacaatgcaa    960
ggttcggtac gtgtggcgca aatgtgccat gaatttggcc tgacctgggg ttcacactct   1020
aacaaccact tcgatatttc cctggcgatg tttacccatg ttgccgccgc tgcaccgggt   1080
aaaattactg ctattgatac gcactggatt tggcaggaag caatcagcg cctgaccaaa    1140
gaaccgtttg agatcaaagg cgggctggta caggtgccag aaaaaccggg gctgggtgta   1200
gaaatcgata tggatcaagt gatgaaagcc catgagctgt atcagaaaca cgggcttggc   1260
gcgcgtgacg atgcgatggg aatgcagtat ctgattcctg ctggacgtt cgataacaag    1320
cgcccgtgca tggtgcgtta a                                             1341

<210> SEQ ID NO 70
<211> LENGTH: 1341
<212> TYPE: DNA
<213> ORGANISM: Pseudomonas stutzeri

<400> SEQUENCE: 70
atgaccaccg ccatgtcggg cacgccccgc atcaccgaac tcaccgtcgt gcccgtcgcc     60
gggcaggaca gcatgctgat gaacctcagc ggcgcccatg ggccctggtt cacccgcaac    120
atcctcatcc tcaaggacag cgccggccac gtcggcgtcg gcgaagtgcc gggcggcgaa    180
gccatccgcc agaccctcga cgatgcccgt gccctgctgg tcggcgaacc gatcggccag    240
tacaacgcgc tgctcggcaa ggtgcgccgc gccttcgccg accgtgacgc cggcggccgc    300
ggcctgcaga ccttcgacct gcgcatcgcc attcacgccg tcaccgcgct ggagtcggcg    360
ctgctcgacc tgctcggcca gcacctcgag gtgccggtcg ccgccttgct cggcgaaggc    420
cagcagcgtg acgaagtgga atgctcggc tacctgttct tcatcggcga tcgcaacagg     480
accgacctcg gctaccgcga cgaatccaac tccgacgacg cctggtttcg cgtgcgcaac    540
gaggaggcca tgacgccgga cgcatcgtc cgccaggccg aggcggccta cgagcgctac    600
ggcttcaagg acttcaagct caagggcggc gtactgcgcg gcgaagagga agtcgaggcg    660
atccgcgccc tggcccagcg cttccccgac gcccgcgtga ctctggaccc caacggcgcc    720
tggtcgctgg acgaagccag cggcctgtgt cgcgacctgc acggcgtgct ggcctatgcc    780
gaagaccct gcggtgccga aacggctat tccggccgcg aggtgatggc cgagttccgc      840
cgcgccaccg gtctgcccac cgcgaccaac atgatcgcca ccgactggcg acagatgagt    900
cacgcggtgt gcctgcactc ggtggacatc ccgctggccg acccgcactt ctggaccatg    960
gccggctctg tgcgcgtggc gcagatgtgc gccgacttcg gcctgacctg gggttcgcac   1020
tcgaacaacc acttcgacat ctccctggcg atgttcaccc acgtggcggc cgccgcgccg   1080
ggtcgcgtca ccgccatcga cacccactgg atctggcagg acggccagca cctgacccgc   1140
gagccgctga agatcgtcag cggcaaggtt gcggtgccgc agaagccggg gctgggcgtc   1200
gagctggact gggatgccct ggagcaggcg catgcccact accaagagaa aggcctgggt   1260
gcccgcgatg acgccatcgc catgcagtac ctgatcccca ctggaccttt caacaacaag   1320
aagccgtgca tggtgcgctg a                                             1341

<210> SEQ ID NO 71
```

<211> LENGTH: 256
<212> TYPE: PRT
<213> ORGANISM: Gluconobacter oxydans

<400> SEQUENCE: 71

```
Met Ser His Pro Asp Leu Phe Ser Leu Ser Gly Ala Arg Ala Leu Val
1               5                   10                  15

Thr Gly Ala Ser Arg Gly Ile Gly Leu Thr Leu Ala Lys Gly Leu Ala
            20                  25                  30

Arg Tyr Gly Ala Glu Val Val Leu Asn Gly Arg Asn Ala Glu Ser Leu
        35                  40                  45

Asp Ser Ala Gln Ser Gly Phe Glu Ala Glu Gly Leu Lys Ala Ser Thr
    50                  55                  60

Ala Val Phe Asp Val Thr Asp Gln Asp Ala Val Ile Asp Gly Val Ala
65                  70                  75                  80

Ala Ile Glu Arg Asp Met Gly Pro Ile Asp Ile Leu Ile Asn Asn Ala
                85                  90                  95

Gly Ile Gln Arg Arg Ala Pro Leu Glu Glu Phe Ser Arg Lys Asp Trp
            100                 105                 110

Asp Asp Leu Met Ser Thr Asn Val Asn Ala Val Phe Phe Val Gly Gln
        115                 120                 125

Ala Val Ala Arg His Met Ile Pro Arg Gly Arg Gly Lys Ile Val Asn
    130                 135                 140

Ile Cys Ser Val Gln Ser Glu Leu Ala Arg Pro Gly Ile Ala Pro Tyr
145                 150                 155                 160

Thr Ala Thr Lys Gly Ala Val Lys Asn Leu Thr Lys Gly Met Ala Thr
                165                 170                 175

Asp Trp Gly Arg His Gly Leu Gln Ile Asn Gly Leu Ala Pro Gly Tyr
            180                 185                 190

Phe Ala Thr Glu Met Thr Glu Arg Leu Val Ala Asp Glu Glu Phe Thr
        195                 200                 205

Asp Trp Leu Cys Lys Arg Thr Pro Ala Gly Arg Trp Gly Gln Val Glu
    210                 215                 220

Glu Leu Val Gly Ala Ala Val Phe Leu Ser Ser Arg Ala Ser Ser Phe
225                 230                 235                 240

Val Asn Gly Gln Val Leu Met Val Asp Gly Gly Ile Thr Val Ser Leu
                245                 250                 255
```

<210> SEQ ID NO 72
<211> LENGTH: 771
<212> TYPE: DNA
<213> ORGANISM: Gluconobacter oxydans

<400> SEQUENCE: 72

| | | |
|---|---|---|
| atgtctcacc cggatctgtt tagcttaagt ggcgcacgcg cattagttac tggtgcctct | 60 |
| cgtggtattg gtttaaccct ggccaaaggt ttagcccgtt atggtgccga agtggtttta | 120 |
| aatggccgta atgccgaaag cctggattct gcccaaagtg gctttgaagc cgaaggctta | 180 |
| aaagcatcta ccgctgtgtt tgacgtgacc gatcaagatg cagtcattga cggcgtggca | 240 |
| gcaattgaac gcgatatggg tccgattgat atcctgatca acaatgcggg cattcaacgc | 300 |
| agagccccgt tagaagaatt ttctcgcaaa gactgggacg atctgatgag caccaacgtt | 360 |
| aacgccgtgt tctttgtggg acaagccgtt gccagacaca tgattcctag aggtcgcggt | 420 |
| aaaatcgtca acatctgttc agtgcagagc gaactggcaa gaccgggtat tgcaccttat | 480 |
| accgccacaa aaggagccgt caaaaatctg accaaaggta tggccaccga ttggggtcgt | 540 |

```
catggtttac agattaatgg cttagcaccg ggctattttg ccaccgagat gaccgaacgc    600
ttagttgccg acgaagaatt taccgactgg ttatgcaaac gcacccctgc aggcagatgg    660
ggccaagttg aagaattagt aggcgcagcc gtgtttttaa gtagtagagc ctcaagcttc    720
gtgaatggcc aagtcctgat ggttgatggt ggaattactg tgagcctgta a             771
```

METHOD FOR SYNTHESIZING FDCA AND DERIVATES THEREOF

CROSS-REFERENCE TO RELATED APPLICATIONS

This application is a utility application which claims the benefit of priority under 35 U.S.C. §119(e) of U.S. provisional application Ser. No. 61/704,408, filed Sep. 21, 2012, which is hereby incorporated by reference in its entirety, including all tables, figures, and claims.

INCORPORATION OF SEQUENCE LISTING

The material in the accompanying Sequence Listing is hereby incorporated by reference into this application. The accompanying sequence listing text file, name SGI1660-1_ST25, was created on Dec. 16, 2013 and is 162 KB. The file can be assessed using Microsoft Word on a computer that uses Windows OS.

BACKGROUND OF THE INVENTION

In recent years, an increasing effort has been devoted to identify new and effective ways to use renewable feedstocks for the production of organic chemicals. Among a plethora of downstream chemical processing technologies, the conversion of biomass-derived sugars to value-added chemicals is considered very important. In particular, six-carboned carbohydrates, i.e. hexoses such as fructose and glucose, are widely recognized the most abundant monosaccharides existing in nature, therefore can be suitably and economically used as the chemical feedstocks.

The production of furans and furan derivatives from sugars has attracted increasing attention in chemistry and in catalysis studies, and is believed to have the potential to provide one of the major routes to achieving sustainable energy supply and chemicals production. Indeed, dehydration and/or oxidation of the sugars available within biorefineries with integrated biomass conversion processes can lead to a large family of products including a wide range of furans and furan derivatives.

Among the furans having the most commercial values, furan-2,5-dicarboxylic acid (also known as 2,5-furandicarboxylic acid, hereinafter abbreviated as FDCA) is a valuable intermediate with various uses in several industries including pharmaceuticals, pesticides, antibacterial agents, fragrances, agricultural chemicals, as well as in a wide range of manufacturing applications of polymer materials, e.g. bioplastic resins. As such, FDCA is considered a green alternative of terephthalic acid (TPA), a petroleum-based monomer that is one of the largest-volume petrochemicals produced yearly worldwide. In fact, the US Department of Energy has identified FDCA as one of the top 12 priority compounds made from sugars into a value-added chemical for establishing the "green" chemistry of the future, and as such, it has been named one of the "sleeping giants" of the renewable intermediate chemicals (Werpy and Petersen, *Top Value Added Chemicals from Biomass*. US Department of Energy, Biomass, Vol 1, 2004).

Although various methods have been proposed for commercial scale production of FDCA (for review, see, e.g., Tong et al., *Appl. Catalysis A: General*, 385, 1-13, 2010), the main industrial synthesis of FDCA currently relies on a chemical dehydration of hexoses, such as glucose or fructose, to the intermediate 5-hydroxymethylfurfural (5-HMF), followed by a chemical oxidation to FDCA. However, it has been reported that current FDCA production processes via dehydration are generally nonselective, unless immediately upon their formation, the unstable intermediate products can be transformed to more stable materials. Thus, the primary technical barrier in the production and use of FDCA is the development of an effective and selective dehydration process from biomass-derived sugars.

It is therefore desirable to develop methods for production of this highly important compound, as well as many other chemicals and metabolites, by alternative means that not only would substitute renewable for petroleum-based feedstocks, but also use less energy and capital-intensive technologies. In particular, the selective control of sugar dehydration could be a very powerful technology, leading to a wide range of additional, inexpensive building blocks.

SUMMARY OF THE INVENTION

The present invention provides methods for producing a product of one or more enzymatic pathways. The pathways used in the methods of the invention involve one or more conversion steps such as, for example, an enzymatic conversion of guluronic acid into D-glucarate (Step 7); an enzymatic conversion of 5-ketogluconate (5-KGA) into L-Iduronic acid (Step 15); an enzymatic conversion of L-Iduronic acid into Idaric acid Step 7b); and an enzymatic conversion of 5-ketocluconate into 4,6-dihydroxy 2,5-diketo hexanoate (2,5-DDH) (Step 16). In some embodiments the methods of the invention produce 2,5-furandicarboxylic acid (FDCA) as a product. The methods include both enzymatic and chemical conversions as steps. Various pathways are also provided for converting glucose into 5-dehdyro-4-deoxy-glucarate (DDG), and for converting glucose into FDCA. The methods can also involve the use of engineered enzymes that perform reactions with high specificity and efficiency.

In a first aspect the invention provides a method for producing a product of an enzymatic or chemical pathway from a starting substrate. The pathway can contain any one or more of the following conversion steps: an enzymatic conversion of guluronic acid into D-glucarate (Step 7); an enzymatic conversion of 5-ketogluconate (5-KGA) into L-Iduronic acid (Step 15); an enzymatic conversion of L-Iduronic acid into Idaric acid (Step 7b); and an enzymatic conversion of 5-ketocluconate into 4,6-dihydroxy 2,5-diketo hexanoate (2,5-DDH) (Step 16); an enzymatic conversion of 1,5-gluconolactone to gulurono-lactone (Step 19).

In one embodiment the product of the enzymatic pathway is 5-dehydro-4-deoxy-glucarate (DDG). In various embodiments the substrate of the method can be glucose, and the product can be 5-dehydro-4-deoxy-glucarate (DDG). The method can involve the steps of the enzymatic conversion of D-glucose to 1,5-gluconolactone (Step 1); the enzymatic conversion of 1,5-gluconolactone to gulurono-lactone (Step 19); the enzymatic conversion of gulurono-lactone to guluronic acid (Step 1B); the enzymatic conversion of guluronic acid to D-glucarate (Step 7); and the enzymatic conversion of D-glucarate to 5-dehydro-4-deoxy-glucarate (DDG) (Step 8).

In another method of the invention the substrate is glucose and the product is DDG, and the method involves the steps of the conversion of D-glucose to 1,5-gluconolactone (Step 1); the conversion of 1,5-gluconolactone to gluconic acid (Step 1a); the conversion of gluconic acid to 5-ketoglucon-ate (5-KGA) (Step 14); the conversion of 5-ketogluconate (5-KGA) to L-Iduronic acid (Step 15); the conversion of L-Iduronic acid to Idaric acid (Step 7b); and the conversion of Idaric acid to DDG (Step 8a).

In another method of the invention the substrate is glucose and the product is DDG and the method involves the steps of the conversion of D-glucose to 1,5-gluconolactone (Step 1); the conversion of 1,5-gluconolactone to gluconic acid (Step 1a); the conversion of gluconic acid to 5-ketogluconate (5-KGA) (Step 14); the conversion of 5-ketogluconate (5-KGA) to 4,6-dihydroxy 2,5-diketo hexanoate (2,5-DDH) (Step 16); the conversion of 4,6-dihydroxy 2,5-diketo hexanoate (2,5-DDH) to 4-deoxy-5-threo-hexosulose uronate (DTHU) (Step 4); and the conversion of 4-deoxy-5-threo-hexosulose uronate (DTHU) to DDG (Step 5).

In another method of the invention the substrate is glucose and the product is DDG, and the method involves the steps of: the conversion of D-glucose to 1,5-gluconolactone (Step 1); the conversion of 1,5-gluconolactone to gluconic acid (Step 1a); the conversion of gluconic acid to 5-ketogluconate (5-KGA) (Step 14); the conversion of 5-ketogluconate (5-KGA) to L-Iduronic acid (Step 15); the conversion of L-Iduronic acid to 4-deoxy-5-threo-hexosulose uronate (DTHU) (Step 7B); and the conversion of 4-deoxy-5-threo-hexosulose uronate (DTHU) to DDG (Step 5).

Any of the methods disclosed herein can further involve the step of converting the DDG to 2,5-furan-dicarboxylic acid (FDCA). Converting the DDG to FDCA in any of the methods can involve contacting DDG with an inorganic acid to convert the DDG to FDCA.

In another aspect the invention provides a method for synthesizing derivatized (esterified) FDCA. The method involves contacting DDG with an alcohol, an inorganic acid at a temperature in excess of 60 C to form derivatized FDCA. In different embodiments the alcohol is methanol, butanol or ethanol.

In another aspect the invention provides a method for synthesizing a derivative of FDCA. The method involves contacting DDG with an alcohol, an inorganic acid, and a co-solvent to produce a derivative of DDG; optionally purifying the derivative of DDG; and contacting the derivative of DDG with an inorganic acid to produce a derivative of FDCA. The inorganic acid can be sulfuric acid and the alcohol can be ethanol or butanol. In various embodiments the co-solvent can be any of THF, acetone, acetonitrile, an ether, butyl acetate, an dioxane, chloroform, methylene chloride, 1,2-dichloroethane, a hexane, toluene, and a xylene.

In one embodiment in the derivative of DDG is di-ethyl DDG and the derivative of FDCA is di-ethyl FDCA, and in another embodiment the derivative of DDG is di-butyl DDG and the derivative of FDCA is di-butyl FDCA.

In another aspect the invention provides a method for synthesizing FDCA. The method involves contacting DDG with an inorganic acid in a gas phase.

In another aspect the invention provides a method for synthesizing FDCA. The method involves contacting DDG with an inorganic acid at a temperature in excess of 120 C.

In another aspect the invention provides a method for synthesizing FDCA. The method involves contacting DDG with an inorganic acid under anhydrous reaction conditions.

DETAILED DESCRIPTION OF THE INVENTION

Figure 1:
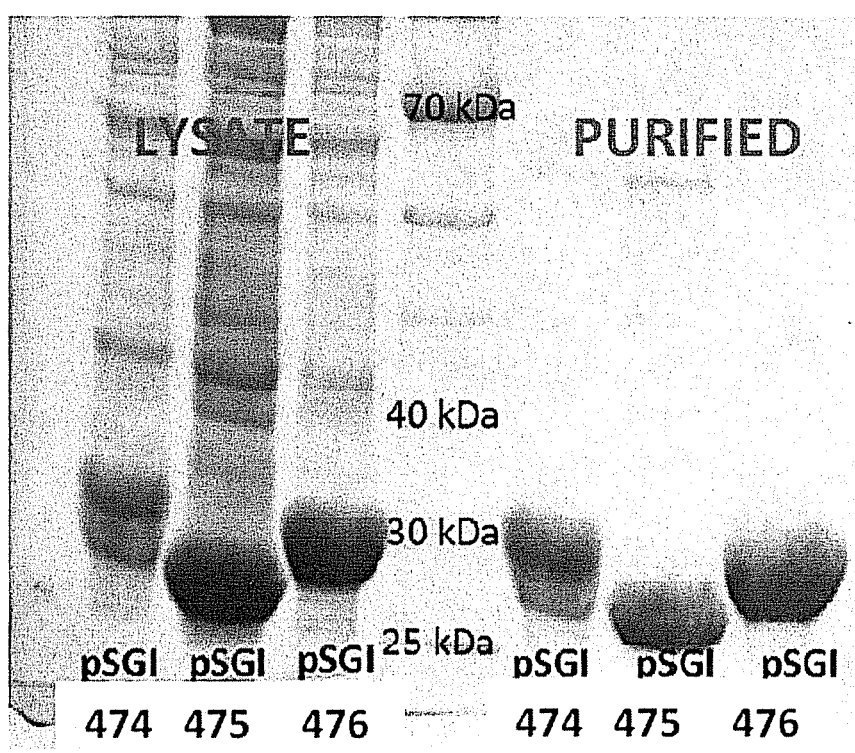
FIG. 1 is a electrophoretic gel of crude lysates and purified enzymes of proteins 474, 475, and 476.

The present invention provides methods for producing a product of an enzymatic pathway. The methods can comprise the enzymatic conversion of a substrate into a product.

By utilizing the enzymatic and chemical pathways of the invention it is possible to synthesize a wide variety of products in a highly efficient and economical manner. One product that can be produced by the methods and pathways of the invention is 2,5-furanyl dicarboxylic acid (FDCA), which can be produced at commercial scales according to the invention. The methods can comprise one or more enzymatic and/or chemical substrate-to-product conversion steps disclosed herein.

The pathways of the invention are comprised of one or more steps. It is understood that a step of a pathway of the invention can involve the forward reaction or the reverse reaction, i.e., the substrate A being converted into intermediate B and product C, while in the reverse reaction substrate C is converted into intermediate B and product A. In the methods both the forward and the reverse reactions are described as the step unless otherwise noted.

The methods involve producing a product of a pathway, which can be an enzymatic pathway. In some embodiments the pathways can include one or more chemical steps. The methods involve one or more enzymatic and/or chemical conversion steps, which convert a substrate to a product. Steps that can be included in the methods include, for example, any one or more of: an enzymatic conversion of guluronic acid into D-glucarate (Step 7); an enzymatic conversion of L-iduronic acid to Idaric acid (7B); an enzymatic conversion of L-Iduronic acid to 4-deoxy-5-threo-hexosulose uronate (DTHU)(7B); an enzymatic conversion of 5-ketogluconate (5-KGA) into L-Iduronic acid (Step 15); an enzymatic conversion of L-Iduronic acid into Idaric acid Step 7B); and an enzymatic conversion of 5-ketocluconate into 4,6-dihydroxy 2,5-diketo hexanoate (2,5-DDH) (Step 16); an enzymatic conversion of 1,5-gluconolactone to gulurono-lactone (Step 19). Any one or more of the forementioned steps can be included in a method or pathway of the invention. An enzymatic step or pathway is a step or pathway that requires an enzyme as a catalyst in the reaction to make the step proceed. Chemical steps can be performed without an enzyme as a catalyst in the reaction. Any one or more of the steps recited in the methods can be an enzymatic step. In some embodiments every step of the pathway is an enzymatic step, while in other embodiments one or more steps in the pathway is a chemical step.

In some embodiments any of the methods can include a step involving the addition of the substrate of the reaction to a reaction mix containing the enzyme that performs the conversion. Thus the method of converting guluronic acid into D-glucarate (step 7) can involve the addition of guluronic acid as starting substrate to the reaction mix; the enzymatic conversion of L-iduronic acid to Idaric acid (7B) can involve the addition of L-Iduronic acid as starting substrate to the reaction mix; the enzymatic conversion of L-Iduronic acid to 4-deoxy-5-threo-hexosulose uronate (DTHU) (7B) can involve the addition of DTHU as starting substrate to the reaction mix. Another step that can be included in any of the methods is a step of purifying from the reaction mixture a reaction product. Thus, a step of purifying D-glucarate or L-Iduronic acid, or Idaric acid, or 4,6-dihydroxy 2,5-diketo hexanoate can be included in any of the methods described herein. Any of the methods disclose can include a step of isolating or purifying DDG or FDCA from the reaction mixture.

The reaction mix used in the methods can be a cell lysate of cells that contain one or more enzymes that perform the enzymatic conversion, but can also be a reaction mixture containing components added by the user to form a reaction mixture, or can contain components purified from a cell lysate, or may be contained in a whole cell biocatalyst.

In various embodiments the methods of the invention are methods of converting glucose to DDG, or glucose to FDCA, or glucose to DTHU or DEHU, or for converting DDG to FDCA. The methods can involve converting the starting substrate in the method into the product. The starting substrate is the chemical entity considered to begin the method and the product is the chemical entity considered to be the final end product of the method. Intermediates are those chemical entities that are created in the method (whether transiently or permanently) and that are present between the starting substrate and the product. In various embodiments the methods and pathways of the invention have about four or about five intermediates or 4-5 intermediates, or about 3 intermediates, or 3-5 intermediates, or less than 6 or less than 7 or less than 8 or less than 9 or less than 10 or less than 15 or less than 20 intermediates, meaning these values not counting the starting substrate or the final end product.

The invention provides methods of producing FDCA and/or DDG, from glucose that have high yields. The theoretical yield is the amount of product that would be formed if the reaction went to completion under ideal conditions. In different embodiments the methods of the invention produce DDG from glucose, fructose, or galactose with a theoretical yield of at least 50% molar, or at least 60% molar or at least 70% molar, or at least 80% molar, at least 90% molar or at least 95% molar or at least 97% molar or at least 98% molar or at least 99% molar, or a theoretical yield of 100% molar. The methods of the invention also can provide product with a carbon conservation of at least 80% or at least 90% or at least 99% or 100%, meaning that the particular carbon atoms present in the initial substrate are present in the end product of the method at the recited percentage. In some embodiments the methods produce DDG and/or FDCA from glucose via dehydration reactions.

Synthesis Routes

The invention also provides specific pathways for synthesizing and producing a desired product. Any of the following described routes or pathways can begin with glucose and flow towards a desired product. In some embodiments D-glucose is the starting substrate and the direction of the pathway towards any intermediate or final product of the pathway is considered to be in the downstream direction, while the opposite direction towards glucose is considered the upstream direction. It will be realized that routes or pathways can flow in either the downstream or upstream direction. It is also understood that glucose, fructose, galactose, or any intermediate in any of the pathways can be the starting substrate in a method of the invention, and DDG, FDCA, or any intermediate in any of the routes or pathways of the invention can be the final end product of a method of the invention. The disclosed methods therefore include any one or more steps disclosed in any of the routes or pathways of the invention for converting any starting substrate or intermediate into any end product or intermediate in the disclosed routes or pathways using one or more of the steps in the disclosed routes or pathways. Thus, for example the methods can be methods for converting glucose to DDG, or glucose to guluronic acid, or glucose to galactarate, or glucose to DTHU, or glucose to DEHU, or for converting glucose to guluronic acid, or for converting glucose to iduronic acid, or for converting glucose to idaric acid, or for converting glucose to glucaric acid, or for converting galactarate to DDG, or for converting guluronic acid to D-glucarate, or for converting 5-KGA to L-Iduronic acid, or for converting L-Iduronic acid to Idaric acid, or for converting 5-KGA to 2,5-DDH or DTHU, or for converting DHG to DEHU. In these embodiments the methods utilize the steps disclosed in the methods and pathways of the invention from glucose as starting substrate to the relevant end product.

Figure 2A:
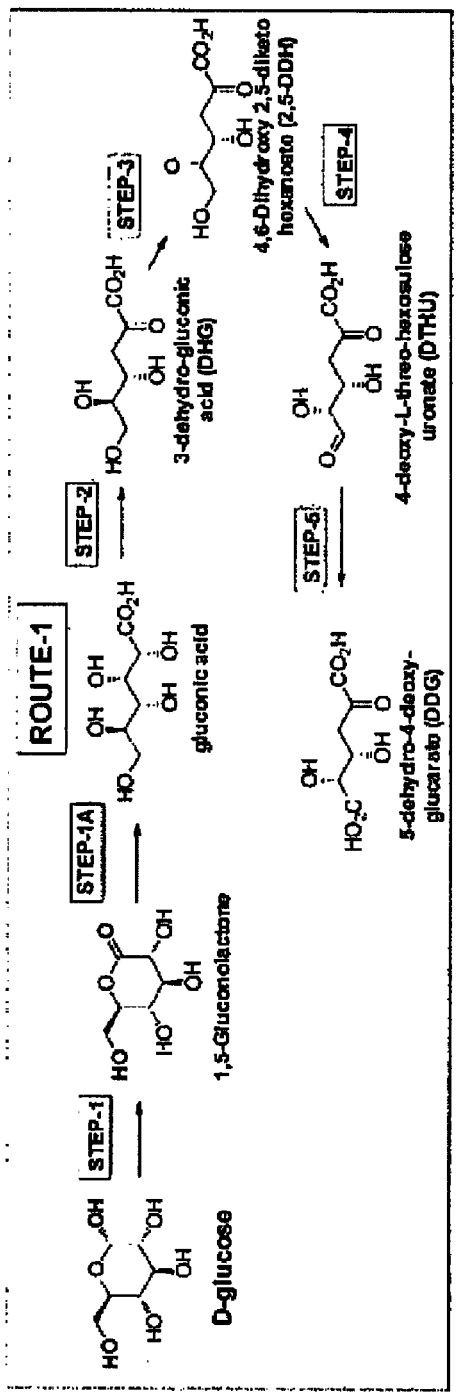
FIGS. 2a-h is a schematic illustration of the pathways of Routes 1, 2, 2A, 2C, 2D, 2E, 2F, respectively.

Route 1 is illustrated in FIG. 2a. Route 1 converts D-glucose (or any intermediate in the pathway) into 5-dehydro-4-deoxy-glucarate (DDG) via an enzymatic pathway via a series of indicated steps. Route 1 converts D-glucose into DDG via a pathway having 1,5-gluconolactone, gluconic acid, 3-dehydro-gluconic acid (DHG), 4,6-dihydroxy 2,5-diketo hexanoate (2,5-DDH), and 4-deoxy-L-threo-hexosulose uronate (DTHU) as intermediates and DDG as the final end product. For any of the pathways additional intermediates not shown can also be present. The steps are the enzymatic conversion of D-glucose to 1,5-gluconolactone (Step 1); the enzymatic conversion of 1,5-gluconolactone to gluconic acid (Step 1A); the enzymatic conversion of gluconic acid to 3-dehydro-gluconic acid (DHG) (Step 2); the enzymatic conversion of 3-dehydro-gluconic acid (DHG) to 4,6-dihydroxy 2,5-diketo hexanoate (2,5-DDH) (Step 3); the enzymatic conversion of 4,6-dihydroxy 2,5-diketo hexanoate (2,5-DDH) to 4-deoxy-L-threo-hexosulose uronate (DTHU) (Step 4); and the enzymatic conversion of 4-deoxy-L-threo-hexosulose uronate (DTHU) to 5-dehydro-4-deoxy glucarate (DDG) (Step 5). Route 1 also comprises sub-routes where the glucose or any intermediate in the pathway is converted into any other downstream intermediate as final product, and each substrate to product sub-route is considered disclosed as if each is set forth herein in full.

Figure 2B:
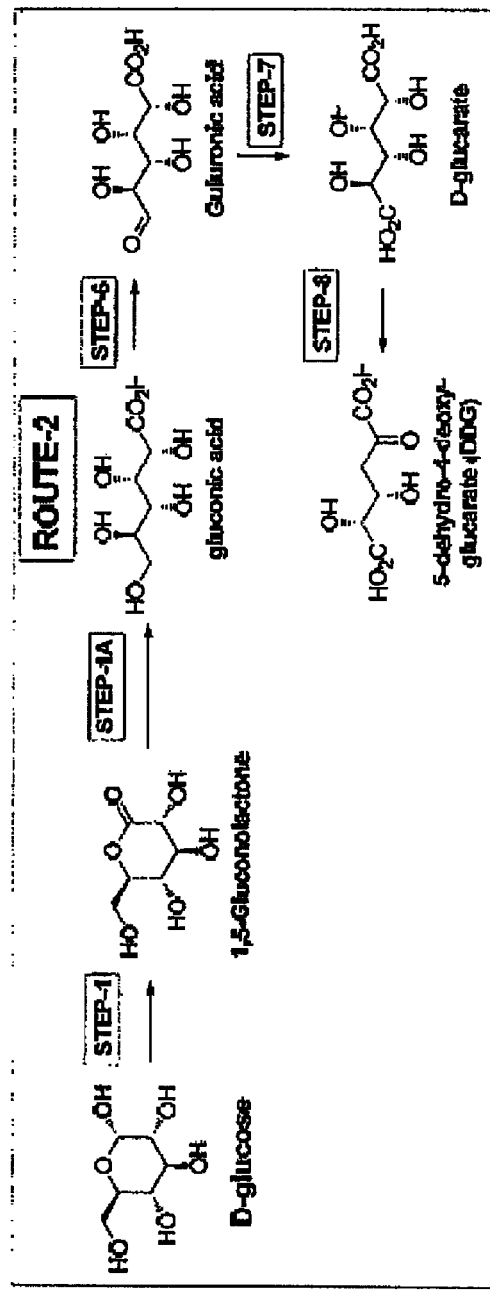

Route 2 is illustrated in FIG. 2b and converts D-glucose into DDG. The steps in the Route 2 pathway are the enzymatic conversion of D-glucose into 1,5-gluconolactone (Step 1); the enzymatic conversion of 1,5-gluconolactone to gluconic acid (Step 1A); the enzymatic conversion of gluconic acid to guluronic acid (Step 6); the enzymatic conversion of guluronic acid to D-glucarate (Step 7); the enzymatic conversion of D-glucarate to DDG (Step 8). Route 2 also comprises sub-routes where glucose or any intermediate in the pathway is converted into any other downstream intermediate as final end product, and each sub-route is considered disclosed as if each is set forth herein in full.

Figure 2C:
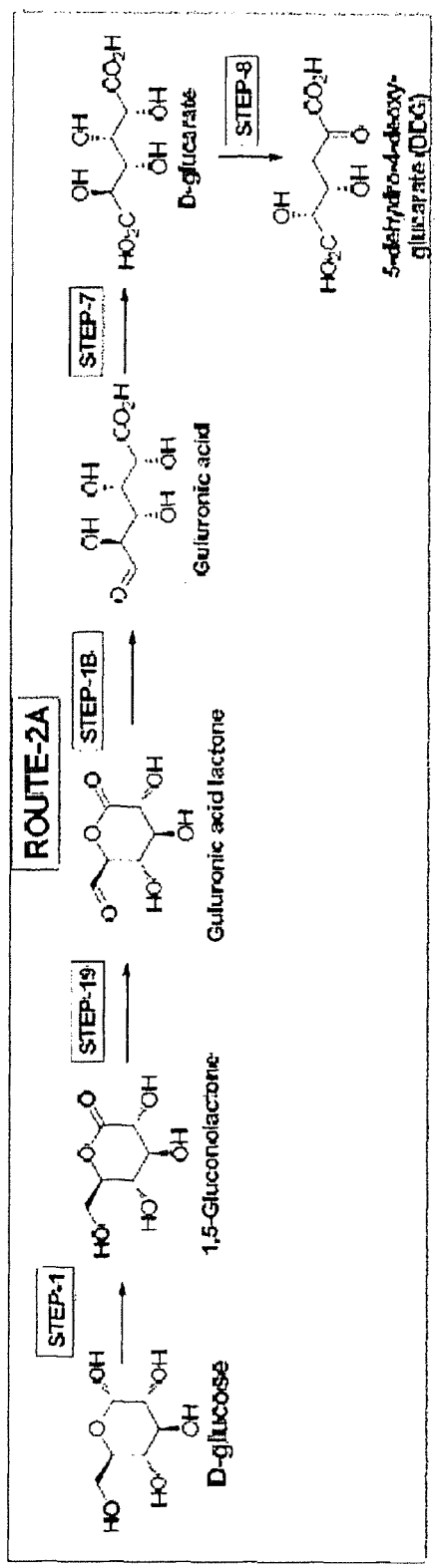

Route 2A is illustrated in FIG. 2c. The steps in Route 2A are the enzymatic conversion of D-glucose to 1,5-gluconolactone (Step 1); the enzymatic conversion of 1,5-gluconolactone to guluronic acid lactone (Step 19); the enzymatic conversion of guluronic acid lactone to guluronic acid (Step 1B); the enzymatic conversion of guluronic acid to D-glucarate (Step 7); the enzymatic conversion of D-glucarate to 5-dehydro-4-deoxy-glucarate (DDG) (Step 8). Route 2A also comprises sub-routes where glucose or any intermediate in the pathway as starting substrate is converted into any other downstream intermediate as final end product, and each sub-route is considered disclosed as if each is set forth herein in full.

Figure 2D:
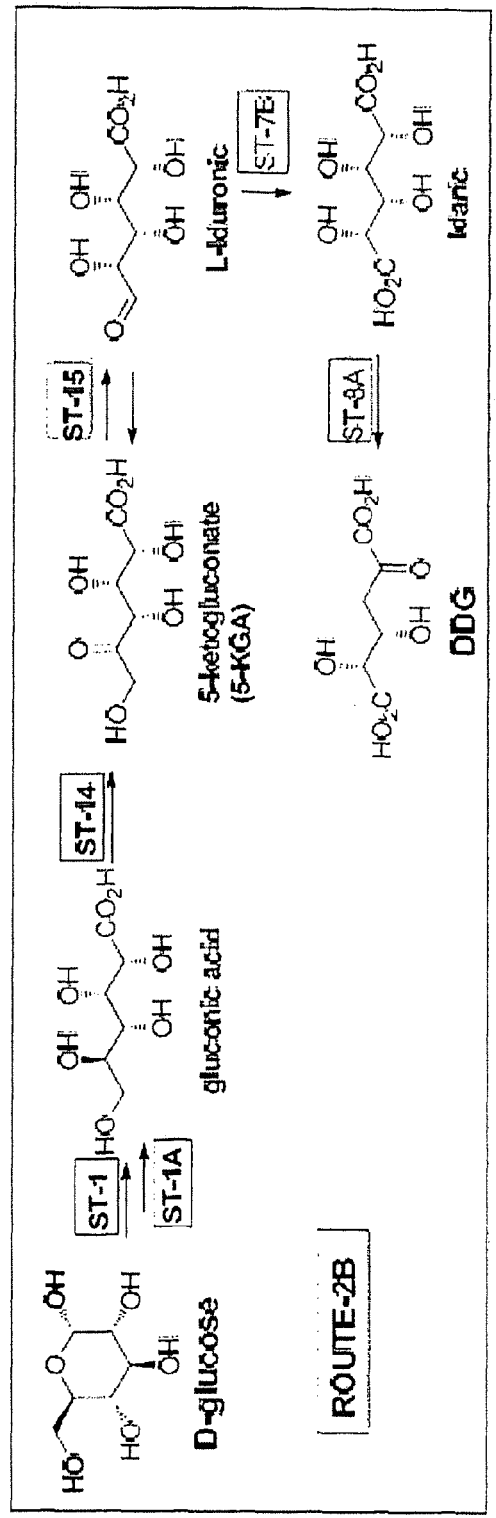

Route 2B is illustrated in FIG. 2d. The steps in Route 2B are the enzymatic conversion of D-glucose into gluconic acid (Steps 1 and 1A); the enzymatic conversion of gluconic acid into 5-ketogluconate (5-KGA) (Step 14); the enzymatic conversion of 5-KGA into L-Iduronic acid (Step 15); the enzymatic conversion of L-Iduronic acid into Idaric acid (Step 7B); the enzymatic conversion of Idaric acid into DDG (Step 8A). Route 2B also comprises sub-routes where glucose or any intermediate in the pathway as starting substrate is converted into any other downstream intermediate as final end product, and each sub-route is considered disclosed as if each is set forth herein in full.

Figure 2E:
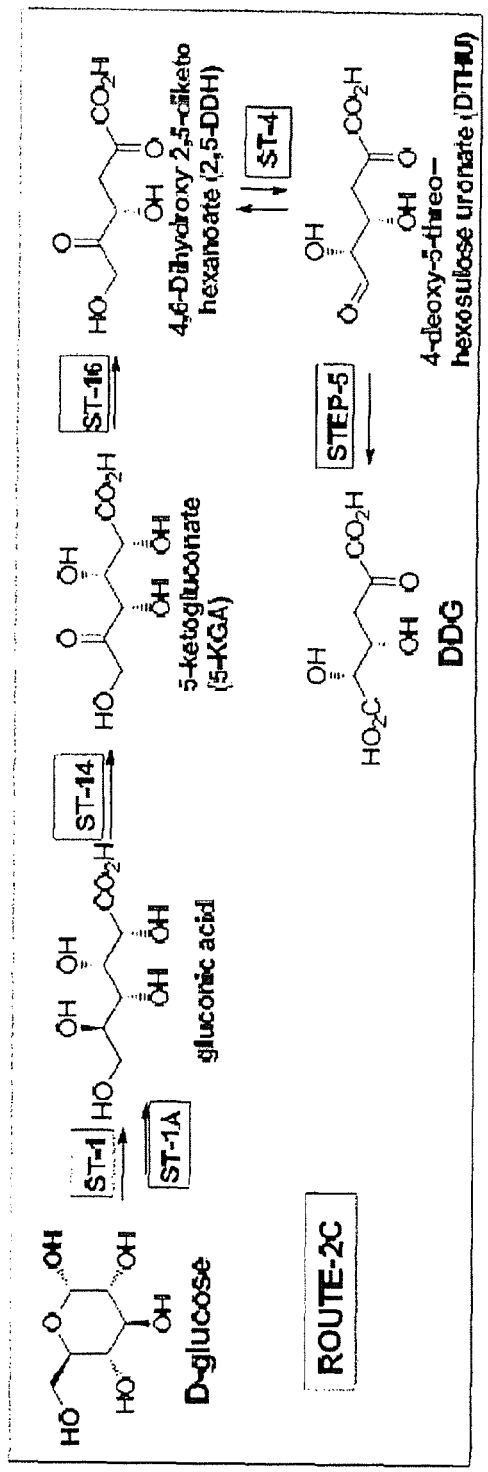

Route 2C is illustrated in FIG. 2e. The steps in Route 2C are the enzymatic conversion of D-glucose to gluconic acid (Steps 1 and 1A); the enzymatic conversion of gluconic acid to 5-ketogluconate (5-KGA) (Step 14); the enzymatic conversion of 5-KGA to 4,6-dihydroxy 2,5-diketo hexanoate (2,5-DDH) (Step 16); the enzymatic conversion of 4,6-dihydroxy 2,5-diketo hexanoate (2,5-DDH) to 4-deoxy-5-threo-hexosulose uronate (DTHU) (Step 4); the enzymatic conversion of DTHU to DDG (Step 5). Route 2C also comprises sub-routes where glucose or any intermediate in the pathway as starting substrate is converted into any other downstream intermediate as final end product, and each sub-route is considered disclosed as if each is set forth herein in full.

Figure 2F:
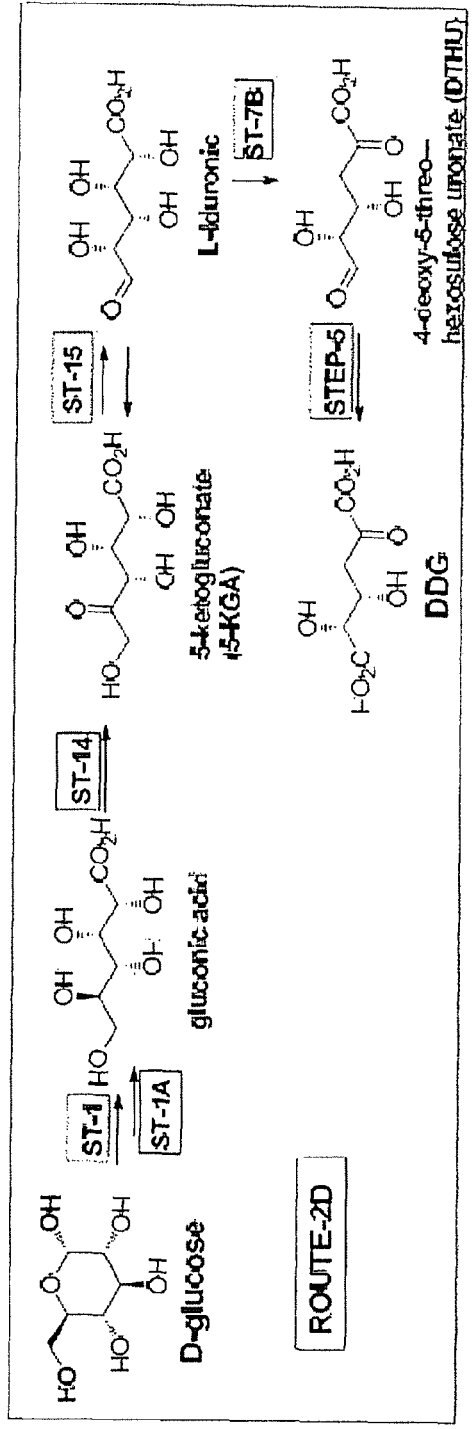

Route 2D is illustrated in FIG. 2f. The steps in Route 2D are the enzymatic conversion of D-glucose to gluconic acid (Steps 1 and 1A); the enzymatic conversion of gluconic acid to 5-ketogluconate (5-KGA) (Step 14); the enzymatic conversion of 5-KGA to Iduronic acid (Step 15); the enzymatic conversion of L-Iduronic acid to DTHU (Step 17); the enzymatic conversion of DTHU to DDG (Step 5). Route 2D also comprises sub-routes where glucose or any intermediate in the pathway as starting substrate is converted into any other downstream intermediate as final end product, and each sub-route is considered disclosed as if each is set forth herein in full.

Figure 2G:
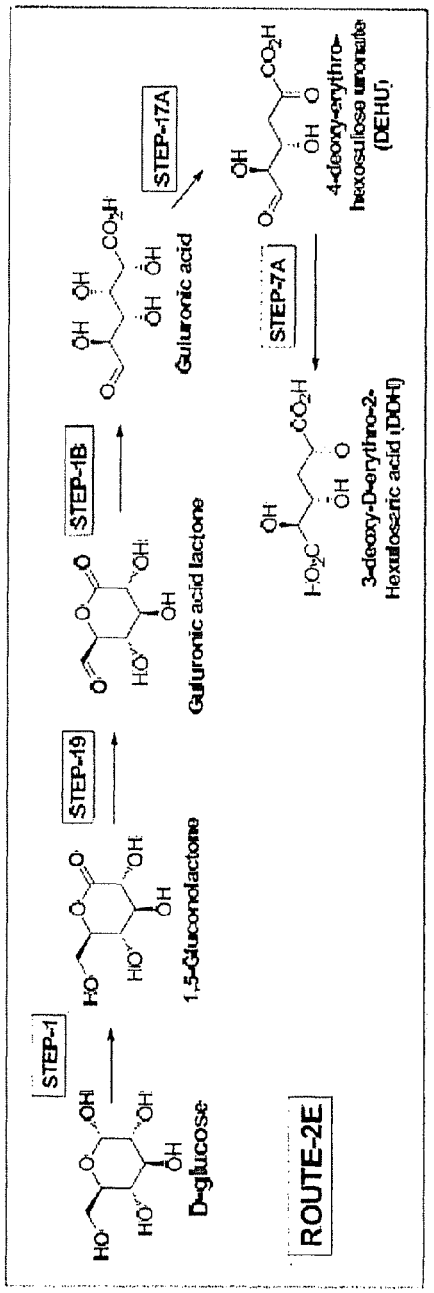

Route 2E is illustrated in FIG. 2g. The steps in Route 2D are the enzymatic conversion of D-glucose to 1,5-gluconolactone (Step 1); the enzymatic conversion of 1,5-gluconolactone to guluronic acid lactone (Step 19); the enzymatic conversion of guluronic acid lactone to guluronic acid (Step 1B); the enzymatic conversion of guluronic acid to 4-deoxy-erythro-hexosulose uronate (DEHU) (Step 17A); the enzymatic conversion of DEHU to 3-deoxy-D-erythro-2-hexylosaric acid (DDH) (Step 7A). Route 2E also comprises sub-routes where glucose or any intermediate in the pathway as starting substrate is converted into any other downstream intermediate as final end product, and each sub-route is considered disclosed as if each is set forth herein in full.

Figure 2H:
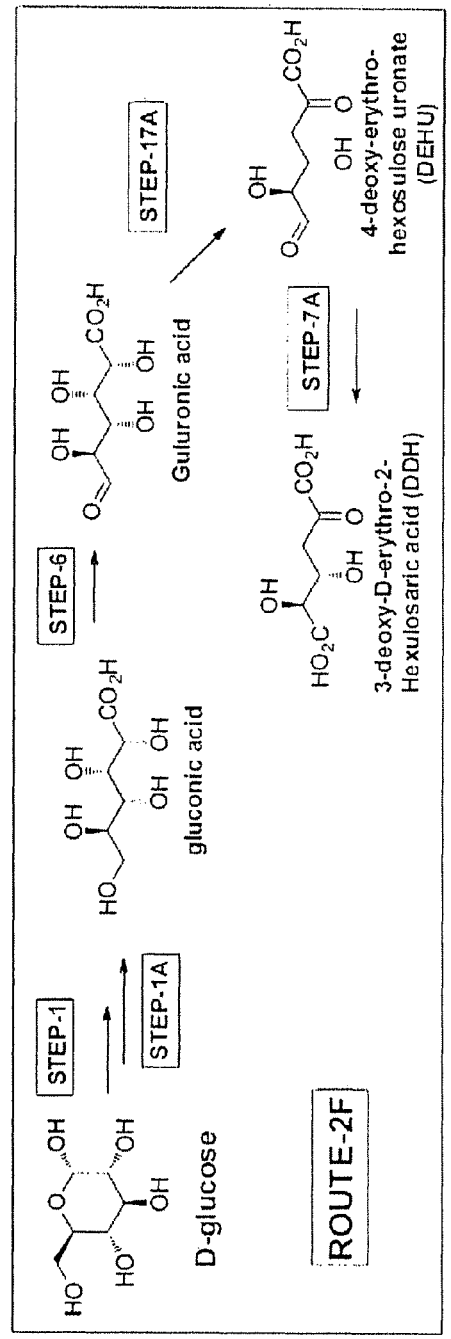

Route 2F is illustrated in FIG. 2h. The steps in Route 2F are the enzymatic conversion of D-glucose to gluconic acid (Steps 1 and 1A); the enzymatic conversion of gluconic acid to guluronic acid (Step 6); the enzymatic conversion of guluronic acid to 4-deoxy-erythro-hexosulose uronate (DEHU) (Step 17); the enzymatic conversion of DEHU to 3-deoxy-D-erythro-2-hexulosaric acid (DDH) (Step 7A). Route 2F also comprises sub-routes where glucose or any intermediate in the pathway as starting substrate is converted into any other downstream intermediate as final end product, and each sub-route is considered disclosed as if each is set forth herein in full.

Figure 3A:
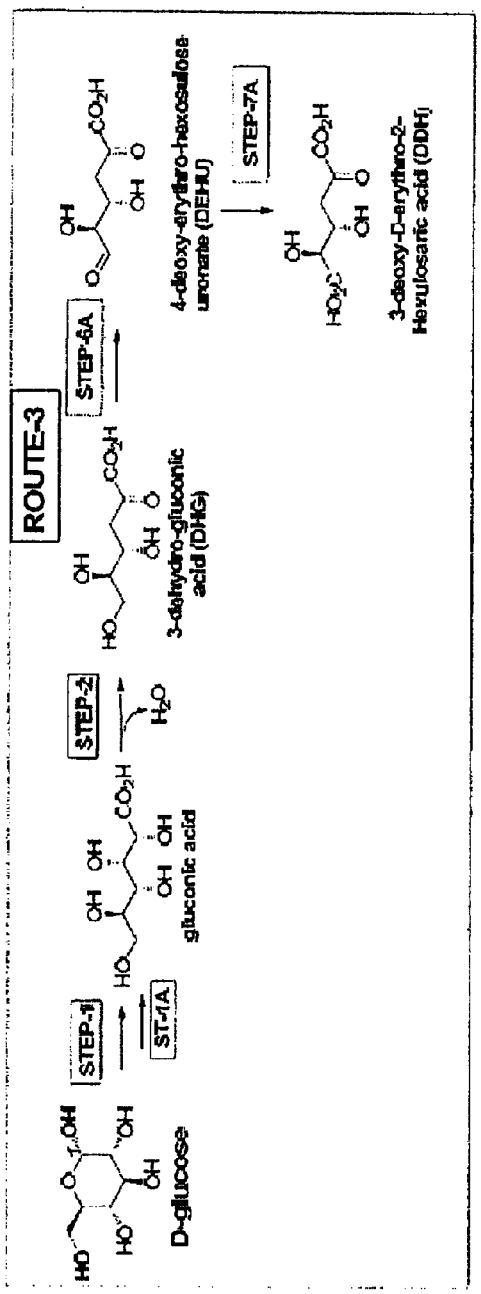
FIGS. 3a-c present a schematic illustration of the pathways of Routes 3, 4, and 5, respectively.

Route 3 is illustrated in FIG. 3a. The steps in Route 3 are the enzymatic conversion of D-glucose to gluconic acid (Steps 1 and 1A); the enzymatic conversion of gluconic acid to 3-dehydro-gluconic acid (DHG) (Step 2); the enzymatic conversion of DHG to 4-deoxy-erythro-hexosulose uronate (DEHU) (Step 6A); the enzymatic conversion of DEHU to DDG (Step 7A). Route 3 also comprises sub-routes where glucose or any intermediate in the pathway as starting substrate is converted into any other downstream intermediate as final end product, and each sub-route is considered disclosed as if each is set forth herein in full.

Figure 3B:
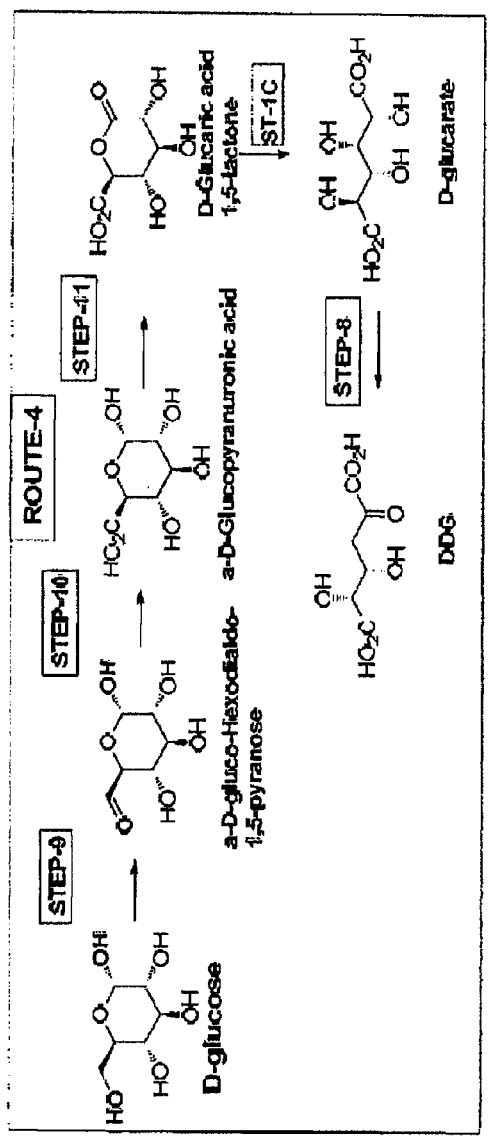

Route 4 is illustrated in FIG. 3b. The steps in Route 4 are the enzymatic conversion of D-glucose to α-D-gluco-hexodialdo-1,5-pyranose (Step 9); the enzymatic conversion of α-D-gluco-hexodialdo-1,5-pyranose to α-D-glucopyranuronic acid (Step 10); the enzymatic conversion of α-D-glucopyranuronic acid to D-glucaric acid 1,5-lactone (Step 11); the enzymatic conversion of D-glucaric acid 1,5-lactone to D-glucarate (Step 1C); the enzymatic conversion of D-glucarate to DDG (Step 8). Route 4 also comprises sub-routes where glucose or any intermediate in the pathway as starting substrate is converted into any other downstream intermediate as final end product, and each sub-route is considered disclosed as if each is set forth herein in full.

Figure 3C:
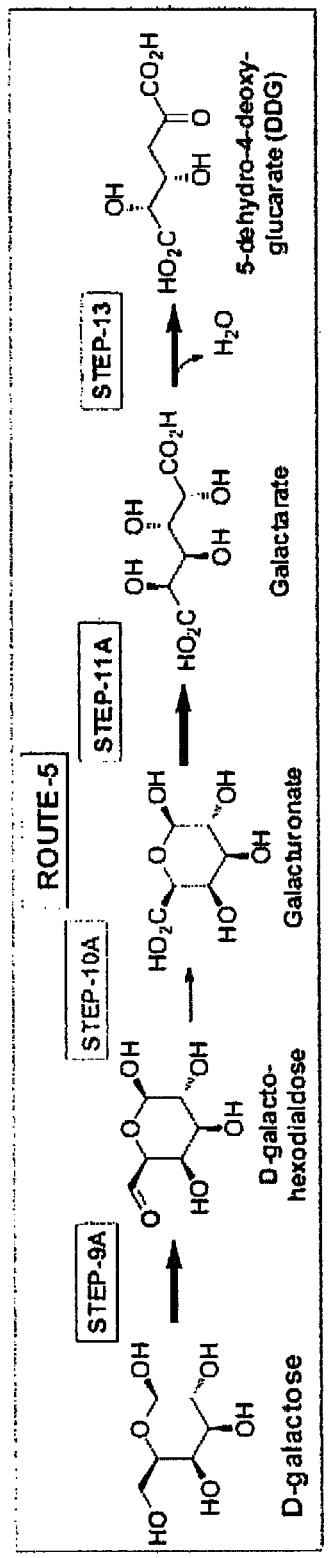

Route 5 is illustrated in FIG. 3c. The steps in Route 5 are the enzymatic conversion of D-galactose to D-galacto-hexodialdose (Step 9A); the enzymatic conversion of D-galacto-hexodialdose to galacturonate (Step 10A); the enzymatic conversion of galacturonate to galactarate (Step 11A); the enzymatic conversion of galactarate to DDG (Step 13). Route 5 also comprises sub-routes where galactose or any intermediate in the pathway as starting substrate is converted into any other downstream intermediate as final product, and each sub-route is considered disclosed as if each is set forth herein in full.

The Enzymatic Steps

There are disclosed a wide variety of enzymes (and nucleic acids that encode the enzymes) that can perform the steps of the methods outlined herein. In addition to the families and classes of enzymes disclosed herein for performing the steps of the invention, additional enzymes (or nucleic acids encoding the enzymes) having a sequence identity to any enzyme or member of a class of enzymes disclosed herein will also be useful in the invention that has a sequence identity of at least 40% or at least 50% or at least 60% or at least 70% or at least 80% or at least 90% or at least 95% or at least 97% or at least 98% or at least 99% to any enzyme or member of an enzyme class disclosed herein. Percent sequence identity or homology with respect to amino acid or nucleotide sequences is defined herein as the percentage of amino acid or nucleotide residues in the candidate sequence that are identical with the known polypeptides, after aligning the sequences for maximum percent identity and introducing gaps, if necessary, to achieve the maximum percent identity or homology. Homology or identity at the nucleotide or amino acid sequence level may be determined using methods known in the art, including but not limited to BLAST (Basic Local Alignment Search Tool) analysis using the algorithms employed by the programs blastp, blastn, blastx, tblastn and tblastx (Altschul (1997), *Nucleic Acids Res.* 25, 3389-3402, and Karlin (1990), *Proc. Natl. Acad. Sci. USA* 87, 2264-2268), which are tailored for sequence similarity searching. Alternatively a functional fragment of any of the enzymes (or nucleic acids encoding such enzymes) disclosed herein may also be used. The term "functional fragment" refers to a polypeptide that has an amino-terminal and/or carboxy-terminal deletion, where the remaining amino acid sequence has at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% sequence identity to the corresponding positions in the reference sequence, and that retains about 75%, 80%, 85%, 90%, 91%, 92%, 93%, 94%, 95%, 96%, 97%, 98%, 99%, or 100% of the activity of the full-length polypeptide. Functional fragments may comprise, e.g., 90% or less, 80% or less, 70% or less, 60% or less, 50% or less, 40% or less, 30% or less, or 20% or less of the full-length polypeptide, and can include, for example, up to about 50%, 55%, 60%, 65%, 70%, 75%, 80%, 85%, 90%, 92%, 93%, 94%, 95%, 96%, 97%, 98%, or 99% of the full-length polypeptide. The EC numbers provided use the enzyme nomenclature of the Nomenclature Committee of the International Union of Biochemistry and Molecular Biology.

Step 1—Conversion (oxidation or dehydrogenation) of glucose to 1,5-gluconolactone. This step can be performed with various enzymes, such as those of the family oxygen dependent glucose oxidases (EC 1.1.3.4) or NAD(P)-dependent glucose dehydrogenases (EC 1.1.1.118, EC 1.1.1.119). *Gluconobacter oxydans* has been shown to efficiently oxidize glucose to gluconic acid and 5-ketogluconate (5-KGA) when grown in a fermentor. Enzymes of the family of soluble and membrane-bound PQQ-dependent enzymes (EC 1.1.99.35 and EC 1.1.5.2) found in *Gluconobacter* and other oxidative bacteria can be used. Quinoprotein glucose is another enzyme that is useful in performing this step. The specific enzyme selected will be dependent on the desired reaction conditions and necessary co-factors that will be present in the reaction, which are illustrated in Table 1.

Step 1A—Conversion (e.g., hydrolysis) of 1,5-gluconolactone to gluconate. This step can be performed chemically in aqueous media and the rate of hydrolysis is dependent on pH (Shimahara, K, Takahashi, T., *Biochim. Biophys. Acta* (1970), 201, 410). Hydrolysis is faster in basic pH (e.g. pH 7.5) and slower in acid pH. Many microorgranisms also contain specific 1,5-glucono lactone hydrolases, and a few of them have been cloned and characterized (EC 3.1.1.17; Shinagawa, E *Biosci. Biotechnol. Biochem.* 2009, 73, 241-244).

Step 1B—Conversion of Guluronic acid lactone to guluronic acid. The chemical hydrolysis of guluronic acid lactone can be done by a spontaneous reaction in aqueous solutions. An enzyme capable of catalyzing this hydrolysis is identified amongst the large number of lactonases (EC 3.1.1.XX and more specifically 3.1.1.17, 3.1.1.25).

Step 2—Conversion of gluconic acid to 3-dehydro gluconic acid (DHG): Several enzymes, such as gluconate dehydratases, can be used in the dehydration of gluconic acid to dehydro gluconic acid (DHG). Examples include those belonging to the gluconate dehydratase family (EC 4.2.139). A specific example of such a dehydratase has been shown to dehydrate gluconate (Kim, S. Lee, S. B. *Biotechnol. Bioprocess Eng.* (2008), 13, 436). Particular examples of enzymes from this family and their cloning are shown in Example 1.

Step 3: Conversion of 3-dehydro-gluconic acid (DHG) to 4,6-dihydroxy 2,5-diketo hexanoate (2,5-DDH). Enzymes, 2-dehydro-3-deoxy-D-gluconate 5-dehydrogenase (or DHG dehydrogenases) (EC 1.1.1.127) for performing this conversion have been described.

Step 4: Conversion of 4,6-dihydroxy 2,5-diketo hexanoate (2,5-DDH) to 4-deoxy-L-threo-hexosulose uronate (DTHU). Enzymes of the family EC 5.3.1.12 can be used in this step, and Step 15 shows that five such enzymes were cloned and shown to have activity for the dehydration of 5-KGA. These enzyme will also show activity towards 2,5-DDH and DTHU.

Step 5: Conversion of DTHU to 5-dehydro-4-deoxy-glucarate (DDG). DDG can be produced from the chemical or enzymatic oxidation of DTHU, for example with a mild chemical catalyst capable of oxidizing aldehydes in the presence of alcohols. Aldehyde oxidases can be used to catalyze this oxidation. Oxidative bacteria such as *Acetobacter* and *Gluconobacter* (Hollmann et al *Green Chem.* 2011, 13, 226) will be useful in screening. Enzymes of the following families can perform this reaction: aldehyde oxidase EC1.2.3.1, aldehyde ferredoxin oxidoreductase (EC1.2.7.5), and in all the families of EC1.2.1.-XX.

Enzymes of the family of uronate dehydrogenases (EC 1.1.1.203) (e.g. see Step 7) will also have this activity. Other enzymes with both alcohol and aldehyde oxidation activity can be used, including enzymes in the alditol oxidase family (see Steps 19 and 6). Other broad substrate oxidases include soluble and membrane bound PQQ-dependent alcohol/aldehyde oxidases. More specifically soluble periplasmic PQQ oxidases enzymes and their homologs belonging into Type I (EC 1.1.91) and II (EC 1.1.2.8) families as well as membrane bound PQQ oxidases belonging into EC 1.1.5.X families are useful. In other embodiments aldehyde dehydrogenases/oxidases that act on DTHU can be used.

Steps 6 and 6A: Conversion of gluconic acid to guluronic acid (6) and conversion of 3-dehydro-gluconic acid (DHG) to 4-deoxy-5-erythro-hexosulose uronate (DEHU)(6A). The enzymes described in Step 5 are useful for these conversions. Other useful enzymes include NAD(P)-dependent dehydrogenases in the EC 1.1.1.XX families and more specifically glucuronate dehydrogenase (EC 1.1.1.19), glucuronolactone reductase (EC 1.1.1.20). In addition, a large number $O_2$-dependent alcohol oxidases with broad substrate range including sugars will be useful (EC 1.1.3.XX), including sorbitol/mannitol oxidases (EC 1.1.3.40), hexose oxidases (EC 1.1.3.5), alcohol oxidases (EC 1.1.3.13) and vanillin oxidase (EC 1.1.3.38). PQQ-dependent enzymes and enzymes present in oxidative bacteria can also be used for these conversions.

Steps 7 and 7B: Conversion of guluronic acid to D-glucaric acid (7) and conversion of L-Iduronic acid to idaric acid (7B). These steps can be accomplished with enzymes of the family of uronate dehydrogenases (EC 1.1.1.203) or the oxidases, as described herein.

Step 7A: Conversion of 4-deoxy-5-erythro-hexosulose uronate (DEHU) to 3-deoxy-D-erythro-2-hexylosaric acid (DDH). The Same enzymes described in Step 5 will be useful for performing this conversion.

Steps 8 and 8A: Conversion of D-glucaric acid to 5-dehydro-4-deoxy-glucarate (DDG) (Step 8) and conversion of Idaric acid to DDG (Step 8A). Enzymes of the family of glucarate dehydratases (EC 4.2.1.40) can be used to perform these steps. Enzymes of this family have been cloned and have been shown to efficiently convert glucarate to DDG. Two D-glucarate dehydratases (EC 4.2.1.40) were cloned as shown in the Table of cloned glucarate dehydratases below. Both enzymes showed very high activity for the dehydration of Glucarate to DDG using the semicarbazide assay, as described in Step 2.

Cloned Glucarate Dehydratases

| Organism | pSGI (Vector) | Gene ID | WT/SYN |
|---|---|---|---|
| E. coli | 353 (pET28) | P0AES2 | WT |
| Pseudomonas (SGI) | 244 | #8114 | WT |

Step 9 and 9A: Conversion of β-glucose to α-D-gluco-hexodialdo-1,5-pyranose (9) and conversion of D-galactose to D-galacto-hexodialdose (9A). Oxidases such as those of the galactose oxidase family (EC 1.1.3.9) can be used in this step. Mutant galactose oxidases are also engineered to have activity on glucose and have been described (Arnold, F. H. et al ChemBioChem, 2002, 3(2), 781).

Step 10: Conversion of α-D-gluco-hexodialdo-1,5-pyranose to α-D-glucopyranuronic acid (step 10) and D-galacto-hexodialdose to galacturonate (10A). This step can be performed using an enzyme of the family of aldehyde dehydrogenases.

Step 11 and 11A: Conversion of α-D-glucopyranuronic acid to glucuronic acid 1,5-lactone. Aldehyde dehydrogenases and oxidases as described in Step 5 will be useful in performing this step. Uronate dehydrogenases described in Steps 7 and 7B can also be useful in performing this step. Step-11A is the conversion of galacturonate to galactarate. The uronate dehydrogenase (EC 1.1.1.203), for example those described in Steps 7 and 7B, will be useful in performing this step.

Step 12: Conversion of fructose to glucose. Glucose and fructose isomerases (EC 5.3.1.5) will be useful in performing this step.

Step 13: Conversion of galactarate to 5-dehydro-4-deoxy-D-glucarate (DDG). Enzymes of the family of galactarate dehydrogenases (EC 4.2.1.42) can be used to perform this step, and additional enzymes can be engineered for performing this step.

Step 14: Conversion of gluconate to 5-ketogluconate (5-KGA). A number of enzymes of the family of NAD(P)-dependent dehydrogenases (EC1.1.1.69) have been cloned and shown to have activity for the oxidation of gluconate or the reduction of 5KGA. For example, the NADPH-dependent gluconate 5-dehydrogenase from *Gluconobacter* (Expasy P50199) was synthesized for optimal expression in *E. coli* as shown herein and was cloned in pET24 (pSGI-383). The enzyme was expressed and shown to have the required activities. Additional enzymes useful for performing this step include those of the family of PQQ-dependent enzymes present in *Gluconobacter* (Peters, B. et al. *Appl. Microbiol Biotechnol.*, (2013), 97, 6397), as well as the enzymes described in Step 6. Enzymes from these families can also be used to synthesize 5KGA from gluconate.

Step 15: Conversion of 5-KGA to L-Iduronic acid. This step can be performed with various enzymes from different isomerase families, as further described in Example 4.

Step 16: Conversion of 5-KGA to (4S)-4,6-dihydroxy 2,5-diketo hexanoate (2,5-DDH). This dehydration can be performed with enzymes in the gluconate dehydratase family (EC 4.2.3.39), such as those described in Example 5 or Step 17.

Step 17 and 17A: L-Iduronate to 4-deoxy-5-threo-hexosulose uronate (DTHU) and Guluronate to 4-deoxy-5-hexoulose uronate (DHU).

Enzymes of the family of dehydratases are identified that can be used in the performance of this step. Enzymes from the families of gluconate or glucarate dehydratases will have the desired activity for performing these steps. Furthermore, many dehydratases of the family (EC 4.2.1.X) will be useful in the performance of these steps. In particular, enzymes that dehydrate 1,2-dyhydroxy acids to selectively produce 2-keto-acids will be useful, such as enzymes of the families: EC 4.2.1.6 (galactonate dehydratase), EC 4.2.1.8 (mannonate dehydratase), EC 4.2.1.25 (arabonate dehydratase), EC 4.2.1.39 (gluconate dehydratase), EC 4.2.1.40 (glucarate dehydratase), EC 4.2.1.67 (fuconate dehydratase), EC 4.2.1.82 (xylonate dehydratase), EC 4.2.1.90 (rhamnonate dehydratase) and dihydroxy acid dehydratases (4.2.1.9). Since known enzyme selectivity is the production of an alpha-keto acid the identified enzymes will produce DEHU and DTHU, respectively, as the reaction products.

Step 19: Conversion of 1,5-gluconolactone to guluronic acid lactone. This step can be performed by enzymes of the family of alditol oxidases (EC 1.1.3.41) or the enzymes described in Step 6.

Methods of Converting DDG to FDCA and of Making Esterified DDG and FDCA

The present invention also provides novel methods of converting DDG to FDCA and FDCA esters. Esters of FDCA include diethyl esters, dibutyl esters, and other esters. The methods involve converting DDG into a DDG ester by contacting DDG with an alcohol, an inorganic acid, and optionally a co-solvent to produce a derivative of DDG. The alcohol can be methanol, ethanol, propanol, butanol, or any C1-C20 alcohol. The inorganic acid can be sulfuric acid. The co-solvent can be any of or any mixture of THF, acetone, acetonitrile, an ether, butyl acetate, an dioxane, chloroform, methylene chloride, 1,2-dichloroethane, a hexane, toluene, and a xylene. The esterified DDG can then be converted into esterified FDCA. The DDG can be optionally purified as a step prior to performing the method. Purifying the DDG can comprise removing water from the solvent comprising the DDG, for example removing greater than 87% of the water or greater than 90% of the water or greater than 95% of the water or greater than 97% or greater than 98% or greater than 99% of the water from the solvent comprising the DDG. Yields of greater than 25% or 30% or 35% or 40% or 45% molar can be obtained.

DDG Purification

DDG purification for dehydration or esterification was performed by acidifying the DDG, e.g., by lowering the pH of the reaction with the addition of conc HCl to pH~2.5. At this pH proteins and any residual glucarate precipitate are removed by filtration and the mixture is lyophilized to give a white powder consisting of DDG and the reaction salts. This DDG can be dehydrated to give 2,5-FDCA, or be esterified to dibutyl-DDG (or di-ethyl DDG) prior to dehydration. This method of purifying or esterifying DDG can be added as a step in any of the methods and pathways disclosed herein that produce DDG.

Methods for Synthesizing FDCA and FDCA Derivatives

The invention also provides various methods of synthesizing FDCA. One method for synthesizing FDCA involves contacting DDG with an alcohol, an inorganic acid at a high temperature to form FDCA. The alcohol can be any alcohol, and examples include (but are not limited to) methanol, ethanol, propanol, and butanol. Diols can also be used. The high temperature can be a temperature greater than 70° C. or greater than 80° C. or greater than 90° C. or greater than 100° C. or greater than 110° C. or greater than 120° C. or greater than 130° C. or greater than 140° C. or greater than 150° C. to form FDCA. Reaction yields of greater than 20% or greater than 30% or greater than 35% or greater than 40% can be achieved.

The invention also provides methods for synthesizing derivatives of FDCA. The methods involve contacting a derivative of DDG with an inorganic acid to produce a derivative of FDCA. The inorganic acid can be, for example, sulfuric acid. Optionally, the derivative of DDG can be purified prior to contacting it with the second inorganic acid. Non-limiting examples of the derivative of DDG that can be used include methyl DDG, ethyl DDG, propyl DDG, butyl DDG, isobutyl DDG, di-methyl DDG, di-ethyl DDG, di-propyl DDG, di-butyl DDG. The derivative of FDCA produced can be methyl FDCA, ethyl FDCA, propyl FDCA, butyl FDCA, di-methyl FDCA, di-ethyl FDCA, di-propyl FDCA, di-butyl FDCA, and isobutyl FDCA. The derivate of FDCA produced corresponds to the derivative of DDG used in the method. The derivative of FDCA can then be de-esterified to produce FDCA. The method can also be conducted in the gas phase, e.g., using the parameters described below.

Another method for synthesizing FDCA or derivatives of FDCA involves contacting DDG or derivatives of DDG (any described herein) with an inorganic acid in a gas phase, which can be done with a short residence time, e.g., of less than 10 seconds or less than 8 seconds, or less than 6 seconds or less than 5 seconds or less than 4 seconds or less than 3 seconds or less than 2 seconds or less than 1 second. The residence time refers to the time that the sample is present in the reaction zone of the high temperature flow through reactor. The method can also be conducted at high temperatures, for example at temperatures greater than 150° C., greater than 200° C., greater than 250° C., greater than 300° C. or greater than 350° C. Yields of greater than 25% or greater than 30%© or greater than 40%© or greater than 45% or greater than 50% molar are obtainable. Another method for synthesizing FDCA involves contacting DDG with an inorganic acid at a temperature in excess of 80° C. or 90° C. or 100° C. or HO ° C. or 120° C. Another method for synthesizing FDCA involves contacting DDG with an inorganic acid under anhydrous reaction conditions. In various embodiments the anhydrous conditions can be established by lyophilizing the DDG in any method of synthesizing FDCA disclosed herein so that the DDG contains less than 10% or less than 9% or less than 8% or less than 7% or less than 6% or less than 5% or less than 4% or less than 3% water or less than 2% water, by weight.

The methods of the invention for synthesizing FDCA described herein provide a significantly higher yield than has been available. In different embodiments molar yields of FDCA (v. DDG) can be obtained of greater than 10% or greater than 15% or greater than 20% or greater than 25% or greater than 30% or greater than 35% or greater than 40% or greater than 45% or greater than 50%.

EXAMPLES

Example 1

Step 2, Gluconic Acid to 3-dehydro-gluconic acid (DHG)

Enzymes with natural activity for the dehydration of gluconate have been discovered (EC 4.2.1.39). Three enzymes from this family were cloned as shown in Table 1. Enzyme pSGI-365 was cloned and shown to be a dehydratase with broad substrate range having strong activity for the dehydration of gluconate (Kim, S. Lee, S. B. *Biotechnol. Bioprocess Eng.* 2008, 13, 436).

TABLE 1

Enzymes used in this experiment and identity homology. All expressed in *P. luorescens*

| Organism | pSGI (Vector) | Gene ID | WT/SYN | Expression Host |
|---|---|---|---|---|
| Achromobacter | 365 (pRANGER) | E3HJU7 | Syn | *P. fluorescens* |
| Achromobacter | 359 (pRANGER) | #0385 | wt | *P. fluorescens* |
| Acinetobacter | 360 (pRANGER) | #0336 | wt | *P. fluorescens* |

| | 359_Achromob | 365_E3HJU7 |
|---|---|---|
| pSGI-360_Acinetobacter (SGI) | 78 | 79 |
| pSGI-359_Achromobacter (SGI) | | 95 |
| pSGI-365 Acromobacter | | |

Figure 4:
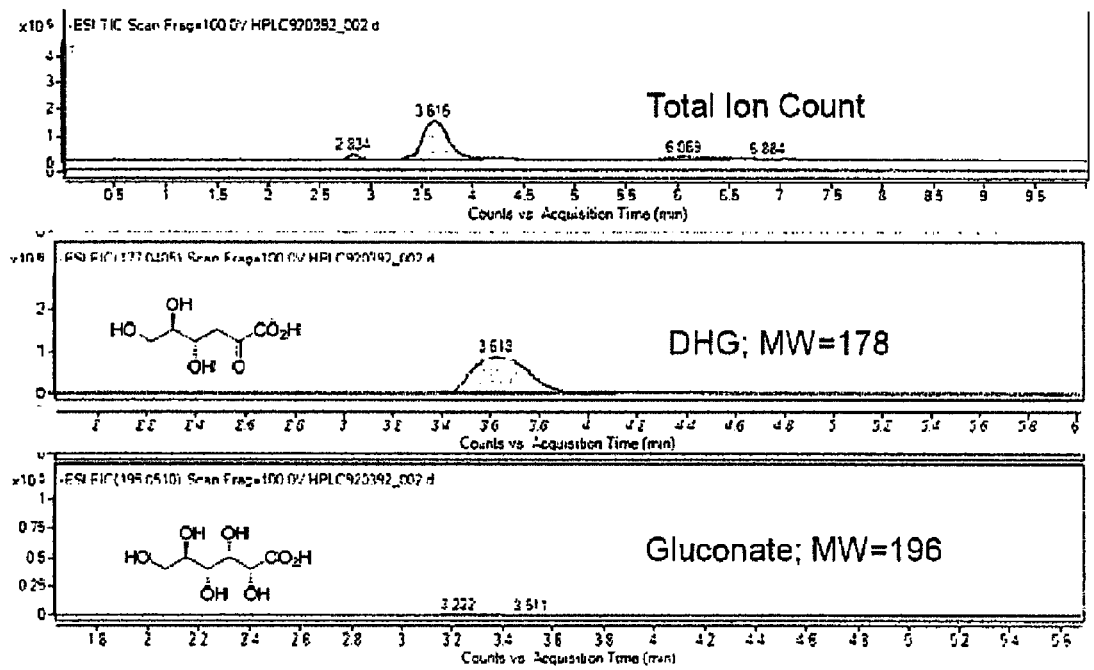
FIG. 4 is an HPCL-MS analysis of the dehydration of gluconate with gluconate dehydratase to produce DHG by pSGI-359.
Figure 5:
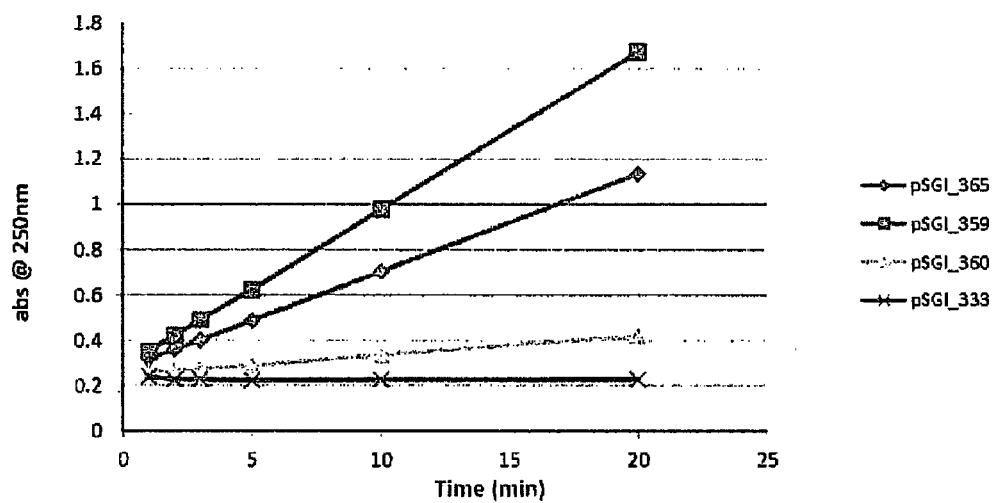
FIG. 5 is a graphical illustration of semicarbizide assay plots for measuring the activity of gluconate dehydratases.

Proteins 359, 360, and 365 showed 2-5 µmole/min per mg of crude enzyme lysate activity for the synthesis of dehydration of gluconate (gel not shown). pSGI-359 was isolated by precipitation with ammonium sulfate and re-dissolving in buffer and assayed by the semicarbazide assay. Activities of 46.2 U/mL, or 5.3 U/mg (1 unit=µmole/min) for the dehydration of gluconate were calculated from semicarbazide assay plots. Reaction buffer (93 mL) containing Kpi 10 mM pH 8.0 with 2 mM MgCl2 and 3.5 gr (0.016 mole) of sodium gluconate was mixed with 7 mL of the previous gluconate dehydratase solution. The reaction was incubated at 45° C. for 16 h before one aliquot was analyzed by HPLC-MS (FIG. 4). As shown in FIG. 4 one new major product with the molecular weight of DHG was produced. The product was also shown to have activity with DHG dehydratases.

All proteins were cloned on the pRANGER™ (Lucigen, Middleton, Wis.) expression vector and were expressed in a *Pseudomonas fluorecens* strain. pRANGER™ is a broad host commercially available plasmid vector containing the pBBR1 replicon, Kanamycin resistance and an pBAD promoter for inducible expression of genes. For the enzyme assay a modification of the semicarbazide assay for the quantification of alpha keto acid was used to calculate the activity of each enzyme (Kim, S.; Lee, S. B. *Biochem J.* 2005, 387, 271). SEQ ID NOs: 30-32 and 33-35 show the amino acid and nucleotide sequences, respectively, of the gluconate dehydratases #0385, #0336, and E3HJU7.

Example 2

Step 3—3-dehydro-gluconic acid (DHG) to (4S)-4, 6-dihydroxy 2,5-diketo hexanoate (2,5-DDH)

Enzymes of the family (EC 1.1.1.127) can be used to perform this step. Two examples are 2-dehydro-3-deoxy-D-gluconate 5-dehydrogenase and DHG dehydrogenases. Five enzymes from this family were cloned as shown in Table 2 below. pRANGER™ vector was used in every case.

TABLE 2

Cloned of DHG oxidoreductase (or 2-dehydro-3-deoxy-D-gluconate 5-dehydrogenase)

| Organism | pSGI (Vector) | Gene ID | WT/SYN | Expression Host |
|---|---|---|---|---|
| Agrobacterium sp (SGI) | 374 | #9041 | WT | P. fluorescens |
| Agrobacterium tumefaciens (SGI) | 375 | #8939 | WT | P. fluorescens |
| E. coli | 376 | P37769 | WT | P. fluorescens |
| Sphingomonas (SGI) | 395 | #5112 | WT | P. fluorescens |
| Hoeflea phototrophica (SGI) | 396 | #7103 | WT | P. fluorescens |

The product prepared from the dehydration of gluconate in Step 2 was used as substrate for assaying the lysates of Table 2. As shown in the following Table 3, enzymes were identified showing activity for the oxidation of DHG in assays measuring NADH formation (absorbance increase at 340 nm).

TABLE 3

Activity calculations for oxidation of DHG to 2,5-DDH using DHG oxidoreductase.
A unit = µmole/min of NADH

| | U/mg (100 mM DHG) | | |
|---|---|---|---|
| ENZ | pH = 7.5 | pH = 8.5 (10 mM DHG) | pH = 9.5 |
| pSGI_395 | 0.012 | 0.070 (0.02) | 0.120 |
| pSGI_396 | 0.033 | 0.139 (0.018) | 0.418 |
| PSGI_374 | 0.007 | 0.043 (0.012) | 0.091 |
| pSGI_376 | 0.007 | 0.121 (0.01) | 1.610 |

Further verification of the formation of 2,5-DDH by these enzymes was shown in Step 16 where the reduction of 2,5-DDH (made from the dehydration of 5KGA) with pSGI-395 at acidic pH was shown.

Example 3

Steps 7 and 7B—Conversion of Guluronic Acid to D-Glucaric Acid (7) and Conversion of L-Iduronic Acid to Marie Acid (7B)

To demonstrate Steps 7 and 7B the following study was performed. Uronate dehydrogenases (EC 1.1.1.203) are enzymes that oxidize glucuronic and galacturonic acid. Three enzymes with sequence similarity to the known uronate dehydrogenase (Expasy: □7CRQ0; Prather, K. J, et al., *J. Bacteriol.* 2009, 191, 1565) were cloned from bacterial strains as shown in Tables 4 & 5.

TABLE 4

Cloned Uronate Dehydrogenases

| Organism | pSGI (pET28) | Gene ID | Expression |
|---|---|---|---|
| Agrobacterium | 474 | #8807 | BL21DE3 |
| Rhizobium | 475 | #8958 | BL21DE3 |
| Pseudomonas | 476 | #1770 | BL21DE3 |

TABLE 5

Sequence Identity

| | 475 | 476 | Q7CRQ0 |
|---|---|---|---|
| 474_Agrobacterium | 73 | 49 | 90 |
| 475_Rhizobium | | 51 | 74 |
| 476_Pseudomonas | | | 50 |

Each protein was expressed with a His tag from pET28 and was purified prior to their screening. Protein gels of the crude lysates and purified enzymes are shown in the gel of FIG. 1. After purification all enzymes were tested for activity against glucuronate, as well as against guluronate and iduronate. Kinetic measurements at different substrate concentrations were performed and the calculated activities and Km values for each enzyme are shown in Table 6. AU enzymes showed good activity for glucuronate, and also for L-iduronate and guluronate.

TABLE 6

Activity and Km value for purified uronate dehydrogenases.

| | Vmax (μM/min/mg); and Km (mM) | | |
|---|---|---|---|
| Enzyme | Glucuronate | Iduronate | Guluronate (Vm only) |
| 474 | 128.2; 0.37 | 0.96; 29.8 | 0.017 |
| 475 | 47.4; 0.22 | 0.59; 42.1 | 0.016 |
| 476 | 90.9; 0.34 | 1.36; 29.6 | 0.014 |

Figure 6A:
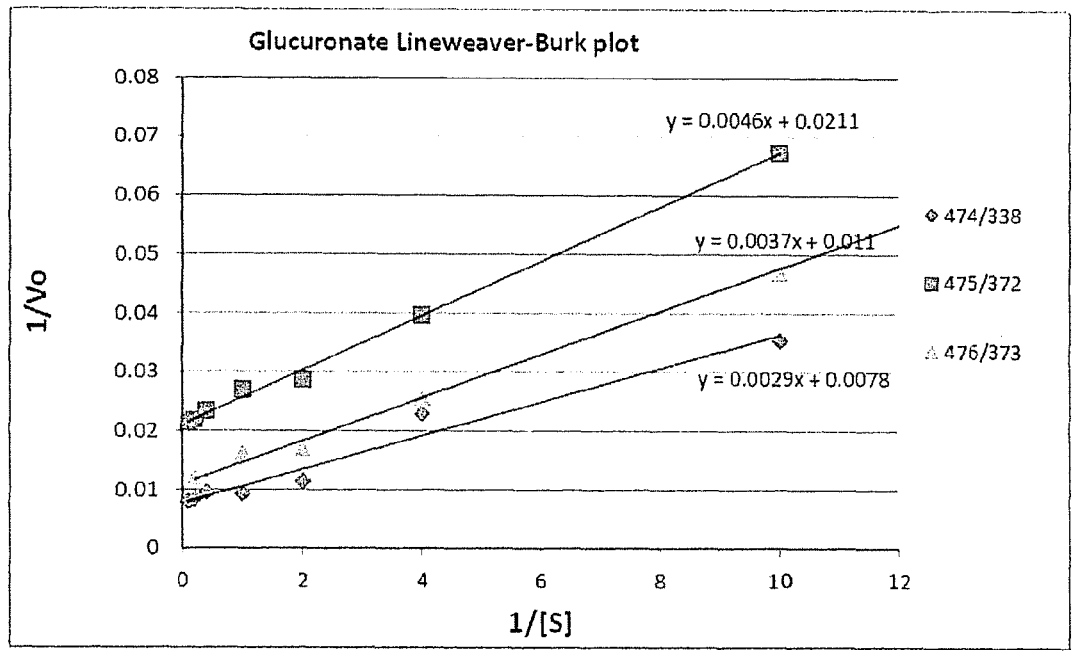
FIGS. 6a and 6b provide Lineweaver-Burk plots for the oxidation of glucuronate and iduronate with three enzymes of the invention.
Figure 6B:
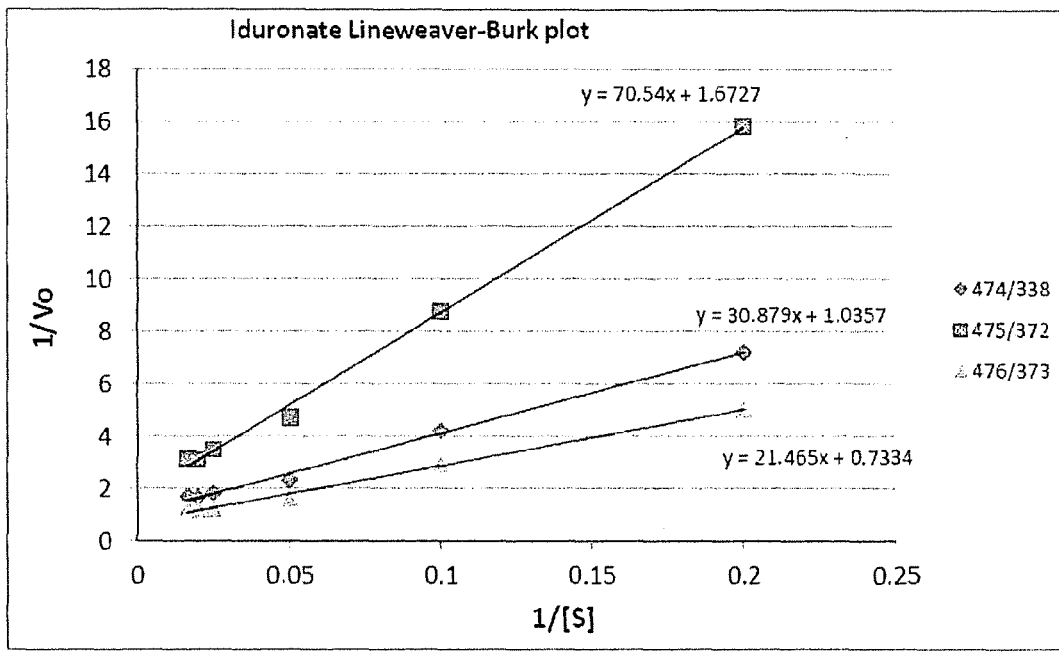

Each plasmid shown in Table 4 was transformed in BL21DE3 *E. coli* cells. Clarified lysates were mixed with equal volume of (25 mL) of equilibration buffer and purified on an Ni NTA column. Activity of each purified enzyme was measured in by mixing 0.050 mL of various dilutions of each purified enzyme with 0.95 mL of reaction buffer (100 mM TrisHCl, pH 8.0, 50 mM NaCl, 0.75 mM NAD+). The reaction progress was measured by monitoring of the formation of NADH at 340 nm. FIGS. 6*a* and 6*b* provide Lineweaver-Burk plots for the oxidation of glucuronate and iduronate, with all three enzymes shown in FIG. 6. Clear positive slopes were obtained with all enzymes giving the activities shown in the table above. Protein sequences of the uronate dehydrogenases are shown as SEQ ID NOs: 1-3 and the genes as SEQ ID NO: 4-6.

Example 4

Step-15: Conversion of 5-ketogluconate (5-KGA) to L-Iduronic Acid (15) or Guluronic Acid (15A)

This example illustrates the identification of an enzyme capable of isomerizing 5-KGA to iduronic acid (Step 15) or guluronic acid (Step 15A). Thirteen enzymes from three different isomerase families were cloned as shown in Table 7, while their % sequence identity is shown in Table 8.

TABLE 7

Isomerases cloned

| EC | Organism | pSGI (pET28) | Gene ID Archetype ® or Expasy | WT/SYN |
|---|---|---|---|---|
| 5.3.1.17 | Rhizobium | 433 | #8938 | WT |
| 5.3.1.17 | E. coli | 434 | Q46938 (Expasy) | WT |
| 5.3.1.17 | Rhizobium | 435 | #3891 | WT |
| 5.3.1.17 | Pannonibacter | 436 | #7102 | WT |
| 5.3.1.n1 | Lactobacillus | 458 | A5YBJ4 (Expasy) | SYN |
| 5.3.1.n1 | Acidophilum | 440 | F0J748 (Expasy) | SYN |
| 5.3.1.n1 | Bacillus | 437 | #9209 | WT |
| 5.3.1.n1 | Ochrobactrum | 438 | #9732 | WT |
| 5.3.1.n1 | Halomonas | 439 | #7403 | WT |
| 5.3.1.12 | Sphingobacteria | 478 | #1874 | WT |
| 5.3.1.12 | Thermotoga | 479 | Q9WXR9 | SYN |
| 5.3.1.12 | Bacillus | 480 | Q9KPI6 | SYN |
| 5.3.1.12 | Bacillus | 481 | O34808 | SYN |

TABLE 8

% Identities of isomerases

| | EC | 436 | 434 | 435 | 458 | 440 | 437 | 438 | 439 | 481 | 480 | 479 | 478 |
|---|---|---|---|---|---|---|---|---|---|---|---|---|---|
| 433 | 5.3.1.17 | 65 | 44 | 43 | 16 | 13 | 18 | 11 | 14 | 6 | 11 | 11 | 7 |
| 436 | 5.3.1.17 | | 45 | 46 | 18 | 14 | 15 | 12 | 13 | 5 | 10 | 11 | 7 |
| 434 | 5.3.1.17 | | | 46 | 17 | 10 | 15 | 10 | 13 | 6 | 10 | 12 | 7 |
| 435 | 5.3.1.17 | | | | 18 | 16 | 18 | 14 | 16 | 9 | 11 | 13 | 7 |
| 458 | 5.3.1.n1 | | | | | 37 | 57 | 41 | 44 | 6 | 7 | 9 | 5 |
| 440 | 5.3.1.n1 | | | | | | 40 | 67 | 50 | 6 | 6 | 6 | 5 |
| 437 | 5.3.1.n1 | | | | | | | 46 | 51 | 8 | 7 | 10 | 6 |
| 438 | 5.3.1.n1 | | | | | | | | 52 | 5 | 5 | 6 | 4 |
| 439 | 5.3.1.n1 | | | | | | | | | 6 | 7 | 8 | 5 |
| 481 | 5.3.1.12 | | | | | | | | | | 7 | 36 | 54 |
| 480 | 5.3.1.12 | | | | | | | | | | | 7 | 7 |
| 479 | 5.3.1.12 | | | | | | | | | | | | 37 |
| 478 | 5.3.1.12 | | | | | | | | | | | | |

As shown in Table 8, enzymes with medium homology (underlined) within each family were selected for cloning. The data demonstrated that enzymes from all families showed activity for the isomerization of 5-KGA giving L-iduronate as the main product. Two enzymes from the 5.3.1.17 family (433 & 434) were also used in the example showing the formation of DDG from 5-ketogluconate (5KGA).

Activity for the isomerization of 5KGA and iduronate using enzymes from Table 7 was measured using an enzymatic method that detected the formation of products by their activity against two different enzymes. For example, isomerization of 5KGA was detected by measuring the activity of the product iduronate using uronate dehydrogenase (pSGI-476). Isomerization of iduronate was detected by measuring the activity 5KGA reductase (pSGI-383, EC 1.1.1.69) of the product 5KGA. Presence of the products was also detected by GC-MS.

Figure 7A:
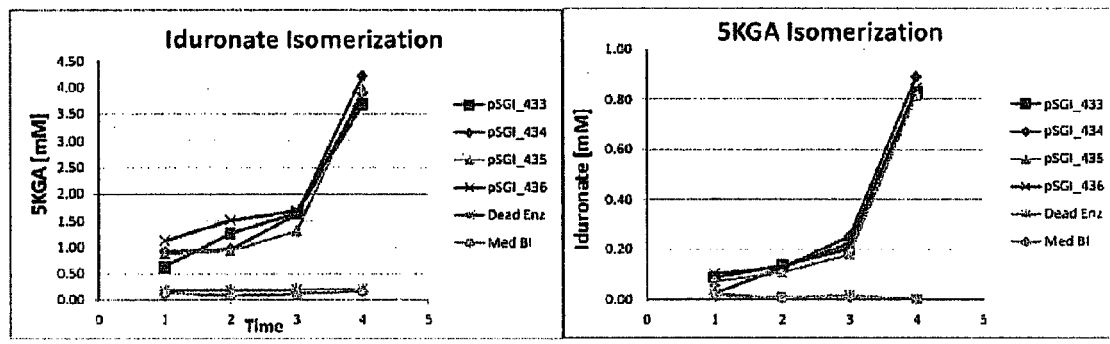
FIG. 7a shows the results of an HPLC analysis of time points for the isomerization of 5KGA and Iduronate using enzymes DTHU isomerases in the EC 5.3.1.17 family. Controls: dead enzyme is a control with heat inactivated enzyme. Med BI refers to reactions without isomerase add/n. Time points, x axis h; 2=1; 3=2 h; 4=16 h.

Enzymes from all families showed varying activity for the isomerization of 5KGA and iduronate. Two enzymes from EC 5.3.1.12 were used in a cell free reaction to isomerize 5KGA and ultimately produce DDG as described in the example. The enzymes were also purified by gel electrophoresis and showed a single band. The purified isomerases were used in reactions using lysate and buffer containing 5KGA or Iduronate. Product formation was demonstrating using both HPLC and the previously described enzymatic methods. Results for 17 h of incubation using both HPLC and enzyme assays are shown in FIG. 7*a*. All enzymes showed good activity for the isomerization of both 5KGA and iduronate. Yields for iduronate isomerization by pSGI433, pSGI 434, pSGI 435, and p SGI 436 were 56%, 48% 42%, (436 not measured), respectively when measured enzymatically and 78.8%, 78.5%, 733% and 76.6%, respectively when measured by HPLC assay. Yields after 16 h for 5KGA isomerization by the same enzymes were 18%, 17%, and 19% respectively (436 not measured) when measured by enzymatic assay, and 16.6%, 17.8%, 16.3%, and 16.9%, respectively, when measured by HPLC assay.

EC 5.3.1.12 Enzymes

Figure 7B:
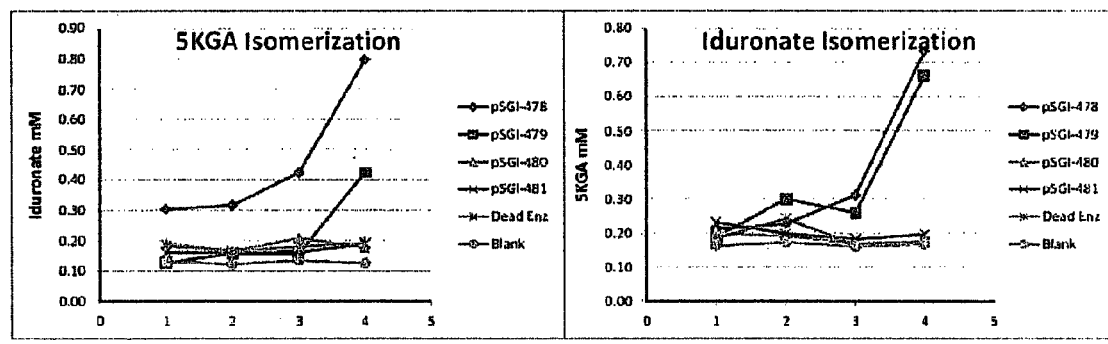
FIG. 7b shows an HPLC analysis of time points for the isomerization of 5KGA and iduronate using enzymes in the EC 5.3.1.17 family. Controls: dead enzyme is a control with heat inactivated enzyme; Med BI: refers to reactions without isomerase add/n. Time points, X axis: 1=0 h; 2=1 h; 3=2 h; 4=17 h.

Enzymes from the EC 5.3.1.12 family (glucuronate isomerases) were also purified by gel electrophoresis, isolated, and used to prepare reactions by mixing with buffer (50 mM HEPES, 1 mM ZnCl2, pH 8.0) that contained 5 mM of 5KGA or Iduronate. The reactions were incubated at 30° C. and analyzed for product formation using both HPLC and enzymatic methods. Results are shown in FIG. 7b.

5.3.1.17 Enzymes

Enzymes pSGI-478 and pSGI-479 (5-dehydro-4-deoxy-D-glucuronate isomerases) showed isomerization activity for both 5KGA and iduronate. This activity was also confirmed with the enzymatic assays as above. Yields for isomerization of iduronate by pSGI-478 and -479 were 50% and 37%, respectively, when measured enzymatically, and 20% and 18% when measured by HPLC. Yields for 5KGA isomerization were 23% and 26%, respectively, when measured enzymatically, and 24% and 16%, respectively when measured by HPLC. Results are shown in FIG. 7a.

5.3.1.n1 Enzymes

Figure 8:
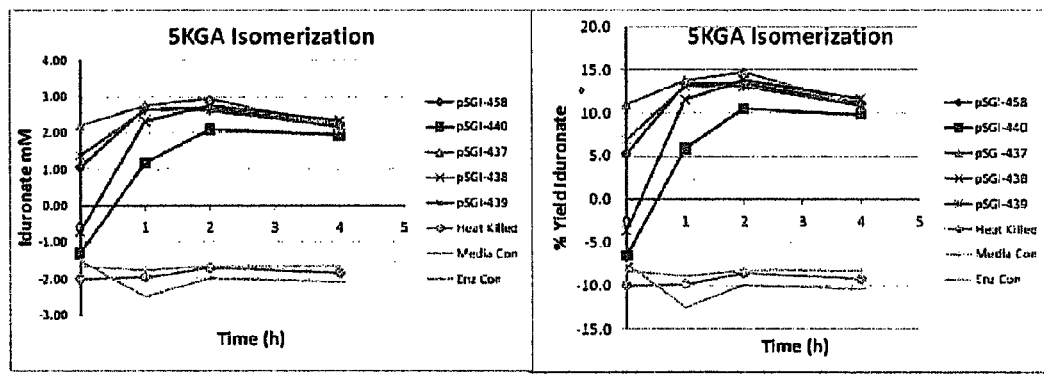
FIG. 8 shows product formation for the isomerization of 5KGA and iduronate with enzymes in the EC 5.3.1.n1 family. The data were obtained from enzymatic assays.

Enzymes in this family were purified by gel electrophoresis. Product formation was measured using enzymatic assays as described above and the results are shown in FIG. 8. All enzymes cloned in this family were shown to have activity for the isomerization of 5KGA and iduronate.

In each case plasmids were transformed in BL21DE3 and proteins purified on a Ni NTA column.

Example 5

Step 16—5-keto-gluconate (5KGA) to (4S)-4,6-dihydroxy 2,5-diketo hexanoate (2,5-DDH)

Figure 9:
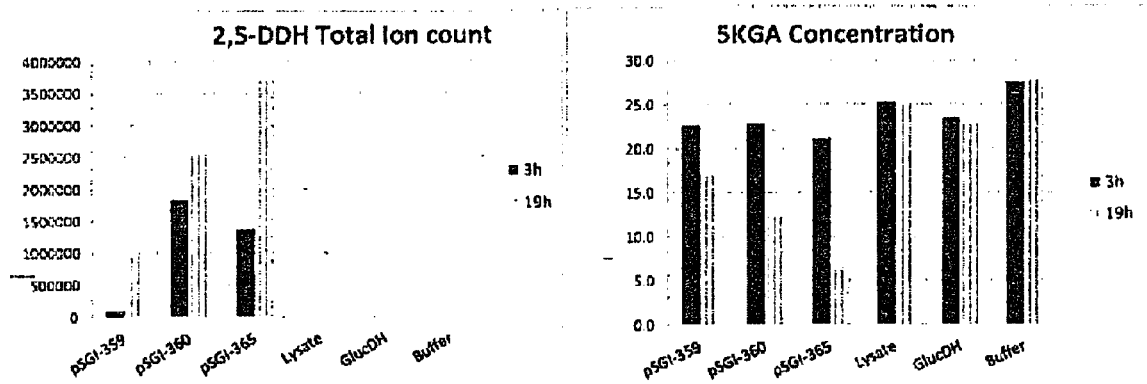
FIG. 9: HPLC analysis of the formation of 2,5-DDH and the reduction of 5 KGA concentration over time. Total ion counts for 2,5-DDH are shown.

The three gluconate dehydratases described in Step 2 (Example 1) were expressed as described in Example 1, along with a purified glucarate dehydratase from Step 8. Enzymatic reactions for activity were performed and HPLC-MS analysis showed the formation of 2,5-DDH (FIG. 9), which was also confirmed by the fact that formation of the new product was accompanied by the reduction of 5-KGA only in the samples containing gluconate dehydratases, as well as by enzymatic assays with DHG dehydratase (pSGI-395). Good slopes at 340 nm indicating large enzyme activity were obtained when NADH, pSGI-395 lysate and aliquots of the previous reactions were mixed (data not shown). This result in combination with the HPLC analysis prove that the gluconate dehydratases examined dehydrate 5KGA to 2,5-DDH.

Example 6

Step 19—Conversion of 1,5-gluconolactone to guluronic acid 6-lactone 1,5-gluconolactone oxidation is a side activity of enzymes from the alditol oxidases (EC 1.1.3.41) family. These enzymes oxidize various alditols such as sorbitol, xylitol, glycerol and others. Enzymes were identified having activity for the oxidation of 1,5-gluconolacone, as shown in Table 6 below.

TABLE 6

Alditol oxidases with activity on 1,5-gluconolactone.

| | | | | 1,5-Gluconolactone | | |
| | | | | Reaction Setup | | |
| Enzyme | Enzyme Source | Sorbitol U/mg | U/mg | Enzyme mg | Substrate mg/mM | Yield |
| --- | --- | --- | --- | --- | --- | --- |
| AO#13 | *Terriglobuds roseus* | 0.23 | 0.02 | 5.3 | 15/85 | 7% |
| AO#22 | *Granulicella mallensis* | 0.27 | 0.015 | 7.6 | 15/85 | 9% |
| AO#28 | *Streptomyces acidiscabies* | 1.30 | 0.010 | 15 | 15/85 | 8% |
| AO#36 | *Actinomycetales* (SGI) | 1.83 | 0.102 | 25 | 90/35 | 46% |
| AO#51 | *Frankia* sp | 0.59 | 0.019 | NT | NT | NT |
| AO#57 | Propionibacteriacaeae (SGI) | 1.47 | 0.051 | 40 | 70/57 | 6% |
| AO#76 | *Streptomyces* sp. | 1.45 | 0.045 | 8.2 | 15/85 | 23% |
| AO#251* | *Paenibacillus* sp. | 0.47 | 0.003 | 24 | 15 8.5 | ~2% |

*crude lysate

Figure 10:
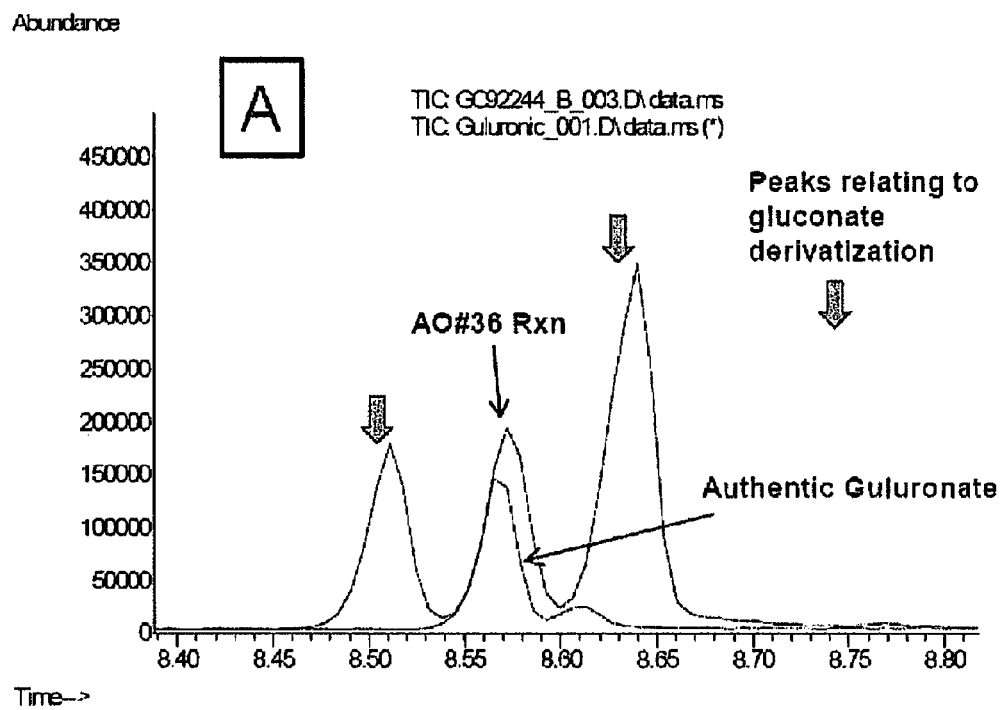
FIG. 10 is a HPLC-MS chromatogram showing the production of guluronic acid lactone from 1,5-gluconolactone. An overlay of a trace of authentic guluronic acid is shown.

Reactions were prepared using lysates of all the purified enzymes shown on Table 6. Reactions were prepared in 50 mM K-phosphate buffer, pH 7.0 with 0.5 mg/mL catalase and incubated at 30° C. A new product was observed by HPLC-MS analysis showing the same retention time as guluronate after comparison with authentic standards (FIG. 10). This was confirmed by GC-MS, where the product also had the same MS fingerprint as guluronate. It is therefore clear that all the alditol oxidases described in the Table oxidize the 6-OH of 1,5-gluconolactone to produce the guluronic acid lactone. All alditol oxidases were cloned in pET28a with a HisTag and were expressed in BL21DE3 and purified on a Ni NTA column.

Example 7

Synthesis of FDCA and Other Intermediates

Purified DDG mono potassium salt was used for the dehydration to 2,5-FDCA. Sulfuric acid was added to DDG and the reaction stirred at 60° C. The in situ yield was calculated (by HPLC-MS) to be ~24% and ~27%.

The reaction solutions were combined and then diluted by pouring into ice (to neutralize the heat). Approximately equivalent volume of THF was added, and the solution transferred to a separation funnel. Sodium chloride salt was added until separation was achieved. The solution was agitated between additions for best possible dissolution. The aqueous layer was removed, and the THF layer washed 3× more with sat. NaCL solution. Sodium sulfate was added and the solution left sitting overnight. Two layers formed again overnight. The aqueous layer was discarded and then silica gel was added to the solution. It was then concentrated down to solids via rotovap. The solids were loaded into a silica flash column and then separated via chromatographically. The fraction was concentrated and dried. The isolated yield was 1739 mg. Corrected yield: 24.9%. $^1$H and $^{13}$C NMR and HPLC-MS analysis confirmed the product Dehydration of DDG Dibutyl-2,5-FDCA in BuOH/H$_2$SO$_4$ Dehydration of un-derivitized lyophilized DDG containing the dehydration salts in BuOH was done using a Dean-Stark apparatus. Under these conditions, DDG was added to BuOH, and then H2SO4 was added and the reaction heated at 140° C. After stirring for 4 h HPLC-MS analysis shows the disappearance of DDG and the formation of dibutyl-2,5-FDCA. The in situ yield was calculated (by HPLC-MS) to be 36.5%.

The mixture was extracted with water, 1% NaOH, and again with water. Then the organic layer was concentrated to a final mass of 3721 g. A portion of this mass (3.4423 g) was removed and 0.34 g of dibutyl-2,5-FDCA was purified using HPLC. Extrapolating the yield of the isolated product to the total amount of compound isolated from the reaction (37.21 g) and taking into account the amount of salts present in the original DDG (~60% pure by weight) the reaction yield was calculated to be 42%. $^1$H and $^{13}$C NMR and HPLC-MS analysis confirmed the product Synthesis of Dibutyl DDG In another aspect the invention provides a method for synthesizing a derivative of DDG. The method involves contacting DDG with an alcohol, an inorganic acid, and optionally a co-solvent to produce a derivative of DDG. Optionally the derivative of DDG can be purified. The reaction can have a yield of the derivative of DDG of at least 10% molar yield or at least 15% molar yield or at least 20% molar yield or at least 25% or at least 30% or at least 35% molar yield or at least 40% molar yield. The inorganic acid can be sulfuric acid and the alcohol can be methanol, ethanol, propanol, butanol, isobutanol, or any C1-C20 alcohol. In various embodiments the co-solvent can be any of THF, acetone, acetonitrile, an ether, butyl acetate, an dioxane, chloroform, methylene chloride, 1,2-dichloroethane, a hexane, toluene, and a xylene. When the alcohol is ethanol the DDG derivative will be DDG mono-ethyl ester and/or DDG diethyl ester. When the alcohol is butanol the DDG derivative will be DDG mono-butyl ester and/or DDG dibutyl ester.

DDG mono-potassium salt was used for derivatization according to the following protocol. In a IL Morton type indented reaction vessel equipped with a mechanical stirrer and heating mantle was charged with 60:40 DDG:KCl (31.2 mmol), BuOH, and heptane. In a separate vial, sulfuric acid was added to water, and allowed to cool after dissolution. The solution was then added to the flask. The solution was kept at 30° C.

The precipitate was filtered off concentrated. The remaining gel was dissolved in EtOAc, and then TLC plates were spotted with the solutions and the plates were sprayed with a phosphomolybdic acid mixture, and then heated to at least 150° C. on a hot plate to identify the DDG-DBE fraction.

Isolated yield: 4.62 g (15.2 mmol, 47% yield), >98% purity. $^1$H and $^{13}$C NMR and HPLC-MS analysis confirmed the product.

Different solvents can be used in the synthesis of DDG esters, such as mixtures of BuOH (5%-95% v/v) with co-solvents such as THF, acetone, acetonitrile, ethers (dibutyl, ditheyl etc), esters such as Butyl-acetate, 1,6-dioxane, chloroform, methylene chloride, 1,2-dichloroethane, hexanes, toluene, and xylenes may be used as cosolvents. Reaction catalysts such as acids (sulfuric, hydrochloric, polyphosphoric or immobilized acids such as DOWEX) or bases (pyridine, ethyl-amine, diethyl-amine, boron trifluoride) or other catalysts commonly used for the esterification of carboxylic acids.

Dehydration of dibutyl-DDG to dibutyl-FDCA in n-BuOH/H$_2$SO$_4$

A stock solution of DDG-DBE (di-butyl ester) was made in butanol and transferred to a clean, dry 100 mL round-bottomed flask equipped with a stir bar. To the flask, 25 mL of conc. sulfuric acid was added. The flask was sealed and then stirred at 60° C. for 2 hrs. The in situ yield was calculated to be ~56%. The reaction solution was concentrated and the residue was dissolved in MTBE and transferred to a separation funnel, and then washed with water. The recovered organic layer was concentrated and then separated via HPLC for an isolated yield: 250.7 mg (~90% purity) and 35% isolated yield (corrected for purity). $^1$C and $^{13}$C NMR and HPLC-MS analysis confirmed the product.

Example 8

Cell Free Synthesis of DDG and FDCA and Derivatives from 5-KGA (Route 2A)

This example illustrates the enzymatic conversion of 5KGA to DDG using purified enzymes according to Scheme 6 (a sub-Scheme of 2B), and also illustrates the DDG produced being dehydrated to FDCA using chemical steps. The Scheme involves the steps of isomerization of 5KGA (Step 15) and the subsequent oxidation to idaric acid (Step 7B). DDG was also dehydrated under differing chemical conditions to FDCA. The last step (Step-8A) was performed using glucarate dehydratase from *E. coli*.

Figure 11:
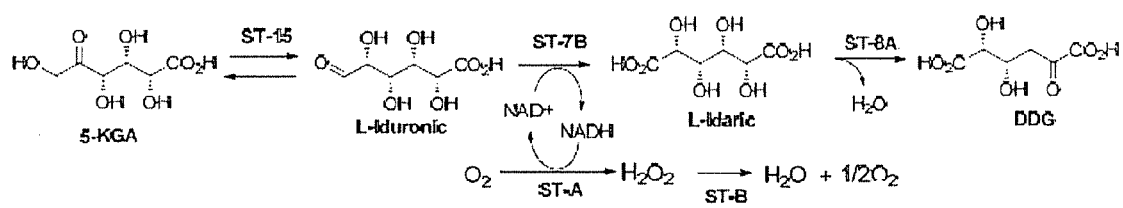
FIG. 11 is a schematic illustration of the Scheme 6 reaction pathway.

Scheme 6 is illustrated in FIG. 11. The scheme was performed using a cell free enzymatic synthesis of DDG from 5-KGA. The Scheme involves the performance of steps 15, 7B and 8A. Two additional proteins were used to complete the reaction path, the first being NADH-oxidase (Step A) that is recycling the NAD+ cofactor in the presence of oxygen, and catalase (Step B) that decomposes the peroxide produced from the action of NADH oxidase. The enzymes are shown in the following Table 7. All enzymes contained a HisTag and were purified using an Ni-NTA column. Yields for this synthesis of DDG were calculated to be at least 88-97%.

TABLE 7

| STEP | Enzyme | EC | Organism |
|------|--------|-----|----------|
| 15 | pSGI-433 (DTHU_IS) | 5.3.1.17 | *Rhizobium* (SGI) |
| 15 | pSGI-434 (DTHU_IS) | 5.3.1.17 | *E. coli* |
| 7B | pSGI-476 (UroDH) | 1.1.1.203 | *Pseudomonas* (SGI) |
| 8A | pSGI-353 (GlucDH) | 4.2.1.40 | *E. coli* |

TABLE 7-continued

| STEP | Enzyme | EC | Organism |
|------|--------|------|----------|
| A | pSGI-431 (NADH_OX) | 1.6.3.1 | Thermus thermophiilus |
| B | Catalase | 1.11.1.6 | Corynbacterium |

Figure 12A:
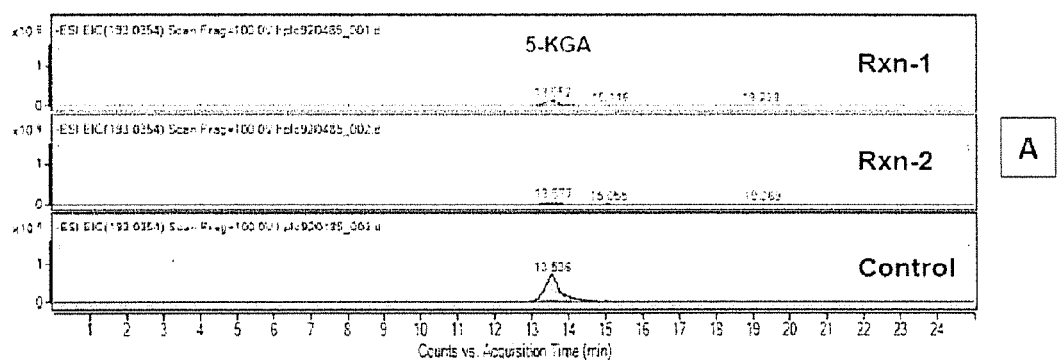
FIGS. 12a and 12b are LC-MS chromatograms showing S-KGA and DDG reaction products, respectively.
Figure 12B:
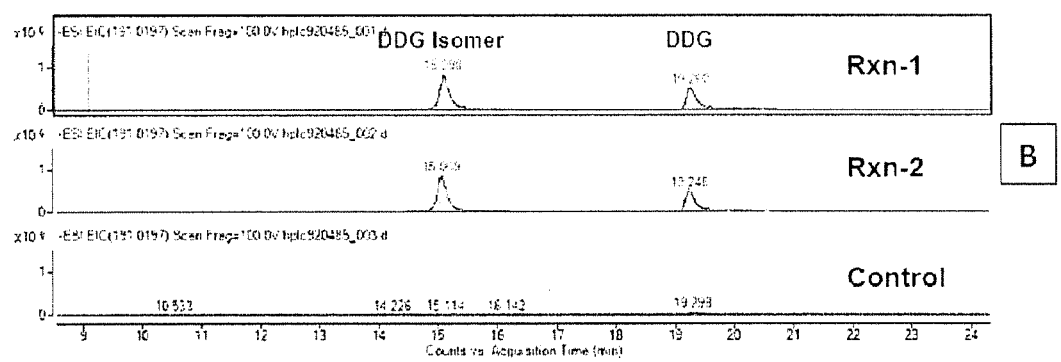

500 mL of liquid culture was purified for each isomerase for the reaction. Besides the enzymes shown on Table 7, each reaction contained 50 mM TrisHCl (pH 8.0), 50 mM NaCl, 1 mM $ZnCl_2$ and 2 mM $MgCl_2$, 1 mM $MnCl_2$ and 1 mM $NAD^+$. Reactions were analyzed by HPLC after 16 h of incubation and FIG. 12 presents the chromatograms.

Figure 13:
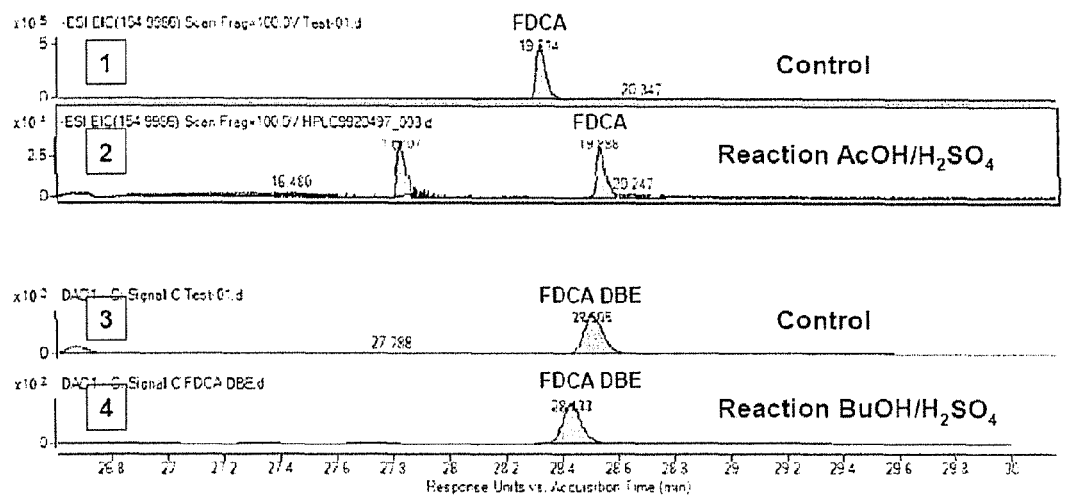
FIG. 13 is a an LC-MS chromatogram showing FDCA and FDCA dibutyl ester derivative reaction products.
Figure 14A:
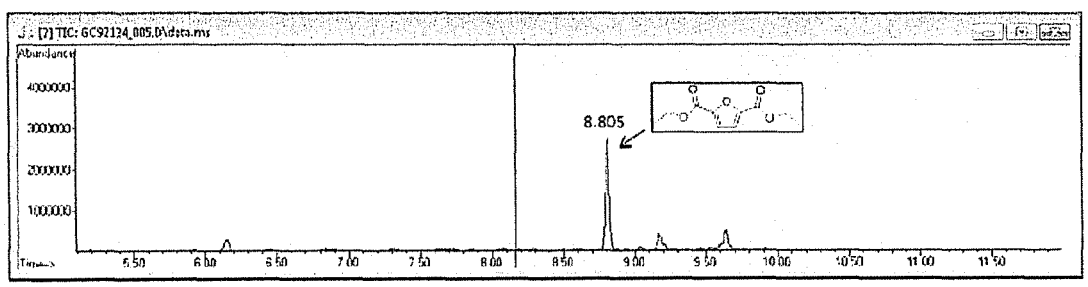
FIG. 14a is a GC-MS analysis of a crude reaction sample of the diethyl-FDCA synthesis from the reaction of DDG with ethanol. Single peak corresponded to diethyl-FDCA.
Figure 14B:
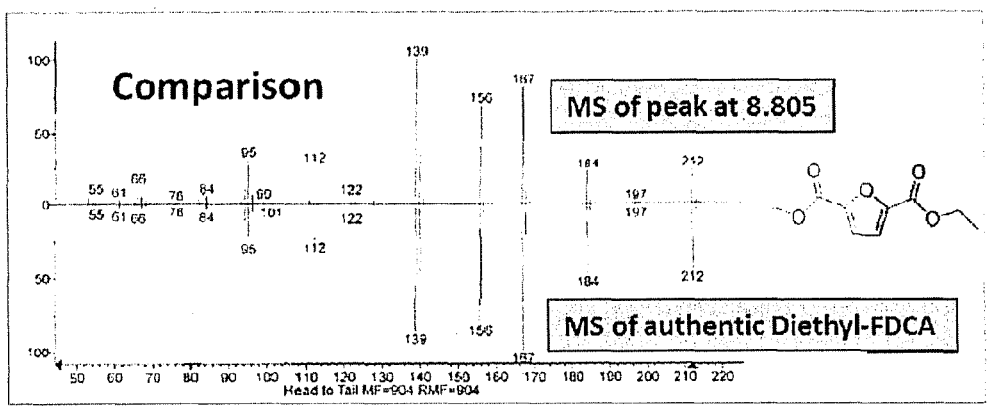
FIG. 14b is an MS fragmentation of the major product from the reaction of DDG with ethanol.

For dehydration to FDCA, the reaction mixtures of both samples were combined and lyophilized into a white powder, which was split into two samples and each dissolved in AcOH with 0.25M $H_2SO_4$ or in 4.5 mL BuOH with 0.25M $H_2SO_4$. Both reactions were heated in sealed vials for 2-4 h at 120° C. Reaction products are shown in FIG. 13.

Samples 1 and 2 represent authentic standard and the 3 h time point from the reaction in AcOH/$H_2SO_4$, respectively. Spiking of sample 2 with sample 1 gave a single peak further verifying the FDCA product. Samples 1 and 3 (FIG. 13) represent authentic standard and the 4 h time point from the reaction in BuOH/$H_2SO_4$, respectively. The formation of FDCA from the enzymatic reactions further confirms the presence of DDG in these samples.

Example 9

Synthesis of DDG from Glucose and Gluconate

This example shows the enzymatic conversion of glucose and gluconate to DDG. The reaction was conducted with purified enzymes, and crude lysates as a catalyst. Enzymes and substrates were combined in a bio-reactor as shown in the Table below:

| | Substrate | ST-1 | ST-14 pSGI-504 | ST-15 pSGI-434 | ST-7B pSGI-476 | ST-8A pSGI-353 | ST-A pSGI-431 | ST-B |
|---|---|---|---|---|---|---|---|---|
| Rxn-1 | Glucose 600 mg | 2 mg | 7 mL[1] | 50 mL[2] | 7.5 mL[1] | 1 mL[3] | 4 mL[4] | 2 mg |
| Rxn-2 | Gluconate 700 mg | — | 7 mL | 50 mL | 7.5 mL | 1 mL | 4 mL | 2 mg |

Figure 17:
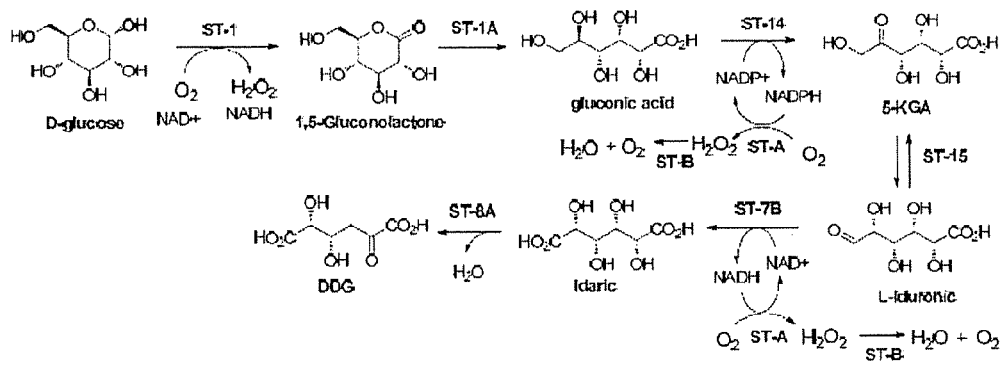
FIG. 17 is a schematic illustration of Scheme 1. Cell free enzymatic synthesis of DDG from glucose. Enzymes are ST-1: glucose oxidase; ST-1A: hydrolysis-chemical; ST-14: gluconate dehydrogenase (pSGI-504); ST-15: 5-dehydro-4-deoxy-D-glucuronate isomerase (DTHU IS, pSGI-434); ST-7B: Uronate dehydrogenase (UroDH, pSGI-476)); ST-8A Glucarate dehydratase (GlucDH, pSGI-353); ST-A: NAD(P)H oxidase (NADH_OX, pSGI-431); ST-B: Catalase.
Figure 17B:
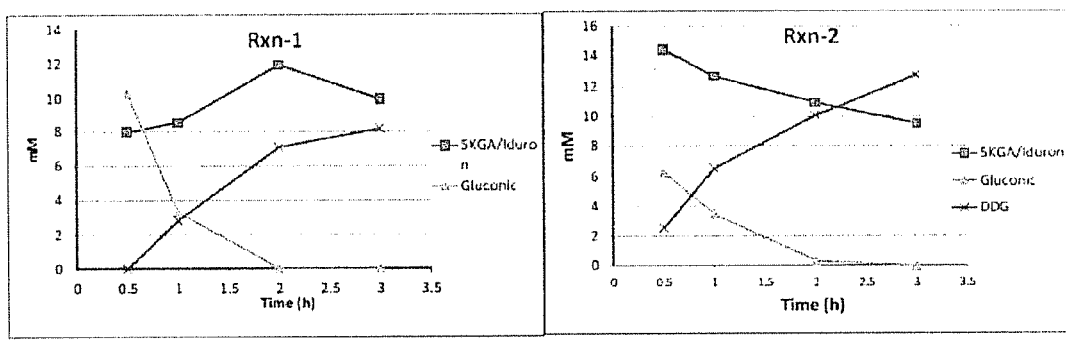
FIG. 17b shows the concentration of reaction intermediates over the first 3 h as analyzed by HPLC. Formation of DDG is shown in both reactions.

[1]Lysate from 500 mL liquid culture of recombinant E. coli with plasmid
[2]Lysate from 2 L liquid culture of BL21DE3/pSGI-434
[3]Purified enzyme, ~30 Units of activity (or 3 mg of purified GlucD)
[4]Lysate from 250 mL of culture The reaction was incubated at 35° C. and dissolved oxygen and pH were kept at 20% and 8 respectively. Time points were analyzed by HPLC-MS and the results are shown in FIG. 17b. Extracted chromatograms verified the DDG mass (not shown) and corresponding MS fragmentation. The results clearly showed production of DDG during incubation of the enzymes with either glucose or gluconate.

Example 10

Construction of Expression Cassettes for Recombinant Gluconate Dehydratases

The following example describes the creation of recombinant nucleic acid constructs that contained coding sequence of a D-glucarate dehydratase activity (GDH, EC 4.2.1.40) for heterologous expression in E. coli cells.

Genes encoding D-Glucarate dehydratase from E. coli (Expasy: P0AES2), Acinetobacter ADP1 (Expasy: P0AES2), as well as a proprietary Pseudomonas bacterial strain (BP1MICT2128114) were PCR-amplified from genomic DNA.

Each of the PCR-amplified genes was subsequently cloned into the bacterial transformation vector pET24a(+), in which the expression of each of the GDH genes was placed under control of a T7 promoter. The nucleotide sequences of each of the PCR-amplified inserts were also verified by sequencing confirmation.

Example 11

E. coli Strains Expressing Recombinant Glucarate Dehydratases

Each of the expression vectors constructed as described in Example 9 was introduced into NovaBlue(DE3) E. coli by heat shock-mediated transformation. Putative transformants were selected on LB agar supplemented with Kanamycin (50 µg/ml). Appropriate PCR primers were used in colony-PCR assays to confirm positive clones that contained each of the expression vectors.

For each expression vector, a bacterial colony was picked from transformation plates and allowed to grow at 30° C. in liquid LB media supplemented with Kanamycin (50 µg/ml) for two days. The culture was then transferred into vials containing 15% glycerol and stored at −80° C. as a frozen pure culture.

Example 11

Demonstration of In Vitro Synthesis of DDG by Using Cell Lysate of Recombinant E. coli Cells Expressing a GDH Enzyme This Example describes how in intro synthesis of DDG intermediate was achieved using recombinant GDH enzymes produced in E. coli cells.

Preparation of Cell Lysates:

Recombinant bacterial strains constructed as described previously in Example 2 were grown individually in 3 mL of liquid LB media supplemented with Kanamycin (50 µg/ml) at 30° C. on a rotating shaker with rotation speed pre-set at 250 rpm for 1 day. This preculture was used to inoculate 100 mL of TB media containing Kanamycin (50 ug/ml), followed by incubation at 30° C. on a rotating shaker pre-set at 250 rpm for 2-3 hour until early log phase ($OD_{600}$~0.5-0.6) before isopropyl D-1 thiogalactopyranoside (IPTG; 0.25 mM final concentration) was added to induce protein expression. Cells were allowed to grow for another 18 hours at 30° C. before they were harvested by centrifugation, resuspended in 15 mL of lysis buffer (10 mM phosphate buffer, pH 7.8, 2 mM $MgCl_2$) and were lysed by sonication. The production of recombinant enzymes in E.

coli cells was quantified using standard pre-cast SDS-PAGE gels system (BioRad), and specific activity was measured according to a procedure described by Gulick et al. (Biochemistry 39, 4590-4602, 2000). Cell lysates were then tested for the ability to convert gram amounts of glucarate to DDG as described in greater details below.

Enzymatic Dehydration of Glucarate:

Five grams of mono-potassium glucarate (~0.02 moles) were added to 85 mL of 5 mM potassium phosphate buffer containing 10 mM MgCl2. The substrate glucarate was found slowly dissolved following the addition of ~2 mL of 5M NaOH. The pH of the reaction was adjusted to about 7.8. Subsequently, 15 mL of a cell lysate containing each of the three recombinant dehydratases in 10 mM phosphate buffer, pH 7.8, as described in Example 3. After incubation with gentle stirring at 30° C. for 1-2 hours, the reactions were analyzed using HPLC-MS techniques. HPLC-MS results indicated a new peak as the only major product with a molecular weight corresponding to predicted product DDG, and trace amounts of the mono-potassium glucarate substrate. No other byproducts were detected by HPLC-MS analysis, indicating that the conversion reaction catalyzed by each of the recombinant enzymes was very efficient and highly specific.

Purification of DDG Product from Enzymatic Reactions:

DDG produced via enzymatic dehydration was purified by using either of the two following techniques.

The enzymatic dehydration reactions were acidified to pH~2.0 with 6M HCl, filtered to eliminate precipitated proteins, and subsequently lyophilized. Methanol (MeOH) was added to the lyophilized powders, followed by gentle stirring for 10-15 minutes to dissolve the DDG product but not the other salts in the dehydration reaction mixtures (such as KCl and phosphates). Substantially pure DDG acid was obtained following filtration of the suspensions and evaporation of MeOH.

In some instances, an alternative procedure was deployed for the purification of DDG salt, in which the first MeOH filtrate was condensed to a volume of ~15-25 mL, then mixed with an equal volume of MeOH containing 0.5M KOH. Potassium salt of DDG precipitated after addition of KOH was subsequently isolated by filtration.

Results of HPLC-MS analyses indicated that DDG product constituted at least 95% of the total products in the samples obtained from either of the two purification techniques.

Example 12

Demonstration of In Vitro Synthesis of FDCA from DDG in One-Step Chemical Reaction Applicants have discovered that the synthesis of FDCA (i.e. the free acid form) could be achieved by a chemical conversion of DDG to FDCA in the presence of H2SO4. The reaction was performed as follows. Approximately 20 mg of DDG acid (crude lyophilized powder with salts previously purified as described in Example 3) and 0.25 M of H2SO4 were added into an air tight sealed tube containing 1 mL of water and 1 mL of DMSO. The DDG was found completely dissolved in this solution. The reaction was stirred at 105° C. for 18 hours. Results of an HPLC-MS analysis performed on a crude reaction sample indicated the formation of FDCA free acid (FDCA: 2,5-furan dicarboxylic acid) as the major product, as well as insignificant amounts of some other unidentified byproducts. As a control in HPLC-MS analysis, a commercial FDCA was analyzed in the same conditions.

Example 13

Demonstration of in vitro synthesis of FDCA-esters (dimethyl-, diethyl-, dibutyl-, and isopropyl-esters)

Synthesis of diethyl-2,5 FDCA from purified DDG

In an air tight sealed tube, 18 mL of EtOH, 0.2 gram (1 mmole) of DDG acid, previously purified as described in Example 11, and 0.25 M of $H_2SO_4$ were added. The DDG acid was not completely dissolved in this solution. The reaction was gently stirred at 105° C. for 18 hours. Results of a GC-MS analysis of a crude reaction sample indicated that the formation of diethyl-FDCA the major product. As a control, an authentic FDCA was chemically synthesized, esterified to diethyl-FDCA and analyzed in the same conditions.

Example 14

Synthesis of dibutyl-2,5 FDCA from Purified DDG

Figure 15A:
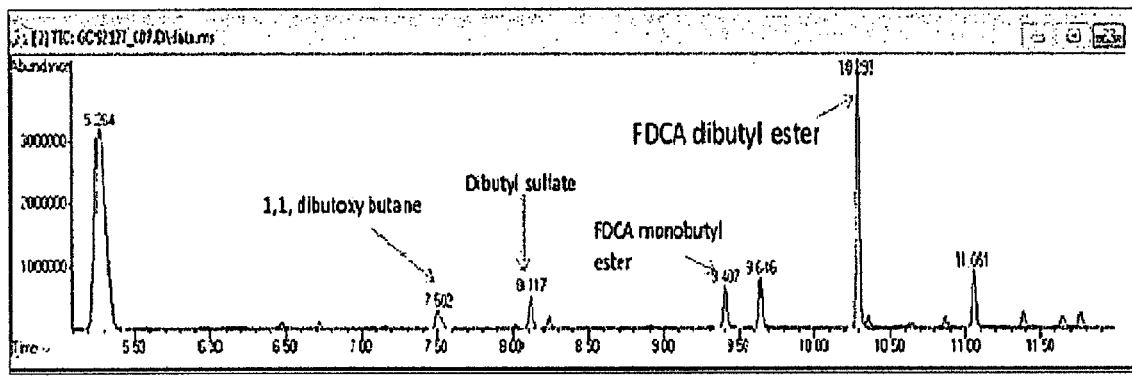
FIG. 15a is a GC-MS analysis of a crude reaction sample of the diethyl-FDCA synthesis from the reaction of DDG with ethanol. Single peak corresponded to diethyl-FDCA.
Figure 15B:
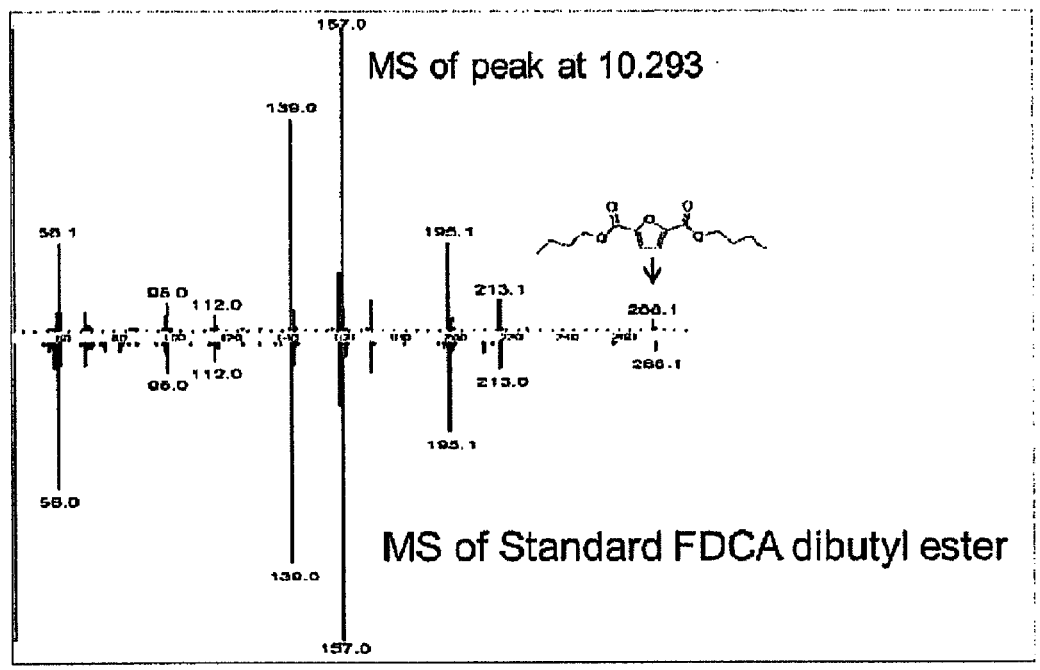
FIG. 15b is a MS fragmentation of the major product from the reaction of DDG with ethanol.

In an air tight sealed tube, 18 mL of n-BuOH, 0.2 gram (1 mmole) of DDG acid, previously purified as described in Example 11, and 0.25 M of $H_2SO_4$ were added. The DDG acid was not completely dissolved in this solution. The reaction was gently stirred at 105° C. for 18 hours. As shown in FIG. 15, results of the GC-MS analysis of a reaction sample indicated that diethyl-FDCA (FDCA: 2,5-furan dicarboxylic acid) was formed as the major product. As a control, an authentic FDCA was chemically synthesized, esterified to diethyl-FDCA, and analyzed in the same conditions.

Example 15

Synthesis of dibutyl-2,5 FDCA from Crude DDG (Unpurified)

0.2 gram (1 mmole) of crude DDG acid, which was an unpurified lyophilized powder obtained directly from the enzymatic dehydration of glucarate as described in Example 11, was added into an air tight sealed tube containing 18 mL of n-BuOH, followed by addition of 0.25 M of $H_2SO_4$. The crude DDG acid was not completely dissolved in this solution. The reaction was gently stirred at 105° C. for 18 hours. Results of a GC-MS analysis of a crude reaction sample indicated that diethyl-FDCA (FDCA: 2,5-furan dicarboxylic acid) was formed as the major product. The GC-MS result indicated that the present of contaminant salts in crude/unpurified lyophilized powder did not significantly affect the reaction outcome. As a control, an authentic FDCA was chemically synthesized, esterified to diethyl-FDCA, and analyzed in the same conditions.

Example 16

In Vitro Production of FDCA and/or Esters Using Immobilized Acids

In industrial practices, immobilized acids offer many advantages for performing dehydrations since they can typically operate in several types of solvent (aqueous, organic or mixed, etc.). In addition, they can be easily recycled and be re-used. Following some examples of the synthesis of esters of FDCA using immobilized AMBERLYST®15 (Rohm and Haas, Philadelphia, Pa.) and DOWEX®50 WX8 (Dow Chemical Co, Midland, Mich.).

Synthesis of dibutyl-FDCA from Crude DDG by Using DOWEX®50 WX8

In an air tight sealed tube, 2 mL of n-Butanol, 20 mg of crude DDG add (unpurified lyophilized powder containing salts) and 200 mg of DOWEX®50 WX8 were combined. The DDG was not completely dissolved in this solution. The reaction was gently stirred at 105° C. for 18 hours. Results of the GC-MS analysis of a crude reaction sample indicated that diethyl-FDCA (FDCA: 2,5-furan dicarboxylic acid) was formed as the major product. This GC-MS result indicated that the present of contaminant salts (phosphate and NaCl) in crude/unpurified lyophilized powder did not significantly affect the reaction outcome. As a control, an authentic FDCA was chemically synthesized esterified to diethyl-FDCA and analyzed in the same conditions.

Synthesis of dibutyl-FDCA from Crude DDG by Using AMBERLYST® 15

In an air tight sealed tube, 2 mL of n-Butanol, 20 mg of crude DDG acid (crude lyophilized powder with salts) and 200 mg of AMBERLYST® 15 (Rohm and Haas, Philadelphia, Pa.) were combined. The DDG was not completely dissolved in this solution. The reaction was gently stirred at 105° C. for 18 hours. Results of the GC-MS analysis of a crude reaction sample indicated that diethyl-FDCA (FDCA: 2,5-furan dicarboxylic acid) was formed as the major product. This GC-MS result indicated that the present of contaminant salts (phosphate and NaCl) in crude/unpurified lyophilized powder did not significantly affect the reaction outcome. As a control, an authentic FDCA was chemically synthesized esterified to diethyl-FDCA and analyzed in the same conditions.

Synthesis of ethyl-FDCA from Crude DDG by Using AMBERLYST® 15

In an air tight sealed tube, 2 mL, of ethanol, 20 mg of crude DDG acid (unpurified lyophilized powder containing salts) and 200 mg of AMBERLYST®15 (Rohm and Haas, Philadelphia, Pa.) were combined. The DDG was not completely dissolved in this solution. The reaction was gently stirred at 105° C. for 18 hours. Results of the GC-MS analysis of a crude reaction sample indicated that diethyl-FDCA (FDCA: 2,5-furan dicarboxylic acid) was formed as the major product. This GC-MS result indicated that the present of contaminant salts (phosphate and NaCl) in crude/unpurified lyophilized powder did not significantly affect the reaction outcome. As a control, a commercial FDCA was chemically esterified to diethyl-FDCA and analyzed in the same conditions.

Synthesis of diethyl-FDCA from Crude DDG by Using DOWEX® 50 WX8

In an air tight sealed tube, 2 mL of ethanol, 20 mg of crude DDG acid (unpurified lyophilized powder containing salts) and 200 mg of DOWEX®50 WX8 were combined. The DDG was not completely dissolved in this solution. The reaction was gently stirred at 105° C. for 18 hours. Results of the GC-MS analysis of a crude reaction sample indicated that diethyl-FDCA (FDCA: 2,5-furan dicarboxylic acid) was formed as the major product. This GC-MS result indicated that the present of contaminant salts (phosphate and NaCl) in crude/unpurified lyophilized powder did not significantly affect the reaction outcome. As a control, a commercial FDCA was chemically esterified to diethyl-FDCA and analyzed in the same conditions.

Example 17

Production of FDCA Derivatives

Figure 16:
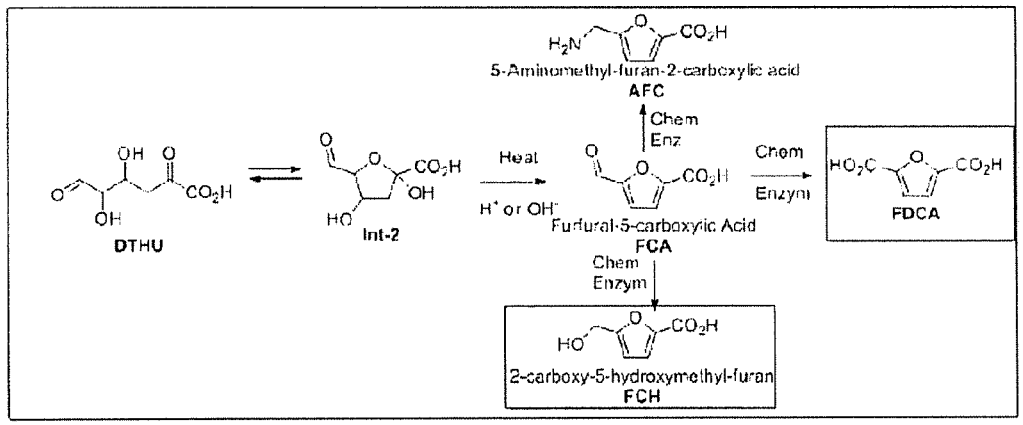
FIG. 16 is a schematic illustration of the synthesis of FDCA and its derivatives from DTHU.

The synthesis of a number of high-value FDCA derivatives is described in FIG. 16 in which dehydration of DTHU produces furfural-5-carboxylic acid, i.e. FCA, which is then chemically or enzymatically oxidized to FDCA, be reduced to FCH, or be transaminated (using chemical reductive amination or transaminase) to amino acid-AFC.

Example 18

Production of di-butyl FDCA in a Gas Phase Reaction

In this example the inlet of the GC was used as a high temperature reactor to catalyze the dehydration of di-butyl DDG to di-butyl FDCA. The resulting products were chromatographically separated detected by mass spectrometry. A solution of di-butyl DDG (10 mM) and sulfuric acid (100 mM) in butanol was placed in a GC vial. The vial was injected into a GC and FDCA Dibutyl ester was observed. The reaction occurred in the 300° C. inlet (residence time 4 seconds). The average yield of 6 injections was 54%.

GC Settings: Direct liquid inject/MS detector
Inlet: 300° C., total flow 29.51 mL/min, split ratio 10:1, split flow 24.1 ml/min, Septum Purge flow 3 mL/min.
GC liner: 4 mm, glass wool (P/N 5183-4647)
Column Flow: 2.41 ml/min He constant pressure control
Oven Program: At 40° C. hold for 2 min, then ramp 25° C./min to 275° C., then ramp 40° C./min to 325° C., hold for 2 min.
Column: HP-SMS, Agilent Technologies, 30 m×0.25 mm×0.25 µm.
Total Runtime: 14.65 minutes
MSD Transfer line: 290° C.
MS Source: 250° C.
MS Quad: 150° C.
Retention times:
2,3-FDCA Dibutyl ester: 9.3 min
2,5-FDCA Dibutyl ester: 93 min All publications and patent applications mentioned in this specification are herein incorporated by reference to the same extent as if each individual publication or patent application was specifically and individually indicated to be incorporated by reference.

No admission is made that any reference constitutes prior art. The discussion of the references states what their authors assert, and the applicants reserve the right to challenge the accuracy and pertinence of the cited documents. It will be clearly understood that although a number of prior art publications are referred to herein, this reference does not constitute an admission that any of these documents forms part of the common general knowledge in the art.

It should also be understood that the foregoing examples are offered to illustrate, but not limit, the invention.

<SEQ ID NO: 1>protein #474
MAMKRLLVTGAAGQLGRVMRKRLASMAEIVRLADLAPLDPAGPNEECMQCDLAD
ADAVDAMVAGCDGIVHLGGISVEKPFEQILQGNIIGLYNLYEAARAHGQPRIIFASSN
HTIGYYPQTERLGPDVPFRPDGLYGVSKCFGESLARMYFEKFGQETALVRIGSCTPEP
LNYRMLSTWFSHDDFVSLIEAAFRAPVLGCPIVWGASANDASWWDNSHLGFIGWKP
KDNAEAFRRKIAETTPQPDARDPIVRFQGGVFVDNPIFKET*

<SEQ ID NO: 2>protein #475
MKRLLITGAAGALGRVMRERLAPMATILRLSDIAPIGAARQNEEIVQCDLADAKAVH
ALVEDCDGIVHLGGVSVERKFSQIVAGNIVGLYNLYEAARAHRMPRIVFASSNHTIGF
YPQTERLSVDHPYRPDGLYGVSKCFGESLAHMYHEKFGQETALVRIGSCVTEPVNH
RMLSTWLSYDDFVSLIEAVFRAPKLGCPVIWGASNNDAGWWDNSAAGFLGWKPKD
NAEIFRSKIEAACERPGSDDPAARWQGGLFTQDPIFPEDE*

<SEQ ID NO: 3>Protein #476
MTTAYTPFNRLLLTGAAGGLGKVLRESLRPYANVLRVSDIAAMSPATGAHEEVQVC
DLADKAAVHQLVEGVDAILHFGGVSVERPFEEILGANICGVFHIYEAARRHGVKRVI
FASSNHVIGFYKQDETIDANCPRRPDSYYGLSKSYGEDMASFYFDRYGIETVSIRIGSS
FPEPHNRRMMSTWLSFADLTQLLERALYTPNVGHTVVYGMSANKNVWWDNHLAA
HLGFQPKDSSEVFRAQIDAQPMPAADDPAMVFQGGAFVAAGPFGDD*

SEQ ID NO: 4 SGI-474-#8807-DNA
ATGGCAATGAAACGGCTTCTTGTTACCGGTGCTGCGGGCCAGCTTGGCCGCGTTA
TGCGCAAACGCCTTGCATCGATGGCCGAGATCGTTCGCCTTGCCGATCTCGCCCC
GCTCGATCCGGCAGGCCCGAACGAGGAATGCATGCAATGCGACCTTGCGGATGC
AGACGCCGTTGACGCCATGGTTGCCGGTTGCGACGGCATCGTTCACCTCGGCGGC
ATATCGGTGGAGAAGCCTTTCGAACAAATCCTTCAGGGCAACATCATCGGGCTGT
ATAATCTCTATGAGGCCGCCCGCGCCCACGGCCAGCCGCGCATCATCTTCGCCAG
TTCGAACCATACGATCGGTTATTACCCGCAGACGGAGAGGCTTGGACCGGATGTT
CCCTTCCGCCCGGATGGGCTTTACGGCGTCTCCAAATGTTTCGGCGAGAGCCTTG
CCCGCATGTATTTCGAGAAATTCGGCCAGGAGACCGCACTTGTCCGCATCGGCTC
CTGCACGCCGGAACCCCTTAATTACCGCATGCTGTCCACCTGGTTTTCGCATGAC
GATTTCGTCTCGCTGATCGAGGCGGCGTTCCGCGCCCCCGTGCTCGGCTGCCCCA
TCGTCTGGGGGCGTCGGCCAACGATGCGAGCTGGTGGGACAATTCGCATCTCG
GCTTTATTGGATGGAAACCGAAGGACAATGCCGAGGCCTTCCGCCGGAAGATTG
CCGAAACGACGCCGCAGCCGGACGCGCGCGACCCGATTGTCCGCTTTCAGGGTG
GCGTGTTTGTCGACAACCCGATCTTCAAGGAGACGTGA

SEQ ID NO: 5 pSGI-475-#7895-DNA
ATGAAGAGACTTCTGATTACCGGCGCAGCGGGTGCACTGGGCCGCGTGATGCGG
GAAAGGCTCGCACCCATGGCAACGATTCTGCGCCTTTCCGATATCGCCCCGATTG
GAGCGGCCCGCCAGAACGAGGAAATCGTCCAGTGCGATCTTGCCGATGCCAAAG
CAGTGCATGCTCTGGTCGAAGATTGCGACGGGATCGTCCATCTCGGTGGCGTCTC
AGTAGAGCGCAAGTTCTCGCAGATCGTCGCCGGCAACATCGTCGGCCTTTACAAT
CTCTACGAAGCCGCACGCGCGCATCGGATGCCGCGCATCGTCTTTGCAAGTTCCA
ATCACACCATCGGCTTTTATCGCAAACCGAACGGTTGTCGGTGGACCATCCCTA
TCGTCCGGACGGGCTCTACGGCGTATCGAAATGTTTCGGCGAGTCTCTGGCGCAT
ATGTACCATGAGAAGTTCGGGCAGGAGACGGCACTCGTGCGCATCGGGTCCTGC
GTGACCGAACCGGTCAACCATCGCATGCTTTCCACCTGGCTTTCCTACGATGATT
TCGTCTCGCTTATCGAGGCCGTATTCCGTGCGCCGAAACTCGGCTGCCCCGTCAT
CTGGGGCGCGTCGAACAACGATGCAGGATGGTGGGACAATTCCGCCGCCGGCTT
TCTCGGCTGGAAGCCGAAAGACAATGCCGAAATCTTCCGTTCGAAGATCGAAGC
CGCTTGCGAACGCCCCGGTTCTGATGATCCGGCCGCCCGCTGGCAAGGCGGGCTC
TTCACGCAGGACCCGATCTTCCCAGAGGACGAGTAA

SEQ ID NO: 6 pSGI-476-#1770-DNA
ATGACCACAGCCTACACCCCCTTCAATCGCCTGCTACTCACCGGAGCGGCAGGCG
GCCTCGGCAAGGTCCTGCGCGAAAGCCTGCGACCCTTATGCCAACGTCCTGCGCGT
CTCCGACATCGCGGCCATGAGCCCTGCCACAGGCGCCCATGAAGAAGTCCAGGT
CTGCGACCTCGCCGATAAAGCGGCGGTCCATCAACTGGTCGAAGGCGTCGACGC
AATCCTGCACTTCGGTGGCGTATCGGTGGAGCGGCCCTTCGAGGAAATCCTCGGG
GCCAATATCTGCGGCGTGTTTCATATCTATGAAGCGGCGCGCCGGCATGGCGTAA
AGCGGGTGATCTTCGCCAGCTCCAACCACGTCATCGGTTTTTATAAGCAGGACGA
AACCATCGACGCCAACTGCCCGCGCCGCCCCGACAGCTACTACGGTCTGTCCAA
GTCCTACGGCGAAGACATGGCCAGCTTCTACTTCGACCGCTACGGCATCGAGACC
GTGAGCATCCGCATCGGCTCCTCGTTCCCCGAGCCGCACAATCGCCGCATGATGA
GCACCTGGCTGAGCTTTGCCGACCTGACGCAGCTGCTCGAACGCGCGCTGTACAC
CCCCAACGTCGGCCACACCGTGGTCTACGGCATGTCCGCTAACAAGAACGTCTG
GTGGGACAACCACCTGGCCGCGCACCTGGGCTTCCAACCGAAGGACAGCTCCGA
GGTGTTCCGTGCGCAGATCGATGCCCAGCCGATGCCCGCCGCCGATGACCCGGC
GATGGTCTTTCAAGGCGGCGCCTTTGTCGCAGCCGGGCCGTTCGGCGACGACTGA

SEQ ID NO: 7 pSGI-433 #8938-Protein
MLNVETRHAVHADHARSLDTEGLRRHFLAQGLFAEGEIRLIYTHYDRFVMGGAVPD
GAPLVLDHVEETKTPGFLDRREMGIVNIGAEGSVHAGNESWSLNRGDVLYLGMGAG
PVTFEGAGRFYLVSAPAHRSLPNRLVTPADSKEVKLGALETSNKRTINQFIHPLVMES
CQLVLGYTTLEDGSVWNTMPAHVHDRRMEAYLYFGMDETSRVLHLMGEPQQTRH
LFVANEEGAISPPWSIHAGAGIGSYTFIWAMAGDNVDYTDMEFIQPGDLR*

SEQ ID NO: 8 pSGI-434_Q46938-Protein
MDVRQSIHSAHAKTLDTQGLRNEFLVEKVFVADEYTMVYSHIDRIIVGGIMPITKTVS
VGGEVGKQLGVSYFLERRELGVINIGGAGTITVDGQCYEIGHRDALYVGKGAKEVV
FASIDTGTPAKFYYNCAPAHTTYPTKKVTPDEVSPVTLGDNLTSNRRTINKYFVPDVL
ETCQLSMGLTELAPGNLWNTMPCHTHERRMEVYFYFNMDDDACVFHMMGQPQET
RHIVMHNEQAVISPSWSIHSGVGTKAYTFIWGMVGENQVFDDMDHVAVKDLR SEQ ID NO: 9 pSGI-435; gene #3891-Protein
MTMKILYGAGPEDVKGYDTQRLRDAFLLDDLFADDRVSFTYTHVDRLILGGAVPVT
TSLTFGSGTEIGTPYLLSAREMGIANLGGTGTIEVDGQRFTLENRDVLYVGRGARQM
TASSLSAERPARFYMNSVPAGADFPHRLITRGEAKPLDLGDARRSNRRRLAMYIHPE
VSPSCLLLMGITDLAEGSAWNTMPPHLHERRMEAYCYFDLSPEDRVIHMMGRPDET
RHLVVADGEAVLSPAWSIHMGAGTGPYAFVWGMTGENQEYNDVAPVAVADLK*

SEQ ID NO: 10 pSGI-436; gene #7102-Protein
MLTVETRHAIDPQTAKRMDTEELRKHFHMGSLFAAGEIRLVYTHYDRMIVGAAVPS
GAPLVLDQVKECGTASILDRREMAVVNVGASGKVSAAGETYAMERGDVLYLPLGS
GKVTFEGEGRFYILSAPAHAAYPARLIRIGEAEKVKLGSAETSNDRTIYQFVHPAVMT
SCQLVVGYTQLHNGSVWNTMPAHVHDRRMEAYLYFDMKPEQRVFHFMGEPQETR
HLVMKNEDAVVSPPWSIHCGAGTGSYTFIWAMAGDNVDYKDVEMVAMEDLR*

SEQ ID NO: 11 pSGI-437; gene #9209-Protein
MSYLLRKPQSNEVSNGVKLVHEVTKSNSDLTYVEFKVLDLASGSSYAEELKKQEICI
VAVTGNITVTDHESTFENIGTRESVFERKPTDSVYISNDRSFEITAVSDARVALCYSPS
EKQLPTKLIKAEDNGIEHRGKFSNKRTVHNILPDSDPSANSLLVVEVYTDSGNWSSYP
PHKHDQDNLPEESFLEETYYHELDPGQGFVFQRVYTDDRSIDETMTVENENVVIVPA
GYHPVGVPDGYTSYYLNVMAGPTRKWKFHNDPAHEWILER*

SEQ ID NO: 12 pSGI-438; gene #9732-Protein
MANLLRKPNGTHGKVHDITPENAKWGYVGFGLFRLKSGESVSEKTGSTEVILVLVE
GKAKISASGEDFGEMGERLNVFEKLPPHCLYVPAESDWHATATTDCVLAVCTAPGK
PGRKAQKLGPESLTLEQRGKGANTRFIHNIAMESRDVADSLLVTEVFTPQGNWSSYP
PHRHDEDNFPDMTYLEETYYHRLNPAQGFGFQRVFTEDGSLDETMAVSDGDVVLVP
KGHHPCGAPYGYEMYYLNVMAGPLRKWRFKNHPDHDWIFKRDNP*

SEQ ID NO: 13 pSGI-439; gene #7403-Protein
MASLLVRPTAPDAQGTVIDVTPESAGWTHVGFRVHKLAKGQRLEASSDDQEVCLVL
LTGRATVTCGEHRFEDIGQRMDIFEQIPPYAVYLPDHVSYAVEATTDLELAVCTAPG
HGNHAPRLIAPDNIKQSTRGQGTNTRVHDILPETEPADSLLVVEVFTPAGNWSSYPP
HKHDVDNLPHESHLEETYYHRINPEQGFAFQRVYTDDRSLDETMAVENGCCVLVPK
GYHPVGASHGYSLYYLNVMAGPKRAWKFHNDPDHEWLMNAG*

SEQ ID NO: 14 pSGI-440; gene F0J748-Protein
MPDLLRKPFGTHGKVHDITPAAAGWRHVGFGLYRLRAGEFAAEATGGNEVILVMV
EGKASIRAAGRDWGVLGERMSVFEKSPPHSLYVPNGAEWALVAETDCIVAVCSAPG
RGGHAARRIGPEGIVLTARGEGTNTRHINNIAMEAEDYCDALLVTEVFTPAGHWSSY
PSHRHDEDDDPRITYLEETYYHRLNPASGFGVQRVYTDDRALDQTMAVSDGDVVLV
PRGHHPCAAPYGIEMYYLNVMAGPLRKWRFLPDPELGIAK SEQ ID NO: 15 pSGI-458; gene A5YBJ4-Protein
MSLLYHKQNQELSSGVRLIQDVNASNSPMKYTAVKVLEFSADSSYEETLEAFEAGIV
VLEGKVTITADDQTFEDVGQRTSIFDKIPTDSVYVSTGLAFGIRAKQAAKILIAYAPTN
QTFP
VRLIRGNIHQVEHRGKYNNKRLVQNILPDNLPFADKLLLVEVYTDSANWSSYPPHRH
DHDDDLPAESLLEEIYYHEMRPKQGFVFQRVYTDDLSLDETMAVQNQDVVVVPKGY
HPVGVPDGYDSYYLNVMAGPTRVWHFHNAPERAWIIDRQ SEQ ID NO: 16 pSGI-478; gene #1874-Protein
MKKFMDENFLLQTETAQKLYHNHAANMPIFDYHCHINPKDIAEDRMFKTITEIWLY
GDHYKWRAMRTNGVDERFCTGDASDWEKFEKWAETVPHTLRNPLYHWTHLELKK
FFGINEILSPKNAREIYDACNEKLQTPAYSCRNIIRMANVHTICTTDDPVDTLEYHQQI
KEDGFEVAVLPAWRPDKAMMVEDPKFFNDYMDQLAEAAGIHIESFEDLMEALDTR
HQYFHDNGCRLSDHGLDTVFAEDYTEEEIKAIFKKIRGGSRLSETEILKFKSCMLYEY
GVMDHSRGWTQQLHIGAQRNNNTRLFKKLGPDTGFDSIGDKPIAEPLAKLLDRLDQ
ENKLCKTVLYNLNPRDNELYATMLGNFQDGSVPGKIQYGSGWWFLDQKDGMIKQ
MNALSNLGLLSRFVGMLTDSRSFLSYTRHEYFRRTLCNLLGNDVENGEIPADMELLG
SMVENICFNNAKNYFNF*

SEQ ID NO: 17 pSGI-479; gene Q9WXR9-Protein
MFLGEDYLLTNRAAVRLFNEVKDLPIVDPHNHLDAKDIVENKPWNDIWEVEGATDH
YVWELMRRCGVSEEYITGSRSNKEKWLALAKVFPRFVGNPTYEWIHLDLWRRFNIK
KVISEETAEEIWEETKKKLPEMTPQKLLRDMKVEILCTTDDPVSTLEHHRKAKEAVE
GVTILPTWRPDRAMNVDKEGWREYVEKMGERYGEDTSTLDGFLNALWKSHEHFKE
HGCVASDHALLEPSVYYVDENRARAVHEKAFSGEKLTQDEINDYKAFMMVQFGKM
NQETNWVTQLHIGALRDYRDSLFKTLGPDSGGDISTNFLRIAEGLRYFLNEFDGKLKI
VLYVLDPTHLPTISTIARAFPNVYVGAPWWFNDSPFGMEMHLKYLASVDLLYNLAG
MVTDSRKLLSFGSRTEMFRRVLSNVVGEMVEKGQIPIKEARELVKHVSYDGPKALFF
G -continued SEQ ID NO: 18 pSGI-480; gene Q9KFI6-Protein
MSINSREVLAEKVKNAVNNQPVTDMHTHLFSPNFGEILLWDIDELLTYHYLVAEVM
RWTDVSIEAFWAMSKREQADLIWEELFIKRSPVSEACRGVLTCLQGLGLDPATRDLQ
VYREYFAKKTSEEQVDTVLQLANVSDVVMTNDPFDDNERISWLEGKQPDSRFHAAL
RLDPLLNEYEQTKHRLRDWGYKVNDEWNEGSIQEVKRFLTDWIERMDPVYMAVSL
PPTFSFPEESNRGRIIRDCLLPVAEKHNIPFAMMIGVKKRVHPALGDAGDFVGKASM
DGVEHLLREYPNNKFLVTMLSRENQHELVVLARKFSNLMIFGCWWFMNNPEIINEM
TRMRMEMLGTSFIPQHSDARVLEQLIYKWHHSKSIIAEVLIDKYDDILQAGWEVTEE
EIKRDVADLFSRNFWRFVGRNDHVTSVKVEQQT SEQ ID NO: 19 pSGI-481; gene O34808-Protein
MEPFMGKNFLLKNETAVSLYHNYAKDMPIIDYHCHLSPKEIYENKTFQNITEAWLYG
DHYKWRIMRANGIEETYITGDAPDEEKFMAWAKTVPMAIGNPLYNWTHLELQRFFG
IYEILNEKSGSAIWKQTNKLLKGEGFGARDLIVKSNVKVVCTTDDPVDSLEYHLLLK
EDKDFPVSVLPGFRPDKGLEINREGFPEWVQALEDAAAISITTYDEFLKALEKRVRFF
HSAGGRVSDHAIDTMVFAETTKEEAGRIFSDRLQGTEVSCEDKKFKTYTLQFLCGL
YAELDWAMQFHINALRNTNTKMMKRLGPDTGYDSMNDEEIAKPLYKLLNSVEMKN
QLPKTILYSLNPNDNYVIASMINSFQDGITPGKIQFGTAWWFNDTKDGMLDQMKALS
NVGLFSRFIGMLTDSRSFLSYTRHEYFRRIVCNLIGEWVENGEVPRDMELLGSIVQGI
CYDNAKHYFQFQEEKANV SEQ ID NO: 20 pSGI-433; gene #8938-DNA
ATGCTCAACGTGGAAACGAGGCACGCCGTTCACGCGGATCACGCGAGATCACTC
GACACAGAGGGCCTGCGCCGGCACTTCCTGGCCCAGGGCCTGTTTGCGGAGGGC
GAGATACGGCTGATCTATACGCATTATGATCGATTCGTCATGGGAGGCGCCGTGC
CGGACGGCGCGCCACTTGTGCTCGATCATGTCGAGGAGACGAAAACGCCGGGCT
TTCTCGACCGACGGGAGATGGGAATCGTCAATATCGGTGCTGAGGGCAGCGTGC
ATGCCGGCAACGAAAGCTGGTCGCTGAACCGTGGTGACGTACTTTATCTCGGCAT
GGGGGCGGGACCGGTCACCTTCGAAGGGGCTGGGCGCTTCTACCTCGTCTCGGC
ACCGGCGCATCGCAGCCTGCCCAACCGGCTCGTCACGCCGGCCGACAGCAAGGA
GGTCAAGCTTGGCGCTCTCGAGACTTCCAACAAACGCACCATCAATCAGTTCATT
CATCCCCTGGTCATGGAAAGCTGCCAGCTCGTGCTGGGATATACCACGCTGGAGG
ACGGCTCGGTCTGGAATACCATGCCCGCGCATGTGCACGACCGACGCATGGAGG
CCTATCTCTATTTCGGCATGGATGAGACATCGCGGGTTCTGCATCTGATGGGCGA
GCCGCAGCAAACGAGGCATCTCTTCGTCGCCAATGAGGAAGGGGCGATCTCTCC
GCCGTGGTCCATCCATGCGGGAGCAGGCATTGGCAGCTATACCTTCATCTGGGCC
ATGGCGGGCGACAATGTCGATTATACCGACATGGAGTTCATCCAGCCGGGAGAT
CTTCGATGA SEQ ID NO: 21 pSGI-434; gene Q46938-Protein
ATGGACGTAAGACAGAGCATCCACAGTGCGCACGCAAAAACGCTGGATACCCAA
GGGCTGCGCAATGAATTTTTGGTTGAAAAGGTATTTGTCGGCGATGAGTACACCA
TGGTTTACAGCCACATTGACCGAATTATTGTTGGCGGCATTATGCCGATAACTAA
AACGGTTTCCGTTGGCGGGGAAGTTGGTAAACAACTCGGCGTAAGCTATTTCCTT
GAACGTCGCGAGTTAGGTGTTATCAATATTGGCGGTGCCGGTACGATTACTGTCG
ATGGCCAATGCTATGAAATCGGTCACCGCGACGCCCTGTATGTTGGTAAAGGTGC
AAAAGAAGTTGTCTTTGCCAGTATTGATACCGGCACTCCGGCGAAGTTTTATTAC
AATTGCGCACCCGCGCATACGACGTATCCCACCAAAAAAGTCACACCGGACGAA
GTATCTCCAGTCACGTTAGGCGATAACCTCACCAGTAACCGTCGCACGATTAACA
AATATTTTGTCCCGGATGTACTGGAAACCTGCCAATTGAGTATGGGGCTGACGGA
GCTGGCTCCGGGTAACTTGTGGAACACCATGCCGTGTCACACCCACGAGCGCCG
GATGGAAGTTTATTTCTATTTCAATATGGATGATGACGCCTGCGTTTTCCACATGA
TGGGGCAGCCGCAAGAAACGCGTCATATTGTGATGCATAACGAGCAGGCGGTGA
TCTCCCCGAGCTGGTCGATCCATTCCGGTGTCGGAACCAAAGCTTATACCTTTAT
CTGGGGCATGGTCGGTGAAAACCAGGTCTTTGATGATATGGACCATGTGGCCGTT
AAAGATTTGCGCTAG SEQ ID NO: 22 pSGI-435; gene #3891-Protein
ATGACGATGAAGATACTCTACGGCGCCGGACCGGAGGATGTGAAAGGGTATGAC
ACGCAGCGCCTGCGCGACGCCTTCCTGCTGGACGACCTCTTCGCCGACGACCGGG
TCAGTTTCACATATACCCATGTCGATCGCCTCATCCTCGGCGGGGCCGTCCCGGT
GACGACGAGCCTCACCTTCGGCTCCGGCACGGAGATCGGAACGCCCTACCTGCTT
TCCGCCCGCGAGATGGGGATCGCCAATCTCGGCGGCACGGGCACGATCGAGGTG
GATGGCCAGCGCTTCACGCTCGAAAACCGCGACGTGCTCTATGTCGGTCGCGGC
GCCCGGCAGATGACCGCCTCCAGCCTGTCGGCGGAGAGGCCAGCCCGCTTCTAC
ATGAATTCCGTGCCCGCCGGCGCCGATTTCCCGCACCGTCTGATCACCCGCGGAG
AGGCCAAGCCCCTCGATCTCGGCGATGCGCGCCGCTCGAACAGGCGCCGGCTCG
CAATGTACATCCATCCGGAGGTCTCGCCGTCCTGCCTGCTGCTCATGGGCATCAC
CGATCTTGCCGAGGGCAGCGCCTGGAACACCATGCCGCCGCATCTGCACGAGCG
GCGGATGGAGGCCTATTGCTACTTCGATCTCTCGCCCGAGGACCGGGTCATCCAC
ATGATGGGTCGGCCGGACGAAACCCGCCACCTTGTCGTGGCCGACGGCGAGGCG
GTCCTCTCTCCCGCCTGGTCGATCCATATGGGTGCCGGGACGGGGCCCTACGCCT
TCGTCTGGGGCATGACCGGCGAAAACCAGGAATACAACGACGTCGCTCCCGTAG
CCGTGGCTGATCTCAAATGA SEQ ID NO: 23 pSGI-436; gene #7102-Protein
ATGCTGACCGTCGAAACCCGCCACGCCATTGATCCGCAGACCGCAAAGCGGATG
GACACGGAAGAGCTGCGCAAGCATTTCCACATGGGCAGCCTGTTTGCTGCCGGT
GAAATCCGCCTCGTCTACACCCACTATGACCGCATGATCGTCGGCGCTGCCGTGC
CCTCGGGCGCGCCGCTGGTGCTGGATCAGGTCAAGGAATGCGGCACCGCCAGCA -continued
TCCTCGACCGCCGCGAGATGGCTGTCGTCAACGTCGGCGCCAGCGGCAAGGTCT
CTGCAGCAGGCGAAACCTACGCCATGGAACGCGGCGACGTGCTCTATCTGCCGC
TGGGCTCCGGCAAGGTGACCTTCGAAGGCGAAGGCCGCTTCTACATTCTCTCCGC
TCCGGCCCACGCTGCTTACCCGGCCCGCCTGATCCGCATCGGCGAGGCCGAGAA
GGTCAAGCTCGGCTCGGCCGAGACCTCCAACGACCGCACCATCTACCAGTTCGTG
CATCCGGCGGTGATGACTTCCTGCCAACTCGTCGTCGGCTACACCCAGCTGCACA
ACGGCTCTGTCTGGAACACCATGCCCGCCCACGTGCATGACCGGCGCATGGAGG
CCTATCTCTATTTCGACATGAAGCGGAGCAGCGCGTGTTCCACTTCATGGGCGA
GCCGCAGGAAACCCGCCATCTGGTCATGAAGAACGAGGATGCGGTGGTCTCCCC
GCCCTGGTCCATCCACTGCGGCGCAGGCACCGGCAGCTACACCTTCATCTGGGCC
ATGGCCGGCGACAACGTCGACTACAAGGACGTGGAAATGGTCGCCATGGAGGAT
CTGCGGTGA SEQ ID NO: 24 pSGI-437; gene #9209-DNA
ATGAGTTATTTGTTGCGTAAGCCGCAGTCGAATGAAGTGTCTAATGGGGTCAAAC
TGGTGCACGAAGTAACGAAATCCAACTCTGATCTCACCTATGTAGAGTTTAAAGT
GTTAGATCTCGCTTCCGGTTCCAGCTATGCAGAAGAATTGAAAAAACAGGAAAT
CTGTATTGTCGCGGTAACGGGAAACATTACAGTGACCGATCACGAGTCGACTTTT
GAGAATATCGGCACGCGTGAAAGCGTATTCGAACGAAAACCGACAGACAGCGTC
TATATTTCAAATGACCGTTCCTTTGAGATCACAGCGGTCAGCGACGCAAGAGTGG
CGCTTTGCTATTCTCCATCGGAAAAACAGCTTCCGACAAAGCTGATCAAAGCGGA
AGACAATGGCATTGAGCATCGCGGGAAGTTTTCAAACAAACGTACTGTTCACAA
CATTCTTCCGGATTCAGACCCTTCAGCTAACAGCCTATTAGTAGTTGAAGTCTAT
ACAGACAGCGGCAACTGGTCCAGCTATCCGCCTCATAAACATGATCAAGACAAT
TTGCCGGAGGAATCTTTTTTAGAAGAAACGTACTACCATGAGTTAGACCCGGGAC
AGGGCTTTGTGTTTCAGCGTGTATACACAGATGACCGCTCGATTGACGAGACAAT
GACTGTAGAAAATGAAAACGTTGTCATCGTTCCTGCAGGATACCACCCGGTAGG
CGTGCCGGACGGATACACATCCTACTATTTAAATGTCATGGCAGGGCCGACGCG
GAAATGGAAGTTTCATAATGACCCGGCGCATGAGTGGATTTTAGAACGTTAA SEQ ID NO: 25 pSGI-438; gene #9732-DNA
ATGGCCAATTTGTTGCGCAAGCCCAACGGCACGCATGGCAAGGTCCACGACATC
ACTCCGGAAAACGCCAAATGGGGTTATGTCGGGTTCGGGCTCTTTCGTCTCAAAT
CCGGCGAGAGTGTCTCCGAAAAGACCGGATCGACGGAGGTGATCCTTGTTCTTGT
GGAAGGCAAGGCAAAGATTTCCGCTTCTGGCGAGGATTTCGGCGAGATGGGTGA
ACGCTTAAACGTGTTCGAGAAACTGCCGCCACACTGCCTCTATGTGCCTGCTGAA
AGCGACTGGCATGCAACCGCCACGACAGATTGTGTTCTGGCTGTTTGCACCGCAC
CGGGCAAGCCAGGCCGCAAGGCACAGAAGCTTGGGCGGAAAGCTTGACACTTG
AACAACGCGGAAAAGGTGCCAATACCCGCTTTATCCATAATATCGCAATGGAAA
GCCGCGATGTTGCCGATAGCCTTCTTGTTACCGAGGTATTCACACCGCAGGGAAA
CTGGTCGTCCTATCCACCCCACAGACACGACGAAGACAATTTTCCGGATATGACC
TATCTGGAAGAGACCTATTATCACCGTCTCAACCCGGCGCAGGGCTTCGGCTTCC
AGCGTGTTTTCACCGAAGACGGAAGCCTTGATGAAACCATGGCGGTCTTCTGACG
GAGACGTCGTGCTTGTACCAAAAGGCCACCATCCATGTGGCGCGCCCTATGGCTA
CGAGATGTATTATCTCAATGTGATGGCCGGTCCCTTGCGCAAATGGCGCTTCAAG
AACCATCCCGACCATGACTGGATTTTCAAACGCGACAATCCGTAA SEQ ID NO: 26 pSGI-439; gene #7403-DNA
ATGGCTTCCCTACTGGTACGCCCCACCGCCCCAGATGCCCAGGGCACCGTGATTG
ACGTTACCCCTGAATCTGCTGGCTGGACGCACGTTGGCTTTCGGGTGCATAAACT
CGCCAAGGGCCAGCGCCTGGAGGCCAGCAGCGATGATCAGGAAGTCTGCCTGGT
GCTGCTCACCGGTCGCGCCACGGTAACTTGCGGCGAGCACCGCTTTGAAGATATT
GGCCAGCGTATGGATATTTTTGAGCAGATCCCTCCCTATGCGGTTTACCTACCTG
ACCATGTTAGCTACGCGGTGGAAGCGACCACAGACTTAGAGCTAGCGGTGTGCA
CCGCCCCTGGGCATGGCAACCATGCCCCACGGCTCATCGCGCCTGACAACATCA
AGCAAAGCACCCGTGGCCAGGGCACCAACACCCGCCATGTTCACGATATTCTGC
CGGAAACCGAGCCCGCCGATAGCCTATTAGTAGTCGAAGTATTCACACCTGCGG
GTAACTGGTCGAGCTACCCGCCCCACAAACACGATGTGGATAACTTACCCCACG
AATCACATCTGGAAGAGACCTACTACCACCGCATTAACCCTGAACAAGGGTTCG
CCTTCCAGCGCGTTTACACCGATGACCGCAGCCTTGATGAAACCATGGCGGTGGA
AAACGGCTGCTGTGTGTTGGTTCCCAAGGGTTACCATCCGGTGGGCGCCTCCCAT
GGCTACTCGCTCTACTACTTAAATGTGATGGCGGGGCCCAAGCGGGCATGGAAA
TTTCACAACGACCCCGACCACGAATGGCTGATGAACGCTGGATAG SEQ ID NO: 27 pSGI-440; gene F0J748-DNA
ATGCCGGACTTACTGAGAAAACCGTTTGGCACCCATGGCAAAGTGCACGATATT
ACCCCAGCAGCAGCAGGTTGGAGACATGTTGGTTTTGGCTTATATCGCTTAAGAG
CGGGCGAATTTGCAGCAGAAGCGACAGGCGGCAATGAAGTTATTCTGGTGATGG
TTGAGGGCAAAGCGTCTATTAGAGCAGCAGGCAGAGATTGGGGCGTTTTAGGCG
AACGTATGAGCGTCTTCGAAAAAAGTCCACCACATTCCCTGTATGTCCCGAATGG
TGCAGAATGGGCCTTAGTAGCCGAAACAGATTGCATTGTAGCAGTGTGTAGCGCT
CCGGGTAGAGGAGGTCATGCTGCAAGAAGAATTGGTCCTGAAGGTATTGTGTTA
ACCGCCAGAGGTGAAGGCACCAATACACGCCACATCAACAACATCGCCATGGAA
GCCGAAGATTATTGTGATGCCCTGTTAGTCACCGAAGTGTTCACCCCAGCCGGCC
ATTGGAGCTCTTATCCATCTCATCGTCATGATGAAGACGACGATCCGCGCATCAC
CTATTTAGAAGAGACCTACTATCATCGCTTAAATCCTGCCTCGGGCTTTGGCGTTC
AACGCGTCTATACCGATGATCGCGCCTTAGATCAAACCATGGCGGTTTCTGATGG
CGATGTTGTTTTAGTTCCTCGCGGCCATCATCCGTGTGCAGCCCCGTATGGTATTG
AAATGTATTACCTGAACGTCATGGCCGGCCCGTTACGTAAATGGCGCTTTTTACC
TGATCCTGAACTTGGCATTGCGAAATAA -continued SEQ ID NO: 28 pSGI-458; gene ASYBJ4-DNA
ATGTCTCTGCTGTACCACAAGCAGAACCAGGAACTGAGTAGTGGTGTGCGCCTG
ATCCAAGATGTTAATGCCAGCAATAGCCCGATGAAATATACCGCCGTGAAAGTG
CTGGAGTTTAGCGCCGATAGCAGCTATGAGGAAACCTTAGAGGCCTTTGAAGCC
GGCATTGTTGTGTTAGAGGGCAAAGTGACCATCACCGCCGACGATCAAACCTTCG
AAGATGTGGGTCAAAGAACCTCGATCTTCGACAAAATCCCCGACCGATAGCGTTT
ATGTGTCTACCGGTTTAGCCTTCGGTATTCGCGCCAAACAAGCCGCCAAAATCTT
AATCGCGTATGCTCCGACCAATCAGACCTTCCCAGTTCGCTTAATTCGCGGCAAT
ATCCACCAGGTGGAACATCGCGGCAAGTACAACAACAAACGCTTAGTGCAGAAC
ATTCTCCCCGGATAATCTCCCGTTCGCCGATAAATTACTGCTGGTTGAGGTGTACA
CCGATAGCGCCAATTGGAGCTCCTATCCGCCGCATAGACATGATCACGATGATTT
ACCGGCCGAAAGTCTGTTAGAGGAGATCTACTATCACGAAATGCGCCCGAAGCA
GGGCTTCGTCTTTCAACGCGTGTATACCGATGATCTGAGTCTGGATGAGACCATG
GCCGTTCAAAATCAAGATGTTGTCGTTGTCCCGAAAGGCTATCATCCGGTTGGTG
TCCCCGACGGCTATGATTCGTATTACCTGAACGTGATGGCCGGCCCGACAAGAGT
GTGGCATTTTCATAATGCTCCGGAACATGCCTGGATTATTGATCGCCAGTAA SEQ ID NO: 29 pSGI-478; gene #1874-DNA
ATGAAAAAATTTATGGATGAAAATTTTCTGTTGCAAACCGAAACAGCGCAGAAA
TTGTATCATAATCACGCGGCAAACATGCCGATTTTCGATTACCACTGCCACATTA
ACCCCAAAGACATCGCGGAAGACCGGATGTTTAAAACCATCACCGAAATCTGGT
TGTACGGCGATCATTATAAATGGCGCGCCATGCGTACAAACGGCGTTGACGAGC
GCTTTTGCACCGGCGATGCAAGCGATTGGGAAAAGTTTGAAAAGTGGGCCGAAA
CGGTTCCTCATACCCTGCGTAATCCGCTTTATCACTGGACACACCTGGAGCTAAA
GAAATTTTTCGGGATTAACGAGATCCTGAGTCCGAAAAATGCCCGGGAAATTTAT
GATGCCTGTAACGAAAAACTGCAAACGCCCGCGTATAGTTGCCGCAACATCATC
CGGATGGCCAATGTGCATACAATCTGTACCACCGACGACCCGGTTGACACACTG
GAATATCATCAGCAAATTAAAGAAGACGGCTTTGAAGTGGCCGGTTTTACCTGCCT
GGCGTCCGGATAAAGCGATGATGGTGGAAGACCCGAAGTTCTTTAACGACTATA
TGGACCAGTTGGCCGAAGCTGCCGGTATCCATATCGAATCGTTTGAGGATTTGAT
GGAAGCCTTGGATACGCGTCACCAGTATTTTCATGATAATGG1TGCCGTTTGTCC
GACCACGGGCTGGATACCGTTTTTGCTGAAGATTATACGGAGGAAGAAATTAAA
GCGATCTTCAAAAAAATCCGTGGCGGCAGCAGGCTTAGCGAAACGGAAATCCTG
AAATTCAAGTCCTGCATGTTGTACGAATATGGGGTGATGACCATTCGCGCGGCT
GGACACAACAATTGCACATTGGCGCACAACGCAACAACAACACCCGTTTGTTCA
AAAAATTAGGTCCCGACACTGGTTTCGATTCGATTGGCGATAAGCCGATCGCTGA
ACCATTGGCCAAATTGCTCGACCGCCTGGATCAGGAAAACAAATTGTGCAAAAC
GGTTTTGTATAATCTGAATCCGCGTGATAACGAGTTGTACGCTACCATGTTGGGC
AACTTTCAGGACGGATCGGTTCCCGGGAAAATTCAATACGGCTCGGGTTGGTGGT
TTCTCGATCAGAAAGACGGCATGATTAAACAGATGAATGCCCTTTCCAATCTGGG
TTTGCTGAGCCGTTTCGTAGGCATGCTGACCGACTCAAGGAGCTTCCTTTCGTAC
ACCCGTCACGAATATTTCCGTCGTACCCTTTGCAACCTGCTTGGGAATGATGTTG
AAAACGGGGAGATTCCGGCAGATATGGAGCTTTTGGGCAGTATGGTTGAGAATA
TTTGTTTTAATAACGCGAAGAACTATTTTAATTTTTAG SEQ ID NO: 30 pSGI-479; gene Q9WXR9-DNA
ATGTTTCTGGGCGAAGACTATCTGCTGACCAATCGTGCGGCAGTTCGTCTGTTCA
ACGAAGTGAAAGATCTGCCGATCGTTGATCCGCATAACCACCTGGATGCGAAAG
ATATCGTGGAAAACAAACCGTGGAACGACATCTGGGAAGTGGAAGGTGCGACCG
ATCACTATGTGTGGGAACTGATGCGTCGTTGTGGTGTTAGCGAAGAATATATTAC
CGGCTCTCGTAGCAACAAAGAAAAATGGCTGGCGCTGGCGAAAGTGTTTCCGCG
TTTTGTGGGTAATCCGACGTACGAATGGATCCACCTGGATCTGTGGCGTCGTTTC
AACATCAAAAAAGTCATCAGCGAAGAAACCGCGGAAGAAATCTGGGAAGAAAC
CAAAAAAAAACTGCCGGAGATGACCCCGCAGAAACTGCTGCGCGACATGAAAGT
GGAAATCCTGTGCACCACCGATGATCCGGTGTCTACCCTGGAACATCACCGTAAA
GCGAAAGAAGCCGTGGAAGGCGTGACCATTTTACCGACCTGGCGTCCGGATCGT
GCAATGAATG1TGATAAAGAAGGTTGGCGTGAATATGTTGAAAAAATGGGTGAA
CGCTATGGCGAAGATACCAGCACCCTGGATGGTTTTCTGAATGCCCTGTGGAAAA
GCCACGAACACTTCAAAGAACACGGCTGTGTGGCGAGCGATCATGCGCTGCTGG
AACCGAGCGTGTACTACGTGGATGAAAACCGCGCGCGTGCAGTTCATGAAAAAG
CATTTTCTGGTGAAAAACTGACTCAAGATGAAATCAACGACTATAAAGCGTTCAT
GATGGTGCAGTTCGGCAAAATGAACCAGGAAACCAACTGGGTGACCCAGCTGCA
CATTGGTGCCCTGCGCGATTACCGCGATAGCCTGTTCAAAACCCTGGGCCCGGAT
TCTGGTGGCGATATCAGCACCAACTTTCTGCGTATTGCTGAAGGTCTGCGCTTATTT
TCTGAACGAATTTGATGGTAAACTGAAATTGTGCTGTACGTGCTGGATCCGACC
CATTTACCGACCATTTCGACCATTGCACGTGCGTTCCCGAACGTGTATGTGGGTG
CACCGTGGTGGTTCAACGATAGCCCGTTCGGCATGGAAATGCACCTGAAATACCT
GGCGAGCGTTGATCTGCTGTACAATCTGGCTGGTATGGTTACCGATTCACGTAAA
TTACTGAGTTTTGGTTCTCGTACCGAAATGTTTCGTCGCGTTCTGTCTAATGTGGT
TGGCGAAATGGTGGAAAAAGGCCAGATCCCGATCAAAGAAGCGCGCGAACTGGT
GAAACACGTGAGCTACGACGGCCCGAAAGCCCTGTTCTTTGGCTGA SEQ ID NO: 31 pSGI-480; gene Q9KFI6-DNA
ATGAGCATCAACAGCCGTGAAGTTCTGGCGGAAAAAGTGAAAAACGCGGTGAAC
AACCAGCCGGTTACCGATATGCATACCCACCTGTTTAGCCCGAACTTTGGCGAAA
TTCTGCTGTGGGACATCGATGAACTGCTGACCTATCACTACCTGGTTGCGGAAGT
TATGCGTTGGACCGATGTGAGCATTGAAGCGTTTTGGGCAATGAGCAAACGTGA
ACAGGCCGATCTGATTTGGGAAGAACTGTTCATCAAACGCAGCCCGGTGAGCGA
AGCATGTCGTGGCGTTCTGACCTGTTTACAAGGTTTAGGTCTGGATCCGGCAACT
CGTGATTTACAGGTGTATCGTGAATACTTCGCCAAAAAAACCAGCGAGGAACAG
GTGGATACCGTTCTGCAGCTGGCAAATGTGAGCGATGTGGTGATGACCAATGATC CGTTCGATGATAATGAACGCATCAGCTGGCTGGAAGGCAAACAGCCGGATAGCC
GCTTTCATGCAGCGTTACGTCTGGATCCGCTGCTGAATGAATATGAACAGACCAA
ACATCGTCTGCGTGATTGGGGTTATAAAGTGAACGACGAATGGAACGAAGGCAG
CATCCAGGAAGTGAAACGCTTTCTGACCGACTGGATTGAACGTATGGATCCGGTG
TATATGGCGGTGAGCTTACCGCCGACCTTCAGCTTTCCGGAAGAATCGAACCGTG
GCCGCATTATCCGTGATTGTCTGTTACCGGTTGCAGAAAAACATAACATCCCGTT
TGCAATGATGATTGGCGTGAAAAAACGCGTGCATCCGGCGTTAGGTGATGCAGG
CGATTTTGTGGGTAAAGCAAGTATGGATGGCGTTAACACCTGCTGCGCGAATAC
CCGAACAACAAATTCCTGGTGACCATGCTGAGCCGCGAAAACCAGCAGAACTG
GTGGTTCTGGCGCGTAAATTTAGTAACCTGATGATTTTTGGTTGTTGGTGGTTTAT
GAACAACCCGGAGATCATCAACGAAATGACCCGCATGCGCATGGAAATGCTGGG
TACCAGCTTTATCCCGCAGCACAGCGATGCCCGTGTTCTGGAACAGCTGATCTAT
AAATGGCACCACAGCAAAAGCATCATCGCGGAAGTCCTGATCGACAAATACGAC
GACATCCTGCAAGCAGGTTGGGAAGTTACCGAAGAAGAAATCAAACGTGATGTG
GCAGATCTGTTTAGCCGCAACTTTTGGCGCTTTGTGGGCCGTAACGATCACGTGA
CCAGCGTGAAAGTGGAACAGCAGACCTGA SEQ ID NO: 32 pSGI-481; gene O34808-DNA
ATGGAACCGTTTATGGGCAAAAACTTCCTGCTGAAAAACGAGACCGCGGTGAGC
CTGTACCACAACTACGCGAAAGATATGCCGATCATCGACTACCATTGCCATCTGA
GCCCGAAAGAAATCTACGAGAACAAAACCTTCCAGAACATCACCGAAGCGTGGC
TGTACGGCGATCACTACAAATGGCGCATCATGCGTGCGAATGGCATCGAAGAAA
CCTATATTACCGGTGATGCACCGGACGAAGAAAAATTCATGGCGTGGGCGAAAA
CCGTGCCGATGGCCATTGGTAATCCGCTGTATAACTGGACCCATCTGGAACTGCA
ACGTTTTTTTGGCATCTACGAAATCCTGAACGAAAAAGCGGCAGCGCGATCTGG
AAACAGACCAACAAACTGCTGAAAGGCGAAGGCTTTGGTGCGCGTGATCTGATC
GTGAAAAGCAACGTTAAAGTGGTGTGCACCACCGACGATCCGGTGGATTCTCTG
GAATACCATCTGCTGCTGAAAGAAGACAAAGACTTCCCGGTTAGCGTTTTACCGG
GTTTTCGTCCGGATAAAGGTCTGGAAATCAACCGTGAAGGCTTTCCGGAATGGGT
TCAAGCCCTGGAAGATGCGGCCGCAATTAGCATTACGACCTATGATGAATTTCTG
AAAGCGCTGGAAAAACGCGTGCGCTTCTTCCATAGTGCGGGTGGTCGTGTTAGCG
ATCATGCAATCGATACCATGGTTTTCGCCGAAACCACCAAAGAAGAAGCGGGTC
GCATTTTAGTGATCGTCTGCAAGGCACCGAAGTTAGCTGCGAAGACGAGAAAA
AATTCAAAACCTACACCCTGCAGTTTCTGTGTGGCCTGTATGCCGAACTGGACTG
GGCAATGCAGTTTCACATCAACGCGCTGCGCAACACCAACACCAAAATGATGAA
ACGCCTGGGTCCGGATACCGGTTATGATAGCATGAACGATGAAGAAATCGCGAA
ACCGCTGTACAAACTGCTGAACAGCGTGGAAATGAAAAACCAACTGCCGAAAAC
CATCCTGTACAGCCTGAACCCGAACGACAACTACGTGATCGCGAGCATGATCAA
CAGCTTCCAGGATGGCATCACCCCGGGCAAAATTCAGTTTGGCACCGCATGGTGG
TTCAACGATACCAAAGATGGTATGCTGGATCAGATGAAAGCACTGAGCAATGTG
GGCCTGTTTAGCCGTTTTATTGGCATGCTGACCGATAGCCGTAGCTTTCTGAGCTA
TACCCGTCACGAATACTTTCGCCGCATTGTGTGTAACCTGATCGGCAATGGGTG
GAAAACGGCGAAGTTCCGCGCGATATGGAACTGCTGGGTAGTATTGTGCAAGGT
ATTTGCTACGATAACGCGAAACATTACTTCCAGTTCCAGGAGGAAAAAGCGAAC
GTGTGA SEQ ID NO: 33 pSGI-359-0385-Protein
MSQTPRKLRSQKWFDDPAHADMTAIYVERYLNYGLTRQELQSGRPIIGIAQTGSDLAPCNRH
HLALAERVKAGIRDAGGIPMEFPVHPLAEQGRRPTAALDRNLAYLGLVEILHGYPLDGVVLT
TGCDKTTPACLMAAATVDLPAIVLSGGPMLDGWHDGQRVGSGTVIWHARNLMAAGKLDY
EGFMTLATASSPSVGHCNTMGTALSMNSLAEALGMSLPTCASIPAPYRERAQMAYATGMRI
CDMVREDLRPSHILTRQAFENAIVVASALGASTNCPPHLIAMARHAGIDLSLDDWQRLGEDV
PLLVNCVPAGEHLGEGFHRAGGVPAVMHELFAAGRLHPDCPTVSGKTIGDIAAGAKTRDAD
VIRSCAAPLKHRAGFIVLSGNFFDSAIIKMSVVGEAFRRAYLSEPGSENAFEARAIVFEGPEDY
HARIEDPALNIDEHCILVIRGAGTVGYPGSAEVVNMAPPSHLIKRGVDSLPCLGDGRQSGTSG
SPSILNMSPEAAVGGGLALLRTGDKIRVDLNQRSVTALVDDAEMARRKQEPPYQAPASQTP
WQELYRQLVGQLSTGGCLEPATLYLKVIETRGDPRHSH SEQ ID NO: 34 pSGI-360-0336-Protein
MSERIKKMNDQNKRIFLRSQEWFDDPEHADMTALYVERYMNYGLTRAELQSGRPIIGIAQTG
SDLTPCNRHHKELAERVKAGIRDAGGIPMEFPVHPIAEQTRRPTAALDRNLAYLGLVEILHGY
PLDGVVLTTGCDKTTPACLMAAATTDIPAIVLSGGPMLDGHFKGELIGSGTVLWHARNLLAT
GEIDYEGFMEMTTSASPSVGHCNTMGTALSMNALAEALGMSLPTCASIPAPYRERGQMAYM
TGKRICEMVLEDLRPSKIMNKQSFENAIAVASALGASSNCPPHLIAIARHMGIELSLEDWQRV
GENIPLIVNCMPAGKYLGEGFHRAGGVPAVLHELQKASVLHEGCASVSGKTMGEIAKNAKT
SNVDVIFPYEQPLKHGAGFIVLSGNFFDSAIMKMSVVGEAFKKTYLSDPNGENSFEARAIVFE
GPEDYHARINDPALDIDEHCILVIRGAGTVGYPGSAEVVNMAPPAELIKKGIDSLPCLGDGRQ
SGTSASPSILNMSPEAAVGGGIALLKTNDRLRIDLNKRSVNVLISDEELEQRRREWKPTVSSSQ
TPWQEMYRNMVGQLSTGGCLEPATLYMRVINQDNLPRHSH SEQ ID NO: 35 pSGI-365 E3HJU7-Protein
MSQTPRKLRSQKWFDDPAHADMTAIYVERYLNYGLTRQELQSGRPIIGIAQTGSDLAPCNRH
HLALAERIKAGIRDAGGIPMEFPVHPLAEQGRRPTAALDRNLAYLGLVEILHGYPLDGVVLTT
GCDKTTPACLMAAATVDIPAIVLSGGPMLDGWHDGQRVGSGTVIWHARNLMAAGKLDYEG
FMTLATASSPSIGHCNTMGTALSMNSLAEALGMSLPTCASIPAPYRERGQMAYATGLRICDM
VREDLRPSHVLTRQAFENAIVVASALGASSNCPPHLIAMARHAGIDLSLDDWQRLGEDVPLL
VNCVPAGEHLGEGFHRAGGVPAVLHELAAAGRLHMDCATVSGKTIGEIAAAAKTNNADVIR
SCDAPLKHRAGFIVLSGNFFDSAIIKMSVVGEAFRRAYLSEPGSENAFEARAIVFEGPEDYHAR
IEDPTLNIDEHCILVIRGAGTVGYPGSAEVVNMAPPSHLLKRGIDSLPCLGDGRQSGTSASPSIL
NMSPEAAVGGGLALLRTGDRIRVDLNQRSVIALVDQTEMERRKLEPPYQAPESQTPWQELY
RQLVGQLSTGGCLEPATLYLKVVETRGDPRHSH SEQ ID NO: 36 pSGI-359-0385-DNA
ATGTCTCAGACACCCCGCAAGTTGCGCAGCCAGAAATGGTTCGACGACCCTGCGCATGC
CGATATGACGGCGATTTACGTCGAGCGTTATCTGAATTACGGCCTGACGCGGCAAGAGTT
GCAGTCCGGGCGGCCGATCATCGGCATCGCCCAGACCGGCAGCGATCTGGCGCCCTGCA
ACCGCCATCACCTGGCGCTGGCCGAGCGCGTCAAAGCGGGCATCCGGGACGCGGGCGGC
ATCCCGATGGAGTTCCCCGTGCACCCGCTGGCCGAACAAGGCCGGCGGCCCACGGCCGC
GCTGGACCGCAACCTGGCCTATCTGGGCCTGGTCGAAATCCTGCACGGCTACCCCTTGGA
CGGGGTGGTGCTGACGACTGGCTGCGACAAGACCACGCCTGCCTGCCTGATGGCCGCCG
CCACGGTCGACCTGCCCGCCATCGTGCTGTCCGGCGGCCCCATGCTGGACGGCTGGCACG
ACGGCCAGCGCGTCGGTTCCGGCACCGTCATCTGGCACGCGCGCAACCTGATGGCGGCC
GGCAAGCTTGATTACGAAGGCTTCATGACGCTGGCCACCGCGTCTTCGCCGTCGGTCGGC
CACTGCAACACCATGGGCACGGCGTTGTCGATGAATTCGCTGGCCGAAGCGCTGGGCAT
GTCGCTGCCCACCTGCGCCAGCATTCCCGCCCCCTACCGCGAACGCGCCCAGATGGCCTA
CGCCACCGGCATGCGCATCTGCGACATGGTGCGCGAAGACCTGCGACCCTCCCACATCCT
GACACGGCAGGCATTCGAGAACGCCATCGTCGTGGCATCGGCGCTGGGCGCGTCCACCA
ATTGCCCGCCGCACCTGATCGCGATGGCCCGCCACGCCGGCATCGACCTTAGCCTGGACG
ACTGGCAGCGCCTGGGTGAAGACGTGCCGCTGCTGGTCAACTGCGTGCCGGCGGGCGAG
CATCTGGGCGAGGGCTTCCACCGCGCGGGCGGCGTCCCCGCGGTCATGCATGAACTGTTC
GCCGCCGGGCGCCTTCACCCCGACTGCCCCACCGTATCCGGCAAGACCATCGGGGACAT
CGCCGCGGGCGCCAAGACCCGCGACGCCGACGTCATCCGCAGCTGCGCCGCCCCGCTGA
AACACCGGGCAGGCTTCATCGTGCTGTCGGGCAATTTCTTCGACAGCGCCATCATCAAGA
TGTCGGTCGTAGGCGAAGCGTTCCGCGCGCCTACCTGTCCGAACCCGGCTCAGAGAAC
GCCTTCGAGGCCCGCGCCATCGTGTTCGAAGGCCCCGAGGACTACCACGCGCGCATCGA
AGACCCGGCGCTGAACATCGACGAACACTGCATCCTTGTCATCCGCGGCGCCGGCACCG
TGGGCTACCCGGGCAGCGCCGAAGTGGTCAACATGGCGCCGCCGTCCACCTGATCAAG
CGCGGCGTGGATTCCCTGCCGTGCCTGGGGGATGGCAGGCAAAGCGGCACTTCCGGCAG
CCCGTCCATTTTGAACATGTCCCCTGAAGCAGCAGTCGGGGGAGGATTGGCGCTGCTGCG
CACCGGCGACAAGATCCGTGTCGATCTGAACCAGCGCAGCGTCACCGCCTTGGTCGACG
ACGCGGAAATGGCAAGACGGAAGCAAGAACCGCCCTACCAGGCACCCGCCCTCGCAAAC
GCCCTGGCAAGAGCTGTACCGGCAACTGGTCGGCCAGTTGTCGACGGGCGGCTGCCTGG
AGCCCGCGACGCTATATCTGAAAGTCATCGAAACGCGCGGCGATCCCCGGCACTCTCACT
GA SEQ ID NO: 37 pSGI-360-0336-DNA
ATGAGTGAAAGGATCAAAAAAATGAATGATCAAAATAAACGGATTTTTTTTACGTAGCCA
AGAATGGTTGATGATCCTGAACATGCTGACATGACAGCACTCTATGTTGAGCGTTATAT
GAATTATGGCCTGACCCGTGCCGAGCTACAATCAGGCCGCCCGATTATTGGTATTGCACA
AACTGGCAGTGATTTAACTCCATGTAACCGTCACCACAAAGAACTTGCTGAACGGGTTAA
AGCAGGTATTCGAGATGCGGGAGGTATTCCCATGGAATTCCCCGTTCACCCGATTGCAGA
ACAAACCCGTCGCCCTACTGCTGCACTTGATAGAAATTTAGCTTACTTAGGCTTAGTTGA
AATATTGCATGGTTATCCGCTTGATGGTGTGGTGCTAACCACAGGTTGTGACAAAACTAC
ACCTGCTTGTTTAATGGCTGCCGCAACGACAGATATACCAGCCATTGTGCTTGTCTGGTGG
ACCAATGCTAGATGGTCATTTTAAAGGTGAGTTAATTGGTCTGGGACTGTGCTTTGGCA
TGCAAGAAATTTACTTGCCACGGGTGAAATTGATTATGAAGGGTTCATGGAAATGACCA
CTTCAGCATCGCCTTCGGTCGGACATTGCAACACCATGGGCACTGCACTTTCTATGAATG
CCTTGGCAGAAGCTTTGGGCATGTCTTTACCGACATGTGCAAGTATTCCAGCGCCGTATC
GCGAACGAGGGCAAATGGCCTATATGACAGGCAAAAGAATTTGTGAAATGGTTTTAGAA
GATTTACGCCCTTCTAAAATCATGAACAAACAATCATTTGAAATGCCATCGCGGTAGCT
TCAGCATTAGGGGCATCAAGTAATTGCCCTCCTCACCTCATTGCAATTGCCCGTCATATG
GGCATTGAGCTCAGTTTAGAAGACTGGCAACGCGTTGGGGAGAACATTCCTCTCATTGTG
AACTGTATGCCTGCGGGTAAATATTTAGGTGAAGGTTTTCACCGTGCTGGCGGTGTTCCT
GCTGTTTTGCATGAATTACAAAAGGCCAGCGTTTTACATGAAGGCTGTGCATCAGTCAGC
GGTAAAACGATGGGAGAAATTGCTAAAAATGCTAAAACCTCCAATGTAGATGTTATTTTT
CCATATGAACAACCATTAAAACATGGTGCAGGTTTTATTGTGCTTAGTGGCAATTTCTTC
GACAGCGCCATTATGAAAATGTCTGTTGTGGGTGAAGCATTTAAGAAAACCTATTTATCT
GACCCAAATGGGGAAAATAGCTTTGAAGCACGGGCAATCGTTTTTGAAGGGCCAGAGGA
CTACCATGCACGAATTAATGATCCAGCCTTAGACATTGATGAACATTGTATTTTGGTCAT
TCGTGGCGCTGGAACAGTGGGCTATCCAGGTAGTGCAGAAGTTGTAAATATGGCTCCAC
CCGCAGAGTTAATTAAAAAAGGCATCGATTCACTGCCTTGCTTAGGAGATGGCCGCCAA
AGTGGTACGTCTGCCAGCCCTTCTATTTTAAATATGTCACCCGAAGCGGCGGTAGGCGGT
GGAATTGCATTATTAAAGACCAATGACCGTTTACGCATTGATCTCAATAAACGCTCCGTC
AACGTACTCATTTCTGACGAAGAGTTAGAACAACGCCGCCGTGAGTGGAAACCGACGGT
CTCTTCATCTCAAACACCTTGGCAAGAAATGTATCGCAACATGGTGGGTCAATTATCCAC
TGGCGGTTGTTTGGAACCTGCAACTTTATATATGCGAGTCATAAATCAAGACAACCTTCC
AAGCACACTCTCATTAA SEQ ID NO: 38 pSGI-365 E3HJU7-DNA
ATGAGCCAAACACCGCGTAAATTACGCAGCCAGAAGTGGTTTGACGATCCTGCACATGC
CGATATGACCGCCATCTATGTTGAACGCTACCTGAACTATGCTTAACCCGCCAAGAACT
GCAAAGTGGTCGCCCGATTATTGGTATTGCCCAAACCGGCAGCGATTTAGCCCCGTGTAA
TCGCCATCATTTAGCCTTAGCCGAACGCATTAAAGCAGGCATTAGAGATGCAGGCGGCA
TTCCTATGGAATTTCCCGTTCATCCGCTGGCCGAACAAGGTAGACGTCCTACAGCAGCAT
TAGATCGCAATTTAGCCTATTTAGGCCTGGTGGAAATTTTACACGGCTATCCCCTGGACG
GTGTGGTGCTGACAACCGGTTGCGATAAAACAACACCGGCGTGTTTAATGGCAGCTGCA
ACAGTTGATATTCCGGCGATCGTGTTATCAGGTGGTCCGATGTTAGATGGCTGGCACGAT
GGCCAAAGAGTTGGCAGTGGTACCGTGATTTGGCATGCACGCAATTTAATGGCAGCAGG
CAAACTGGATTATGAAGGCTTCATGACCCTGGCGACAGCCTCTTCTCCGAGTATTGGACA
CTGTAATACCATGGGCACAGCCTTAAGCATGAATAGTCTGGCAGAAGCCCTGGGTATGTC
TTTACCGACCTGTGCGTCTATTCCAGCCCCGTATAGAGAACGCGGTCAAATGGCGTATGC
TACTGGTTTACGCATTTGCGATATGGTGCGCGAAGATTTACGCCCGTCACATGTTTTAAC -continued

```
CCGCCAAGCCTTCGAAAATGCCATTGTTGTTGCCTCAGCCTTAGGTGCAAGCTCTAATTG
TCCCCCTCATTTAATTGCCATGGCCCGTCATGCCGGTATCGACTTAAGCCTGGATGACTG
GCAACGCTTAGGCGAAGATGTTCCGTTACTGGTCAATTGTGTGCCTGCCGGTGAACATTT
AGGTGAAGGATTTCATCGCGCGGGTGGTGTTCCTGCTGTTTTACATGAATTAGCTGCCGC
AGGTCGTTTACATATGGATTGTGCTACCGTTTCTGGCAAGACCATCGGCGAAATTGCAGC
TGCCGCAAAAACCAACAACGCAGACGTGATTCGCTCGTGTGATGCCCCGTTAAAACATA
GAGCCGGCTTTATTGTGTTAAGCGGCAATTTCTTCGACTCCGCCATCATCAAGATGTCCG
TTGTGGGTGAAGCCTTTCGCAGAGCCTATTTAAGTGAACCTGGCAGCGAAAATGCCTTTG
AAGCCCGTGCCATCGTGTTTGAAGGCCCGGAAGACTATCATGCCCGCATTGAAGATCCG
ACCCTGAATATTGATGAACACTGCATTCTGGTGATTCGCGGCGCAGGTACCGTTGGTTAT
CCTGGTAGTGCTGAAGTTGTGAATATGGCCCCGCCGAGCCATTTATTAAAACGCGGTATT
GATTCATTACCTTGCCTGGGAGATGGCCGCCAAAGTGGTACCTCAGCTAGTCCGTCTATC
CTGAATATGAGCCCTGAAGCCGCCGTTGGAGGAGGTTTAGCATTAATTAAGAACCGGTGA
TCGCATTCGCGTCGATCTGAATCAACGCTCAGTCATTGCATTAGTCGACCAGACCGAAAT
GGAACGCCGCAAATTAGAACCACCGTATCAAGCACCTGAAAGCCAAACCCCGTGGCAAG
AACTGTATCGCCAATTAGTCGGTCAACTGTCAACAGGCGGCTGCCTGGAACCAGCCACCT
TATATTTAAAAGTCGTGGAAACCCGTGGAGATCCTCGTCATAGCCATTAA
```

SEQ ID NO: 39 - AO#13-0573
MDRRELLKTSALLMAAAPLARAANVPEDHANVPRTNWSKNFHYSTSRVYAPTTPEEVPAIV
LENGHLKGLGSRHCFNNIADSQYAQISMREVKGIQIDEAAQTVTVGAGIAYGELAPVLDKAG
FALANLASLPHISVGGTIATATHGSGVGNKNLSSATRAIEIVKADGSILRLSRDTDGERFRMA
VVHLGALGVLTKVTLDIVPRFDMSQVVYRNLSFDQLEHNLDTILSSGYSVSLFTDWQRNRVN
QVWIKDKATADAPQKPLPPMFYGATLQTAKLHPIDDHPADACTEQMGSVGPWYLRLPHFK
MEFTPSSGEELQTEYFVARKDGYRAIRAVEKLRDKITPHLFITEIRTIAADDLPMSMAYQRDS
MAIHFTWKPEEFTVRKLLPEIEAALAPFGVRPHWGKIFEIPPSYLHKQYPALPRFRAMAQALD
PGGKFRNAYLDRNIFGA

SEQ ID NO: 40 - AO#22-8001
MDKRDFLKGSATTAVALMMGLNESKAFADDSVPRTNWSGNYHYSTNKVLQPASVAETQD
AVRSVAGVRALGTRHSFNGIADSQIAQISTLKLKDVSLDAKSSTVTVGAGIRYGDLAVQLDA
KGFALHNLASLPHISVGGACATATHGSGMGNGNLATAVKAVEFVAADGSVHTLSRDRDGD
RFAGSVVGLGALGVVTHLTLQVQPRFEMTQVVYRDLPFSELEHHLPEIMGAGYSVSLFTDW
QNGRAGEVWIKRRVDQGGASAPPARFFNATLATTKLHPILDHPAEACTDQLNTVGPWYERL
PHFKLNFTPSSGQELQTEFFVPFDRGYDAIRAVETLRDVITPHLYITELRAVAADDLWMSMAY
QRPSLAIHFTWKPETDAVLKLLPQIEAKLAPFGARPHWAKVFTMKSSHVAPLYPRLKDFLVL
AKSFDPKGKFQNAFLQDHVDIA

SEQ ID NO: 41 - AO#28-9635.1
MTASVTNWAGNISFVAKDVVRPGGVEALRKVVAGNDRVRVLGSGHSFNRIAEPGADGVLV
SLDALPQVIDVDTERRTVRVGGGVKYAELARHVNESGLALPNMASLPHISVAGSVATGTHGS
GVNNGPLATPVREVELLTADGSLVTIGKDDARFPGAVTSLGALGVVVALTLDLEPAYGVEQ
YTFTELPLEGLDFEAVASAAYSVSLFTDWREAGFRQVWVKRRIDEPYAGFPWAAPATEKLHP
VPGMPAENCTDQFGAAGPWHERLPHFKAEFTPSSGDELQSEYLLPREHALAALDAVGNVRE
TVSTVLQICEVRTIAADTQWLSPAYGRDSVALHFTWTDDMDAVLPAVRAVESALDGFGARP
HWGKVFTTAPAALRERYPRLDDFRTLRDELDPAGKFTNAFVRDVLEG

SEQ ID NO: 42 - AO#36-7049
MTLERNWAGTHTFAAPRIVNATSIDEVRALVAEAARTGTRVRALGTRHSFTDLADSDGTLIT
VLDIPADPVFDEAAGSVTIGAGTRYGIAAAWLAEHGLAFHNMGSLPHISVGGAIATGTHGSG
NDNGILSSAVSGLEYVDATGELVHVRRGDPGFDGLVVGLGAYGIVVRVTVDVQPAYRVRQD
VYRDVPWDAVLADFEGVTGGAYSVSIFTNWLGDTVEQIWWKTRLVAGDDELPVVPESWLG
VQRDSLTAGNLVETDPDNLTLQGGVPGDWWERLPHFRLESTPSNGDEIQTEYFIDRADGPAA
ITALRALGDRIAPLLLVTELRTAAPDKLWLSGAYHREMLAVHFTWRNLPEEVRAVLPAIEEA
LAPFDARPHWGKLNLLTAERIAEVVPRLADARDLFEELDPAGTFSNAHLERIGVRLPR

SEQ ID NO: 43 - AO#51-9823
MRDAAAANWAGNVRFGAARVVAPESVGELQEIVAGSRKARALGTGHSFSRIADTDGTLIAT
ARLPRRIQIDDGSVTVSGGIRYGDLARELAPNGWALRNLGSLPHISVAGACATGTHGSGDRN
GSLATSVAALELVTASGELVSVRRGDEDFDGHVIALGALGVTVAVTLDLVPGFQVRQLVYE
GLTRDTLLESVQEIFAASYSVSVFTGWDPESSQLWLKQRVDGPGDDGEPPAERFGARLATRP
LHPVPGIDPTHTTQQLGVPGPWHERLPHFRLDFTPSAGDELQTEYFVAREHAAAAIEALFAIG
AVVRPALQISEIRTVAADALWLSPAYRRDVMALHFTWISAEGTVMPAVAAVERALAPFDPV
PHWGKVFALPPAAVRAGYPRAAEFLALAARRDPEAVFRNQYLDAYLPAA

SEQ ID NO: 44 - AO#57-0794
MTQRNWAGNVSYSSSRVAEPASVDDLTALVESEPRVRPLGSRHCFNDIADTPGVHVSLARLR
GEEPRLTAPGTLRTPAWLRYGDLVPVLREAGAALANLASLPHISVAGAVQTGTHGSGDRIGT
LATQVSALELVTGTGEVLRLERGEPDFDGAVVGLGALGVLTHVELDVSPARDVAQHVYEGV
RLDDVLADLGAVTGAGDSVSMFTHWQDPAVVSQVWVKSGGDVDDAAIRDAGGRPADGPR
HPIAGIDPTPCTPQLGEPGPWYDRLPHFRLEFTPSVGEELQSEYLVDRDDAVDAIRAVQDLAP
RIAPLLFVCEIRTMASDGLWLSPAQGRDTVGLHFTWRPDESAVRQLLPEIERALPASARPHW
GKVFTLPGHDVAARYPRWADFVALRRRLDPERRFANAYLERLGL

SEQ ID NO: 45 - AO#76-BAA19135
MTPAEKNWAGNITFGAKRLCVPRSVRELRETVAASGAVRPLGTRHSFNTVADTSGDHVSLA
GLPRVVDIDVPGRAVSLSAGLRFGEFAAELHARGLALANLGSLPHISVAGAVATGTHGSGVG
NRSLAGAVRALSLVTADGETRTLRRTDEDFAGAVVSLGALGVVTSLELDLVPAFEVRQWVY
EDLPEATLAARFDEVMSAAYSVSVFTDWRPGPVGQVWLKQRVGDEGARSVMPAEWLGAR
LADGPRHPVPGMPAGNCTAQQGVPGPWHERLPHFRMEFTPSNGDELQSEYFVARADAVAA

-continued
YEALARLRDRIAPVLQVSELRTVAADDLWLSPAHGRDSVAFHFTWVPDAAAVAPVAGAIEE
ALAPFGARPHWGKVFSTAPEVLRTLYPRYADFEELVGRHDPEGTFRNAFLDRYFRR SEQ ID NO: 46 - AO#251-F3MC79
MGDKLNWAGNYRYRSMELLEPKSLEEVKDLVVSRTSIRVLGSCHSFNGIADTGGSHLSLRK
MNRVIDLDRVQRTVTVEGGIRYGDLCRYLNDHGYALHNLASLPHISVAGAVATATHGSGDL
NASLASSVRAIELMKSDGEVTVLTRGTDPEFDGAVVGLGGLGVVTKLKLDLVPSFQVSQTVY
DRLPFSALDHGIDEILSSAYSVSLFTDWAEPIFNQVWVKRKVGINGEDETSPDFFGALPAPEKR
HMVLGQSVVNCSEQMGDPGPWYERLPHFRMEFTPSAGNELQSEYFVPRRHAVEAMRALGK
LRDRIAPLLFISEIRTIASDTFWMSPCYRQDSVGLHFTWKPDWERVRQLLPLIERELEPFAARP
HWAKLFTMESEMIQARYERLADFRQLLLRYDPIGKFRNTFLDHYIMH SEQ ID NO: 47 - AO#13-0573-DNA
ATGGATCGTCGTGAACTGCTGAAAACCTCTGCACTGCTGATGGCAGCAGCACCGTTAGCA
CGTGCAGCAAATGTTCCGGAAGATCATGCAAATGTTCCGCGTACCAATTGGAGCAAAAA
CTTCCACTATAGCACCAGCCGCGTTTATGCACCGACTACCCCGGAAGAAGTTCCGGCAAT
TGTTCTGGAAAATGGTCATCTGAAAGGTCTGGGTTCTCGTCACTGCTTCAACAACATCGC
CGATAGCCAGTATGCGCAGATCAGCATGCGCGAAGTTAAAGGCATTCAGATCGATGAAG
CCGCACAAACCGTTACCGTGGGTGCAGGTATTGCGTATGGTGAATTAGCACCGGTGCTGG
ATAAAGCGGGTTTTGCACTGGCAAATTTAGCAAGTTTACCGCATATCAGCGTGGGTGGCA
CCATTGCAACCGCAACACATGGCTCTGGCGTTGGTAACAAAAACCTGTCTTCTGCAACCC
GTGCAATTGAAATCGTGAAAGCGGATGGCAGCATTCTGCGTCTGTCGCGTGATACTGATG
GTGAACGTTTTCGTATGGCGGTGGTTCATCTGGGTGCATTAGGTGTTTTAACCAAAGTTA
CCCTGGATATCGTGCCGCGCTTCGATATGTCTCAGGTGGTGTATCGCAACCTGTCCTTTGA
TCAGCTGGAACACAACCTGGATACCATTCTGAGCTCTGGCTATAGCGTTAGCCTGTTCAC
CGACTGGCAGCGTAATCGTGTTAATCAGGTGTGGATCAAAGATAAAGCGACCGCGGATG
CACCGCAAAACCGTTACCTCCGATGTTTATGGTGCGACCCTGCAAACCGCAAAACTGC
ATCCGATCGATGATCATCCGGCAGATGCATGTACCGAACAAATGGGTAGTGTTGGTCCGT
GGTATTTACGTCTGCCGCATTTCAAAATGGAGTTTACCCCGAGCAGCGGTGAAGAATTAC
AGACCGAATACTTCGTGGCGCGCAAAGATGGCTATCGCGCAATTCGTGCCGTGGAAAAA
CTGCGCGATAAAATTACCCCGCACCTGTTTATCACCGAAATCCGCACCATTGCAGCAGAT
GATCTGCCGATGAGCATGGCATATCAACGTGACAGTATGGCGATTCATTTTACCTGGAAA
CCGGAAGAACCGACCGTGCGTAAATTACTGCCGGAAATCGAAGCAGCACTGGCGCCGTT
TGGTGTTCGTCCGCATTGGGGCAAAATTTTTGAAATTCCGCCGAGCTATCTGCATAAACA
GTATCCGGCACTGCCGCGTTTTCGCGCAATGGCACAGGCATTAGATCCTGGTGGCAAATT
TCGTAATGCATATCTGGATCGTAACATCTTTGGCGCGTAG SEQ ID NO: 48 - AO#22-8001-DNA
ATGGACAAACGCGATTTCCTGAAAGGTAGCGCAACCACCGCAGTTGCACTGATGATGGG
TCTGAATGAAAGCAAAGCGTTTGCGGATGATAGCGTTCCGCGTACCAATTGGAGCGGCA
ACTACCATTATAGCACCAACAAAGTGCTGCAGCCGGCAAGTGTTGCAGAAACCCAAGAT
GCAGTTCGTAGTGTTGCAGGTGTTCGTGCATTAGGTACTCGTCATAGCTTTAACGGCATC
GCGGATAGCCAGATTGCCCAGATTAGTACCCTGAAACTGAAAGATGTGAGCTGGATGC
GAAAAGCTCGACCGTGACCGTTGGTGCAGGTATTCGTTATGGTGATCTGGCGGTTCAGCT
GGATGCGAAAGGTTTTGCTCTGCATAATCTGGCAAGTCTGCCGCATATTTCTGTTGGTGG
TGCATGTGCAACTGCGACCCATGGTTCAGGTATGGGTAATGGTAATTTAGCAACCGCAGT
TAAAGCGGTGGAATTTGTTGCGGCGGATGGTAGCGTGCATACCCGTCTCGTGATCGTGA
TGGTGATCGTTTTGCGGGCTCTGTTGTTGGTCTGGGTGCATTAGGTGTTGTTACCCATTTA
ACCCTGCAAGTTCAGCCACGTTTCGAAATGACCCAGGTGGTGTACCGTGATCTGCCATTT
AGTGAACTGGAACATCATCTGCCGGAAATTATGGGTGCCGGTTATAGCGTGTCCCTGTTT
ACCGATTGGCAGAATGGTCGTGCAGGTGAAGTGTGGATCAAACGTGCCGTTGAAATCAAGG
TGGTGCAAGTGCTCCTCCAGCTCGTTTTTTTAATGCAACCTTAGCAACCACCAAACTGCA
CCCGATCCTGGATCATCCTGCTGAAGCATGTACCGATCAGTTAAATACCGTAGGTCCGTG
GTATGAACGTTTACCGCACTTCAAACTGAACTTCACCCCGAGCAGTGGCCAAGAATTACA
GACCGAGTTTTTCGTGCCGTTCGATCGCGGCTATGACGCCATTCGTGCCGTTGAAACTTT
ACGTGATGTGATTACCCCGCACCTGTATATCACCGAACTGCGTGCAGTTGCAGCTGATGA
TTTATGGATGAGCATGGCATATCAACGTCCGAGTCTGGCAATCCATTTTACCTGGAAACC
GGAAACCGATGCAGTGCTGAAATTACTGCCGCAGATTGAAGCGAAACTGGCCCCGTTTG
GTGCTCGTCCGCATTGGGCAAAAGTTTTTACCATGAAAAGCAGCCATGTGGCCACCGCTGT
ATCCGCGCCTGAAAGATTTTCTGGTTCTGGCAAAATCCTTTGATCCGAAAGGCAAATTCC
AAAACGCGTTTCTGCAGGACCATGTGGACATCGCATAG SEQ ID NO: 49 - AO#28-9635-DNA
ATGACCGCATCTGTGACCAATTGGGCGGGTAACATCAGCTTTGTGGCGAAAGATGTTGTT
CGTCCGGGTGGTGTTGAAGCACTGCGTAAAGTTGTTGCGGGTAATGATCGTGTTCGTGTT
CTGGGTTCTGGTCATAGCTTTAACCGTATCGCTGAACCGGGTGCTGATGGTGTTCTGGTT
AGCCTGGATGCATTACCGCAAGTGATTGATGTTGATACCGAACGTCGTACCGTGCGTGTT
GGTGGTGGTGTTAAATACGCGAACTGGCTCGTCATGTGAATGAATCTGGTCTGGCACTG
CCGAATATGGCATCTCTGCCGCATATTTCTGTTGCAGGTCTGTTGCAACTGGTACCCATG
GTTCTGGTGTGAATAATGGCCCGTTAGCAACCCCGGTTCGTGAAGTTGAATTATTAACCG
CGGATGGCTCTCTGGTGACCATCGGTAAAGATGATGCGCGTTTTCCGGGTGCAGTTACTT
CTCTGGGTGCGCTGGGTGTTGTTGCACTGACCTTAGATTTAGAACCGGCGTATGGTG
TTGAACAGTATACCTTTACCGAATTACCGCTGGAAGGTCTGGACTTCGAAGCAGTTGCGA
GTGCAGCATATTCTGTTAGCCTGTTCACCGATTGGCGTGAAGCTGGTTTTCGCCAAGTTTG
GGTGAAACGCCGCATTGATGAACCGTACGCGGGCTTTCCGTGGGCAGCACCGGCAACTG
AAAAATTACATCCGGTTCGGGTATGCCAGCAGAAATTGTATGATCAATTTGGTCCAG
CAGGTCCATGGCATGAACGTTTACCGCATTTTAAAGCGGAATTTACCCCGTCTAGCGGTG
ATGAATTACAGAGCGAATATCTGCTGCCGCGTGAACATGCACTGGCGGCACTGGATGCA
GTGGGCAACGTGCGTGAAACCGTTTCTACCGTGCTGCAGATTTGCGAAGTTCGTACCATT
GCAGCAGATACCCAGTGGTTAAGTCCGGCTTATGGTCGTGATAGTGTTGCATTACATTTT
ACTTGGACCGATGATATGGATGCAGTTTTACCTGCAGTTCGTGCCGTTGAAAGCGCGCTG -continued
GATGGCTTTGGTGCTCGCCCGCATTGGGGTAAAGTGTTTACCACCGCACCGGCAGCATTA
CGTGAACGTTATCCGCGTCTGGATGATTTTCGTACCCTGCGTGATGAATTAGATCCGGCA
GGCAAATTTACTAATGCATTTGTTCGTGATGTTCTGGAAGGTTAG SEQ ID NO 50 - AO#36-7049-DNA
ATGACCCTGGAACGTAATTGGGCAGGTACCCATACCTTTGCAGCACCGCGTATTGTTAAT
GCAACCAGCATCGATGAAGTTCGTGCGTTAGTGGCAGAAGCAGCACGTACCGGTACCCG
TGTTCGTGCATTAGGTACTCGTCATTCTTTTACCGATCTGGCAGATAGCGATGGTACCCTG
ATTACCGTGCTGGATATTCCGGCAGATCCAGTTTTCGATGAAGCAGCAGGTAGCGTTACC
ATTGGTGCAGGTACCCGTTATGGTATTGCAGCAGCAGGTTAGCAGAACATGGTCTGGCG
TTTCACAACATGGGTAGCCTGCCGCATATTAGCGTTGGTGGTGCAATTGCAACCGGTACC
CATGGTAGTGGTAATGATAACGGCATTCTGAGTAGCGCAGTTAGTGGTCTGGAATATGTT
GATGCGACCGGTGAACTGGTTCATGTGCGTCGTGGTGATCCTGGTTTTGATGGTCTGGTT
GTTGGTTTAGGCGCGTATGGTATTGTGGTTCGTGTGACGGTGGATGTTCAACCGGCATAT
CGTGTTCGCCAGGATGTGTATCGTGATGTTCCGTGGGATGCAGTTCTGGCAGATTTTGAA
GGTGTTACAGGTGGTGCGTATAGCGTTAGCATCTTTACCAACTGGCTGGGTGATACGGTG
AACAGATTTGGTGGAAAACCCGTCTGGTTGCAGGTGATGATGAACTGCCGGTGGTTCC
GGAAAGCTGGCTGGGTGTTCAACGTGAT1CTTTAACCGCAGGTAATCTGGTTGAAACCGA
TCCGGATAATTTAACCCTGCAAGGTGGTGTTCCGGGTGATTGGTGGGAACGTTTACCGCA
TTTTCGTCTGGAAAGTACCCCGTCTAATGGTGATGAAATCCAGACCGAATACTTCATCGA
TCGCGCGGATGGTCCGGCGGCAATTACCGCACTGCGTGCATTAGGTGATCGTATTGCTCC
GTTACTGTTAGTTACCGAATTACGTACCGCAGCTCCAGATAAACTGTGGCTGAGTGGCGC
ATATCATCGCGAAATGTTAGCGGTCCATTTTACCTGGCGTAATTTACCGGAAGAAGTGCG
TGCAGTTTTACCAGCGATCGAAGAAGCCCTGGCGCCGTTTGATGCTCGTCCGCATTGGGG
TAAACTGAATCTGTTAACCGCAGAACGTATTGCAGAAGTTGTTCCGCGTCTGGCTGATGC
ACGTGATCTGTTTGAAGAACTGGACCCGGCTGGTACCTTTTCTAATGCTCATCTGGAACG
TATTGGTGTTCGTTTACCGCGTTAG SEQ ID NO: 51 - AO#51-9823-DNA
ATGCGTGATGCAGCAGCAGCAAATTGGGCAGGTAATGTGCGTTTTGGTGCAGCACGTGTT
GTTGCACCGGAAAGTGTTGGTGAACTGCAGGAAATTGTTGCAGGTAGCCGTAAAGCACG
TGCATTAGGTACCGGTCATAGCTTTAGCCGTATTGCAGATACCGATGGTACCCTGATTGC
TACCGCACGTTTACCACGTCGTATTCAGATCGATGATGGCAGCGTTACCGTTTCTGGTGG
TATCCGTTATGGCGATCTGGCCCGTGAATTAGCACCGAATGGTTGGGCATTACGTAATCT
GGGTTCTTTACCGCACATTTCAGTTGCAGGTGCATGTGCAACCGGTACCCATGGTTCAGG
TGATCGTAATGGTAGTCTGGCAACCTCTGTTGCAGCGTTAGAATTAGTTACCGCGTCTGG
TGAATTAGTGAGCGTTCGTCGTGGCGATGAAGATTTCGATGGCCATGTGATTGCGCTGGG
TGCACTGGGTGTTACTGTTGCAGTTACCCTGGATTTAGTTCCGGGTTTTCAGGTTCGTCAG
CTGGTGTATGAAGGTCTGACCCGTGATACCTTACTGGAAAGTGTGCAGGAAATCTTTGCT
GCGAGCTATAGTGTTAGCGTGTTTACCGGTTGGGACCCGAAAGTTCTCAACTGTGGCTG
AAACAGCGCGTTGATGGTCCGGGCGATGATGGTGAACCACCGGCAGAACGTTTTGGTGC
ACGTTTAGCAACTCGTCCGTTACATCCAGTTCCGGGTATTGATCCGACTCATACTACTCA
ACAATTAGGTGTTCCAGGTCCGTGGCATGAACGTTTACCGCATTTTCGTCTGGATTTTACC
CCTTCTGCAGGTGATGAACTGCAAACCGAATACTTCGTGGCCCGCGAACATGCAGCGGC
GGCGATTGAAGCACTGTTTGCGATTGGTGCGGTTGTTCGTCGGCATTACAAATTAGCGA
AATTCGTACCGTTGCAGCTGATGCATTATGGCTGTCTCCGGCATATCGTCGTGATGTTATG
GCGTTACATTTTACCTGGATTAGCGCAGAAGGTACCGTTATGCCAGCAGTTGCAGCAGTG
GAACGTGCACTGGCGCCGTTTGATCCGGTTCCTCATTGGGGTAAAGTTTTTGCGCTGCCG
CCAGCAGCAGTTCGTGCTGGTTATCCTCGTGCAGCAGAATTTTTAGCATTAGCAGCTCGT
CGTGATCCGGAAGCAGTTTTTCGTAATCAGTATTTAGATGCATATTTACCGGCAGCATAG SEQ ID NO: 52 - AO#57-0794-DNA
ATGACCCAGCGTAATTGGGCGGGTAATGTGAGCTATAGTAGCAGCCGTGTTGCAGAACC
AGCAAGTGTGGATGATTTAACCGCACTGGTTGAAAGTGAACCGCGTGTTCGTCCGTTAGG
TAGTCGTCATTGCTTCAACGATATCGCCGATACCCCAGGTGTTCATGTTTCTGGCACGT
CTGCGTGGTGAAGAACCGCGTTTAACAGCACCGGGTACCTTACGTACTCCAGCTTGGTTA
CGTTATGGTGATTTAGTTCCGGTTCTGCGTGAAGCAGGTGCAGCATTAGCAAATTTAGCA
TCTCTGCCGCATATTAGCGTTGCAGGTGCAGTTCAAACCGGTACCCATGGTTCAGGTGAT
CGTATTGGCACTCTGGCAACCCAAGTTAGCGCCCTGGAATTAGTGACCGGCACCGGTGA
AGTTTTACGCTTAGAACGTGGTGAACCTGATTTTGATGGTGCGGTTGTTGGTTTAGGTGC
GTTAGGTGTTCTGACTCATGTGGAATTAGATGTTAGTCCGGCGCGTGATGTTGCACAGCA
CGTGTATGAAGGTGTTCGTCTGGATGATGTTCTGGCGGATTTAGGCGCGGTTACTGGCGC
AGGTGATTCGGTGAGCATGTTTACCCATTGGCAAGATCCGGCAGTTGTTAGTCAGGTTTG
GGTTAAAAGTGGCGGTGATGTGGATGATGCAGCAATTCGTGATGCAGGTGGTCGTCCGG
CAGATGGTCCGCGTCATCCAATTGCAGGTATTGATCCGACTCCATGTACTCCACAATTAG
GTGAACCAGGTCCGTGGTATGATCGTCTGCCGCATTTTCGTCTGGAATTTACCCCGAGTG
TTGGTGAAGAACTGCAAAGTGAATATCTGGTTGATCGCGATGATGCCGTTGATGCAATTC
GTGCGGTGCAGGATTTAGCCCCGCGTATTGCGCCGCTGCTGTTTGTTTGCGAAATTCGTA
CCATGGCAAGTGATGGTTTATGGCTGAGCCCGGCACAAGGTCGTGATACCGTTGGTCTGC
ATTTTACCTGGCGTCCTGATGAATCTGCAGTTCGTCAATTATTACCGGAAATTGAACGTG
CTTTACCGGCAAGTGCTCGTCCGCATTGGGGTAAAGTGTTTACCCTGCCGGGCCATGATG
TTGCAGCACGTrATCCGCGTTGGGCAGATTTTGTTGCATTACGTCGTCGTTTAGATCCGGA
ACGTCGTTTCGCGAATGCATACCTGGAACGTTTAGGTCTGTAG SEQ ID NO 53 - AO#76-BAA19135-DNA
ATGACTCCGGCGGAAAAAAATTGGGCGGGCAACATCACCTTTGGTGCAAAACGTCTGTG
TGTTCCGCGTTCTGTTCGTGAACTGCGTGAAACCGTTGCAGCATCTGGTGCAGTTCGTCC
GTTAGGTACTCGTCATAGCTTTAATACCGTTGCAGATACCAGTGGTGATCATGTTAGTCT
GGCAGGTTTACCGCGTGTTGTGGACATCGATGTTCCGGGTCGTGCAGTTTCTCTGTCTGCT
GGTCTGCGTTTTGGTGAATTTGCGGCTGAATTACATGCACGTGGTCTGGCGCTGGCAAAT
TTAGGTTCTCTGCCGCATATTAGCGTTGCAGGTGCAGTTGCAACCGGTACTCATGGTTCT -continued
```
GGTGTTGGTAATCGTTCTTTAGCAGGTGCAGTTCGTGCTTTATCTCTGGTAACCGCCGATG
GTGAAACCCGTACCTTACGTCGTACCGATGAAGATTTTGCAGGTGCAGTGGTTTCTCTGG
GTGCACTGGGTGTTGTTACTTCTCTGGAACTGGATTTAGTTCCGGCGTTCGAAGTGCGTC
AGTGGGTGTACGAAGATCTGCCGGAAGCAACTTTAGCAGCTCGTTTTGATGAAGTTATGT
CAGCAGCGTATAGCGTGTCCGTGTTCACCGATTGGCGTCCGGGTCCTGTTGGTCAAGTTT
GGCTGAAACAACGTGTTGGTGATGAAGGTGCTCGTAGTGTTATGCCAGCAGAATGGTTA
GGTGCACGTTTAGCAGATGGTCCGCGTCATCCAGTTCCAGGTATGCCTGCAGGTAATTGT
ACAGCACAACAAGGTGTTCCAGGTCCGTGGCATGAACGTTTACCGCATTTTCGCATGGAA
TTTACCCCGTCTAACGGCGATGAACTGCAAAGCGAATATTTTGTGGCGCGTGCAGATGCA
GTTGCAGCGTATGAAGCATTAGCACGTCTGCGTGATCGTATTGCGCCGG1TCTGCAAGTT
AGCGAATTACGTACCGTTGCAGCAGATGATCTGTGGCTGAGTCCGGCACATGGTCGTGAT
AGTGTTGCGTTTCATTTTACCTGGGTTCCGGATGCAGCAGCAGTTGCACCGGTTGCAGGT
GCTATTGAAGAAGCATTAGCACCGTTTGGTGCACGTCCACATTGGGGTAAAGTTTTTAGC
ACCGCACCGGAAGTTTTACGTACCTTATATCCGCGTTATGCCGATTTCGAAGAACTGGTG
GGCCGCCATGATCCGGAAGGCACCTTTCGTAATGCATTTTTAGATCGCTACTTTCGTCGCT
AG SEQ ID NO: 54 - AO#251-F3MC79-DNA
ATGGGCGATAAACTGAATTGGGCGGGCAACTATCGTTATCGCAGCATGGAACTGCTGGA
ACCGAAAAGCCTGGAAGAAGTGAAAGATCTGGTGGTTAGCCGTACCAGCATTCGTGTTC
TGGGTAGCTGTCATAGCTTTAACGGCATTGCGGATACCGGTGGTAGTCATCTGAGTCTGC
GCAAAATGAACCGCGTGATTGATCTGGATCGTGTTCAGCGTACCGTTACCGTTGAAGGTG
GTATTCGTTACGGTGATCTGTGCCGCTATCTGAACGATCATGGTTATGCCCTGCATAATCT
GGCCAAGCTTACCGCACATCAGCGTTGCAGGTGCAGTTGCAACCGCAACCCATGGTTCTGG
TGATCTGAATGCAAGTCTGGCAAGCTCTGTTCGTGCAATTGAACTGATGAAAAGCGATGG
CGAAGTTACGGTTCTGACCCGTGGTACCGATCCGGAATTTGATGGTGCAGTTGTTGGTCT
GGGTGGTTTAGGTGTTGTGACCAAACTGAAACTGGATCTGGTTCCGAGCTTTCAGGTGTC
GCAGACCGTGTATGATCGTCTGCCGTTTAGCGCACTGGATCATGGCATCGATGAAATTCT
GAGTAGTGCATATAGCGTTAGCCTGTTCACCGATTGGGCGGAACCGATCTTTAATCAGGT
GTGGGTGAAACGCAAAGTGGGCATTAACGGCGAAGATGAAACCAGTCCGGATTTTTTTG
GCGCATTACCGGCACCGGAAAAACGCCACATGGTTCTGGGTCAGAGCGTGGTGAATTGC
AGCGAACAAATGGGTGATCCTGGTCCGTGGTATGAACGTTTACCGCATTTTCGCATGGAA
TTTACCCCGAGTGCAGGCAATGAATTACAGAGCGAATATTTTGTGCCGCGTCGTCATGCG
GTTGAAGCAATGCGTGCGTTAGGTAAACTGCGTGATCGTATTGCACCCACTGCTGTTCATC
AGCGAAATCCGCACCATTGCGAGCGATACCTTCTGGATGAGCCCGTGTTATCGTCAGGAT
TCTGTTGGTCTGCATTTTACCTGGAAACCGGATTGGGAACGTGTTCGTCAGTTATTACCGC
TGATTAACGTGAACTGGAACCGTTTGCGGCACGTCCGCATTGGGCGAAACTGTTTACCA
TGGAAAGCGAAATGATTCAGGCGCGCTATGAACGTCTGGCGGATTTTCGTCAGCTGCTGC
TGCGTTATGATCCGATTGGCAAATTCCGTAACACCTTTCTGGATCACTACATCATGCACT
AA SEQ ID NO: 55 pSGI-431 Q72LK2-Protein
MEATLPVLDAKTAALKRRSIRRYRKDPVPEGLLREILEAALRAPSAWNLQPWRIVVVRDPAT
KRALREAAFGQAHVEEAPVVLVLYADLEDALAHLDEVIHPGVQGERREAQKQAIQRAFAA
MGQEARKAWASGQSYILLGYLLLLLEAYGLGSVPMLGFDPERVKAILGLPSHAAIPALVALG
YPAEEGYPSHRLPLERVVLWR SEQ ID NO: 56 pSGI-431 Q72LK2-DNA
ATGGAAGCAACCTTACCGGTGTTAGACGCGAAAACCGCAGCACTGAAACGTCGTAGCAT
TCGCCGTTATCGCAAAGATCCAGTTCCGGAAGGTTTACTGCGCGAAATTCTGGAAGCAGC
ATTACGTGCACCGTCTGCATGGAATTTACAACCGTGGCGTATTGTGGTGGTTCGTGATCC
GGCAACTAAACGTGCATTACGTGAAGCAGCATTTGGTCAAGCCCATGTGGAAGAAGCAC
CGGTTGTTCTGGTTCTGTACGCAGATCTGGAAGATGCACTGGCACATCTGGATGAAGTGA
TTCATCCGGGCGTTCAAGGTGAACGTCGTGAAGCGCAGAAACAAGCAATTCAGCGTGCA
TTTGCAGCAATGGGTCAGGAAGCTCGTAAAGCTTGGGCAAGCGGTCAAAGTTATATTCTG
CTGGGTTATCTGCTGCTGCTGCTGGAAGCATATGGTCTGGGTTCTGTTCCGATGCTGGGTT
TTGATCCTGAACGTGTTAAAGCGATTCTGGGCCTGCCGTCACATGCAGCGATTCCGGCAT
TAGTTGCACTGGGTTATCCGGCTGAAGAAGGTTATCCGAGTCATCGTTTACCGCTGGAAC
GTGTTGTTTTATGGCGTTGA SEQ ID NO: 57: pSGI-374 #9041 Protein
MLKNPFSLQGRKALVTGANTGLGQAIAVGLAAAGAEVVCAARRAPDETLEMIASDGGKASA
LSIDFADPLAAKDSFAGAGFDILVNNAGIIRRADSVEFSELDWDEVMDVNLKALFFTTQAFAK
ELLAKGRSGKVVNIASLLSFQGGIRVPSYTAAKHGVAGLTKLLANEWAAKGINVNAIAPGYI
ETNNTEALRADAARNKAILERIPAGRWGRSEDIAGAAVFLSSAAADYVHGAILNVDGGWLA
R SEQ ID NO: 58 pSGI-375 #8939 Protein
MIAGVGGEARELALDLSDPMAAKDVFAEGAYDLLINNAGIIRRADAVDFSEDDWDAVMDV
NLKAVFFTSQAFARALMSRNASGKIVNIASLLSFQGGIRVASYTAAKHGVAGITRLLANEWA
SRGINVNAIAPGYIATNNTEALRADEERNAAILARIPAGRWGRAEDIAGTAVYLCSPAADYV
HGAILNVDGGWLAR SEQ ID NO: 59 pSGI-376 P37769-Protein
MILSAFSLEGKVAVVTGCDTGLGQGMALGLAQAGCDIVGINIVEPTETIEQVTALGRRFLSLT
ADLRKIDGIPALLDRAVAEFGHIDILVNNAGLIRREDALEFSEKDWDDVMNLNIKSVFFMSQA
AAKHFIAQGNGGKIINIASMLSFQGGIRVPSYTASKSGVMGVTRLMANEWAKHNINVNAIAP
GYMATNNTQQLRADEQRSAEILDRIPAGRWGLPSDLMGPIVFLASSASDYVNGYTIAVDGG
WLAR
```

SEQ ID NO: 60 pSGI-395 #5112 Protein
MPGMTTPFDLHGKTAIVTGANTGIGQAIALSLAQAGADIAAVGRTPAQDTVDQVRALGRRA
DIISADLSTIEPVQRVLDETLEKLGALDILVNNAGIIRRADSVDFTEEDWDAVIDTNLKTTFFLC
QAAGRHMLAQGAGKIINIASLLSFQGGIRVPSYTASKSGVAGLTKLLANEWAAKGVNVNAIA
PGYIATNNTAALQADETRNRQIQERIPAGRWGDPADIGGAAVFLASSAADYIHGHTLAVDGG
WLAR SEQ ID NO: 61 pSGI-396 #7103-Protein
MNPFSLEGKTALVTGANTGIGQAIAMALGRAGADVICAGRSSCAETVALIAGSKGKARELVL
DFADPMAARDVFAAEPVDILVNNAGIIRRADAVDFTEADWDEVMDVNLKAVFFTCQAFGK
AVLGRGGNGKIVNIASLISFQGGIRVPSYTASKHGVAGITKLLANEWAAKGINVNAIAPGYIE
TNNTEALRADPVRNKAILERIPAGRWGQASDIGEAAVFLASPAANYIHGAVLNVDGGWLAR SEQ ID NO: 62 pSGI-374 #9041 DNA
ATGAAGAATCCCTTTTCGCTTCAGGGGCGTAAGGCGCTCGTCACCGGCGCGAATACGGGGCTTGGC
CAGGCGATTGCGGTTGGGCTCGCCGCGGCCGGTGCGGAGGTGGTCTGCGCCGCCCGCCGCGCGCC
GGATGAAACGCTGGAGATGATCGCCAGCGACGGCGGCAAGGCCAGCGCATTGTCCATCGATTTTG
CCGATCCGCTGGCGGCGAAGGACAGTTTTGCCGGCGCCGGTTTCGATATTCTCGTCAACAATGCCG
GTATCATCCGCCGTGCCGATTCCGTCGAGTTCTCCGAACTCGACTGGGACGAGGTGATGGACGTCA
ATCTCAAGGCGCTGTTTTTCACCACCCAGGCTTTTGCGAAAGAGCTGCTGGCGAAAGGCCGGTCCG
GCAAGGTGGTCAATATCGCTTGCTCCTTTCCTTTCAGGGCGGTATTCGCGTGCCGTCCTATACGGC
GGCGAAACATGGTGTCGCCGGCCTAACCAAACTCCTGGCGAATGAATGGGCCGCCAAGGGCATCA
ATGTGAATGCCATTGCGCCCGGTTATATCGAAACCAACAATACCGAGGCGCTACGCGCCGATGCG
GCTCGTAACAAGGCCATTCTCGAGCGCATCCCGGCCGGCCGCTGGGGGCGCTCGGAAGACATCGC
CGGGGCGGCGGTTTTCCTGTCATCTGCGGCGGCGGACTATGTGCATGGCGCCATTCTCAACGTCGA
TGGCGGCTGGCTGGCGCGCTGA SEQ ID NO: 63 pSGI-375 #8939 DNA
ATGATCGCCGGCGTGGGGGGAGAAGCAAGGGAGCTGGCGCTCGATCTGTCCGATCCCATGGCGGC
AAAAGATGTTTTTGCTGAAGGCGCTTACGACCTCCTCATCAACAATGCCGGCATCATCCGCCGTGC
CGATGCAGTCGATTTCTCCGAGGATGACTGGGACGCGGTGATGGACGTGAACCTGAAAGCCGTCT
TCTTCACCTCGCAAGCCTTTGCGCGGGCTCTCATGTCCAGAAACGCAAGCGGAAAGATCGTTAACA
TTGCATCCCTTCTGTCGTTTCAAGGCGGCATTCGCGTTGCCTCCTACACGGCCGCCAAGCACGGTGT
GGCAGGCATCACCAGACTGTTGGCAAACGAATGGGCGTCCCGGCATCAACGTCAATGCGATAG
CGCCCGGTTACATTGCCACGAACAACACGGAAGCGCTTGAGCCGACGAGGAGCGCAACGCGGCG
ATCCTCGCACGCATTCCGGCTGGCCGCTGGGGGCGGGCGGAGGATATTGCGGGTACTGCTGTCTAT
CTTTGTTCGCCGGCAGCCGATTATGTTCATGGCGCCATTCTAAACGTCGATGGCGGTTGGCTCGCG
CGCTGA SEQ ID NO: 64 pSSI-376 P37769-DNA
ATGATTTTAAGTGCATTTTCTCTCGAAGGTAAAGTTGCGGTCGTCACTGGTTGTGATACTG
GACTGGGTCAGGGGATGGCGTTGGGGCTGGCGCAAGCGGGCTGTGACATTGTTGGCATT
AACATCGTTGAACCGACTGAAACCATCGAGCAGGTCACAGCGCTGGGGCGTCGTTTTTA
AGCCTGACCGCCGATCTGCGAAAGATTGATGGTATTCCAGCACTGCTGGATCGCGGTA
GCGGAGTTTGGTCATATTGATATCCTGGTGAATAACGCCGGATTGATTCGCCGCGAAGAT
GCTCTCGAGTTCAGCGAAAAGGACTGGGACGATGTCATGAACCTGAATATCAAGAGCGT
ATTCTTCATGTCTCAGGCAGCGGCGAAACACTTTATCGCGCAAGGCAATGGCGGCAAGA
TTATCAATATCGCGTCAATGCTCTCCTTCCAGGGCGGGATCCGTGTGCCTTCTTATACCGC
ATCAAAAAGCGGCGTGATGGGTGTGACGCGATTGATGGCGAACGAATGGGCTAAACACA
ACATTAATGTTAATGCGATAGCCCCGGGTTACATGGCGACCAACAATACTCAACAACTAC
GGGCAGATGAACAACGTAGCGCGGAAATTCTCGACCGCATTCCAGCTGGTCGTTGGGGA
CTGCCGAGTGACCTGATGGGGCCGATAGTGTTCCTTGCCTCCAGCGCTTCAGATTATGTG
AATGGTTATACCATTGCCGTGGATGGCGGTTGGCTGGCGCGTTAA SEQ ID NO: 65 pSGI-395 #5112 DNA
ATGCCCGGCATGACCACTCCTTTCGATCTTCATGGCAAGACCGCGATCGTCACCGGCGCCAATACC
GGCATCGGCCAGGCCATTGCCCTGTCGCTCGCGCAGGCCGGCGCGGATATCGCCGCCGTCGGCCG
CACGCCCGCACAGGACACGGTCGATCAGGTCCGCGCGCTCGGCCGCCGGGCGGACATTATCTCGG
CCGACCTTTCGACCATCGAACCGGTTCAGCGCGTCCTCGACGAAACGCTGGAAAAGCTTGGTGCCT
TGGACATACTGGTCAACAATGCCGGCATCATCCGCCGCGCCGACAGCGTCGATTTCACCGAGGAG
GATTGGGACGCGGTGATCGACACCAATCTCAAGACCACCTTCTTCCTCTGTCAGGCCGCCGGTCGC
CACATGCTTGCCCAAGGCGCTGGCAAGATCATCAACATCGCCTCGCTTCTTTCCTTCCAGGGCGGC
ATTCGCGTGCCGAGCTACACCGCGTCCAAAAGCGGCGTGCCGGCGCTGACCAAGCTGCTCGCCAA
CGAATGGGCGGCCAAGGGCGTCAATGTGAACGCCATCGCGCCGGGCTATATCGCCACCAACAACA
CCGCCGCTCCAGGCCGACGAAACCCGCAACCGCCAGATCCAGGAGCGCATCCCGGCTGGCCGC
TGGGGCGACCCCGCCGACATTGGCGGCGCGGCCGTGTTCCTGGCGTCCAGCGCCGCCGATTATATC
CATGGCCACACGCTCGCCGTCGACGGCGGCTGGCTCGCGCGCTGA SEQ ID NO: 66 pSGI-396 #7I03-DNA
ATGAACCCCTTCTCGCTTGAGGGCAAGACCGCCTTGTGACCGGTGCCAATACGGGCATCGGTCAG
GCCATCGCCATGGCGCTTGGCCGCGCCGGGGCGGACGTCATCTGCGCGGGACGCTCGTCCTGTGCG
GAGACCGTTGCCCTCATCGCTGGCAGCAAGGGCAAGGCGCGCGAACTGGTGCTCGACTTCGCCGA
CCCGATGGCCGCCGTGACGTGTTCGCCGCCGAACCGGTGGACATTCTCGTCAACAACGCGGGCA
TCATCCGGCGCGCCGATGCAGTGGATTTCACCGAGGCGACTGGGATGAGGTGATGGACGTGAAC
CTGAAGGCCGTGTTCTTCACCTGCCAGGCCTTCGGCAAGGCCGTTCTTGGCCGTGGAGGAAACGGC
AAGATCGTCAACATTGCCTCGCTCCTGTCATTCCAGGGTGGTATCCGGGTGCCGTCCTACACGGCC
TCGAAGCATGGTGTTGCAGGCATCACCAAGCTTCTGGCCAACGAATGGGCGGCGAAGGGCATCAA
TGTGAATGCCATCGCCCCCGGTTACATCGAAACGAACAATACCGAAGCACTGCGGGCGGACCCGG
TGCGCAACAAGGCCATCCTTGAGCGTATCCCTGCCGGCCGCTGGGGCCAGGCCTCGGACATCGGC GAAGCCGCCGTGTTCCTTGCCTCTCCGGCTGCCAATTACATCCATGGTGCAGTGCTGAATGTTGAC
GGAGGCTGGCTTGCCCGCTGA SEQ ID NO: 67 pSGI-353 P0AES2
MSSQFTTPVVTEMQVIPVAGHDSMLMNLSGAHAPFFTRNIVIIKDNSGHTGVGEIPGGEKIRK
TLEDAIPLVVGKTLGEYKNVLTLVRNTFADRDAGGRGLQTFDLRTTIHVVTGIEAAMLDLLG
QHLGVNVASLLGDGQQRSEVEMLGYLFFVGNRKATPLPYQSQPDDSCDWYRLRHEEAMTP
DAVVRLAEAAYEKYGFNDFKLKGGVLAGEEEAESIVALAQRFPQARITLDPNGAWSLNEAIK
IGKYLKGSLAYAEDPCGAEQGFSGREVMAEFRRATGLPTATNMIATDWRQMGHTLSLQSVD
IPLADPHFWTMQGSVRVAQMCHEFGLTWGSHSNNHFDISLAMFTHVAAAAPGKITAIDTHW
IWQEGNQRLTKEPFEIKGGLVQVPEKPGLGVEIDMDQVMKAHELYQKHGLGARDDAMGMQ
YLIPGWTFDNKRPCMVR SEQ ID NO: 68 pSGI-244 #8114
MTTAMSGTPRITELTVVPVAGQDSMLMNLSGAHGPWFTRNILILKDSAGHVGVGEVPGGEAI
RQTLDDARALLVGEPIGQYNALLGKVRRAFADRDAGGRGLQTFDLRIAIHAVTALESALLDL
LGQHLEVPVAALLGEGQQRDEVEMLGYLFFIGDRNRTDLGYRDESNSDDAWFRVRNEEAM
TPERIVRQAEAAYERYGFKDFKLKGGVLRGEEEVEAIRALAQRFPDARVTLDPNGAWSLDEA
SGLCRDLHGVLAYAEDPCGAENGYSGREVMAEFRRATGLPTATNMIATDWRQMSHAVCLH
SVDIPLADPHFWTMAGSVRVAQMCADFGLTWGSHSNNHFDISLAMFTHVAAAAPGRVTAID
THWIWQDGQHLTREPLKIVSGKVAVPQKPGLGVELDWDALEQAHAHYQEKGLGARDDAIA
MQYLIPNWTFNNKKPCMVR SEQ ID NO: 69 pSGI-353 P0AES2-DNA
ATGAGTTCTCAATTTACGACGCCTGTTGTTACTGAAATGCAGGTTATCCCGGTGGCGGGTCATGAC
AGTATGCTGATGAATCTGAGTGGTGCACACGCACCGTTCTTTACGCGTAATATTGTGATTATCAAA
GATAATTCTGGTCACACTGGCGTAGGGGAAATTCCCGGCGGCGAGAAAATCCGTAAAACGCTGGA
AGATGCGA1TCCGCTGGTGGTAGGTAAAACGCTGGGTGAATACAAAAACGTTCTGACGCTGGTGC
GTAATACTTTTGCCGATCGTGATGCTGGTGGGCGCGGTTTGCAGACATTTGACCTACGTACCACTA
TTCATGTAGTTACCGGGATAGAAGCGGCAATGCTGGATCTGCTGGGGCAGCATCTGGGGGTAAAC
GTGGCATCGCTGCTGGGCGATGGTCAACAGCGTAGCGAAGTCGAAATGCTCGGTTATCTGTTCTTC
GTCGGTAATCGCAAAGCCACGCCGCTGCCGTATCAAAGCCAGCCGGATGACTCATGCGACTGGTA
TCGCCTGCGTCATGAAGAAGCGATGACGCCGGATGCGGTGGTGCGCCTGGCGGAAGCGGCATATG
AAAAATATGGCTTCAACGATTTCAAACTGAAGGGCGGTGTACTGGCCGGGGAAGAAGAGGCCGAG
TCTATTGTGGCACTGGCGCAACGCTTCCCGCAGGCGCGTATTACGCTCGATCCTAACGGTGCCTGG
TCGCTGAACGAAGCGATTAAAATCGGTAAATACCTGAAAGGTTCGCTGGCTTATGCAGAAGATCC
GTGTGGTGCGGAGCAAGGTTTCTCCGGGCGTGAAGTGATGGCAGAGTTCCGTCGCGCGACAGGTC
TACCGACTGCAACCAATATGATCGCCACCGACTGGCGGCAAATGGGCCATACGCTCTCCCTGCAAT
CCGTTGATATCCCGCTGGCGGATCCGCATTTCTGGACAATGCAAGGTTCGGTACGTGTGGCGCAAA
TGTGCCATGAATTTGGCCTGACCTGGGGTTCACACTCTAACAACCACTTCGATATTTCCCTGGCGAT
GTTTACCCATGTTGCCGCCGCTGCACCGGGTAAAATTACTGCTATTGATACGCACTGGATTTGGCA
GGAAGGCAATCAGCGCCTGACCAAAGAACCGTTTGAGATCAAAGGCGGGCTGGTACAGGTGCCAG
AAAAACCGGGGCTGGGTGTAGAAATCGATATGGATCAAGTGATGAAAGCCCATGAGCTGTATCAG
AAACACGGGCTTGGCGCGCGTGACGATGCGATGGGAATGCAGTATCTGATTCCTGGCTGGACGTT
CGATAACAAGCGCCCGTGCATGGTGCGTTAA SEQ ID NO: 70 pSGI-244 #8114
ATGACCACCGCCATGTCGGGCACGCCCCGCATCACCGAACTCACCGTCGTGCCCGTCGCCGGGCA
GGACAGCATGCTGATGAACCTCAGCGGCGCCCATGGGCCCTGGTTCACCCGCAACATCCTCATCCT
CAAGGACAGCGCCGGCCACGTCGGCGTCGGCGAAGTGCCGGGCGGCGAAGCCATCCGCCAGACCC
TCGACGATGCCCGTGCCCTGCTGGTCGGCGAACCGATCGGCCAGTACAACGCTGCTCGGCAAG
GTGCGCCGCGCCTTCGCCGACCGTGACGCCGGCGGCCGCGGCCTGCAGACCTTCGACCTGCGCATC
GCCATTCACGCCGTCACCGCGCTGGAGTCGGCGCTGCTCGACCTGCTCGGCCAGCACCTCGAGGTG
CCGGTCGCCGCCTTGCTCGGCGAAGGCCAGCAGCGTGACGAAGTGGAAATGCTCGGCTACCTGTT
CTTCATCGGCGATCGCAACAGGACCGACCTCGGCTACCGCGACGAATCCAACTCCGACGACGCCT
GGTTTCGCGTGCGCAACGAGGAGGCCATGACGCCGGAGCGCATCGTCCGCCAGGCCGAGGCGGCC
TACGAGCGCTACGGCTTCAAGGACTTCAAGCTCAAGGGCGGCGTACTGCGCGGCGAAGAGGAAGT
CGAGGCGATCCGCGCCCTGGCCCAGCGCTTCCCCGACGCCCGCGTGACTCTGGACCCCAACGGCG
CCTGGTCGCTGGACGAAGCCAGCGGCCTGTGTCGCGACCTGCACGGCGTGCTGGCCTATGCCGAA
GACCCCTGCGGTGCCGAGAACGGCTATTCCGGCCGCGAGGTGATGGCCGAGTTCCGCCGCGCCAC
CGGTCTGCCCACCGCGACCAACATGATCGCCACCGACTGGCGACAGATGAGTCACGCGGTGTGCC
TGCACTCGGTGGACATCCCGCTGGCCGACCCGCACTTCTGGACCATGGCCGGCTCTGTGCGCGTGG
CGCAGATGTGCGCCGACTTCGGCCTGACCTGGGGTTCGCACTCGAACAACCACTTCGACATCTCCC
TGGCGATGTTCACCCACGTGGCGGCCGCCGCGCCGGGTCGCGTCACCGCCATCGACACCCACTGG
ATCTGGCAGGACGGCCAGCACCTGACCCGCGAGCGCTGAAGATCGTCAGCGGCAAGGTTGCGGT
GCCGCAGAAGCCGGGCTGGGCGTCGAGCTGGACTGGGATGCCCTGGAGCAGGCGCATGCCCACT
ACCAAGAGAAAGGCCTGGGTGCCCGCGATGACGCCATCGCCATGCAGTACCTGATCCCCAACTGG
ACCTTCAACAACAAGAAGCCGTGCATGGTGCGCTGA SEQ ID NO: 71 pSGI-383 P50199
MSHPDLFSLSGARALVTGASRGIGLTLAKGLARYGAEVVLNGRNAESLDSAQSGFEAEGLKA
STAVFDVTDQDAVIDGVAAIERDMGPIDILINNAGIQRRAPLEEFSRKDWDDLMSTNVNAVFF
VGQAVARHMIPRGRGKIVNICSVQSELARPGIAPYTATKGAVKNLTKGMATDWGRHGLQIN
GLAPGYFATEMTERLVADEEFTDWLCKRTPAGRWGQVEELVGAAVFLSSRASSFVNGQVL
MVDGGITVSL SEQ ID NO: 72 pSGI-383 P50199-DNA
ATGTCTCACCCGGATCTGTTTAGCTTAAGTGGCGCACGCGCATTAGTTACTGGTGCCTCTCGTGGTA
TTGGTTTAACCCTGGCCAAAGGTTTAGCCCGTTATGGTGCCGAAGTGGTTTTAAATGGCCGTAATG
CCGAAAAGCCTGGATTCTGCCCAAAGTGGCTTTGAAGCCGAAGGCTTAAAAGCATCTACCGCTGTGT
TTGACGTGACCGATCAAGATGCAGTCATTGACGGCGTGGCAGCAATTGAACGCGATATGGGTCCG -continued
ATTGATATCCTGATCAACAATGCGGGCATTCAACGCAGAGCCCCGTTAGAAGAATTTTCTCGCAAA
GACTGGGACGATCTGATGAGCACCAACGTTAACGCCGTGTTCTTTGTGGGACAAGCCGTTGCCAGA
CACATGATTCCTAGAGGTCGCGGTAAAATCGTCAACATCTGTTCAGTGCAGAGCGAACTGGCAAG
ACCGGGTATTGCACCTTATACCGCCACAAAAGGAGCCGTCAAAAATCTGACCAAAGGTATGCCA
CCGATTGGGGTCGTCATGGTTTACAGATTAATGGCTTAGCACCGGGCTATTTTGCCACCGAGATGA
CCGAACGCTTAGTTGCCGACGAAGAATTTACCGACTGGTTATGCAAACGCACCCCTGCAGGCAGA
TGGGGCCAAGTTGAAGAATTAGTAGGCGCAGCCGTGTTTTTAAGTAGTAGAGCCTCAAGCTTCGTG
AATGGCCAAGTCCTGATGGTTGATGGTGGAATTACTGTGAGCCTGTAA

---

What is claimed is:

1. A method for synthesizing a derivative of FDCA comprising:
contacting DDG with an alcohol and an inorganic acid at a temperature in excess of 60° C. to form a derivative of FDCA.

2. The method of claim 1 wherein the alcohol is butanol or ethanol and the derivative of FDCA is a butyl or ethyl derivative of FDCA, respectively.

3. The method of claim 1 having a yield of at least 25% molar.

4. A method of synthesizing a derivative of DDG comprising:
contacting DDG with an alcohol, an inorganic acid, and optionally a co-solvent to produce a derivative of DDG.

5. The method of claim 4 wherein:
a) the alcohol is ethanol or butanol;
b) the inorganic acid is sulfuric acid; and
c) the co-solvent is selected from the group consisting of: THF, acetone, acetonitrile, an ether, ethyl acetate, butyl acetate, an dioxane, chloroform, methylene chloride, 1,2-dichloroethane, a hexane, a heptane, toluene, carbon tetrachloride, petroleum ether, and a xylene.

6. A method for synthesizing a derivative of FDCA comprising:
contacting a derivative of DDG with an inorganic acid to produce a derivative of FDCA.

7. The method of claim 6 having a yield of greater than 25% molar.

8. The method of claim 6 wherein the derivative of DDG is selected from the group consisting: methyl-DDG, ethyl-DDG, butyl-DDG, di-methyl DDG, diethyl-DDG, and di-butyl DDG; and
the derivative of FDCA is a methyl, ethyl, butyl, dimethyl, diethyl, or dibutyl derivative of FDCA, respectively.

9. The method of claim 8 further comprising that the derivative of FDCA is de-esterified to yield FDCA.

10. The method of claim 6 further comprising a step of polymerizing the derivative of FDCA.

11. A method for synthesizing FDCA comprising:
contacting DDG with an inorganic acid in a gas phase at a temperature greater than 70° C. to synthesize FDCA.

12. A method for synthesizing FDCA comprising:
contacting DDG with an inorganic acid in a gas phase at a temperature in excess of 120° C. to synthesize FDCA.

13. A method for synthesizing FDCA comprising:
contacting DDG with an inorganic acid under anhydrous reaction conditions to synthesize FDCA.

14. The method of claim 1 wherein:
the alcohol is selected from: butanol, ethanol, methanol, and propanol;
the acid is sulfuric acid;
the contacting occurs at a temperature of greater than 70° C.; and
thereby synthesizing a butyl, ethyl, methyl, or propyl derivative of FDCA, respectively.

15. The method of claim 14 wherein the contacting occurs in a gas phase at a temperature of greater than 150° C.

16. The method of claim 5 further comprising a step of removing water from a solvent comprising the DDG prior to performing the method.

17. The method of claim 16 wherein greater than 90% of the water is removed from the solvent comprising the DDG prior to performing the method.

18. The method of claim 8 wherein the contacting occurs in the gas phase at a temperature of at least 90° C.

19. The method of claim 11 wherein the inorganic acid is sulfuric acid.

20. The method of claim 12 wherein the inorganic acid is sulfuric acid.

21. The method of claim 13 wherein the contacting occurs at a temperature of greater than 80° C.

22. The method of claim 13 wherein the DDG is comprised in a solvent that contains less than 10% water (w/w).

23. The method of claim 22 wherein the DDG is comprised in a solvent that contains less than 5% water (w/w).

24. The method of claim 8 further comprising a step of polymerizing the derivative of FDCA.

* * * * *